(12) United States Patent
Dennis et al.

(10) Patent No.: US 8,436,147 B2
(45) Date of Patent: May 7, 2013

(54) ANTIBODIES AND IMMUNOCONJUGATES AND USES THEREFOR

(75) Inventors: Mark S. Dennis, San Carlos, CA (US); Bonnee Rubinfeld, Danville, CA (US); Paul Polakis, Mill Valley, CA (US); Aya Jakobovits, Beverly Hills, CA (US)

(73) Assignee: Genentech, Inc., South San Francisco, CA (US)

( * ) Notice: Subject to any disclaimer, the term of this patent is extended or adjusted under 35 U.S.C. 154(b) by 133 days.

(21) Appl. No.: 11/978,122

(22) Filed: Oct. 26, 2007

(65) Prior Publication Data

US 2009/0280056 A1    Nov. 12, 2009

Related U.S. Application Data

(60) Provisional application No. 60/863,295, filed on Oct. 27, 2006, provisional application No. 60/868,707, filed on Dec. 5, 2006, provisional application No. 60/921,300, filed on Mar. 30, 2007, provisional application No. 60/937,857, filed on Jun. 29, 2007.

(51) Int. Cl.
    *C12P 21/08*    (2006.01)

(52) U.S. Cl.
    USPC .............. 530/387.3; 530/350; 530/388.1; 530/391.1; 530/391.3; 530/391.5; 530/391.7; 530/391.9

(58) Field of Classification Search ............ 530/350, 530/387.3, 388.1, 391.1, 391.3, 391.5, 391.7, 530/391.9
    See application file for complete search history.

(56) References Cited

U.S. PATENT DOCUMENTS

| | | | |
|---|---|---|---|
| 4,140,707 A | 2/1979 | Cleare et al. | |
| 4,808,614 A | 2/1989 | Hertel et al. | |
| 4,814,470 A | 3/1989 | Colin et al. | |
| 5,416,064 A | 5/1995 | Chari et al. | |
| 5,859,205 A * | 1/1999 | Adair et al. ............... | 530/387.3 |
| 5,869,045 A | 2/1999 | Hellstrom et al. | |
| 6,048,970 A | 4/2000 | Lal et al. | |
| 6,329,503 B1 | 12/2001 | Afar et al. | |
| 6,342,219 B1 | 1/2002 | Thorpe et al. | |
| 6,800,746 B2 | 10/2004 | Xu et al. | |
| 6,833,438 B1 | 12/2004 | Afar et al. | |
| 6,887,975 B2 | 5/2005 | Afar et al. | |
| 7,053,186 B2 | 5/2006 | Afar et al. | |
| 7,091,186 B2 | 8/2006 | Senter et al. | |
| 7,166,714 B2 | 1/2007 | Afar et al. | |
| 7,319,006 B2 | 1/2008 | Afar et al. | |
| 7,455,991 B2 | 11/2008 | Afar et al. | |
| 7,485,299 B2 | 2/2009 | Afar et al. | |
| 7,494,646 B2 * | 2/2009 | Jakobovits et al. ........ | 424/130.1 |
| 7,498,298 B2 | 3/2009 | Doronina et al. | |
| 7,575,749 B2 | 8/2009 | Afar et al. | |
| 7,611,904 B2 | 11/2009 | Afar et al. | |
| 7,642,054 B2 | 1/2010 | Afar et al. | |
| 7,727,533 B2 | 6/2010 | Afar et al. | |
| 7,745,394 B2 | 6/2010 | Doronina et al. | |
| 7,884,179 B2 | 2/2011 | Faris et al. | |
| 7,928,201 B2 | 4/2011 | Afar et al. | |
| 7,939,503 B2 | 5/2011 | Jacobovits et al. | |
| 7,947,276 B2 | 5/2011 | Jacobovits et al. | |
| 7,947,459 B2 | 5/2011 | Hubert et al. | |
| 7,964,566 B2 | 6/2011 | Doronina et al. | |
| 7,968,307 B2 | 6/2011 | Afar et al. | |
| 7,994,135 B2 | 8/2011 | Doronina et al. | |
| 8,008,442 B2 | 8/2011 | Jacobovits et al. | |
| 8,013,135 B2 | 9/2011 | Jacobovits et al. | |
| 8,053,551 B2 | 11/2011 | Afar et al. | |
| 8,241,626 B2 | 8/2012 | Hubert et al. | |
| 2002/0022248 A1 | 2/2002 | Xu et al. | |
| 2003/0060612 A1 | 3/2003 | Goddard et al. | |
| 2003/0064397 A1 | 4/2003 | Spancake et al. | |
| 2003/0149531 A1 | 8/2003 | Hubert et al. | |
| 2006/0073150 A1 | 4/2006 | Faris et al. | |
| 2007/0134253 A1 | 6/2007 | Afar et al. | |
| 2008/0226657 A1 | 9/2008 | Doronina et al. | |
| 2008/0248053 A1 | 10/2008 | Doronina et al. | |
| 2010/0272742 A1 | 10/2010 | Afar et al. | |
| 2011/0318371 A1 | 12/2011 | Afar et al. | |
| 2012/0003247 A1 | 1/2012 | Doronina et al. | |
| 2012/0142607 A1 | 6/2012 | Jacobovits et al. | |

FOREIGN PATENT DOCUMENTS

| | | |
|---|---|---|
| EA | 005601 B1 | 4/2005 |
| EP | 0 834 563 | 4/1998 |
| EP | 0834563 | 4/1998 |
| EP | 1308459 | 5/2003 |
| GB | 2136425 | 9/1984 |
| JP | 11164691 | 6/1999 |
| WO | WO 94/09150 | 4/1994 |
| WO | WO 95/14772 | 6/1995 |

(Continued)

OTHER PUBLICATIONS

Hillier, et al., "The WashU-Merck EST Project," EMBL Sequence Database, XP002128081, Aug. 25, 1996.

"WUGC:H_RG041D11.1 Protein (WUGSC: H_DJ1121E10.1 Protein) (Fragment)," EMBL Sequence Database, XP002128083, May 1, 1999.

"Homo Sapiens PAC Clone DJ1121E10 from 7q21.1-q2, Complete Sequence," EMBL Sequence Database, XP002128084, Jun. 15, 1998.

"Human BAC Clone RG016J04 from 7q21, Complete Sequence," EMBL Sequence Database, XP002128082, May 13, 1997.

Abu-Threideh et al., GENBANK, (Accession No. 095034), National Library of Medicine, Bethesda MD, May I, 1999.

Abu-Threideh et al., Jun. 1998, EMBL/GEN13ANIC/DDBJ Databases.

(Continued)

*Primary Examiner* — Stephen L Rawlings
*Assistant Examiner* — Brad Duffy
(74) *Attorney, Agent, or Firm* — Stephanie Yonker; Ginger R. Dreger; Arnold & Porter, LLP

(57) ABSTRACT

Anti-STEAP-1 antibodies and immunoconjugates thereof are provided. Methods of using anti-STEAP-1 antibodies and immunoconjugates thereof are provided.

44 Claims, 45 Drawing Sheets
(29 of 45 Drawing Sheet(s) Filed in Color)

FOREIGN PATENT DOCUMENTS

| WO | WO 98/18489 | 5/1998 |
|---|---|---|
| WO | WO 98/37093 | 8/1998 |
| WO | WO 98/37418 | 8/1998 |
| WO | WO 98/53071 | 11/1998 |
| WO | WO 99/06548 | 2/1999 |
| WO | WO 99/61469 | 2/1999 |
| WO | WO 99/62941 | 12/1999 |
| WO | WO 00/04149 | 1/2000 |
| WO | WO 00/35937 | 6/2000 |
| WO | WO 00/77021 | 12/2000 |
| WO | WO 01/12662 | 2/2001 |
| WO | WO 01/24118 | 4/2001 |
| WO | WO 01/25272 | 4/2001 |
| WO | WO 01/72962 | 4/2001 |
| WO | WO 01/34802 | 5/2001 |
| WO | WO 01/40276 | 6/2001 |
| WO | WO 01/51633 | 7/2001 |
| WO | WO 01/57190 | 8/2001 |
| WO | WO 01/57276 | 8/2001 |
| WO | WO 01/57277 | 8/2001 |
| WO | WO 01/60860 | 8/2001 |
| WO | WO 01/73032 | 10/2001 |
| WO | WO 01/75067 | 10/2001 |
| WO | WO 01/86003 | 11/2001 |
| WO | WO 01/94629 | 12/2001 |
| WO | WO 01/96388 | 12/2001 |
| WO | WO 02/10449 | 2/2002 |
| WO | WO 02/16429 | 2/2002 |
| WO | WO 02/26822 | 4/2002 |
| WO | WO 02/057303 | 7/2002 |
| WO | WO 02/059260 | 8/2002 |
| WO | WO 02/095010 | 11/2002 |
| WO | WO 02/102993 | 12/2002 |
| WO | WO 02/102994 | 12/2002 |
| WO | WO 03/004622 | 1/2003 |
| WO | WO 03/009814 | 2/2003 |
| WO | WO 2004/010957 | 2/2004 |
| WO | WO 2005/081711 | 9/2005 |
| WO | WO 2005/113601 A2 | 12/2005 |
| WO | WO 03/022995 | 3/2006 |
| WO | WO 2006/034488 A2 | 3/2006 |

OTHER PUBLICATIONS

Alberts et al., Molecular Biology of the Cell, 3rd edition (1994) p. 465.
Bellone et al., Immunology Today (1999) 20(10):457-462.
Bowie et al. (1990) Science 247:1306-1310.
Burgess et al., J. Cell Biol. 111:2129-2138, (1990).
Cate et al., GENBANK, (Accession No. W86309), National Library of Medicine, Bethesda MD, Nov. 1998.
Challita-Eid Pia M., et al., "Monoclonal antibodies to six-transmembrane epithelial antigen of the prostate-1 inhibit intercellular communication in vitro and growth of human tumor xenografts in vivo", vol. 67, No. 12, pp. 5798-5805, (2007).
Database EMBL Nucleotide and Protein Sequences, Aug. 25, 1996, XP002128081, AA032221, Hinxton, GB.
Database EMBL Nucleotide and Protein Sequences, Jun. 15, 1998, X.P002128084, AC004969 (clone D11121E10), Hinxton, GB.
Database EMBL, "Human BAC clone CTB-167B5 form 7q21, 'complete sequence," Jun. 17, 1998 XP002173859 (Accession AC 003991 (Waterstone, R.)).
Diss et al. "Expression of skeletal muscle-type voltage-gated Na+ channel in rat and human prostate cancer cell lines," FEBS Letters 427:5-10, (1998).
Dulcert et al., GENBANK, (Accession No. Y11840), National Library of Medicine, Bethesda MD, Feb. 11, 1999.
Faris M., et al., "Validation of STEAP-1 as a cell surface cancer therapeutic target", Proceedings of the annual meeting of the American Association for Cancer Research, vol. 43, p. 947, (2002).
Fu et al (EMBO Journal, 1996, vol. 15, pp. 4392-4401.
Goldenberg, clinical Therapeutics, 20(2): 309-318, (1999).
Greenspan et al., Nature Biotechnology 7:936-937, (1999).
Grimes et al., "Electrophysiological characterization of voltage-gated Na+ current expressed in the highly metastatic Mat-LyLu cell line of rat prostate cancer," Journal of Cellular Physiology 175:50-58, (1998).
Gura, Science, 278:1041-1042, (1997).
Gutierrez et al., "Activation of a $Ca^{2+}$ -permeable cation channel by.two different inducers of appoptosis in a human prostatic cancer cell line," Journal of Physiology 517.1:95-107, (1999).
Haverstick et al., "Inhibition of human prostate cancer proliferation in vitro and in a mouse model by a compound synthesized to block $Ca^{2+}$ Entry'," Cancer Research pp. 1002-1008, (2000).
Herbert et al., The Dictionary of Immunology, Academic Press, 4th edition, (1995).
Hubert et al., PNAS USA 96(25):14523-14528, (1999).
Lazar, et al., Mol. Cell Biol., 8(3): 1247-1252, (1988).
Lepple-Wienhues et al., "K + Channels and the intracellular calcium signal in human melanoma cell proliferation," J. Membrane Biol. 151:149-157, (1996).
Marino et al., "Association between cell membrane potential and breast cancer," Tumor Biol. 15:82-89, (1994).
McClean and Hill, Eur. J. of Cancer, vol. 29A, pp. 2243-2248, (1993).
Nie, et al., "Inhibition of proliferation of MCF-7 breast cancer cells by a blocker of $CA^{2+}$-permeable channel", Cell Calcium, 22(2): 75-82, (1997).
Pancrazio, et al., "Voltage-dependent ion channels in small-cell lung cancer cells", Cancer Research, 49: 5901-5906, (1989).
Reiger, et al., Glossary of Genetics and Cytogenetics, Springer-Verlag, p. 17, (1976).
Shantz and Pegg, Int J of Biochem. and Cell Biol., vol. 31, pp. 107-122, (1999).
Spitler, Cancer Biotherapy, 10:1-3, (1995).
Doronina et al., "Development of potent monoclonal antibody auristatin conjugates for cancer therapy", Nature Biotechnol. 21: 778-784; 941 (2003).
Opposition Brief filed by Laboratorio Franco to Colombian Patent No. 09-034.904, Jan. 25, 2011 (English translation).
Elbashir, et al., "Duplexes of 21-nucleotide RNAs mediate RNA interference in cultured mammalian cells", Nature, vol. 411, pp. 494-498, (2001).
Saffran, et al., "Anti-PSCA mAbs inhibit tumor growth and metastasis formation and prolong the survival of mice bearing human prostate cancer xenografts", PNAS, vol. 98, No. 5, pp. 2658-2663, (2001).
Yang, et al., "Murine six-transmembrane epithelial antigen of the prostate, prostate stem cell antigen and prostate-specific membrane antigen: Prostate-specific cell-surface antigens highly expressed in prostate cancer of transgenic adenocarcinoma mouse prostate mice", Cancer Research, vol. 61, No. 15, pp. 5857-5860, (2001).
U.S. Appl. No. 13/397,644 dated Feb. 15, 2012, Doronina et al.
English translation of Russian Decision on grant, received in corresponding RU Patent Application No. 2009119976.
Roitt et al., "Interaction of Antibodies with Antigens"; *Immunology*," transl. from Engl.: Mir. 2000 pp. 110, 150; and English translation.

\* cited by examiner

Alignment of Light Chain Sequences

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | | |
| | | | | | | | | | | | | | | | | | | | | | | | | | | | | | Kabat – CDR L1 | | | | | | | | | | | | | | |
| | | | | | | | | | | | | | | | | | | | | | | | | | | | | | | Chothia – CDR L1 | | | | | | | | | | | | |
| | | | | | | | | | | | | | | | | | | | | | | | | | | | | | | | | | | | | Contact – CDR L1 | | | | | | |
| huKI | D | I | Q | M | T | Q | S | P | S | S | L | S | A | S | V | G | D | R | V | T | I | T | C | R | A | S | Q | S | I | S | N | Y | L | A | W | Y | Q | Q |
| mu120 | D | V | V | M | T | Q | T | P | L | S | L | P | V | S | L | G | D | Q | A | S | I | S | C | K | S | S | Q | S | L | L | Y | R | S | N | Q | K | N | Y | L | A | W | Y | L |
| 120 graft | D | I | Q | M | T | Q | S | P | S | S | L | S | A | S | V | G | D | R | V | T | I | T | C | K | S | S | Q | S | L | L | Y | R | S | N | Q | K | N | Y | L | A | W | Y | Q |
| 120.v24 | D | I | Q | * | * | * | * | * | * | * | * | * | * | * | * | * | * | * | * | * | * | * | * | K | S | S | Q | S | L | L | Y | R | S | N | Q | K | N | Y | L | A | W | Y | Q |

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | Kabat – CDR L2 | | | | | | | | | | | | | | | | | | | | | | | | | | | | | | |
| | | | | | | | | | | | | | | Chothia – CDR L2 | | | | | | | | | | | | | | | | | | | | | | | | | | | | |
| | | | | | | | | | | | | | | Contact – CDR L2 | | | | | | | | | | | | | | | | | | | | | | | | | | | | |
| huKI | Q | K | P | G | K | A | P | K | L | L | I | Y | A | A | S | S | L | E | S | G | V | P | S | R | F | S | G | S | G | S | G | T | D | F | T | L | T | I | S | S | L | Q | P |
| mu120 | Q | K | P | G | Q | S | P | K | L | L | I | Y | W | A | S | T | R | E | S | G | V | P | D | R | F | T | G | S | G | S | G | T | D | F | T | L | T | I | S | S | V | K | A |
| 120 graft | Q | K | P | G | K | A | P | K | L | L | I | Y | W | A | S | T | R | E | S | G | V | P | S | R | F | S | G | S | G | S | G | T | D | F | T | L | T | I | S | S | L | Q | P |
| 120.v24 | Q | * | * | * | * | * | * | * | * | * | * | * | W | A | S | T | R | E | S | * | * | * | * | * | * | * | * | * | * | * | * | * | * | * | * | * | * | * | * | * | * | * | * |

| Kabat# | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|
| | | | | | | | | Kabat – CDR L3 | | | | | | | | | | | | | | | | | | | |
| | | | | | | | | | Chothia – CDR L3 | | | | | | | | | | | | | | | | | | |
| | | | | | | | | | Contact – CDR L3 | | | | | | | | | | | | | | | | | | |
| huKI | E | D | F | A | T | Y | Y | C | Q | Q | Y | N | S | L | P | W | T | F | G | Q | G | T | K | V | E | I | K | R | (SEQ ID NO:4) |
| mu120 | E | D | L | A | V | Y | Y | C | Q | Q | Y | Y | R | T | P | R | T | F | G | G | G | T | K | V | E | I | K | R | (SEQ ID NO:5) |
| 120 graft | E | D | F | A | T | Y | Y | C | Q | Q | Y | Y | R | T | P | R | T | F | G | Q | G | T | K | V | E | I | K | R | (SEQ ID NO:6) |
| 120.v24 | * | * | * | * | * | * | * | * | Q | Q | Y | Y | R | T | P | R | T | F | * | * | * | * | * | * | * | * | * | * | |

| | | | |
|---|---|---|---|
| I | | | |
| A | QVQLVQSGAEVKKPGASVKVSCKASGYTFT -H1- | WVRQAPGQGLEWMG | -H2- |
| B | QVQLVQSGAEVKKPGASVKVSCKAS -H1- | WVRQAPGQGLEWM | -H2- |
| C | QVQLVQSGAEVKKPGASVKVSCKAS -H1- | WVRQAPGQGLEWM | -H2- |
| D | QVQLVQSGAEVKKPGASVKVSCKAS -H1- | WVRQAPGQGLEWM | -H2- |
| II | | | |
| A | QVQLQESGPGLVKPSQTLSLTCTVSGGSVS -H1- | WIRQPPGKGLEWIG | -H2- |
| B | QVQLQESGPGLVKPSQTLSLTCTVS -H1- | WIRQPPGKGLEWI | -H2- |
| C | QVQLQESGPGLVKPSQTLSLTCTVS -H1- | WIRQPPGKGLEWI | -H2- |
| D | QVQLQESGPGLVKPSQTLSLTCTVS -H1- | WIRQPPGKGLEWI | -H2- |
| III | | | |
| A | EVQLVESGGGLVQPGGSLRLSCAASGFTFS -H1- | WVRQAPGKGLEWVS | -H2- |
| B | EVQLVESGGGLVQPGGSLRLSCAAS -H1- | WVRQAPGKGLEWV | -H2- |
| C | EVQLVESGGGLVQPGGSLRVSCAAS -H1- | WVRQAPGKGLEWV | -H2- |
| D | EVQLVESGGGLVQPGGSLRLSCAAS -H1- | WVRQAPGKGLEWV | -H2- |
| Acceptor-1 | | | |
| A | EVQLVESGGGLVQPGGSLRLSCAASGFNIK -H1- | WVRQAPGKGLEWVS | -H2- |
| B | EVQLVESGGGLVKPGGSLRLSCAAS -H1- | WVRQAPGKGLEWV | -H2- |
| C | EVQLVESGGELVQPGGSLRLSCAAS -H1- | WVRQAPGKGLEWV | -H2- |
| Acceptor-2 | | | |
| A | EVQLVESGGGLVQPGGSLRLSCAASGFNIK -H1- | WVRQAPGKGLEWVS | -H2- |
| B | EVQLVESGGGLVQPGGSLRLSCAAS -H1- | WVRQAPGKGLEWV | -H2- |
| C | EVQLVESGGGLVQPGGSLRLSCAAS -H1- | WVRQAPGKGLEWV | -H2- |
| D | EVQLVESGGGLVQPGGSLRLSCAAS -H1- | WVRQAPGKGLEWV | -H2- |

Figure 3A

| | | SEQ ID NOs: |
|---|---|---|
| RVTITADTSTSTAYMELSSLRSEDTAVYYCAR ...WGQGTLVTVSS | 26, 27, 28, 29 |
| RVTITADTSTSTAYMELSSLRSEDTAVYYCAR ...WGQGTLVTVSS | 30, 31, 28, 29 |
| RVTITADTSTSTAYMELSSLRSEDTAVYYCAR ...WGQGTLVTVSS | 30, 31, 32, 29 |
| RVTITADTSTSTAYMELSSLRSEDTAVYYC... ...WGQGTLVTVSS | 30, 31, 33, 29 |
| RVTISVDTSKNQFSLKLSSVTAADTAVYYCAR ...WGQGTLVTVSS | 34, 35, 36, 29 |
| RVTISVDTSKNQFSLKLSSVTAADTAVYYCAR ...WGQGTLVTVSS | 37, 38, 36, 29 |
| RVTISVDTSKNQFSLKLSSVTAADTAVYYCA  ...WGQGTLVTVSS | 37, 38, 39, 29 |
| RVTISVDTSKNQFSLKLSSVTAADTAVYYC   ...WGQGTLVTVSS | 37, 38, 40, 29 |
| RFTISRDNSKNTLYLQMNSLRAEDTAVYYCAR ...WGQGTLVTVSS | 41, 42, 43, 29 |
| RFTISRDNSKNTLYLQMNSLRAEDTAVYYCAR ...WGQGTLVTVSS | 44, 45, 43, 29 |
| RFTISRDNSKNTLYLQMNSLRAEDTAVYYCAR ...WGQGTLVTVSS | 44, 45, 46, 29 |
| RFTISRDNSKNTLYLQMNSLRAEDTAVYYC   ...WGQGTLVTVSS | 44, 45, 47, 29 |
| RFTIS DSKNTYLQMNSLRAEDTAVYYCR    ...WGQGTLVTVSS | 48, 42, 49, 29 |
| RFTIS DSKNTYLQMNSLRAEDTAVYYCR    ...WGQGTLVTVSS | 44, 45, 49, 29 |
| RFTIS DSKNTYLQMNSLRAEDTAVYYC     ...WGQGTLVTVSS | 44, 45, 50, 29 |
| RFTIS DSKNTYLQMNSLRAEDTAVYYCAR   ...WGQGTLVTVSS | 48, 42, 51, 29 |
| RFTIS DSKNTYLQMNSLRAEDTAVYYCAR   ...WGQGTLVTVSS | 44, 45, 51, 29 |
| RFTIS DSKNTYLQMNSLRAEDTAVYYCA    ...WGQGTLVTVSS | 44, 45, 52, 29 |
| RFTIS DSKNTYLQMNSLRAEDTAVYYC     ...WGQGTLVTVSS | 44, 45, 53, 29 |

Figure 3B kv1  DIQMTQSPSSLSASVGDRVTITC -L1- WYQQKPGKAPKLLIY -L2- GVPSRFSGSGSGTDFTLTISSLQP kv1  DIQMTQSPSSLSASVGDRVTITC -L1- WYQQKPGKAPKLLI   -L2- GVPSRFSGSGSGTDFTLTISSLQP kv2  DIVMTQSPLSLPVTPGEPASISC -L1- WYLQKPGQSPQLLIY -L2- GVPDRFSGSGSGTDFTLKISRVEA kv3  EIVLTQSPGTLSLSPGERATLSC -L1- WYQQKPGQAPRLLIY -L2- GIPDRFSGSGSGTDFTLTISRLEP kv4  DIVMTQSPDSLAVSLGERATINC -L1- WYQQKPGQPPKLLIY -L2- GVPDRFSGSGSGTDFTLTISSLQA

Figure 4A

EDFATYYC -L3- FGQGTKVEIK    SEQ ID NOs: 54, 55, 56, 57

EDFATYYC -L3- FGQGTKVEIK    SEQ ID NOs: 54, 58, 56, 57

EDVGVYYC -L3- FGQGTKVEIK    SEQ ID NOs: 58, 59, 60, 57

EDFAVYYC -L3- FGQGTKVEIK    SEQ ID NOs: 61, 62, 63, 57

EDVAVYYC -L3- FGQGTKVEIK    SEQ ID NOs: 64, 65, 66, 57

Figure 4B

```
          230       240       250       260       270
humIgG1   PAPELLGGPSVFLFPPKPKDTLMISRTPEVTCVVVDVSHEDPEVKFNWYV
humIgG2   PAP-PVAGPSVFLFPPKPKDTLMISRTPEVTCVVVDVSHEDPEVQFNWYV
humIgG3   PAPELLGGPSVFLFPPKPKDTLMISRTPEVTCVVVDVSHEDPEVQFKWYV
humIgG4   PAPEFLGGPSVFLFPPKPKDTLMISRTPEVTCVVVDVSQEDPEVQFNWYV
             ****                                *   * *

280       290       300       310       320
humIgG1   DGVEVHNAKTKPREEQYNSTYRVVSVLTVLHQDWLNGKEYKCKVSNKALP
humIgG2   DGVEVHNAKTKPREEQFNSTFRVVSVLTVVHQDWLNGKEYKCKVSNKGLP
humIgG3   DGVEVHNAKTKPREEQFNSTFRVVSVLTVLHQDWLNGKEYKCKVSNKALP
humIgG4   DGVEVHNAKTKPREEQFNSTYRVVSVLTVLHQDWLNGKEYKCKVSNKGLP
                          *    *         *                *

330       340       350       360       370
humIgG1   APIEKTISKAKGQPREPQVYTLPPSREEMTKNQVSLTCLVKGFYPSDIAV
                          D L
humIgG2   APIEKTISKTKGQPREPQVYTLPPSREEMTKNQVSLTCLVKGFYPSDIAV
humIgG3   APIEKTISKTKGQPREPQVYTLPPSREEMTKNQVSLTCLVKGFYPSDIAV
humIgG4   SSIEKTISKAKGQPREPQVYTLPPSQEEMTKNQVSLTCLVKGFYPSDIAV
          **        *              *

380       390       400       410       420
humIgG1   EWESNGQPENNYKTTPPVLDSDGSFFLYSKLTVDKSRWQQGNVFSCSVMH
humIgG2   EWESNGQPENNYKTTPPMLDSDGSFFLYSKLTVDKSRWQQGNVFSCSVMH
humIgG3   EWESSGQPENNYNTTPPMLDSDGSFFLYSKLTVDKSRWQQGNIFSCSVMH
humIgG4   EWESNGQPENNYKTTPPVLDSDGSFFLYSRLTVDKSRWQEGNVFSCSVMH
              *       *    *                *    * *

430       440
humIgG1   EALHNHYTQKSLSLSPGK    (SEQ ID NO:85)
humIgG2   EALHNHYTQKSLSLSPGK    (SEQ ID NO:86)
humIgG3   EALHNRFTQKSLSLSPGK    (SEQ ID NO:87)
humIgG4   EALHNHYTQKSLSLSLGK    (SEQ ID NO:88)
              **           *
```

A Kappa light chain constant region consensus sequence:

```
RTVAAPSVFIFPPSDEQLKSGTASVVCLLNNFYPREAKVQWK
VDNALQSGNSQESVTEQDSKDSTYSLSSTLTLSKADYEKHKV
YACEVTHQGLSSPVTKSFNRGEC    (SEQ ID NO:89)
```

Figure 5

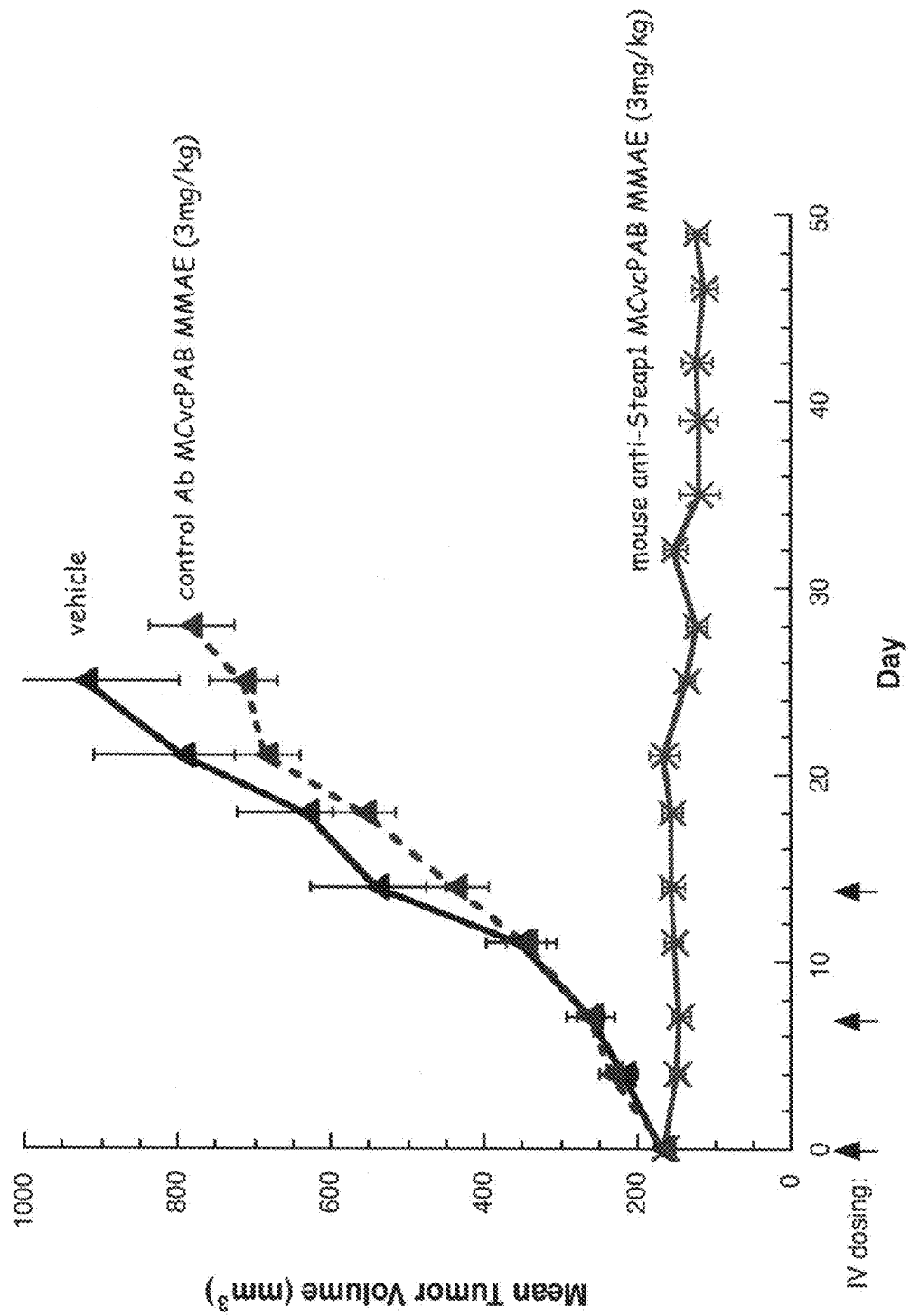

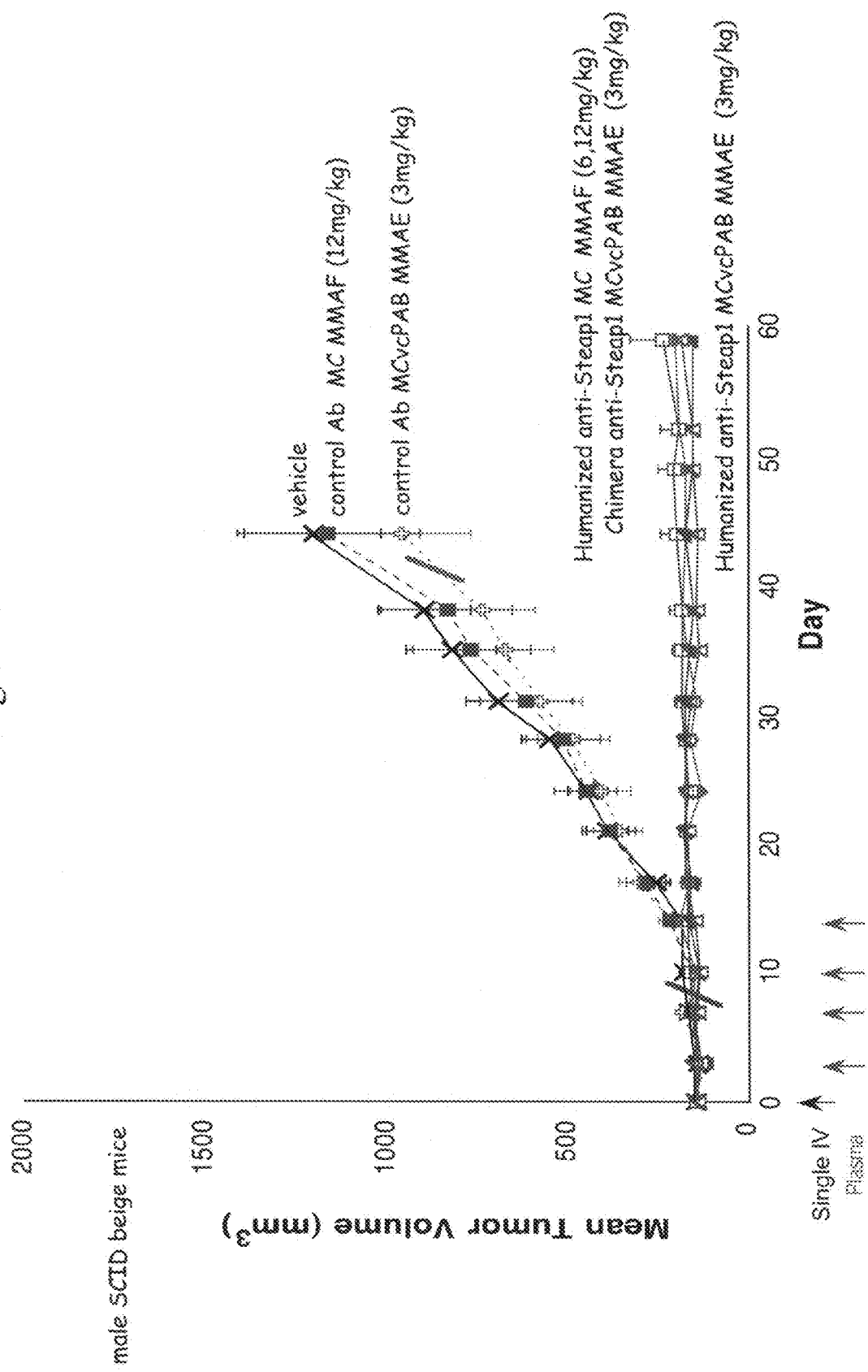

Expression of STEAP1 in prostate cancer models
*Exogenous models*
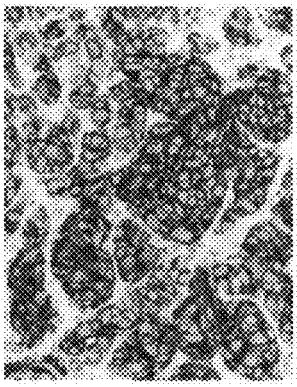
293 STEAP1 LB50
Figure 13A
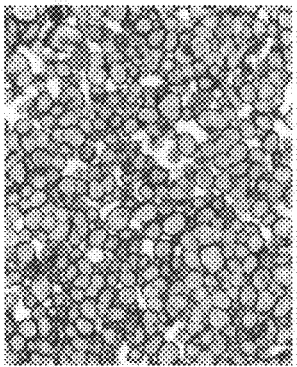
PC3 STEAP1 PS5.4
Figure 13B
*Endogenous models*
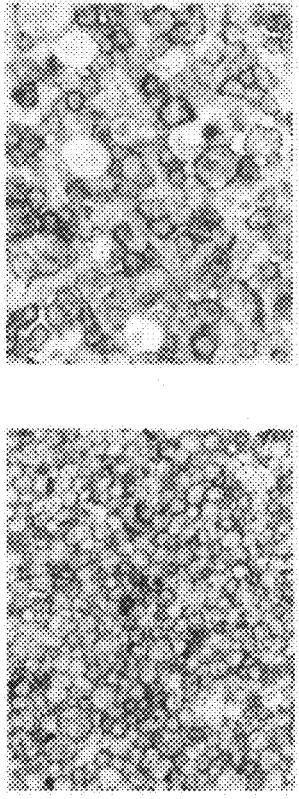
LNCaP
Figure 13C
LuCAP 77
Figure 13D

Thio-LC Variant (V205C) with corresponding sequential numbering

Standardized numbering >> LC-V205C (Kabat numbering)

| Relative position | | | | | | | | | | | | | | |
|---|---|---|---|---|---|---|---|---|---|---|---|---|---|---|
| LC-V210C | V | T | H | Q | G | L | S | S | P | V | T | K | S | F | N | R | G | C | 219 |
| LC-V204C | V | T | H | Q | G | L | S | S | P | V | T | K | S | F | N | R | G | C | 213 |
| LC-V211C | V | T | H | Q | G | L | S | S | P | V | T | K | S | F | N | R | G | C | 220 |
| LC-V205C | V | T | H | Q | G | L | S | S | P | V | T | K | S | F | N | R | G | C | 214 |
| LC-V205C | V | T | H | Q | G | L | S | S | P | V | T | K | S | F | N | R | G | C | 214 |
| LC-V205C | V | T | H | Q | G | L | S | S | P | V | T | K | S | F | N | R | G | C | 214 |
| LC-V210C | V | T | H | Q | G | L | S | S | P | V | T | K | S | F | N | R | G | C | 219 |
| LC-V209C | V | T | H | Q | G | L | S | S | P | V | T | K | S | F | N | R | G | C | 218 |
| LC-V209C | V | T | H | Q | G | L | S | S | P | V | T | K | S | F | N | R | G | C | 218 |
| LC-V205C | V | T | H | Q | G | L | S | S | P | V | T | K | S | F | N | R | G | C | 214 |
| STEAP120-LC-V211C | V | T | H | Q | G | L | S | S | P | V | T | K | S | F | N | R | G | C | 220 |

Figure 17A

Thio-HC Variant (A121C) with corresponding sequential numbering >> HC-A118C (EU Numbering)

| Relative position | Standardized numbering >> | | |
|---|---|---|---|
| HC-A114C | - - - - - LYLWGQGT LVTVSSAS KGPSVFPLAPSSKSTSGG TAAL 138 |
| HC-A123C | - - NSYWYFDVWGQGT LVTVSSAS TKGPSVFPLAPSSKSTSGG TAAL 147 |
| HC-A121C | - - IPRHANVFMWGQGT LVTVSSA ATKGPSVFPLAPSSKSTSGG TA

Thio-Fc Variant (S400C) with corresponding sequential numbering

Standardized numbering >>  Fc-S400C (EU Numbering)

| Relative numbering | | | |
|---|---|---|---|
| HC-S396C | VLDSDGSFFLYSKLTVDKSRWQQGNVFSCSVMHEALHNHYTQKSLS | 438 |
| HC-S405C | VLDSDGSFFLYSKLTVDKSRWQQGNVFSCSVMHEALHNHYTQKSLS | 447 |
| HC-S403C | VLDSDGSFFLYSKLTVDKSRWQQGNVFSCSVMHEALHNHYTQKSLS | 445 |
| HC-S399C | VLDSDGSFFLYSKLTVDKSRWQQGNVFSCSVMHEALHNHYTQKSLS | 441 |
| HC-S403C | VLDSDGSFFLYSKLTVDKSRWQQGNVFSCSVMHEALHNHYTQKSLS | 445 |
| HC-S403C | VLDSDGSFFLYSKLTVDKSRWQQGNVFSCSVMHEALHNHYTQKSLS | 445 |
| HC-S403C | VLDSDGSFFLYSKLTVDKSRWQQGNVFSCSVMHEALHNHYTQKSLS | 445 |
| HC-S406C | VLDSDGSFFLYSKLTVDKSRWQQGNVFSCSVMHEALHNHYTQKSLS | 448 |
| HC-S400C | VLDSDGSFFLYSKLTVDKSRWQQGNVFSCSVMHEALHNHYTQKSLS | 442 |
| HC-S403C | VLDSDGSFFLYSKLTVDKSRWQQGNVFSCSVMHEALHNHYTQKSLS | 445 |
| STEAP120-HC-S407C | VLDSDGSFFLYSKLTVDKSRWQQGNVFSCSVMHEALHNHYTQKSLS | 449 |

Figure 17C

PC3 Steap1 c.PS5.4

120 VL Differences - Kappa I vs IV

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|
|  |  |  |  |  |  |  |  |  |  |  |  |  |  |  |  |  |  |  |  |  |  |  |  |  |  |  |  | Kabat - CDR L1 | | | | | | | | | |
|  |  |  |  |  |  |  |  |  |  |  |  |  |  |  |  |  |  |  |  |  |  |  |  |  |  | Chothia - CDR L1 | | | | | | | | | | | |
|  |  |  |  |  |  |  |  |  |  |  |  |  |  |  |  |  |  |  |  |  |  |  |  |  |  |  |  |  |  |  | Contact - CDR L1 | | | | | |
| 120 | D | I | V | M | S | Q | S | P | S | S | L | A | V | S | V | G | E | K | V | T | M | S | C | K | S | S | Q | S | L | L | Y | R | S | N | Q | K | N |
| Simmons IV 120.v24 | D | I | V | M | T | Q | S | P | D | S | L | A | V | S | L | G | E | R | A | T | I | N | C | K | S | S | Q | S | L | L | Y | R | S | N | Q | K | N |
|  | * |  |  |  | * |  |  |  | * |  |  |  |  |  | * |  |  | * | * |  | * | * |  |  |  |  |  |  |  |  |  |  |  |  |  |  |  |
| 120.v24 | D | I | [Q] | M | T | Q | S | P | [S] | S | L | [S] | A | [S] | V | G | [D] | R | [V] | T | [T] | [T] | C | [T] | S | S | Q | S | L | L | Y | R | S | N | Q | K | N |

| Kabat# | 38 | 39 | 40 | 41 | 42 | 43 | 44 | 45 | 46 | 47 | 48 | A | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  |  |  |  |  |  |  |  |  |  |  |  |  |  |  | Kabat - CDR L2 | | | | | | | | | | | | | | | | | | | | | | | | | | | | | |
|  |  |  |  |  |  |  |  |  |  |  |  |  |  |  | Chothia - CDR L2 | | | | | | | | | | | | | | | | | | | | | | | | | | | | | |
|  |  |  |  |  |  |  |  |  |  |  |  |  | Contact - CDR L2 | | | | | | | | | | | | | | | | | | | | | | | | | | | | | | |
| 120 | L | A | W | Y | Q | Q | K | P | G | Q | S | P | K | L | L | I | Y | W | A | S | T | R | E | S | G | V | P | D | R | F | T | G | S | G | S | G | T | D | F | T | L | T | I | S |
| Simmons IV 120.v24 | L | A | W | Y | Q | Q | K | P | G | Q | [A] | P | K | L | L | I | Y | W | A | S | T | R | E | S | G | V | P | [S] | R | F | S | G | S | G | S | G | T | D | F | T | L | T | I | S |
|  |  |  |  |  |  |  |  |  |  |  | * |  |  |  |  |  |  |  |  |  |  |  |  |  |  |  |  | * |  |  | * |  |  |  |  |  |  |  |  |  |  |  |  |

| Kabat# | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|---|---|---|---|---|---|
|  |  |  |  |  |  |  |  |  | Kabat - CDR L3 | | | | | | | | | | | | | | | | | | | | | | | | | |
|  |  |  |  |  |  |  |  |  | Chothia - CDR L3 | | | | | | | | | | | | | | | | | | | | | | | | | |
|  |  |  |  |  |  |  |  |  | Contact - CDR L3 | | | | | | | | | | | | | | | | | | | | | | | | | |
| 120 | S | V | K | A | E | D | L | A | V | Y | Y | C | Q | Q | Y | Y | N | Y | P |  |  | R | T | F | G | G | G | T | K | V | E | I | K | R |
| Simmons IV | S | S | L | Q | A | E | D | V | A | V | Y | Y | C | Q | Q | Y | Y | N | Y | P |  | R | T | F | G | Q | G | T | K | V | E | I | K | R |
| 120.v24 | S | S | L | Q | [P] | E | D | [F] | A | [T] | Y | Y | C | Q | Q | Y | Y | N | Y | P |  | R | T | F | G | Q | G | T | K | V | E | I | K | R |
|  |  |  |  |  | * |  |  | * |  | * |  |  |  |  |  |  |  |  |  |  |  |  |  |  |  | * |  |  |  |  |  |  |  |  |

Figure 23 (PART 1)

Figure 23 (PART 2)

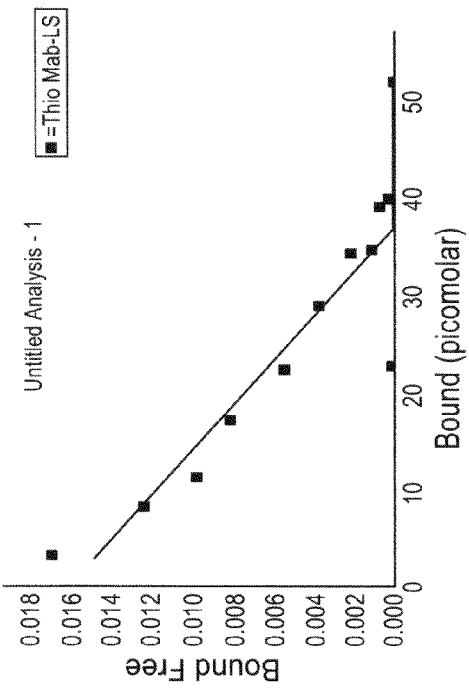
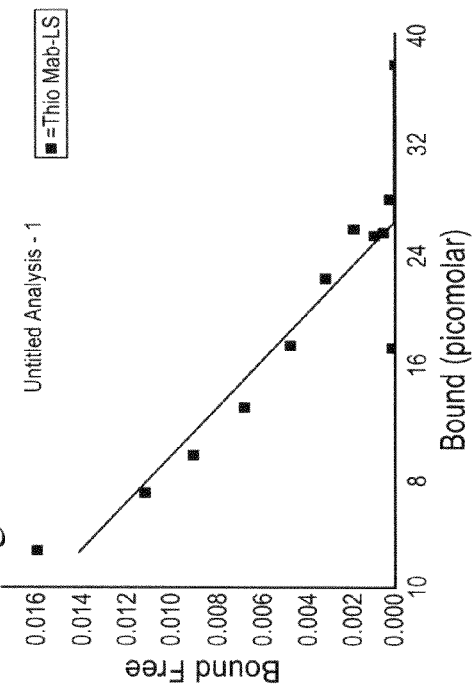
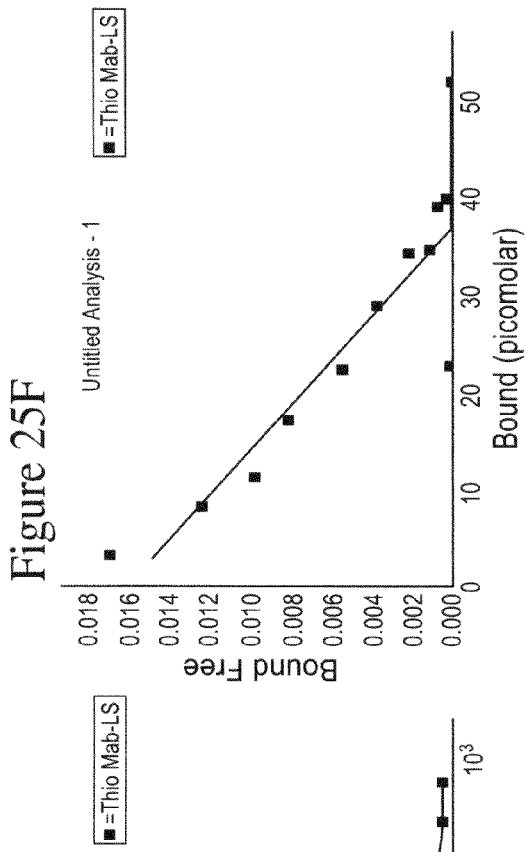
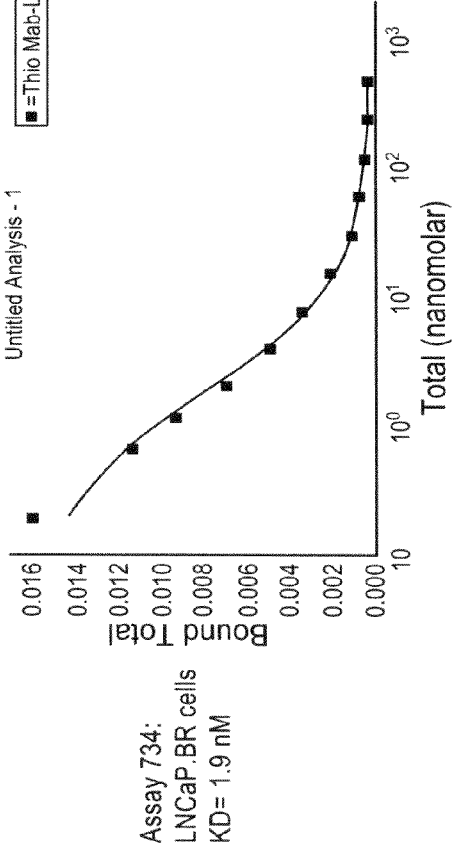
Figure 25E
Figure 25F
Figure 25G
Figure 25H

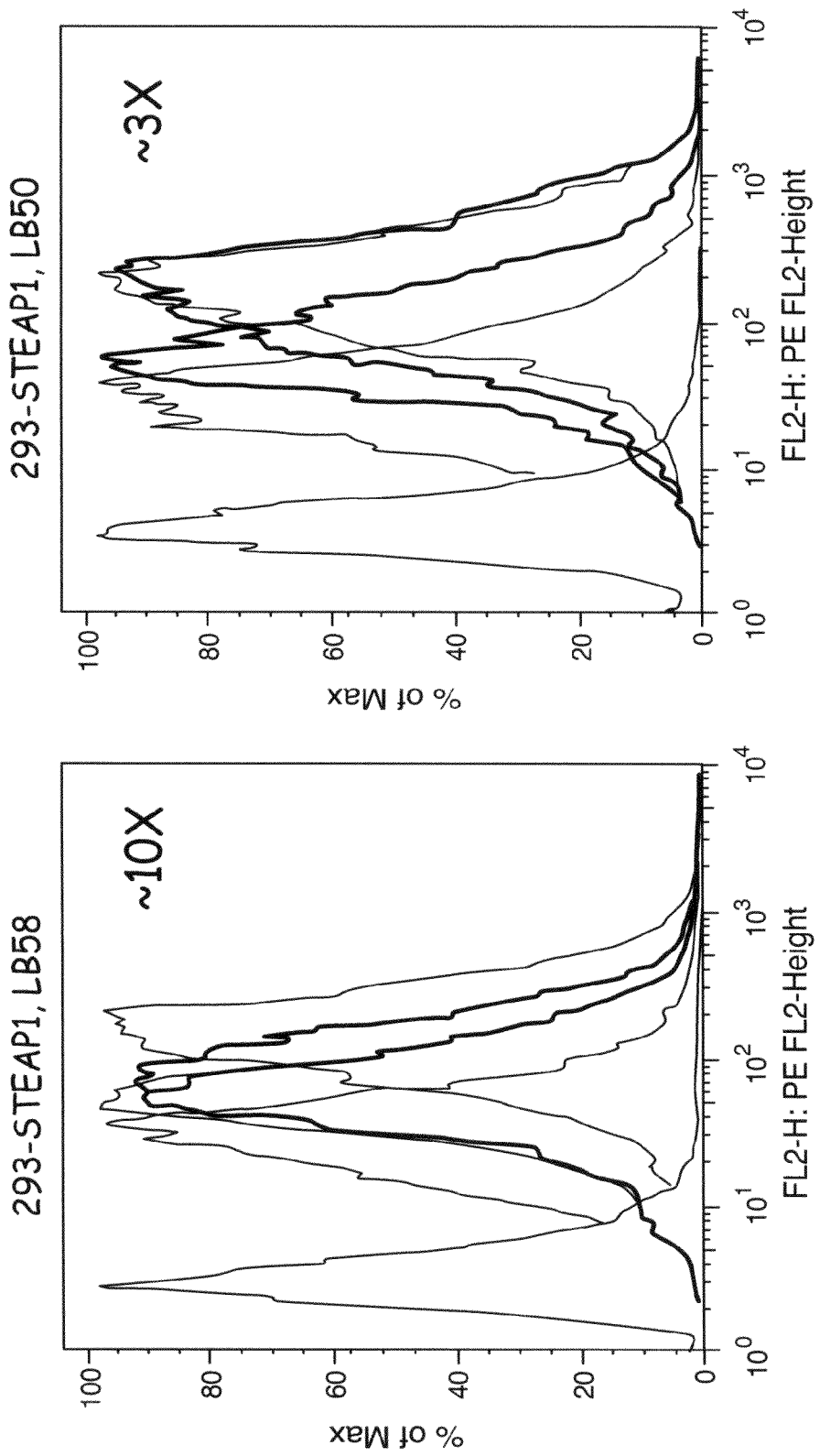

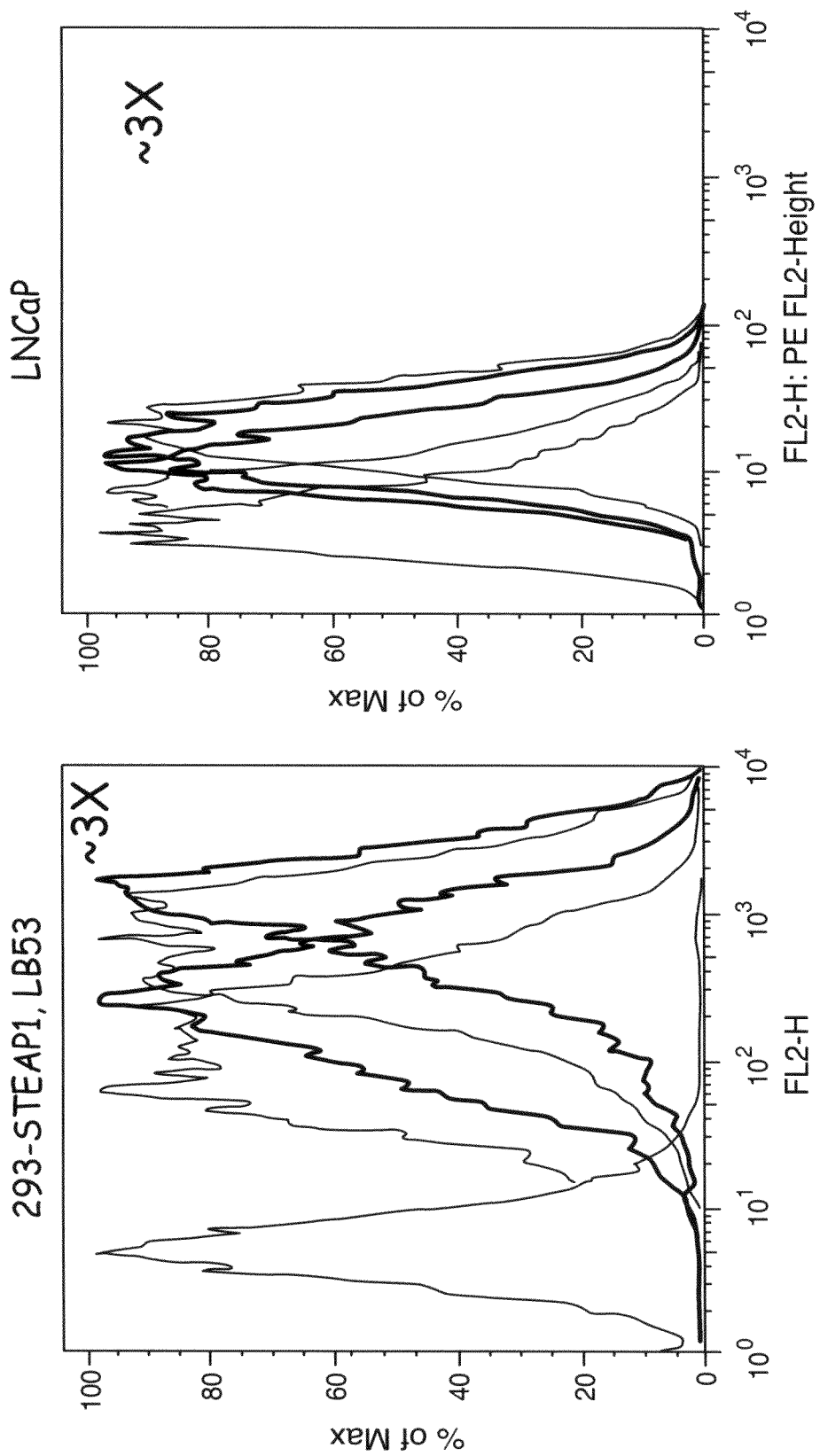

SEQUENCE LISTING

```
<160> NUMBER OF SEQ ID NOS: 139

<210> SEQ ID NO 1
<211> LENGTH: 340
<212> TYPE: PRT
<213> ORGANISM: Homo sapiens

<400> SEQUENCE: 1

Met Glu Ser Arg Lys Asp Ile Thr Asn Gln Glu Glu Leu Trp Lys Met
 1               5                  10                  15

Lys Pro Arg Arg Asn Leu Glu Glu Asp Asp Tyr Leu His Lys Asp Thr
                20                  25                  30

Gly Glu Thr Ser Met Leu Lys Arg Pro Val Leu Leu His Leu His Gln
            35                  40                  45

Thr Ala His Ala Asp Glu Phe Asp Cys Pro Ser Glu Leu Gln His Thr
        50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

Leu Gly Ile Val Ser Leu Leu Leu Gly Thr Ile His Ala Leu Ile Phe
            260                 265                 270

Ala Trp Asn Lys Trp Ile Asp Ile Lys Gln Phe Val Trp Tyr Thr Pro
```

```
            275                 280                 285
Pro Thr Phe Met Ile Ala Val Phe Leu Pro Ile Val Leu Ile Phe
290                 295                 300
Lys Ser Ile Leu Phe Leu Pro Cys Leu Arg Lys Ile Leu Lys Ile
305                 310                 315                 320
Arg His Gly Trp Glu Asp Val Thr Lys Ile Asn Lys Thr Glu Ile Cys
                325                 330                 335
Ser Gln Leu Asn
        340

<210> SEQ ID NO 2
<211> LENGTH: 340
<212> TYPE: PRT
<213> ORGANISM: Mus musculus

<400> SEQUENCE: 2

Met Glu Ile Ser Asp Asp Val Thr Asn Pro Glu Gln Leu Trp Lys Met
1               5                   10                  15
Lys Pro Lys Gly Asn Leu Glu Asp Asp Ser Tyr Ser Thr Lys Asp Ser
                20                  25                  30
Gly Glu Thr Ser Met Leu Lys Arg Pro Gly Leu Ser His Leu Gln His
            35                  40                  45
Ala Val His Val Asp Ala Phe Asp Cys Pro Ser Glu Leu Gln His Thr
        50                  55                  60
Gln Glu Phe Phe Pro Asn Trp Arg Leu Pro Val Lys Val Ala Ala Ile
65                  70                  75                  80
Ile Ser Ser Leu Thr Phe Leu Tyr Thr Leu Arg Glu Ile Ile Tyr
                85                  90                  95
Pro Leu Val Thr Ser Arg Glu Gln Tyr Phe Tyr Lys Ile Pro Ile Leu
                100                 105                 110
Val Ile Asn Lys Val Leu Pro Met Val Ala Ile Thr Leu Leu Ala Leu
            115                 120                 125
Val Tyr Leu Pro Gly Glu Leu Ala Ala Val Val Gln Leu Arg Asn Gly
        130                 135                 140
Thr Lys Tyr Lys Lys Phe Pro Pro Trp Leu Asp Arg Trp Met Leu Ala
145                 150                 155                 160
Lys Lys Gln Phe Gly Leu Leu Ser Phe Phe Ala Val Leu His Ala
                165                 170                 175
Val Tyr Ser Leu Ser Tyr Pro Met Arg Arg Ser Tyr Arg Tyr Lys Leu
            180                 185                 190
Leu Asn Trp Ala Tyr Lys Gln Val Gln Gln Asn Lys Glu Asp Ala Trp
        195                 200                 205
Val Glu His Asp Val Trp Arg Met Glu Ile Tyr Val Ser Leu Gly Ile
    210                 215                 220
Val Gly Leu Ala Ile Leu Ala Leu Leu Ala Val Thr Ser Ile Pro Ser
225                 230                 235                 240
Val Ser Asp Ser Leu Thr Trp Arg Glu Phe His Tyr Ile Gln Ser Lys
                245                 250                 255
Leu Gly Ile Val Ser Leu Leu Leu Gly Thr Val His Ala Leu Val Phe
            260                 265                 270
Ala Trp Asn Lys Trp Val Asp Val Ser Gln Phe Val Trp Tyr Met Pro
        275                 280                 285
Pro Thr Phe Met Ile Ala Val Phe Leu Pro Thr Leu Val Leu Ile Cys
    290                 295                 300
Lys Ile Ala Leu Cys Leu Pro Cys Leu Arg Lys Lys Ile Leu Lys Ile
```

```
                305                 310                 315                 320
Arg Cys Gly Trp Glu Asp Val Ser Lys Ile Asn Arg Thr Glu Met Ala
                    325                 330                 335
Ser Arg Leu Asn
            340

<210> SEQ ID NO 3
<211> LENGTH: 340
<212> TYPE: PRT
<213> ORGANISM: Macaca fascicularis

<400> SEQUENCE: 3

Met Glu Ser Arg Lys Asp Ile Thr Asn Glu Glu Leu Trp Lys Met
 1               5                  10                  15

Lys Pro Arg Arg Asn Leu Glu Glu Asp Tyr Leu His Lys Asp Thr
                20                  25                  30

Gly Glu Thr Ser Met Leu Lys Arg Pro Val Leu Leu His Leu His Gln
                35                  40                      45

Thr Ala His Ala Asp Glu Phe Asp Cys Pro Ser Glu Leu Gln His Thr
 50                      55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Arg Glu Val Ile His
                85                  90                  95

Pro Leu Ala Thr Ser His Gln Gln Tyr Phe Tyr Lys Ile Pro Ile Leu
                100                 105                 110

Val Ile Asn Lys Val Leu Pro Met Val Ser Ile Thr Leu Leu Ala Leu
                115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
                180                 185                 190

Leu Asn Trp Ala Tyr Gln Gln Val Gln Gln Asn Lys Glu Asp Ala Trp
                195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

Leu Gly Ile Val Ser Leu Leu Leu Gly Thr Ile His Ala Leu Ile Phe
                260                 265                 270

Ala Trp Asn Lys Trp Ile Asp Ile Lys Gln Phe Val Trp Tyr Thr Pro
                275                 280                 285

Pro Thr Phe Met Ile Ala Val Phe Leu Pro Val Val Val Leu Ile Phe
                290                 295                 300

Lys Ser Ile Leu Phe Leu Pro Cys Leu Arg Lys Lys Ile Leu Lys Ile
305                 310                 315                 320

Arg His Gly Trp Glu Asp Ile Thr Lys Ile Asn Lys Met Glu Ile Ser
                325                 330                 335

Ser Gln Leu Asn
```

<210> SEQ ID NO 4
<211> LENGTH: 108
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys Arg
            100                 105

<210> SEQ ID NO 5
<211> LENGTH: 114
<212> TYPE: PRT
<213> ORGANISM: Mus musculus

<400> SEQUENCE: 5

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Arg
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Tyr Pro Arg Thr Phe Gly Gly Gly Thr Lys Val Glu Ile
            100                 105                 110

Lys Arg

<210> SEQ ID NO 6
<211> LENGTH: 114
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val

```
                    50                  55                  60
Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                     85                  90                  95

Tyr Tyr Asn Tyr Pro Arg Thr Phe Gly Gln Gly Thr Lys Val Glu Ile
                100                 105                 110

Lys Arg

<210> SEQ ID NO 7
<211> LENGTH: 113
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Val Ile Ser Gly Asp Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Phe Asp Tyr Trp Gly Gln Gly Thr Leu Val Thr Val Ser
                100                 105                 110

Ser

<210> SEQ ID NO 8
<211> LENGTH: 124
<212> TYPE: PRT
<213> ORGANISM: Mus musculus

<400> SEQUENCE: 8

Asp Val Gln Val Gln Glu Ser Gly Pro Gly Leu Val Lys Pro Ser Gln
  1               5                  10                  15

Ser Leu Ser Leu Thr Cys Thr Val Thr Gly Tyr Ser Ile Thr Ser Asp
                 20                  25                  30

Tyr Ala Trp Asn Trp Ile Arg Gln Phe Pro Gly Asn Lys Leu Glu Trp
             35                  40                  45

Met Gly Tyr Ile Ser Asn Ser Gly Ser Thr Ser Tyr Asn Pro Ser Leu
         50                  55                  60

Lys Ser Arg Ile Ser Ile Thr Arg Asp Thr Ser Lys Asn Gln Phe Phe
 65                  70                  75                  80

Leu Gln Leu Ile Ser Val Thr Thr Glu Asp Thr Ala Thr Tyr Tyr Cys
                 85                  90                  95

Ala Arg Glu Arg Asn Tyr Asp Tyr Asp Asp Tyr Tyr Ala Met Asp
                100                 105                 110

Tyr Trp Gly Gln Gly Thr Thr Leu Thr Val Ser Ala
             115                 120

<210> SEQ ID NO 9
<211> LENGTH: 124
<212> TYPE: PRT
```

<213> ORGANISM: Homo sapiens

<400> SEQUENCE: 9

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Tyr Ser Ile Thr Ser Asp
            20                  25                  30
Tyr Ala Trp Asn Trp Val Arg Gln Ala Pro Gly Lys Gly Leu Glu Trp
        35                  40                  45
Val Gly Tyr Ile Ser Asn Ser Gly Ser Thr Tyr Asn Pro Ser Leu
    50                  55                  60
Lys Ser Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Arg Asn Tyr Asp Tyr Asp Asp Tyr Tyr Tyr Ala Met Asp
               100                 105                 110
Tyr Trp Gly Gln Gly Thr Leu Val Thr Val Ser Ser
           115                 120
```

<210> SEQ ID NO 10
<211> LENGTH: 124
<212> TYPE: PRT
<213> ORGANISM: Homo sapiens

<400> SEQUENCE: 10

```
Glu Val Gln Leu Val Glu Ser Gly Gly Gly Leu Val Gln Pro Gly Gly
 1               5                  10                  15
Ser Leu Arg Leu Ser Cys Ala Val Ser Gly Tyr Ser Ile Thr Ser Asp
            20                  25                  30
Tyr Ala Trp Asn Trp Val Arg Gln Ala Pro Gly Lys Gly Leu Glu Trp
        35                  40                  45
Val Gly Tyr Ile Ser Asn Ser Gly Ser Thr Tyr Asn Pro Ser Leu
    50                  55                  60
Lys Ser Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Arg Asn Tyr Asp Tyr Asp Asp Tyr Tyr Tyr Ala Met Asp
               100                 105                 110
Tyr Trp Gly Gln Gly Thr Leu Val Thr Val Ser Ser
           115                 120
```

<210> SEQ ID NO 11
<211> LENGTH: 17
<212> TYPE: PRT
<213> ORGANISM: Homo sapiens

<400> SEQUENCE: 11

```
Lys Ser Ser Gln Ser Leu Leu Tyr Arg Ser Asn Gln Lys Asn Tyr Leu
 1               5                  10                  15
Ala
```

<210> SEQ ID NO 12
<211> LENGTH: 7
<212> TYPE: PRT
<213> ORGANISM: Homo sapiens

<400> SEQUENCE: 12

```
Trp Ala Ser Thr Arg Glu Ser
  1               5

<210> SEQ ID NO 13
<211> LENGTH: 9
<212> TYPE: PRT
<213> ORGANISM: Homo sapiens

<400> SEQUENCE: 13

Gln Gln Tyr Tyr Asn Tyr Pro Arg Thr
  1               5

<210> SEQ ID NO 14
<211> LENGTH: 11
<212> TYPE: PRT
<213> ORGANISM: Homo sapiens

<400> SEQUENCE: 14

Gly Tyr Ser Ile Thr Ser Asp Tyr Ala Trp Asn
  1               5                  10

<210> SEQ ID NO 15
<211> LENGTH: 17
<212> TYPE: PRT
<213> ORGANISM: Homo sapiens

<400> SEQUENCE: 15

Gly Tyr Ile Ser Asn Ser Gly Ser Thr Ser Tyr Asn Pro Ser Leu Lys
  1               5                  10                  15

Ser

<210> SEQ ID NO 16
<211> LENGTH: 15
<212> TYPE: PRT
<213> ORGANISM: Homo sapiens

<400> SEQUENCE: 16

Glu Arg Asn Tyr Asp Tyr Asp Asp Tyr Tyr Ala Met Asp Tyr
  1               5                  10                  15

<210> SEQ ID NO 17
<211> LENGTH: 23
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
  1               5                  10                  15

Asp Arg Val Thr Ile Thr Cys
            20

<210> SEQ ID NO 18
<211> LENGTH: 15
<212> TYPE: PRT
<213> ORGANISM: Homo sapiens

<400> SEQUENCE: 18

Trp Tyr Gln Gln Lys Pro Gly Lys Ala Pro Lys Leu Leu Ile Tyr
  1               5                  10                  15

<210> SEQ ID NO 19
<211> LENGTH: 32
<212> TYPE: PRT
<213> ORGANISM: Homo sapiens
```

```
<400> SEQUENCE: 19

Gly Val Pro Ser Arg Phe Ser Gly Ser Gly Thr Asp Phe Thr
1               5                  10                 15

Leu Thr Ile Ser Ser Leu Gln Pro Glu Asp Phe Ala Thr Tyr Tyr Cys
            20                  25                  30

<210> SEQ ID NO 20
<211> LENGTH: 11
<212> TYPE: PRT
<213> ORGANISM: Homo sapiens

<400> SEQUENCE: 20

Phe Gly Gln Gly Thr Lys Val Glu Ile Lys Arg
1               5                  10

<210> SEQ ID NO 21
<211> LENGTH: 25
<212> TYPE: PRT
<213> ORGANISM: Homo sapiens

<400> SEQUENCE: 21

Glu Val Gln Leu Val Glu Ser Gly Gly Gly Leu Val Gln Pro Gly Gly
1               5                  10                 15

Ser Leu Arg Leu Ser Cys Ala Ala Ser
            20                  25

<210> SEQ ID NO 22
<211> LENGTH: 13
<212> TYPE: PRT
<213> ORGANISM: Homo sapiens

<400> SEQUENCE: 22

Trp Val Arg Gln Ala Pro Gly Lys Gly Leu Glu Trp Val
1               5                  10

<210> SEQ ID NO 23
<211> LENGTH: 32
<212> TYPE: PRT
<213> ORGANISM: Homo sapiens

<400> SEQUENCE: 23

Arg Phe Thr Ile Ser Arg Asp Asn Ser Lys Asn Thr Leu Tyr Leu Gln
1               5                  10                 15

Met Asn Ser Leu Arg Ala Glu Asp Thr Ala Val Tyr Tyr Cys Ala Arg
            20                  25                  30

<210> SEQ ID NO 24
<211> LENGTH: 11
<212> TYPE: PRT
<213> ORGANISM: Homo sapiens

<400> SEQUENCE: 24

Trp Gly Gln Gly Thr Leu Val Thr Val Ser Ser
1               5                  10

<210> SEQ ID NO 25
<211> LENGTH: 25
<212> TYPE: PRT
<213> ORGANISM: Homo sapiens

<400> SEQUENCE: 25

Glu Val Gln Leu Val Glu Ser Gly Gly Gly Leu Val Gln Pro Gly Gly
1               5                  10                 15
```

```
Ser Leu Arg Leu Ser Cys Ala Val Ser
            20                  25

<210> SEQ ID NO 26
<211> LENGTH: 30
<212> TYPE: PRT
<213> ORGANISM: Homo sapiens

<400> SEQUENCE: 26

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr
            20                  25                  30

<210> SEQ ID NO 27
<211> LENGTH: 14
<212> TYPE: PRT
<213> ORGANISM: Homo sapiens

<400> SEQUENCE: 27

Trp Val Arg Gln Ala Pro Gly Gln Gly Leu Glu Trp Met Gly
 1               5                  10

<210> SEQ ID NO 28
<211> LENGTH: 32
<212> TYPE: PRT
<213> ORGANISM: Homo sapiens

<400> SEQUENCE: 28

Arg Val Thr Ile Thr Ala Asp Thr Ser Thr Ser Thr Ala Tyr Met Glu
 1               5                  10                  15

Ile Ser Ser Leu Arg Ser Glu Asp Thr Ala Val Tyr Tyr Cys Ala Arg
            20                  25                  30

<210> SEQ ID NO 29
<211> LENGTH: 11
<212> TYPE: PRT
<213> ORGANISM: Homo sapiens

<400> SEQUENCE: 29

Trp Gly Gln Gly Thr Leu Val Thr Val Ser Ser
 1               5                  10

<210> SEQ ID NO 30
<211> LENGTH: 25
<212> TYPE: PRT
<213> ORGANISM: Homo sapiens

<400> SEQUENCE: 30

Gln Val Gln Leu Val Gln Ser Gly Ala Glu Val Lys Lys Pro Gly Ala
 1               5                  10                  15

Ser Val Lys Val Ser Cys Lys Ala Ser
            20                  25

<210> SEQ ID NO 31
<211> LENGTH: 13
<212> TYPE: PRT
<213> ORGANISM: Homo sapiens

<400> SEQUENCE: 31

Trp Val Arg Gln Ala Pro Gly Gln Gly Leu Glu Trp Met
 1               5                  10
```

```
<210> SEQ ID NO 32
<211> LENGTH: 31
<212> TYPE: PRT
<213> ORGANISM: Homo sapiens

<400> SEQUENCE: 32

Arg Val Thr Ile Thr Ala Asp Thr Ser Thr Ser Thr Ala Tyr Met Glu
 1               5                  10                  15

Leu Ser Ser Leu Arg Ser Glu Asp Thr Ala Val Tyr Tyr Cys Ala
             20                  25                  30

<210> SEQ ID NO 33
<211> LENGTH: 30
<212> TYPE: PRT
<213> ORGANISM: Homo sapiens

<400> SEQUENCE: 33

Arg Val Thr Ile Thr Ala Asp Thr Ser Thr Ser Thr Ala Tyr Met Glu
 1               5                  10                  15

Leu Ser Ser Leu Arg Ser Glu Asp Thr Ala Val Tyr Tyr Cys
             20                  25                  30

<210> SEQ ID NO 34
<211> LENGTH: 30
<212> TYPE: PRT
<213> ORGANISM: Homo sapiens

<400> SEQUENCE: 34

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Val Ser
             20                  25                  30

<210> SEQ ID NO 35
<211> LENGTH: 14
<212> TYPE: PRT
<213> ORGANISM: Homo sapiens

<400> SEQUENCE: 35

Trp Ile Arg Gln Pro Pro Gly Lys Gly Leu Glu Trp Ile Gly
 1               5                  10

<210> SEQ ID NO 36
<211> LENGTH: 32
<212> TYPE: PRT
<213> ORGANISM: Homo sapiens

<400> SEQUENCE: 36

Arg Val Thr Ile Ser Val Asp Thr Ser Lys Asn Gln Phe Ser Leu Lys
 1               5                  10                  15

Leu Ser Ser Val Thr Ala Ala Asp Thr Ala Val Tyr Tyr Cys Ala Arg
             20                  25                  30

<210> SEQ ID NO 37
<211> LENGTH: 25
<212> TYPE: PRT
<213> ORGANISM: Homo sapiens

<400> SEQUENCE: 37

Gln Val Gln Leu Gln Glu Ser Gly Pro Gly Leu Val Lys Pro Ser Gln
 1               5                  10                  15

Thr Leu Ser Leu Thr Cys Thr Val Ser
             20                  25
```

```
<210> SEQ ID NO 38
<211> LENGTH: 13
<212> TYPE: PRT
<213> ORGANISM: Homo sapiens

<400> SEQUENCE: 38

Trp Ile Arg Gln Pro Pro Gly Lys Gly Leu Glu Trp Ile
1               5                   10

<210> SEQ ID NO 39
<211> LENGTH: 31
<212> TYPE: PRT
<213> ORGANISM: Homo sapiens

<400> SEQUENCE: 39

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala
            20                  25                  30

<210> SEQ ID NO 40
<211> LENGTH: 30
<212> TYPE: PRT
<213> ORGANISM: Homo sapiens

<400> SEQUENCE: 40

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 41
<211> LENGTH: 30
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 42
<211> LENGTH: 14
<212> TYPE: PRT
<213> ORGANISM: Homo sapiens

<400> SEQUENCE: 42

Trp Val Arg Gln Ala Pro Gly Lys Gly Leu Glu Trp Val Ser
1               5                   10

<210> SEQ ID NO 43
<211> LENGTH: 32
<212> TYPE: PRT
<213> ORGANISM: Homo sapiens

<400> SEQUENCE: 43

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 44
```

```
<211> LENGTH: 25
<212> TYPE: PRT
<213> ORGANISM: Homo sapiens

<400> SEQUENCE: 44

Glu Val Gln Leu Val Glu Ser Gly Gly Gly Leu Val Gln Pro Gly Gly
 1               5                  10                  15

Ser Leu Arg Leu Ser Cys Ala Ala Ser
            20                  25

<210> SEQ ID NO 45
<211> LENGTH: 13
<212> TYPE: PRT
<213> ORGANISM: Homo sapiens

<400> SEQUENCE: 45

Trp Val Arg Gln Ala Pro Gly Lys Gly Leu Glu Trp Val
 1               5                  10

<210> SEQ ID NO 46
<211> LENGTH: 31
<212> TYPE: PRT
<213> ORGANISM: Homo sapiens

<400> SEQUENCE: 46

Arg Phe Thr Ile Ser Arg Asp Asn Ser Lys Asn Thr Leu Tyr Leu Gln
 1               5                  10                  15

Met Asn Ser Leu Arg Ala Glu Asp Thr Ala Val Tyr Tyr Cys Ala
            20                  25                  30

<210> SEQ ID NO 47
<211> LENGTH: 30
<212> TYPE: PRT
<213> ORGANISM: Homo sapiens

<400> SEQUENCE: 47

Arg Phe Thr Ile Ser Arg Asp Asn Ser Lys Asn Thr Leu Tyr Leu Gln
 1               5                  10                  15

Met Asn Ser Leu Arg Ala Glu Asp Thr Ala Val Tyr Tyr Cys
            20                  25                  30

<210> SEQ ID NO 48
<211> LENGTH: 30
<212> TYPE: PRT
<213> ORGANISM: Homo sapiens

<400> SEQUENCE: 48

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys
            20                  25                  30

<210> SEQ ID NO 49
<211> LENGTH: 32
<212> TYPE: PRT
<213> ORGANISM: Homo sapiens

<400> SEQUENCE: 49

Arg Phe Thr Ile Ser Ala Asp Thr Ser Lys Asn Thr Ala Tyr Leu Gln
 1               5                  10                  15

Met Asn Ser Leu Arg Ala Glu Asp Thr Ala Val Tyr Tyr Cys Ser Arg
            20                  25                  30
```

```
<210> SEQ ID NO 50
<211> LENGTH: 31
<212> TYPE: PRT
<213> ORGANISM: Homo sapiens

<400> SEQUENCE: 50

Arg Phe Thr Ile Ser Ala Asp Thr Ser Lys Asn Thr Ala Tyr Leu Gln
 1               5                  10                  15

Met Asn Ser Leu Arg Ala Glu Asp Thr Ala Val Tyr Tyr Cys Ser
            20                  25                  30

<210> SEQ ID NO 51
<211> LENGTH: 32
<212> TYPE: PRT
<213> ORGANISM: Homo sapiens

<400> SEQUENCE: 51

Arg Phe Thr Ile Ser Ala Asp Thr Ser Lys Asn Thr Ala Tyr Leu Gln
 1               5                  10                  15

Met Asn Ser Leu Arg Ala Glu Asp Thr Ala Val Tyr Tyr Cys Ala Arg
            20                  25                  30

<210> SEQ ID NO 52
<211> LENGTH: 31
<212> TYPE: PRT
<213> ORGANISM: Homo sapiens

<400> SEQUENCE: 52

Arg Phe Thr Ile Ser Ala Asp Thr Ser Lys Asn Thr Ala Tyr Leu Gln
 1               5                  10                  15

Met Asn Ser Leu Arg Ala Glu Asp Thr Ala Val Tyr Tyr Cys Ala
            20                  25                  30

<210> SEQ ID NO 53
<211> LENGTH: 30
<212> TYPE: PRT
<213> ORGANISM: Homo sapiens

<400> SEQUENCE: 53

Arg Phe Thr Ile Ser Ala Asp Thr Ser Lys Asn Thr Ala Tyr Leu Gln
 1               5                  10                  15

Met Asn Ser Leu Arg Ala Glu Asp Thr Ala Val Tyr Tyr Cys
            20                  25                  30

<210> SEQ ID NO 54
<211> LENGTH: 23
<212> TYPE: PRT
<213> ORGANISM: Homo sapiens

<400> SEQUENCE: 54

Asp Ile Gln Met Thr Gln Ser Pro Ser Ser Leu Ser Ala Ser Val Gly
 1               5                  10                  15

Asp Arg Val Thr Ile Thr Cys
            20

<210> SEQ ID NO 55
<211> LENGTH: 15
<212> TYPE: PRT
<213> ORGANISM: Homo sapiens

<400> SEQUENCE: 55

Trp Tyr Gln Gln Lys Pro Gly Lys Ala Pro Lys Leu Leu Ile Tyr
 1               5                  10                  15
```

```
<210> SEQ ID NO 56
<211> LENGTH: 32
<212> TYPE: PRT
<213> ORGANISM: Homo sapiens

<400> SEQUENCE: 56

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 57
<211> LENGTH: 10
<212> TYPE: PRT
<213> ORGANISM: Homo sapiens

<400> SEQUENCE: 57

Phe Gly Gln Gly Thr Lys Val Glu Ile Lys
1               5                   10

<210> SEQ ID NO 58
<211> LENGTH: 14
<212> TYPE: PRT
<213> ORGANISM: Homo sapiens

<400> SEQUENCE: 58

Trp Tyr Gln Gln Lys Pro Gly Lys Ala Pro Lys Leu Leu Ile
1               5                   10

<210> SEQ ID NO 59
<211> LENGTH: 15
<212> TYPE: PRT
<213> ORGANISM: Homo sapiens

<400> SEQUENCE: 59

Trp Tyr Leu Gln Lys Pro Gly Gln Ser Pro Gln Leu Leu Ile Tyr
1               5                   10                  15

<210> SEQ ID NO 60
<211> LENGTH: 32
<212> TYPE: PRT
<213> ORGANISM: Homo sapiens

<400> SEQUENCE: 60

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 61
<211> LENGTH: 23
<212> TYPE: PRT
<213> ORGANISM: Homo sapiens

<400> SEQUENCE: 61

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 62
<211> LENGTH: 15
<212> TYPE: PRT
<213> ORGANISM: Homo sapiens
```

```
<400> SEQUENCE: 62

Trp Tyr Gln Gln Lys Pro Gly Gln Ala Pro Arg Leu Leu Ile Tyr
1               5                   10                  15

<210> SEQ ID NO 63
<211> LENGTH: 32
<212> TYPE: PRT
<213> ORGANISM: Homo sapiens

<400> SEQUENCE: 63

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 64
<211> LENGTH: 23
<212> TYPE: PRT
<213> ORGANISM: Homo sapiens

<400> SEQUENCE: 64

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 65
<211> LENGTH: 15
<212> TYPE: PRT
<213> ORGANISM: Homo sapiens

<400> SEQUENCE: 65

Trp Tyr Gln Gln Lys Pro Gly Gln Pro Pro Lys Leu Leu Ile Tyr
1               5                   10                  15

<210> SEQ ID NO 66
<211> LENGTH: 32
<212> TYPE: PRT
<213> ORGANISM: Homo sapiens

<400> SEQUENCE: 66

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 67
<211> LENGTH: 23
<212> TYPE: PRT
<213> ORGANISM: Mus musculus

<400> SEQUENCE: 67

Asp Ile Val Met Ser Gln Ser Pro Ser Ser Leu Ala Val Ser Val Gly
1               5                   10                  15

Glu Lys Val Thr Met Ser Cys
            20

<210> SEQ ID NO 68
<211> LENGTH: 15
<212> TYPE: PRT
<213> ORGANISM: Mus musculus

<400> SEQUENCE: 68
```

Trp Tyr Gln Gln Lys Pro Gly Gln Ser Pro Lys Leu Leu Ile Tyr
1               5                   10                  15

<210> SEQ ID NO 69
<211> LENGTH: 32
<212> TYPE: PRT
<213> ORGANISM: Mus musculus

<400> SEQUENCE: 69

Gly Val Pro Asp Arg Phe Thr Gly Ser Gly Ser Gly Thr Asp Phe Thr
1               5                   10                  15

Leu Thr Ile Ser Ser Val Lys Ala Glu Asp Leu Ala Val Tyr Tyr Cys
            20                  25                  30

<210> SEQ ID NO 70
<211> LENGTH: 11
<212> TYPE: PRT
<213> ORGANISM: Mus musculus

<400> SEQUENCE: 70

Phe Gly Gly Gly Thr Lys Val Glu Ile Lys Arg
1               5                   10

<210> SEQ ID NO 71
<211> LENGTH: 25
<212> TYPE: PRT
<213> ORGANISM: Mus musculus

<400> SEQUENCE: 71

Asp Val Gln Val Gln Glu Ser Gly Pro Gly Leu Val Lys Pro Ser Gln
1               5                   10                  15

Ser Leu Ser Leu Thr Cys Thr Val Thr
            20                  25

<210> SEQ ID NO 72
<211> LENGTH: 13
<212> TYPE: PRT
<213> ORGANISM: Mus musculus

<400> SEQUENCE: 72

Trp Ile Arg Gln Phe Pro Gly Asn Lys Leu Glu Trp Met
1               5                   10

<210> SEQ ID NO 73
<211> LENGTH: 32
<212> TYPE: PRT
<213> ORGANISM: Mus musculus

<400> SEQUENCE: 73

Arg Ile Ser Ile Thr Arg Asp Thr Ser Lys Asn Gln Phe Phe Leu Gln
1               5                   10                  15

Leu Ile Ser Val Thr Thr Glu Asp Thr Ala Thr Tyr Tyr Cys Ala Arg
            20                  25                  30

<210> SEQ ID NO 74
<211> LENGTH: 12
<212> TYPE: PRT
<213> ORGANISM: Mus musculus

<400> SEQUENCE: 74

Trp Gly Gln Gly Thr Thr Leu Thr Val Ala Ser Ala
1               5                   10

<210> SEQ ID NO 75
<211> LENGTH: 13
<212> TYPE: PRT
<213> ORGANISM: Homo sapiens

<400> SEQUENCE: 75

Trp Ile Arg Gln Ala Pro Gly Lys Gly Leu Glu Trp Val
1               5                   10

<210> SEQ ID NO 76
<211> LENGTH: 13
<212> TYPE: PRT
<213> ORGANISM: Homo sapiens

<400> SEQUENCE: 76

Trp Val Arg Gln Ala Pro Gly Lys Gly Leu Glu Trp Met
1               5                   10

<210> SEQ ID NO 77
<211> LENGTH: 13
<212> TYPE: PRT
<213> ORGANISM: Homo sapiens

<400> SEQUENCE: 77

Trp Ile Arg Gln Ala Pro Gly Lys Gly Leu Glu Trp Met
1               5                   10

<210> SEQ ID NO 78
<211> LENGTH: 32
<212> TYPE: PRT
<213> ORGANISM: Homo sapiens

<400> SEQUENCE: 78

Arg Ile Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 79
<211> LENGTH: 32
<212> TYPE: PRT
<213> ORGANISM: Homo sapiens

<400> SEQUENCE: 79

Arg Phe Thr Ile Ser Arg Asp Asn Ser Lys Asn Thr Phe Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 80
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Cys Asp Lys Thr His Thr Gly Gly Gly Ser Gln Arg Leu Met Glu Asp
1               5                   10                  15

Ile Cys Leu Pro Arg Trp Gly Cys Leu Trp Glu Asp Asp Phe
            20                  25                  30

<210> SEQ ID NO 81
<211> LENGTH: 20

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Arg Leu Met Glu Asp Ile Cys Leu Pro Arg Trp Gly Cys Leu Trp
1               5                   10                  15

Glu Asp Asp Phe
            20

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Arg Leu Ile Glu Asp Ile Cys Leu Pro Arg Trp Gly Cys Leu Trp
1               5                   10                  15

Glu Asp Asp Phe
            20

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Arg Leu Ile Glu Asp Ile Cys Leu Pro Arg Trp Gly Cys Leu Trp Glu
1               5                   10                  15

Asp Asp

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Cys Leu Pro Arg Trp Gly Cys Leu Trp
1               5                   10

<210> SEQ ID NO 85
<211> LENGTH: 218
<212> TYPE: PRT
<213> ORGANISM: Homo sapiens

<400> SEQUENCE: 85

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60
```

```
Glu Gln Tyr Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Ser Asn
                 85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 86
<211> LENGTH: 217
<212> TYPE: PRT
<213> ORGANISM: Homo sapiens

<400> SEQUENCE: 86

Pro Ala Pro Pro Val Ala Gly Pro Ser Val Phe Leu Phe Pro Pro Lys
  1               5                  10                  15

Pro Lys Asp Thr Leu Met Ile Ser Arg Thr Pro Glu Val Thr Cys Val
                 20                  25                  30

Val Val Asp Val Ser His Glu Asp Pro Glu Val Gln Phe Asn Trp Tyr
             35                  40                  45

Val Asp Gly Val Glu Val His Asn Ala Lys Thr Lys Pro Arg Glu Glu
 50                  55                  60

Gln Phe Asn Ser Thr Phe Arg Val Val Ser Val Leu Thr Val Val His
 65                  70                  75                  80

Gln Asp Trp Leu Asn Gly Lys Glu Tyr Lys Cys Lys Val Ser Asn Lys
                 85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

```
<210> SEQ ID NO 87
<211> LENGTH: 168
<212> TYPE: PRT
<213> ORGANISM: Homo sapiens

<400> SEQUENCE: 87

Pro Ala Pro Glu Leu Leu Gly Gly Pro Ser Val Phe Leu Phe Pro Pro
 1               5                  10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45

Tyr Val Ala Pro Ile Glu Lys Thr Ile Ser Lys Thr Lys Gly Gln Pro
 50                  55                  60

Arg Glu Pro Gln Val Tyr Thr Leu Pro Pro Ser Arg Glu Glu Met Thr
 65                  70                  75                  80

Lys Asn Gln Val Ser Leu Thr Cys Leu Val Lys Gly Phe Tyr Pro Ser
            85                  90                  95

Asp Ile Ala Val Glu Trp Glu Ser Ser Gly Gln Pro Glu Asn Asn Tyr
        100                 105                 110

Asn Thr Thr Pro Pro Met Leu Asp Ser Asp Gly Ser Phe Phe Leu Tyr
    115                 120                 125

Ser Lys Leu Thr Val Asp Lys Ser Arg Trp Gln Gln Gly Asn Ile Phe
130                 135                 140

Ser Cys Ser Val Met His Glu Ala Leu His Asn Arg Phe Thr Gln Lys
145                 150                 155                 160

Ser Leu Ser Leu Ser Pro Gly Lys
                165

<210> SEQ ID NO 88
<211> LENGTH: 218
<212> TYPE: PRT
<213> ORGANISM: Homo sapiens

<400> SEQUENCE: 88

Pro Ala Pro Glu Phe Leu Gly Gly Pro Ser Val Phe Leu Phe Pro Pro
 1               5                  10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
 50                  55                  60

Glu Gln Phe Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Ser Asn
            85                  90                  95

Lys Gly Leu Pro Ser Ser Ile Glu Lys Thr Ile Ser Lys Ala Lys Gly
        100                 105                 110

Gln Pro Arg Glu Pro Gln Val Tyr Thr Leu Pro Pro Ser Gln Glu Glu
    115                 120                 125

Met Thr Lys Asn Gln Val Ser Leu Thr Cys Leu Val Lys Gly Phe Tyr
130                 135                 140

Pro Ser Asp Ile Ala Val Glu Trp Glu Ser Asn Gly Gln Pro Glu Asn
145                 150                 155                 160
```

```
Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215

<210> SEQ ID NO 89
<211> LENGTH: 107
<212> TYPE: PRT
<213> ORGANISM: Homo sapiens

<400> SEQUENCE: 89

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 90
<211> LENGTH: 114
<212> TYPE: PRT
<213> ORGANISM: Mus musculus

<400> SEQUENCE: 90

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Arg
            20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Tyr Pro Arg Thr Phe Gly Gln Gly Thr Lys Val Glu Ile
            100                 105                 110

Lys Arg

<210> SEQ ID NO 91
<211> LENGTH: 114
<212> TYPE: PRT
<213> ORGANISM: Mus musculus

<400> SEQUENCE: 91
```

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Asn Tyr Pro Arg Thr Phe Gly Gln Gly Thr Lys Val Glu Ile
            100                 105                 110

Lys Arg

<210> SEQ ID NO 92
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Tyr Pro Arg Thr Phe Gly Gln Gly Thr Lys
            100                 105

<210> SEQ ID NO 93
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Thr Tyr Tyr Cys Gln Gln
                85                  90                  95

Tyr Tyr Asn Tyr Pro Arg Thr Phe Gly Gln Gly Thr Lys
            100                 105

<210> SEQ ID NO 94
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Gln Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Tyr Arg
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Tyr Pro Arg Thr Phe Gly Gln Gly Thr Lys
            100                 105

<210> SEQ ID NO 95
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Asp Ile Val Met Thr Gln Ser Pro Asp Ser Leu Ala Val Ser Val Gly
 1               5                  10                  15

Glu Arg Ala Thr Ile Asn Cys Lys Ser Ser Gln Ser Leu Leu Tyr Arg
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Phe Ala Val Tyr Tyr Cys Gln Gln
                85                  90                  95

Tyr Tyr Asn Tyr Pro Arg Thr Phe Gly Gln Gly Thr Lys
            100                 105

<210> SEQ ID NO 96
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 96

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Asn Tyr Pro Arg Thr Phe Gly Gln Gly Thr Lys
            100                 105

<210> SEQ ID NO 97
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Gln Met Thr Gln Ser Pro Asp Ser Leu Ser Ala Ser Val Gly
 1               5                  10                  15

Glu Arg Ala Thr Ile Asn Cys Lys Ser Ser Gln Ser Leu Leu Tyr Arg
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Asn Tyr Pro Arg Thr Phe Gly Gln Gly Thr Lys
            100                 105

<210> SEQ ID NO 98
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Asp Ser Leu Ser Ala Ser Val Gly
 1               5                  10                  15

Glu Arg Ala Thr Ile Asn Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Gln Gln
                85                  90                  95

Tyr Tyr Asn Tyr Pro Arg Thr Phe Gly Gln Gly Thr Lys
            100                 105

<210> SEQ ID NO 99
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Leu Leu Tyr Arg
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Tyr Pro Arg Thr Phe Gly Gln Gly Thr Lys
            100                 105

<210> SEQ ID NO 100
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Met Thr Gln Ser Pro Asp Ser Leu Ser Ala Ser Val Gly
1               5                  10                  15

Glu Arg Ala Thr Ile Asn Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Pro Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Ala Glu Asp Phe Ala Thr Tyr Tyr Cys Gln Gln
                85                  90                  95

Tyr Tyr Asn Tyr Pro Arg Thr Phe Gly Gln Gly Thr Lys
            100                 105

<210> SEQ ID NO 101
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 101

Asp Ile Gln Met Thr Gln Ser Pro Asp Ser Leu Ser Ala Ser Val Gly
1               5                   10                  15

Glu Arg Ala Thr Ile Asn Cys Lys Ser Ser Gln Ser Leu Leu Tyr Arg
            20                  25                  30

Ser Asn Gln Lys Asn Tyr Leu Ala Trp Tyr Gln Gln Lys Pro Gly Gln
        35                  40                  45

Ala Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Asn Tyr Pro Arg Thr Phe Gly Gln Gly Thr Lys
                100                 105

<210> SEQ ID NO 102
<211> LENGTH: 15
<212> TYPE: PRT
<213> ORGANISM: Homo sapiens

<400> SEQUENCE: 102

Trp Lys Met Lys Pro Arg Arg Asn Leu Glu Glu Asp Asp Tyr Leu
1               5                   10                  15

<210> SEQ ID NO 103
<211> LENGTH: 20
<212> TYPE: PRT
<213> ORGANISM: Homo sapiens

<400> SEQUENCE: 103

Glu Val Thr His Gln Gly Leu Ser Ser Pro Val Thr Lys Ser Phe Asn
1               5                   10                  15

Arg Gly Glu Cys
            20

<210> SEQ ID NO 104
<211> LENGTH: 20
<212> TYPE: PRT
<213> ORGANISM: Homo sapiens

<400> SEQUENCE: 104

Glu Val Thr His Gln Gly Leu Ser Ser Pro Val Thr Lys Ser Phe Asn
1               5                   10                  15

Arg Gly Glu Cys
            20

<210> SEQ ID NO 105
<211> LENGTH: 20
<212> TYPE: PRT
<213> ORGANISM: Homo sapiens

<400> SEQUENCE: 105

Glu Val Thr His Gln Gly Leu Ser Ser Pro Val Thr Lys Ser Phe Asn
1               5                   10                  15

Arg Gly Glu Cys
            20

<210> SEQ ID NO 106
<211> LENGTH: 20
<212> TYPE: PRT

<213> ORGANISM: Homo sapiens

<400> SEQUENCE: 106

Glu Val Thr His Gln Gly Leu Ser Ser Pro Val Thr Lys Ser Phe Asn
1               5                   10                  15

Arg Gly Glu Cys
            20

<210> SEQ ID NO 107
<211> LENGTH: 20
<212> TYPE: PRT
<213> ORGANISM: Homo sapiens

<400> SEQUENCE: 107

Glu Val Thr His Gln Gly Leu Ser Ser Pro Val Thr Lys Ser Phe Asn
1               5                   10                  15

Arg Gly Glu Cys
            20

<210> SEQ ID NO 108
<211> LENGTH: 20
<212> TYPE: PRT
<213> ORGANISM: Homo sapiens

<400> SEQUENCE: 108

Glu Val Thr His Gln Gly Leu Ser Ser Pro Val Thr Lys Ser Phe Asn
1               5                   10                  15

Arg Gly Glu Cys
            20

<210> SEQ ID NO 109
<211> LENGTH: 20
<212> TYPE: PRT
<213> ORGANISM: Homo sapiens

<400> SEQUENCE: 109

Glu Val Thr His Gln Gly Leu Ser Ser Pro Val Thr Lys Ser Phe Asn
1               5                   10                  15

Arg Gly Glu Cys
            20

<210> SEQ ID NO 110
<211> LENGTH: 20
<212> TYPE: PRT
<213> ORGANISM: Homo sapiens

<400> SEQUENCE: 110

Glu Val Thr His Gln Gly Leu Ser Ser Pro Val Thr Lys Ser Phe Asn
1               5                   10                  15

Arg Gly Glu Cys
            20

<210> SEQ ID NO 111
<211> LENGTH: 20
<212> TYPE: PRT
<213> ORGANISM: Homo sapiens

<400> SEQUENCE: 111

Glu Val Thr His Gln Gly Leu Ser Ser Pro Val Thr Lys Ser Phe Asn
1               5                   10                  15

Arg Gly Glu Cys
            20

<210> SEQ ID NO 112
<211> LENGTH: 20
<212> TYPE: PRT
<213> ORGANISM: Homo sapiens

<400> SEQUENCE: 112

Glu Val Thr His Gln Gly Leu Ser Ser Pro Val Thr Lys Ser Phe Asn
1               5                   10                  15

Arg Gly Glu Cys
            20

<210> SEQ ID NO 113
<211> LENGTH: 20
<212> TYPE: PRT
<213> ORGANISM: Homo sapiens

<400> SEQUENCE: 113

Glu Val Thr His Gln Gly Leu Ser Ser Pro Val Thr Lys Ser Phe Asn
1               5                   10                  15

Arg Gly Glu Cys
            20

<210> SEQ ID NO 114
<211> LENGTH: 39
<212> TYPE: PRT
<213> ORGANISM: Homo sapiens

<400> SEQUENCE: 114

Leu Tyr Leu Trp Gly Gln Gly Thr Leu Val Thr Val Ser Ser Ala Ser
1               5                   10                  15

Thr Lys Gly Pro Ser Val Phe Pro Leu Ala Pro Ser Ser Lys Ser Thr
            20                  25                  30

Ser Gly Gly Thr Ala Ala Leu
        35

<210> SEQ ID NO 115
<211> LENGTH: 44
<212> TYPE: PRT
<213> ORGANISM: Homo sapiens

<400> SEQUENCE: 115

Asn Ser Tyr Trp Tyr Phe Asp Val Trp Gly Gln Gly Thr Leu Val Thr
1               5                   10                  15

Val Ser Ser Ala Ser Thr Lys Gly Pro Ser Val Phe Pro Leu Ala Pro
            20                  25                  30

Ser Ser Lys Ser Thr Ser Gly Gly Thr Ala Ala Leu
        35                  40

<210> SEQ ID NO 116
<211> LENGTH: 44
<212> TYPE: PRT
<213> ORGANISM: Homo sapiens

<400> SEQUENCE: 116

Ile Pro Arg His Ala Asn Val Phe Trp Gly Gln Gly Thr Leu Val Thr
1               5                   10                  15

Val Ser Ala Ser Thr Lys Gly Pro Ser Val Phe Pro Leu Ala Pro
            20                  25                  30

Ser Ser Lys Ser Thr Ser Gly Gly Thr Ala Ala Leu
        35                  40

<210> SEQ ID NO 117
<211> LENGTH: 43
<212> TYPE: PRT
<213> ORGANISM: Homo sapiens

<400> SEQUENCE: 117

Trp Thr Ser Gly Leu Asp Tyr Trp Gly Gln Gly Thr Leu Val Thr Val
1               5                   10                  15

Ser Ser Ala Ser Thr Lys Gly Pro Ser Val Phe Pro Leu Ala Pro Ser
            20                  25                  30

Ser Lys Ser Thr Ser Gly Gly Thr Ala Ala Leu
        35                  40

<210> SEQ ID NO 118
<211> LENGTH: 44
<212> TYPE: PRT
<213> ORGANISM: Homo sapiens

<400> SEQUENCE: 118

Asp Gly Phe Tyr Ala Met Asp Tyr Trp Gly Gln Gly Thr Leu Val Thr
1               5                   10                  15

Val Ser Ser Ala Ser Thr Lys Gly Pro Ser Val Phe Pro Leu Ala Pro
            20                  25                  30

Ser Ser Lys Ser Thr Ser Gly Gly Thr Ala Ala Leu
        35                  40

<210> SEQ ID NO 119
<211> LENGTH: 44
<212> TYPE: PRT
<213> ORGANISM: Homo sapiens

<400> SEQUENCE: 119

Ile Ser Ile Ala Gly Met Asp Tyr Trp Gly Gln Gly Thr Leu Val Thr
1               5                   10                  15

Val Ser Ser Ala Ser Thr Lys Gly Pro Ser Val Phe Pro Leu Ala Pro
            20                  25                  30

Ser Ser Lys Ser Thr Ser Gly Gly Thr Ala Ala Leu
        35                  40

<210> SEQ ID NO 120
<211> LENGTH: 44
<212> TYPE: PRT
<213> ORGANISM: Homo sapiens

<400> SEQUENCE: 120

Ser Trp Asp Trp Tyr Phe Asp Val Trp Gly Gln Gly Thr Leu Val Thr
1               5                   10                  15

Val Ser Ser Ala Ser Thr Lys Gly Pro Ser Val Phe Pro Leu Ala Pro
            20                  25                  30

Ser Ser Lys Ser Thr Ser Gly Gly Thr Ala Ala Leu
        35                  40

<210> SEQ ID NO 121
<211> LENGTH: 45
<212> TYPE: PRT
<213> ORGANISM: Homo sapiens

<400> SEQUENCE: 121

Arg Ser His Val Gly Tyr Phe Asp Val Trp Gly Gln Gly Thr Leu Val
1               5                   10                  15

Thr Val Ser Ser Ala Ser Thr Lys Gly Pro Ser Val Phe Pro Leu Ala
            20                  25                  30

```
Pro Ser Ser Lys Ser Thr Ser Gly Gly Thr Ala Ala Leu
        35                  40                  45

<210> SEQ ID NO 122
<211> LENGTH: 41
<212> TYPE: PRT
<213> ORGANISM: Homo sapiens

<400> SEQUENCE: 122

Ile Arg Leu Asp Tyr Trp Gly Gln Gly Thr Leu Val Thr Val Ser Ser
1               5                   10                  15

Ala Ser Thr Lys Gly Pro Ser Val Phe Pro Leu Ala Pro Ser Ser Lys
            20                  25                  30

Ser Thr Ser Gly Gly Thr Ala Ala Leu
        35                  40

<210> SEQ ID NO 123
<211> LENGTH: 44
<212> TYPE: PRT
<213> ORGANISM: Homo sapiens

<400> SEQUENCE: 123

Arg Gly Asp Tyr Ser Met Asp Tyr Trp Gly Gln Gly Thr Leu Val Thr
1               5                   10                  15

Val Ser Ser Ala Ser Thr Lys Gly Pro Ser Val Phe Pro Leu Ala Pro
            20                  25                  30

Ser Ser Lys Ser Thr Ser Gly Gly Thr Ala Ala Leu
        35                  40

<210> SEQ ID NO 124
<211> LENGTH: 46
<212> TYPE: PRT
<213> ORGANISM: Homo sapiens

<400> SEQUENCE: 124

Tyr Asp Asp Tyr Tyr Tyr Ala Met Asp Tyr Trp Gly Gln Gly Thr Leu
1               5                   10                  15

Val Thr Val Ser Ser Ala Ser Thr Lys Gly Pro Ser Val Phe Pro Leu
            20                  25                  30

Ala Pro Ser Ser Lys Ser Thr Ser Gly Gly Thr Ala Ala Leu
        35                  40                  45

<210> SEQ ID NO 125
<211> LENGTH: 46
<212> TYPE: PRT
<213> ORGANISM: Homo sapiens

<400> SEQUENCE: 125

Val Leu Asp Ser Asp Gly Ser Phe Phe Leu Tyr Ser Lys Leu Thr Val
1               5                   10                  15

Asp Lys Ser Arg Trp Gln Gln Gly Asn Val Phe Ser Cys Ser Val Met
            20                  25                  30

His Glu Ala Leu His Asn His Tyr Thr Gln Lys Ser Leu Ser
        35                  40                  45

<210> SEQ ID NO 126
<211> LENGTH: 46
<212> TYPE: PRT
<213> ORGANISM: Homo sapiens

<400> SEQUENCE: 126
```

Val Leu Asp Ser Asp Gly Ser Phe Phe Leu Tyr Ser Lys Leu Thr Val
1               5                   10                  15

Asp Lys Ser Arg Trp Gln Gln Gly Asn Val Phe Ser Cys Ser Val Met
            20                  25                  30

His Glu Ala Leu His Asn His Tyr Thr Gln Lys Ser Leu Ser
        35                  40                  45

<210> SEQ ID NO 127
<211> LENGTH: 46
<212> TYPE: PRT
<213> ORGANISM: Homo sapiens

<400> SEQUENCE: 127

Val Leu Asp Ser Asp Gly Ser Phe Phe Leu Tyr Ser Lys Leu Thr Val
1               5                   10                  15

Asp Lys Ser Arg Trp Gln Gln Gly Asn Val Phe Ser Cys Ser Val Met
            20                  25                  30

His Glu Ala Leu His Asn His Tyr Thr Gln Lys Ser Leu Ser
        35                  40                  45

<210> SEQ ID NO 128
<211> LENGTH: 46
<212> TYPE: PRT
<213> ORGANISM: Homo sapiens

<400> SEQUENCE: 128

Val Leu Asp Ser Asp Gly Ser Phe Phe Leu Tyr Ser Lys Leu Thr Val
1               5                   10                  15

Asp Lys Ser Arg Trp Gln Gln Gly Asn Val Phe Ser Cys Ser Val Met
            20                  25                  30

His Glu Ala Leu His Asn His Tyr Thr Gln Lys Ser Leu Ser
        35                  40                  45

<210> SEQ ID NO 129
<211> LENGTH: 46
<212> TYPE: PRT
<213> ORGANISM: Homo sapiens

<400> SEQUENCE: 129

Val Leu Asp Ser Asp Gly Ser Phe Phe Leu Tyr Ser Lys Leu Thr Val
1               5                   10                  15

Asp Lys Ser Arg Trp Gln Gln Gly Asn Val Phe Ser Cys Ser Val Met
            20                  25                  30

His Glu Ala Leu His Asn His Tyr Thr Gln Lys Ser Leu Ser
        35                  40                  45

<210> SEQ ID NO 130
<211> LENGTH: 46
<212> TYPE: PRT
<213> ORGANISM: Homo sapiens

<400> SEQUENCE: 130

Val Leu Asp Ser Asp Gly Ser Phe Phe Leu Tyr Ser Lys Leu Thr Val
1               5                   10                  15

Asp Lys Ser Arg Trp Gln Gln Gly Asn Val Phe Ser Cys Ser Val Met
            20                  25                  30

His Glu Ala Leu His Asn His Tyr Thr Gln Lys Ser Leu Ser
        35                  40                  45

<210> SEQ ID NO 131
<211> LENGTH: 46

<212> TYPE: PRT
<213> ORGANISM: Homo sapiens

<400> SEQUENCE: 131

Val Leu Asp Ser Asp Gly Ser Phe Phe Leu Tyr Ser Lys Leu Thr Val
1               5                   10                  15

Asp Lys Ser Arg Trp Gln Gln Gly Asn Val Phe Ser Cys Ser Val Met
            20                  25                  30

His Glu Ala Leu His Asn His Tyr Thr Gln Lys Ser Leu Ser
        35                  40                  45

<210> SEQ ID NO 132
<211> LENGTH: 46
<212> TYPE: PRT
<213> ORGANISM: Homo sapiens

<400> SEQUENCE: 132

Val Leu Asp Ser Asp Gly Ser Phe Phe Leu Tyr Ser Lys Leu Thr Val
1               5                   10                  15

Asp Lys Ser Arg Trp Gln Gln Gly Asn Val Phe Ser Cys Ser Val Met
            20                  25                  30

His Glu Ala Leu His Asn His Tyr Thr Gln Lys Ser Leu Ser
        35                  40                  45

<210> SEQ ID NO 133
<211> LENGTH: 46
<212> TYPE: PRT
<213> ORGANISM: Homo sapiens

<400> SEQUENCE: 133

Val Leu Asp Ser Asp Gly Ser Phe Phe Leu Tyr Ser Lys Leu Thr Val
1               5                   10                  15

Asp Lys Ser Arg Trp Gln Gln Gly Asn Val Phe Ser Cys Ser Val Met
            20                  25                  30

His Glu Ala Leu His Asn His Tyr Thr Gln Lys Ser Leu Ser
        35                  40                  45

<210> SEQ ID NO 134
<211> LENGTH: 46
<212> TYPE: PRT
<213> ORGANISM: Homo sapiens

<400> SEQUENCE: 134

Val Leu Asp Ser Asp Gly Ser Phe Phe Leu Tyr Ser Lys Leu Thr Val
1               5                   10                  15

Asp Lys Ser Arg Trp Gln Gln Gly Asn Val Phe Ser Cys Ser Val Met
            20                  25                  30

His Glu Ala Leu His Asn His Tyr Thr Gln Lys Ser Leu Ser
        35                  40                  45

<210> SEQ ID NO 135
<211> LENGTH: 46
<212> TYPE: PRT
<213> ORGANISM: Homo sapiens

<400> SEQUENCE: 135

Val Leu Asp Ser Asp Gly Ser Phe Phe Leu Tyr Ser Lys Leu Thr Val
1               5                   10                  15

Asp Lys Ser Arg Trp Gln Gln Gly Asn Val Phe Ser Cys Ser Val Met
            20                  25                  30

His Glu Ala Leu His Asn His Tyr Thr Gln Lys Ser Leu Ser

<210> SEQ ID NO 136
<211> LENGTH: 109
<212> TYPE: PRT
<213> ORGANISM: Homo sapiens

<400> SEQUENCE: 136

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Leu Tyr Arg
            20                  25                  30
Ser Asn Gln Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Asn Tyr Pro Arg Thr Phe Gly Gln Gly Thr Lys
            100                 105

<210> SEQ ID NO 137
<211> LENGTH: 109
<212> TYPE: PRT
<213> ORGANISM: Homo sapiens

<400> SEQUENCE: 137

Asp Ile Gln Met Thr Gln Ser Pro Asp Ser Leu Ser Ala Ser Val Gly
1               5                   10                  15
Glu Arg Ala Thr Ile Asn Cys Lys Ser Ser Gln Ser Leu Leu Tyr Arg
            20                  25                  30
Ser Asn Gln Lys Asn Tyr Leu Ala Trp Tyr Gln Gln Lys Pro Gly Lys
        35                  40                  45
Ala Pro Lys Leu Leu Ile Tyr Trp Ala Ser Thr Arg Glu Ser Gly Val
50                  55                  60
Pro Ser Arg Phe Ser Gly Ser Gly Ser Gly Thr Asp Phe Thr Leu Thr
65                  70                  75                  80
Ile Ser Ser Leu Gln Pro Glu Asp Phe Ala Thr Tyr Tyr Cys Gln Gln
                85                  90                  95
Tyr Tyr Asn Tyr Pro Arg Thr Phe Gly Gln Gly Thr Lys
            100                 105

<210> SEQ ID NO 138
<211> LENGTH: 32
<212> TYPE: PRT
<213> ORGANISM: Homo sapiens

<400> SEQUENCE: 138

Arg Phe Thr Ile Ser Arg Asp Thr Ser Lys Asn Thr Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 139
<211> LENGTH: 32
<212> TYPE: PRT
<213> ORGANISM: Homo sapiens

```
<400> SEQUENCE: 139

Gly Val Pro Ser Arg Phe Ser Gly Ser Arg Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

ANTIBODIES AND IMMUNOCONJUGATES AND USES THEREFOR

CROSS-REFERENCE TO RELATED APPLICATIONS

This is a non-provisional application claiming priority under 35 U.S.C. §119(e) from U.S. Provisional Patent Application No. 60/863,295, filed Oct. 27, 2006, U.S. Provisional Patent Application No. 60/868,707, filed Dec. 5, 2006, U.S. Provisional Patent Application No. 60/921,300, filed Mar. 30, 2007, and U.S. Provisional Patent Application No. 60/937,857, filed on Jun. 29, 2007, the entire disclosures of which are expressly incorporated by reference herein.

SEQUENCE LISTING

The instant application contains a Sequence Listing which has been submitted via EFS-Web and is hereby incorporated by reference in its entirety. Said ASCII copy, created on Aug. 24, 2012, is named GNE0160R4.txt, and is 72,508 bytes in size.

Incorporation of Sequence Listing

This application includes a Sequence Listing submitted via EFS-Web as a computer-readable form 71,839 byte file entitled "GNE-0160R4.txt" created on Jul. 15, 2009, which is hereby incorporated herein by reference in its entirety.

FIELD OF THE INVENTION

The present invention relates to anti-STEAP-1 antibodies and immunconjugates thereof. The invention further relates to methods of using anti-STEAP-1 antibodies and immunconjugates thereof.

BACKGROUND

In humans, prostate cancer is one of the most commonly diagnosed malignancies in males and is the second leading cause of cancer related death in men. The American Cancer Society estimates that for the year 2000, 180,400 new cases of prostate cancer will be diagnosed with 31,900 deaths from the disease. In advanced stages, prostate cancer metastasizes to the bone. While advances in early diagnosis and treatment of locally confined tumors have been achieved, prostate cancer is incurable once it has metastasized. Patients with metastatic prostate cancer on hormonal therapy will eventually develop an androgen-refractory (androgen independent) state that will lead to disease progression and death. Currently, prostate-specific antigen (PSA) is the most widely used tumor marker for screening, diagnosis, and monitoring prostate cancer. However, widespread use of PSA as a tool for screening is controversial since PSA fails to discriminate accurately between benign and malignant prostate disease.

Depending on the stage of the cancer, prostate and bladder cancer treatment involves one or a combination of the following therapies: surgery to remove the cancerous tissue, radiation therapy, chemotherapy, androgen deprivation (e.g., hormonal therapy) in the case of prostate cancer. While surgical or radiation therapy significantly improves survival in patients with early stages of the disease, the therapeutic options are very limited for advanced cases, particularly for tumor recurrences following hormone ablation. The majority of patients who undergo hormone therapy progress to develop androgen-independent disease. Currently, there is no effective treatment for the 20-40% of prostate cancer patients who develop recurrent disease after surgery or radiation therapy, or for those in whom the cancer has metastasized at the time of diagnosis. Chemotherapy has its toxic side effects, especially in elderly patients. Development of new forms of therapy especially for disease refractory to androgen deprivation is an urgent need in the management of prostatic carcinoma.

The identification of a novel cell surface antigen, STEAP-1 has been described (see U.S. Pat. No. 6,329,503). STEAP-1 is member of cell surface serpentine transmembrane antigens. It is expressed predominantly in the prostate cancer, and thus members of this family have been termed "STEAP" (Six Transmembrane Epithelial Antigens of the Prostate). Human STEAP proteins exhibit a high degree of structural conservation within the family but show no significant structural homology to any known human proteins. STEAP-1 appears to be a type IIIa membrane protein expressed predominantly in prostate cells in normal human tissues. Structurally, STEAP-1 is a 339 amino acid protein characterized by a molecular topology of six transmembrane domains and intracellular N- and C-termini, suggesting that it folds in a "serpentine" manner into three extracellular and two intracellular loops. STEAP-1 protein expression is maintained at high levels across various states of prostate cancer. STEAP-1 is highly over-expressed in other human cancers such as lung and colon. Murine antibodies have been raised to human STEAP-1 fragments and the antibodies were shown to bind STEAP-1 on the cell surface (see US Patent Application No. 20040253232A1).

Antibody-based therapy has proved very effective in the treatment of various cancers. For example, HERCEPTIN® and RITUXAN® (both from Genentech, S. San Francisco), have been used successfully to treat breast cancer and non-Hodgkin's lymphoma, respectively. HERCEPTIN® is a recombinant DNA-derived humanized monoclonal antibody that selectively binds to the extracellular domain of the human epidermal growth factor receptor 2 (HER2) proto-oncogene. HER2 protein overexpression is observed in 25-30% of primary breast cancers. RITUXAN® is a genetically engineered chimeric murine/human monoclonal antibody directed against the CD20 antigen found on the surface of normal and malignant B lymphocytes. Both these antibodies are produced in CHO cells.

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., Cancer Immunol. Immunother. 21:183-87 (1986)). Toxins used in antibody-toxin conjugates include bacterial toxins such as diphtheria toxin, plant toxins such as ricin, small molecule toxins such as geldanamycin (Kerr et al (1997) Bioconjugate Chem. 8(6):781-784; Mandler et al (2000) Journal of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Himnan et al (1993) Cancer Res. 53:3336-3342). The toxins may effect their cytotoxic and cytostatic effects by mechanisms including tubulin binding, DNA binding, or topoisomerase inhibition (Meyer, D. L. and Senter, P. D. "Recent Advances in Antibody Drug Conjugates for Cancer Therapy" in Annual Reports in Medicinal Chemistry, Vol 38 (2003) Chapter 23, 229-237). Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is being developed for the treatment of cancers that express CanAg antigen, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The same maytansinoid drug moiety, DM1, was linked through a non-disulfide linker, SMCC, to a mouse murine monoclonal antibody, TA.1 (Chari et al. (1992) Cancer Research 52:127-131). This conjugate was reported to be 200-fold less potent than the corresponding disulfide linker conjugate. The SMCC linker was considered therein to be "noncleavable."

Several short peptide compounds have been isolated from the marine mollusk, Dolabella auricularia, and found to have biological activity (Pettit et al (1993) Tetrahedron 49:9151; Nakamura et al (1995) Tetrahedron Letters 36:5059-5062; Sone et al (1995) Journal Org. Chem. 60:4474). Analogs of these compounds have also been prepared, and some were found to have biological activity (for a review, see Pettit et al (1998) Anti-Cancer Drug Design 13:243-277). For example, auristatin E (U.S. Pat. No. 5,635,483) is a synthetic analogue of the marine natural product Dolastatin 10, an agent that inhibits tubulin polymerization by binding to the same site on tubulin as the anticancer drug vincristine (G. R. Pettit, (1997) Prog. Chem. Org. Nat. Prod. 70:1-79). Dolastatin 10, auristatin PE, and auristatin E are linear peptides having four amino acids, three of which are unique to the dolastatin class of compounds, and a C-terminal amide.

The auristatin peptides, auristain E (AE) and monomethylauristatin (MMAE), synthetic analogs of dolastatin, were conjugated to: (i) chimeric monoclonal antibodies cBR96 (specific to Lewis Y on carcinomas); (ii) cAC10 which is specific to CD30 on hematological malignancies (Klussman, et al: (2004), Bioconjugate Chemistry 15(4):765-773; Doronina et al (2003) Nature Biotechnology 21(7):778-784; "Monomethylvaline Compounds Capable of Conjugation to Ligands"; Francisco et al (2003) Blood 102(4):1458-1465; US 2004/0018194; (iii) anti-CD20 antibodies such as Rituxan® (rituximab) (WO 04/032828) for the treatment of CD20-expressing cancers and immune disorders; (iv) anti-EphB2 antibodies 2H9 and anti-IL-8 for treatment of colorectal cancer (Mao, et al (2004) Cancer Research 64(3):781-788); (v) E-selectin antibody (Bhaskar et al (2003) Cancer Res. 63:6387-6394); and (vi) other anti-CD30 antibodies (WO 03/043583). Monomethylauristatin (MMAE) has also been conjugated to 2H9, an antibody against EphB2R which is a type 1 ™ tyrosine kinase receptor with close homology between mouse and human, and is over-expressed in colorectal cancer cells (Mao et al (2004) Cancer Res. 64:781-788).

Monomethylauristatin MMAF, a variant of auristatin E (MMAE) with a phenylalanine at the C-terminus (U.S. Pat. No. 5,767,237; U.S. Pat. No. 6,124,431), has been reported to be less potent than MMAE, but more potent when conjugated to monoclonal antibodies (Senter et al, Proceedings of the American Association for Cancer Research, Volume 45, Abstract Number 623, presented Mar. 28, 2004). Auristatin F phenylene diamine (AFP); a phenylalanine variant of MMAE was linked to an anti-CD70 mAb, 1F6, through the C-terminus of 1F6 via a phenylene diamine spacer (Law et al, Proceedings of the American Association for Cancer Research, Volume 45, Abstract Number 625, presented Mar. 28, 2004).

There exists a need in the art for additional drugs to treat various cancers such as cancers and metatases of cancers in the prostate, lung and colon. Particularly useful drugs for this purpose include prostate, lung or colon cell targeted anti-STEAP-1 antibody-drug conjugates having a significantly lower toxicity, yet useful therapeutic efficiency. These and other limitations and problems of the past are addressed by the present invention.

The recitation of any reference in this application is not an admission that the reference is prior art to this application. All references cited herein, including patents, patent applications and publications, are incorporated by reference in their entirety.

SUMMARY

The invention provides anti-STEAP-1 antibodies and methods of using the same.

In one aspect, an antibody that binds to STEAP-1 is provided, wherein the antibody comprises a light chain variable domain comprising the amino acid sequence shown in FIG. 2A (SEQ ID NO:6) or a heavy chain variable domain comprising the amino acid sequence shown in FIG. 2B (SEQ ID NO:9). In one aspect, an antibody that binds to STEAP-1 is provided, wherein the antibody comprises a light chain variable domain comprising the amino acid sequence shown in FIG. 2A (SEQ ID NO:6) and a heavy chain variable domain comprising the amino acid sequence shown in FIG. 2B (SEQ ID NO:9).

In one aspect, an antibody that binds to STEAP-1 is provided, wherein the antibody comprises a heavy chain variable domain having at least 90%, at least 91%, at least 92%, at least 93%, at least 94%, at least 95%, at least 96%, at least 97%, at least 98%, or at least 99% sequence identity to an amino acid sequence of SEQ ID NOs:9 or 10. In one embodiment, the antibody comprises a heavy chain variable domain of SEQ ID NOs:9 or 10. In one embodiment, the antibody comprises a heavy chain variable domain framework region 1 of SEQ ID NO:25 or a heavy chain variable domain framework region 2 of SEQ ID NO:75 or 76 or 77 or a heavy chain variable domain framework region 3 of SEQ ID NO:78 or 79.

In one aspect, the antibody comprises a light chain variable domain having at least 90%, at least 91%, at least 92%, at least 93%, at least 94%, at least 95%, at least 96%, at least 97%, at least 98%, or at least 99% sequence identity to an amino acid sequence of SEQ ID NO:6. In one embodiment, the antibody comprises a light chain variable domain of SEQ ID NO:6.

In one aspect, an antibody that binds to STEAP-1 is provided, wherein the antibody comprises a heavy chain variable domain having at least 90%, at least 91%, at least 92%, at least 93%, at least 94%, at least 95%, at least 96%, at least 97%, at least 98%, or at least 99% sequence identity to an amino acid sequence of SEQ ID NOs:9 or 10. In one embodiment, the antibody comprises a heavy chain variable domain of SEQ ID NOs:9 or 10. In one embodiment, the antibody comprises a heavy chain variable domain framework region 1 of SEQ ID NO:25 or a heavy chain variable domain framework region 2 of SEQ ID NO:75 or 76 or 77 or a heavy chain variable domain framework region 3 of SEQ ID NO:78 or 79. In an embodiment, the antibody further comprises a light chain variable domain having at least 90%, at least 91%, at least 92%, at least 93%, at least 94%, at least 95%, at least 96%, at least 97%, at least 98%, or at least 99% sequence identity to an amino acid sequence of SEQ ID NO:6. In one embodiment, the antibody comprises a light chain variable domain of SEQ ID NO:6.

In certain embodiments, a polynucleotide encoding any of the above antibodies is provided. In one embodiment, a vector comprising the polynucleotide is provided. In one embodiment, a host cell comprising the vector is provided. In one embodiment, the host cell is eukaryotic. In one embodiment, the host cell is a Chinese hamster ovary (CHO) cell. In one embodiment, a method of making an anti-STEAP-1 antibody is provided, wherein the method comprises culturing the host cell under conditions suitable for expression of the polynucleotide encoding the antibody, and isolating the antibody.

In one aspect, an antibody that binds to STEAP-1 expressed on the surface of a cell is provided. In one embodiment, the antibody binds to an epitope within a region of human or mouse STEAP-1. In one embodiment, the cell is mammalian cell. In one embodiment, the cell is a human cell. In one embodiment, the cell is a cancer cell. In one embodiment the cell is a prostate, lung or colon cell. In one embodiment the cancer cell is a prostate cancer cell. In another embodiment, the cell cell from a metastisis of a primary prostate, lung or colon cancer.

In certain embodiments, any of the above antibodies is a monoclonal antibody. In one embodiment, the antibody is an antibody fragment selected from a Fab, Fab'-SH, Fv, scFv, or (Fab')$_2$ fragment. In one embodiment, the antibody is humanized. In one embodiment, the antibody is human.

In one aspect, a method of detecting the presence of STEAP-1 in a biological sample is provided, the method comprising contacting the biological sample with any of the above antibodies under conditions permissive for binding of the antibody to STEAP-1, and detecting whether a complex is formed between the antibody and STEAP-1. In one embodiment, the biological sample comprises prostate cells. In one embodiment, the biological sample is from a mammal experiencing or suspected of experiencing a prostate cell disorder and/or a cell proliferative disorder of cells or tissues including, but not limited to, prostate, lung, colon, bladder, and ovarian cancer and Ewing's sarcoma as well as metastases of primary prostate, lung, colon, bladder, and ovarian cancers and Ewing's sarcoma. See, for example, (see U.S. Pat. No. 6,329,503; and Rodeberg, D. A. et al., Clin. Cancer Res. 11(12):4545-4552 (2005)).

In one aspect, a method of diagnosing a cell proliferative disorder associated with increased expression of STEAP-1 is provided, the method comprising contacting a test cell with any of the above antibodies; determining the level of expression of STEAP-1 by detecting binding of the antibody to STEAP-1; and comparing the level of expression of STEAP-1 by the test cell with the level of expression of STEAP-1 by a control cell, wherein a higher level of expression of STEAP-1 by the test cell as compared to the control cell indicates the presence of a cell proliferative disorder associated with increased expression of STEAP-1. In one embodiment, the test cell is a cell from a patient suspected of having a cell proliferative disorder, such as a prostate proliferative disorder. In one embodiment, the cell proliferative disorder is selected from prostate cell disorders including but not limited to prostate cancer. In one embodiment, the method comprises determining the level of expression of STEAP-1 on the surface of the test cell (such as, for example, a prostate cancer cell) and comparing the level of expression of STEAP-1 on the surface of the test cell with the level of expression of STEAP-1 on the surface of the control cell (such, for example, as a normal prostate cell other than an abnormally proliferating prostate cell).

In one aspect, a method of diagnosing a cell proliferative disorder associated with an increase in cells, such as prostate cells, expressing STEAP-1 is provided, the method comprising contacting a test cells in a biological sample with any of the above antibodies; determining the level of antibody bound to test cells in the sample by detecting binding of the antibody to STEAP-1; and comparing the level of antibody bound to cells in a control sample, wherein the level of antibody bound is normalized to the number of STEAP-1-expressing cells in the test and control samples, and wherein a higher level of antibody bound in the test sample as compared to the control sample indicates the presence of a cell proliferative disorder associated with cells expressing STEAP-1.

In one aspect, a method of detecting soluble STEAP-1 in blood or serum, the method comprising contacting a test sample of blood or serum from a mammal suspected of experiencing a prostate cell proliferative disorder with an anti-STEAP-1 antibody of the invention and detecting a increase in soluble STEAP-1 in the test sample relative to a control sample of blood or serum from a normal mammal. In an embodiment, the method of detecting is useful as a method of diagnosing a prostate cell proliferative disorder associated with an increase in soluble STEAP-1 in blood or serum of a mammal.

In one aspect, the antibodies of the invention include cysteine engineered antibodies where one or more amino acids of a parent antibody are replaced with a free cysteine amino acid as disclosed in WO2006/034488 (herein incorporated by reference in its entirety). A cysteine engineered antibody comprises one or more free cysteine amino acids having a thiol reactivity value in the range of 0.6 to 1.0. A free cysteine amino acid is a cysteine residue which has been engineered into the parent antibody and is not part of a disulfide bridge. Cysteine engineered antibodies are useful for attachment of cytotoxic and/or imaging compounds at the site of the engineered cysteine through, for example, a maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London).

Cysteine engineered antibodies may be useful in the treatment of cancer and include antibodies specific for cell surface and transmembrane receptors, and tumor-associated antigens (TAA). Such antibodies may be used as naked antibodies (unconjugated to a drug or label moiety) or as antibody-drug conjugates (ADC). Cysteine engineered antibodies of the invention may be site-specifically and efficiently coupled with a thiol-reactive reagent. The thiol-reactive reagent may be a multifunctional linker reagent, a capture label reagent, a fluorophore reagent, or a drug-linker intermediate. The cysteine engineered antibody may be labeled with a detectable label, immobilized on a solid phase support and/or conjugated with a drug moiety. Thiol reactivity may be generalized to any antibody where substitution of amino acids with reactive cysteine amino acids may be made within the ranges in the light chain selected from amino acid ranges: L-10 to L-20; L-38 to L-48; L-105 to L-115; L-139 to L-149; L-163 to L-173; and within the ranges in the heavy chain selected from amino acid ranges: H-35 to H-45; H-83 to H-93; H-114 to H-127; and H-170 to H-184, and in the Fc region within the ranges selected from H-268 to H-291; H-319 to H-344; H-370 to H-380; and H-395 to H-405, where the numbering of amino acid positions begins at position 1 of the Kabat numbering system (Kabat et al. (1991) Sequences of Proteins of Immunological Interest, 5th Ed. Public Health Service, National Institutes of Health, Bethesda, Md.) and continues sequentially thereafter as disclosed in WO 2006/034488. Thiol reactivity may also be generalized to certain domains of an antibody, such as the light chain constant domain (CL) and heavy chain constant domains, CH1, CH2 and CH3. Cysteine replacements resulting in thiol reactivity values of 0.6 and higher may be made in the heavy chain constant domains α, δ, ε, γ, and μ of intact antibodies: IgA, IgD, IgE, IgG, and IgM, respectively, including the IgG subclasses: IgG1, IgG2, IgG3, IgG4, IgA, and IgA2. Such antibodies and their uses are disclosed in WO 2006/034488.

Cysteine engineered antibodies of the invention can comprise a cysteine at one position selected from 15, 43, 110, 144, 168 and 205 of the light chain according to Kabat numbering convention or one position selected from 41, 88, 115, 118, 120, 171, 172, 282, 375, and 400 of the heavy chain according to EU numbering convention.

Cysteine engineered antibodies of the invention preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signalling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis.

An antibody of the invention may be conjugated to other thiol-reactive agents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671). The partner may be a cytotoxic agent (e.g. a toxin such as doxorubicin or pertussis toxin), a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

In one aspect, antibodies of the invention may be conjugated with any label moiety which can be covalently attached to the antibody through a reactive moiety, an activated moiety, or a reactive cysteine thiol group (Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation.

Labelled cysteine engineered antibodies may be useful in diagnostic assays, e.g., for detecting expression of an antigen of interest in specific cells, tissues, or serum. For diagnostic applications, the antibody will typically be labeled with a detectable moiety. Numerous labels are available which can be generally grouped into the following categories:

Radioisotopes (radionuclides), such as $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. Radioisotope labelled antibodies are useful in receptor targeted imaging experiments. The antibody can be labeled with ligand reagents that bind, chelate or otherwise complex a radioisotope metal where the reagent is reactive with the engineered cysteine thiol of the antibody, using the techniques described in Current Protocols in Immunology, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.). Radionuclides can be targeted via complexation with the antibody-drug conjugates of the invention (Wu et al (2005) Nature Biotechnology 23(9): 1137-1146).

Linker reagents such as DOTA-maleimide (4-maleimidobutyramidobenzyl-DOTA) can be prepared by the reaction of aminobenzyl-DOTA with 4-maleimidobutyric acid (Fluka) activated with isopropylchloroformate (Aldrich), following the procedure of Axworthy et al (2000) Proc. Natl. Acad. Sci. USA 97(4):1802-1807). DOTA-maleimide reagents react with the free cysteine amino acids of the cysteine engineered antibodies and provide a metal complexing ligand on the antibody (Lewis et al (1998) Bioconj. Chem. 9:72-86). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.). Receptor target imaging with radionuclide labelled antibodies can provide a marker of pathway activation by detection and quantitation of progressive accumulation of antibodies in tumor tissue (Albert et al (1998) Bioorg. Med. Chem. Lett. 8:1207-1210). The conjugated radio-metals may remain intracellular following lysosomal degradation.

Metal-chelate complexes suitable as antibody labels for imaging experiments are disclosed: U.S. Pat. No. 5,342,606; U.S. Pat. No. 5,428,155; U.S. Pat. No. 5,316,757; U.S. Pat. No. 5,480,990; U.S. Pat. No. 5,462,725; U.S. Pat. No. 5,428,139; U.S. Pat. No. 5,385,893; U.S. Pat. No. 5,739,294; U.S. Pat. No. 5,750,660; U.S. Pat. No. 5,834,456; Hnatowich et al (1983) J. Immunol. Methods 65:147-157; Meares et al (1984) Anal. Biochem. 142:68-78; Mirzadeh et al (1990) Bioconjugate Chem. 1:59-65; Meares et al (1990) J. Cancer 1990, Suppl. 10:21-26; Izard et al (1992) Bioconjugate Chem. 3:346-350; Nikula et al (1995) Nucl. Med. Biol. 22:387-90; Camera et al (1993) Nucl. Med. Biol. 20:955-62; Kukis et al (1998) J. Nucl. Med. 39:2105-2110; Verel et al (2003) J. Nucl. Med. 44:1663-1670; Camera et al (1994) J. Nucl. Med. 21:640-646; Ruegg et al (1990) Cancer Res. 50:4221-4226; Verel et al (2003) J. Nucl. Med. 44:1663-1670; Lee et al (2001) Cancer Res. 61:4474-4482; Mitchell, et al (2003) J. Nucl. Med. 44:1105-1112; Kobayashi et al (1999) Bioconjugate Chem. 10:103-111; Miederer et al (2004) J. Nucl. Med. 45:129-137; DeNardo et al (1998) Clinical Cancer Research 4:2483-90; Blend et al (2003) Cancer Biotherapy & Radiopharmaceuticals 18:355-363; Nikula et al (1999) J. Nucl. Med. 40:166-76; Kobayashi et al (1998) J. Nucl. Med. 39:829-36; Mardirossian et al (1993) Nucl. Med. Biol. 20:65-74; Roselli et al (1999) Cancer Biotherapy & Radiopharmaceuticals, 14:209-20.

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to antibodies using the techniques disclosed in Current Protocols in Immunology, supra, for example. Fluorescent dyes and fluorescent label reagents include those which are commercially available from Invitrogen/Molecular Probes (Eugene, Oreg.) and Pierce Biotechnology, Inc. (Rockford, Ill.).

(c) Various enzyme-substrate labels are available or disclosed (U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, ma late dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al (1981) "Methods for the Preparation of Enzyme-Antibody Conjugates for use in Enzyme Immunoassay", in Methods in Enzym. (ed J. Langone & H. Van Vunakis), Academic Press, New York, 73:147-166.

Examples of enzyme-substrate combinations include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3', 5,5'-tetramethylbenzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review, see U.S. Pat. No. 4,275,149 and U.S. Pat. No. 4,318,980.

A label may be indirectly conjugated with an amino acid side chain, an activated amino acid side chain, a cysteine engineered antibody, and the like. For example, the antibody can be conjugated with biotin and any of the three broad categories of labels mentioned above can be conjugated with avidin or streptavidin, or vice versa. Biotin binds selectively to streptavidin and thus, the label can be conjugated with the antibody in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved (Hermanson, G. (1996) in Bioconjugate Techniques Academic Press, San Diego).

The antibody of the present invention may be employed in any known assay method, such as ELISA, competitive binding assays, direct and indirect sandwich assays, and immunoprecipitation assays (Zola, (1987) Monoclonal Antibodies: A Manual of Techniques, pp. 147-158, CRC Press, Inc.).

A detection label may be useful for localizing, visualizing, and quantitating a binding or recognition event. The labelled antibodies of the invention can detect cell-surface receptors. Another use for detectably labelled antibodies is a method of bead-based immunocapture comprising conjugating a bead with a fluorescent labelled antibody and detecting a fluorescence signal upon binding of a ligand. Similar binding detection methodologies utilize the surface plasmon resonance (SPR) effect to measure and detect antibody-antigen interactions.

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labelling antibodies, preferably with the following properties: (i) the labelled antibody should produce a very high signal with low background so that small quantities of antibodies can be sensitively detected in both cell-free and cell-based assays; and (ii) the labelled antibody should be photostable so that the fluorescent signal may be observed, monitored and recorded without significant photo bleaching. For applications involving cell surface binding of labelled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

Direct quantification of cellular fluorescence intensity and enumeration of fluorescently labelled events, e.g. cell surface binding of peptide-dye conjugates may be conducted on an system (FMAT® 8100 HTS System, Applied Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193-204). Uses of labelled antibodies also include cell surface receptor binding assays, immunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) Proc. Natl. Acad. Sci. USA 95:618-23; U.S. Pat. No. 6,372,907), apoptosis (Vernes, "A novel assay for apoptosis. Flow cytometric detection of phosphatidylserine expression on early apoptotic cells using fluorescein labelled Annexin V" (1995) J. Immunol. Methods 184:39-51) and cytotoxicity assays. Fluorometric microvolume assay technology can be used to identify the up or down regulation by a molecule that is targeted to the cell surface (Swartzman, "A homogeneous and multiplexed immunoassay for high-throughput screening using fluorometric microvolume assay technology", (1999) Anal. Biochem. 271:143-51).

Labelled antibodies of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) Bioconjugate Chem. 15:41-49; (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone-erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labelling methods are well known. See Haugland, 2003, Molecular Probes Handbook of Fluorescent Probes and Research Chemicals, Molecular Probes, Inc.; Brinkley, 1992, Bioconjugate Chem. 3:2; Garman, (1997) Non-Radioactive Labelling: A Practical Approach, Academic Press, London; Means (1990) Bioconjugate Chem. 1:2; Glazer et al (1975) Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGryter, Berlin and New York; and Wong (1991) Chemistry of Protein Conjugation and Cross-linking, CRC Press, Boca Raton, Fla.); De Leon-Rodriguez et al (2004) Chem. Eur. J. 10:1149-1155; Lewis et al (2001) Bioconjugate Chem. 12:320-324; Li et al (2002) Bioconjugate Chem. 13:110-115; Mier et al (2005) Bioconjugate Chem. 16:240-237.

Peptides and proteins labelled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18-34).

The labelled antibodies of the invention may also be used as an affinity purification agent. In this process, the labelled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, that will release the antigen from the polypeptide variant.

Labelling reagents typically bear reactive functionality which may react (i) directly with a cysteine thiol of a cysteine engineered antibody to form the labelled antibody, (ii) with a linker reagent to form a linker-label intermediate, or (iii) with a linker antibody to form the labelled antibody. Reactive functionality of labelling reagents include: maleimide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, and phosphoramidite, although other functional groups can also be used.

An exemplary reactive functional group is N-hydroxysuccinimidyl ester (NHS) of a carboxyl group substituent of a detectable label, e.g. biotin or a fluorescent dye. The NHS ester of the label may be preformed, isolated, purified, and/or characterized, or it may be formed in situ and reacted with a nucleophilic group of an antibody. Typically, the carboxyl form of the label is activated by reacting with some combination of a carbodiimide reagent, e.g. dicyclohexylcarbodiimide, diisopropylcarbodiimide, or a uronium reagent, e.g. TSTU (O—(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester of the label. In some cases, the label and the antibody may be coupled by in situ activation of the label and reaction with the antibody to form the label-antibody conjugate in one step. Other activating and coupling reagents include TBTU (2-(1H-benzotriazo-1-yl)-1-1,3,3-tetramethyluronium hexafluorophosphate), TFFH (N,N',N'',N'''-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydroquinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzenesulfonyl chloride.

Albumin Binding Peptide-Fab Compounds of the Invention:

In one aspect, the antibody of the invention is fused to an albumin binding protein. Plasma-protein binding can be an effective means of improving the pharmacokinetic properties of short lived molecules. Albumin is the most abundant protein in plasma. Serum albumin binding peptides (ABP) can alter the pharmacodynamics of fused active domain proteins, including alteration of tissue uptake, penetration, and diffusion. These pharmacodynamic parameters can be modulated by specific selection of the appropriate serum albumin binding peptide sequence (US 20040001827). A series of albumin binding peptides were identified by phage display screening (Dennis et al. (2002) "Albumin Binding As A General Strategy For Improving The Pharmacokinetics Of Proteins" J Biol. Chem. 277:35035-35043; WO 01/45746). Compounds of the invention include ABP sequences taught by: (i) Dennis et al (2002) J Biol. Chem. 277:35035-35043 at Tables III and IV, page 35038; (ii) US 20040001827 at SEQ ID NOS: 9-22; and (iii) WO 01/45746 at pages 12-13, all of which are incorporated herein by reference. Albumin Binding (ABP)-Fabs are engineered by fusing an albumin binding peptide to, for example, the C-terminus of Fab heavy chain in 1:1 stoichiometric ratio (1 ABP/1 Fab). It was shown that association of these ABP-Fabs with albumin increased antibody half life by more than 25 fold in rabbits and mice. The above described reactive Cys residues can therefore be introduced in these ABP-Fabs and used for site-specific conjugation with cytotoxic drugs followed by in vivo animal studies.

Exemplary albumin binding peptide sequences include, but are not limited to, the amino acid sequences listed in SEQ ID NOS:80-84.

```
CDKTHTGGGSQRLMEDICLPRWGCLWEDDF    SEQ ID NO: 80

QRLMEDICLPRWGCLWEDDF              SEQ ID NO: 81

QRLIEDICLPRWGCLWEDDF              SEQ ID NO: 82

RLIEDICLPRWGCLWEDD                SEQ ID NO: 83

DICLPRWGCLW                       SEQ ID NO: 84
```

Antibody-Drug Conjugates

In another aspect, the invention provides immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In another aspect, the invention further provides methods of using the immunoconjugates. In one aspect, an immunoconjugate comprises any of the above anti-STEAP-1 antibodies covalently attached to a cytotoxic agent or a detectable agent.

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Phammaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7): 778-784) and are under therapeutic development.

Chemotherapeutic agents useful in the generation of immunoconjugates are described herein. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987) Science, 238:1098. Carbon-14-labeled 1-isothiocyanatobenzyl-3-methyldiethylene triaminepentaacetic acid (MX-DTPA) is an exemplary chelating agent for conjugation of radionucleotide to the antibody (WO94/11026).

Conjugates of an antibody and one or more small molecule toxins, such as a calicheamicin, maytansinoids, dolastatins, auristatins, a trichothecene, and CC1065, and the derivatives of these toxins that have toxin activity, are also contemplated herein.

Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides). and those having modifications at other positions Exemplary maytansinoid drug moieties also include those having modifications such as: C-9-SH (U.S. Pat. No. 4,424,219) (prepared by the reaction of maytansinol with $H_2S$ or $P_2S_5$); C-14-alkoxymethyl(demethoxy/$CH_2OR$) (U.S. Pat. No. 4,331,598); C-14-hydroxymethyl or acyloxymethyl ($CH_2OH$ or $CH_2OAc$) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from *Trewia nudlflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

Exemplary embodiments of maytansinoid drug moieties include: DM1; DM3; and DM4, having the structures:

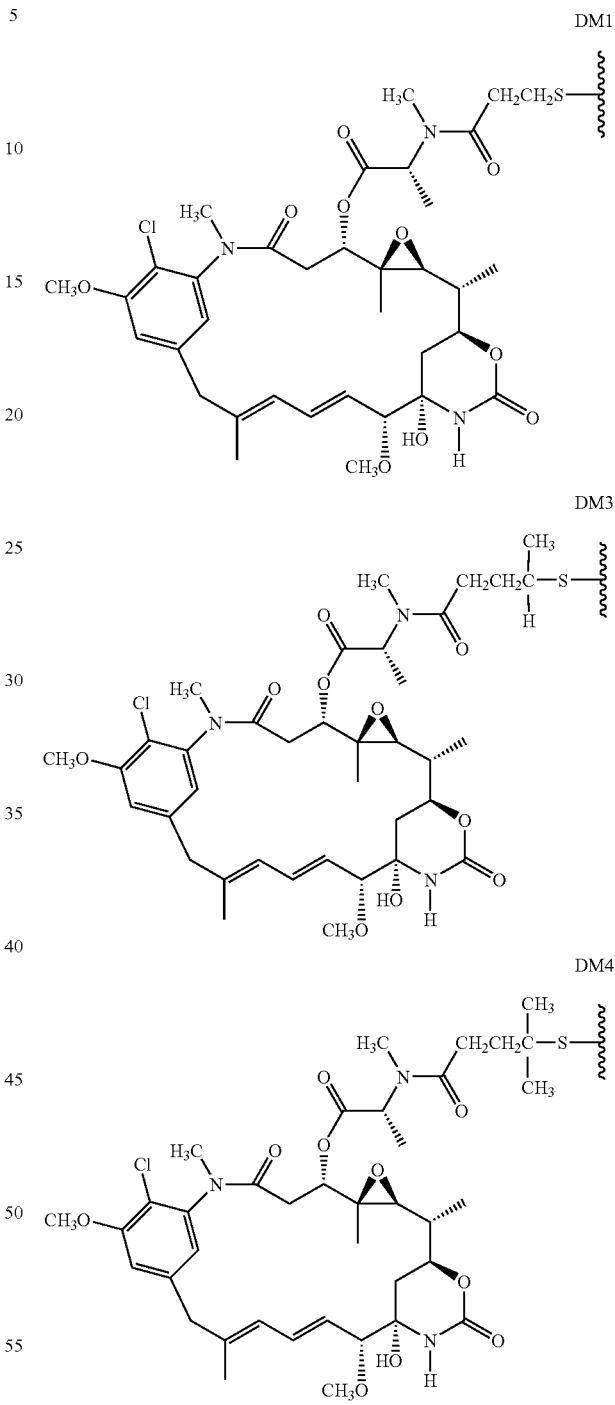

wherein the wavy line indicates the covalent attachment of the sulfur atom of the drug to a linker (L) of an antibody drug conjugate. HERCEPTIN® (trastuzumab) linked by SMCC to DM1 has been reported (WO 2005/037992, which is expressly incorporated herein by reference in its entirety). An antibody drug conjugate of the present invention may be prepared according to the procedures disclosed therein.

Other exemplary maytansinoid antibody drug conjugates have the following structures and abbreviations, (wherein Ab is antibody and p is 1 to about 8):
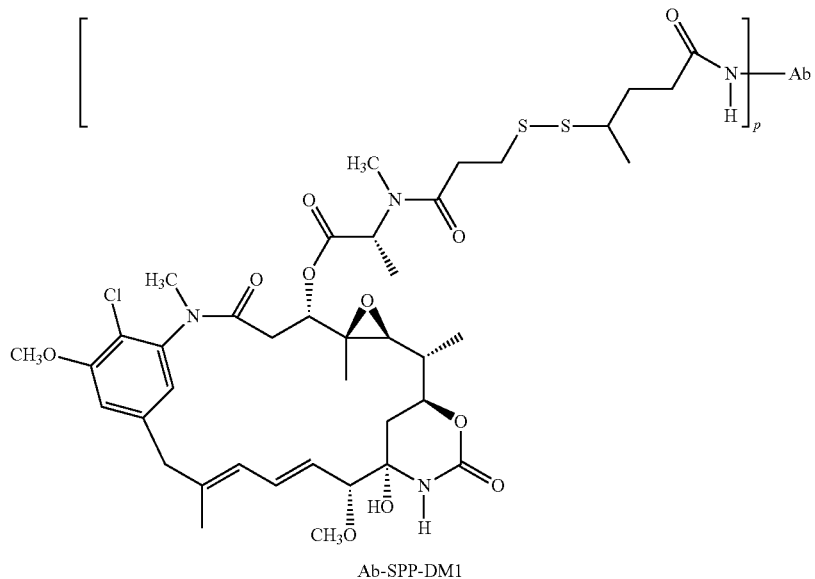
Ab-SPP-DM1
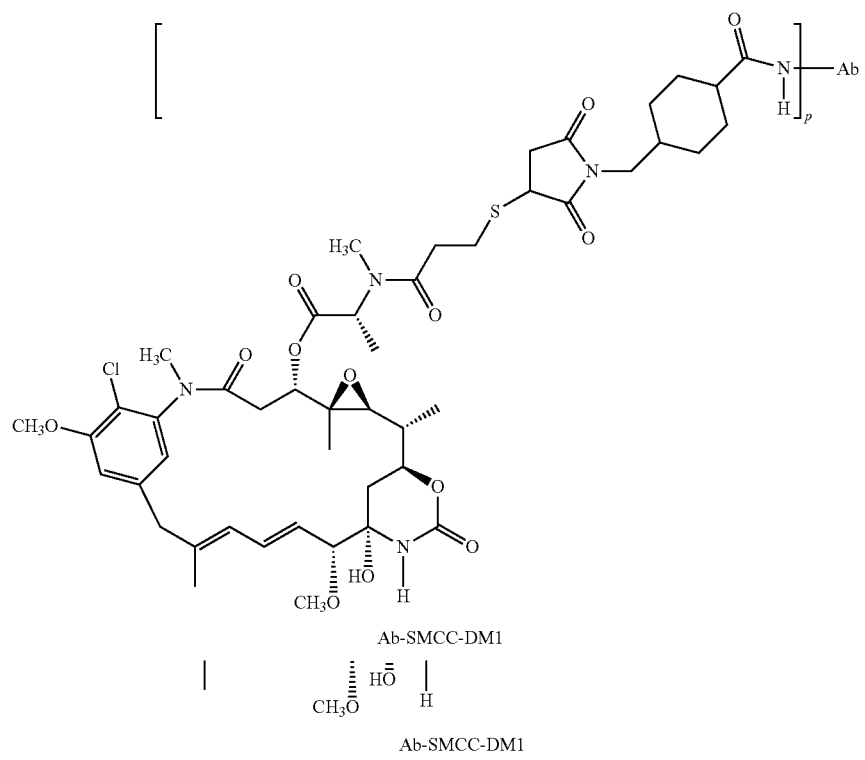
Ab-SMCC-DM1

Exemplary antibody drug conjugates where DM1 is linked through a BMPEO linker to a thiol group of the antibody have the structure and abbreviation:

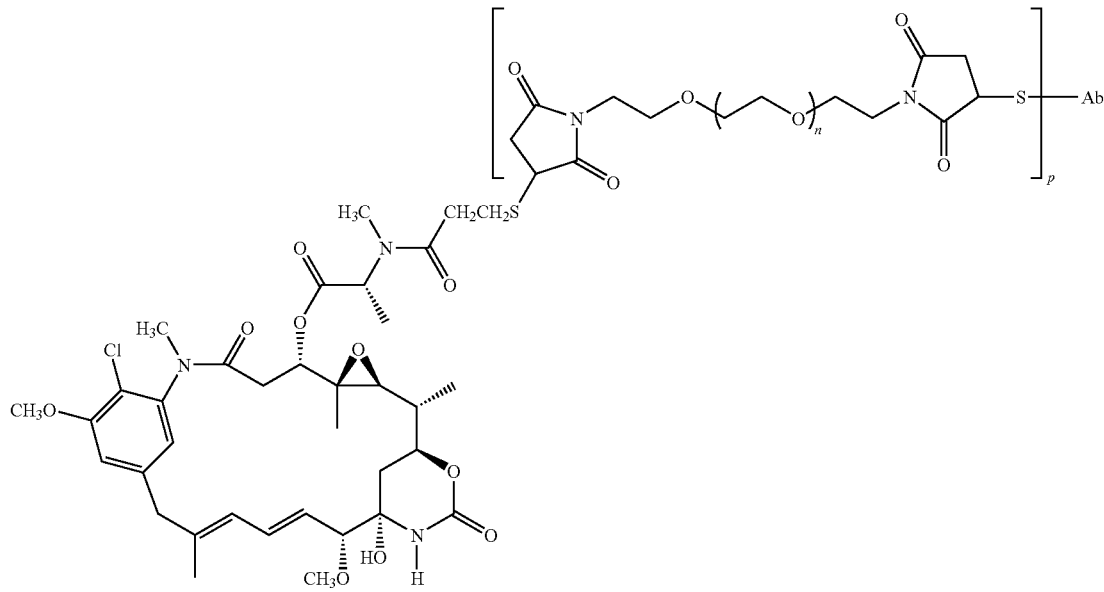

where Ab is antibody; n is 0, 1, or 2; and p is 1, 2, 3, or 4.

Immunoconjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA. 1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Anti-STEAP-1 antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. Nos. 5,208,020, 6,441,163, or EP Patent 0 425 235 B1, Chari et al., Cancer Research 52:127-131 (1992), and US 2005/0169933 A1, the disclosures of which are hereby expressly incorporated by reference. Antibody-maytansinoid conjugates comprising the linker component SMCC may be prepared as disclosed in U.S. patent application Ser. No. 11/141,344, filed 31 May 2005, "Antibody Drug Conjugates and Methods". The linking groups include disulfide groups, thioether groups, acid labile groups, photolabile groups, peptidase labile groups, or esterase labile groups, as disclosed in the above-identified patents. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

In one embodiment, any of the antibodies of the invention (full length or fragment) is conjugated to one or more maytansinoid molecules. In one embodiment of the immunoconjugate, the cytotoxic agent D, is a maytansinoid DM1. In one embodiment of the immunoconjugate, the linker is selected from the group consisting of SPDP, SMCC, IT, SPDP, and SPP.

Auristatins and Dolostatins

In some embodiments, the immunoconjugate comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004, the disclosure of which is expressly incorporated by reference in its entirety.

An exemplary auristatin embodiment is MMAE (wherein the wavy line indicates the covalent attachment to a linker (L) of an antibody drug conjugate).

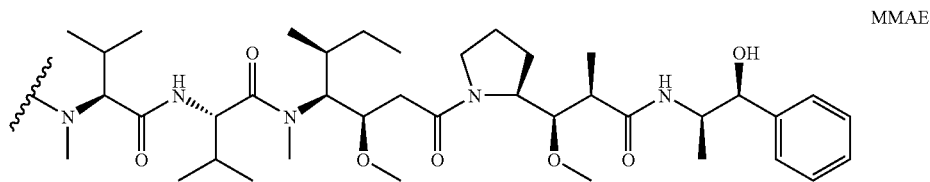 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

Another exemplary auristatin embodiment is MMAF, wherein the wavy line indicates the covalent attachment to a linker (L) of an antibody drug conjugate (US 2005/0238649):

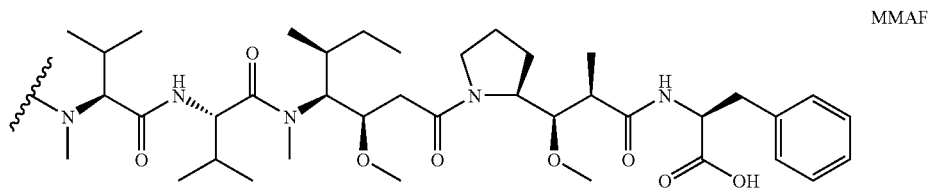 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

MMAF

Additional exemplary embodiments comprising MMAE or MMAF and various linker components (described further herein) have the following structures and abbreviations (wherein Ab means antibody and p is 1 to about 8):

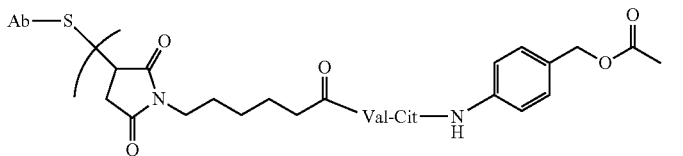

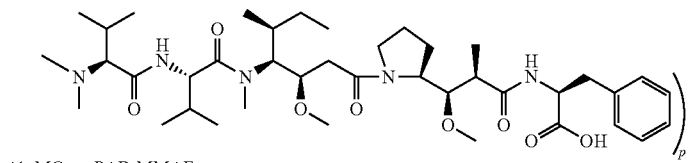

Ab-MC-vc-PAB-MMAF

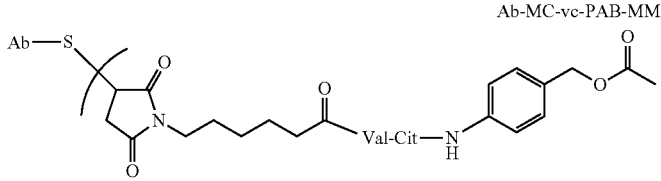

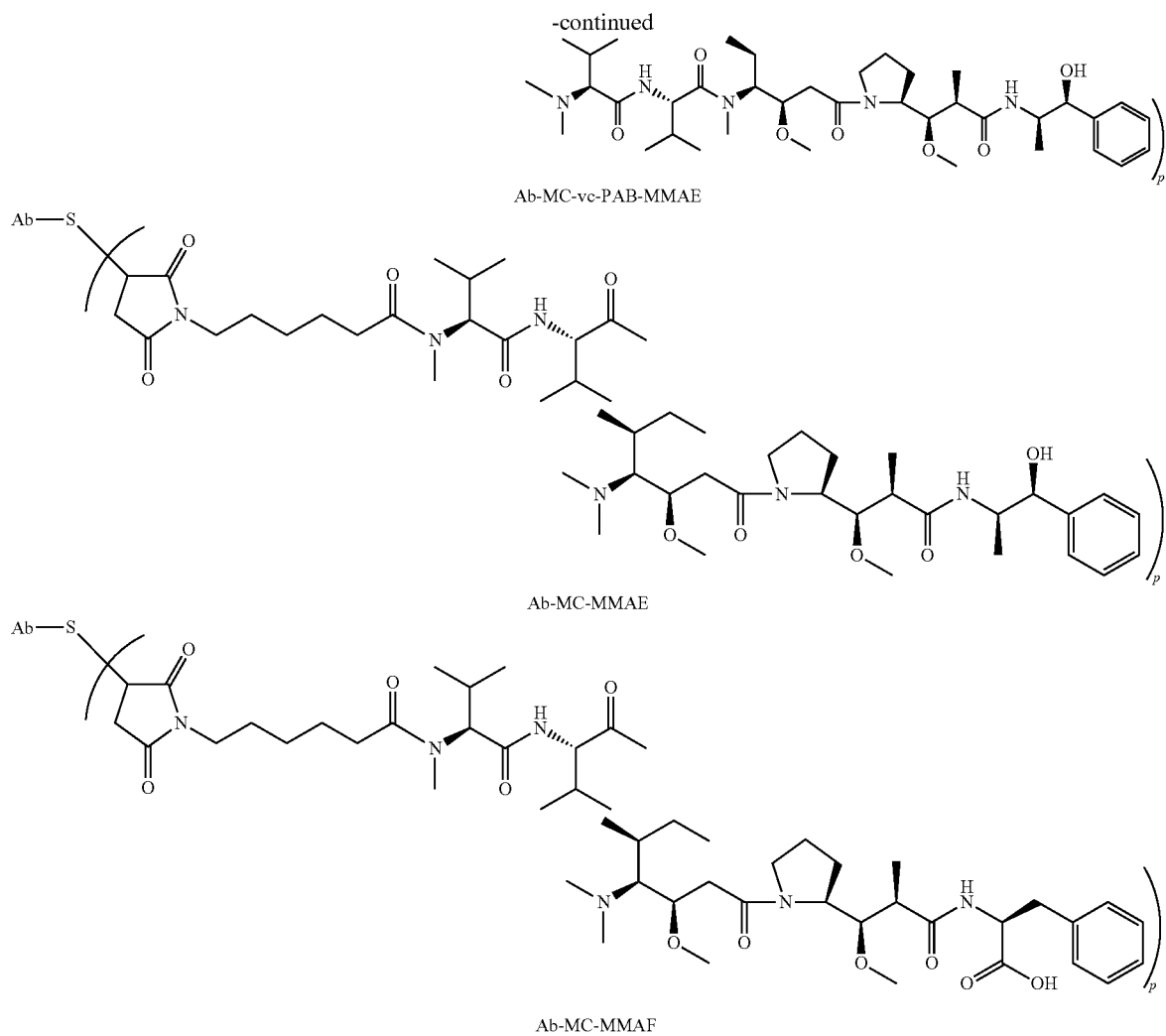

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 15:859-863; and Doronina (2003) Nat Biotechnol 21(7):778-784.

Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053, 394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates:

In the antibody drug conjugates (ADC) of the invention, an antibody (Ab) is conjugated to one or more drug moieties (D), e.g. about 1 to about 20 drug moieties per antibody, through a linker (L). In one embodiment, the number of drug moieties (D) per antibody is from about 1 to about 5, alternatively, from about 2 to about 6, alternatively, from about 2 to about 5, alternatively from about 3 to about 4 drug moieties per antibody. Because the number of drug moieties per antibody is typically an average number over all conjugates in a population of an antibody drug conjugate, the number of drug moieties per antibody may not be a whole number. The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \quad \text{Formula I}$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC'), and N-Succinimidyl (4-iodo-acetyl)aminobenzoate ("SIAB"). In on embodiment, the linker is valine-citrullin-p-aminobenzyloxycaronyl ("vc-PAB"). Additional linker components are known in the art and some are described herein.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease. Exemplary linker component structures are shown below (wherein the wavy line indicates sites of covalent attachment to other components of the ADC):

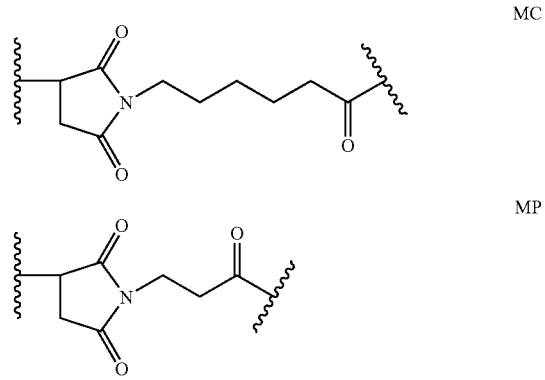

-continued

MPEG

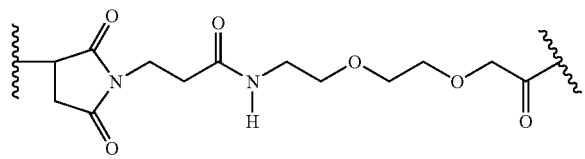

Additional exemplary linker components and abbreviations include (wherein the antibody (Ab) and linker are depicted, and p is 1 to about 8):

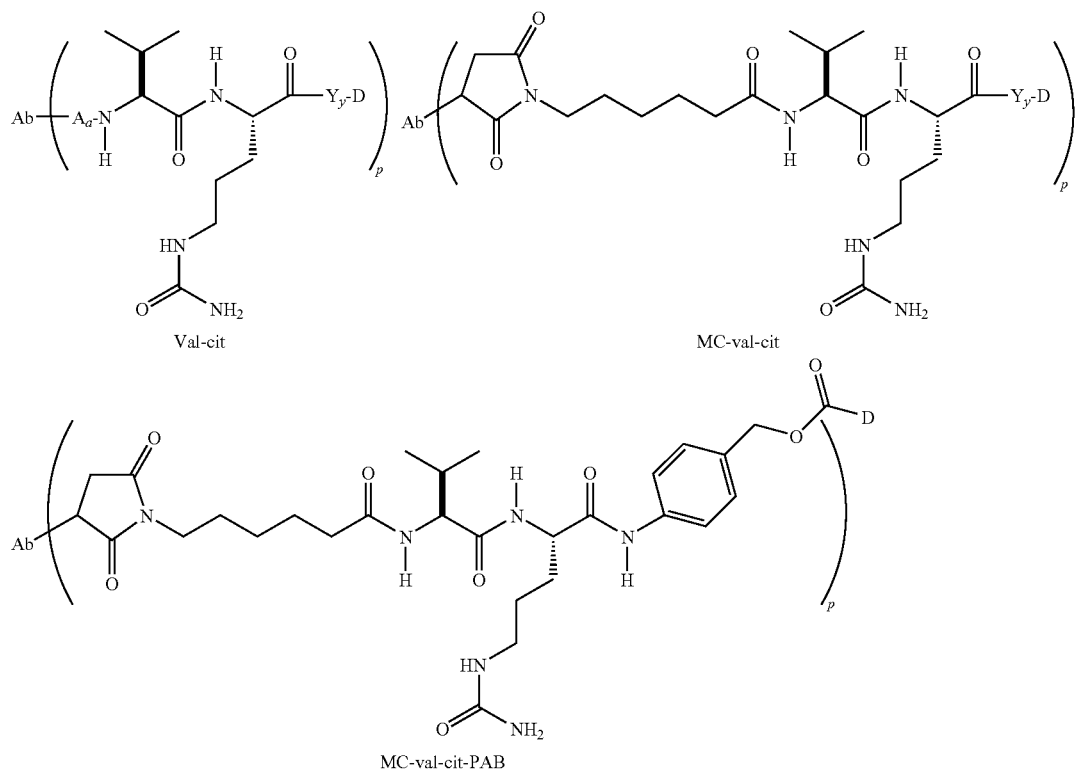

preparing mutant antibodies comprising one or more non-native cysteine amino acid residues).

Antibody drug conjugates of the invention may also be produced by modification of the antibody to introduce electrophilic moieties, which can react with nucleophilic subsituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Methods for the conjugation of linker-drug moieties to cell-targeted proteins such as antibodies, immunoglobulins or Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., fragments thereof are found, for example, in U.S. Pat. No. 5,208,020; U.S. Pat. No. 6,441,163; WO2005037992; WO2005081711; and WO2006/034488, all of which are hereby expressly incorporated by reference in their entirety.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

In one embodiment of the immunoconjugate, the cytotoxic agent, D, is an auristatin of formula $D_E$ or $D_F$

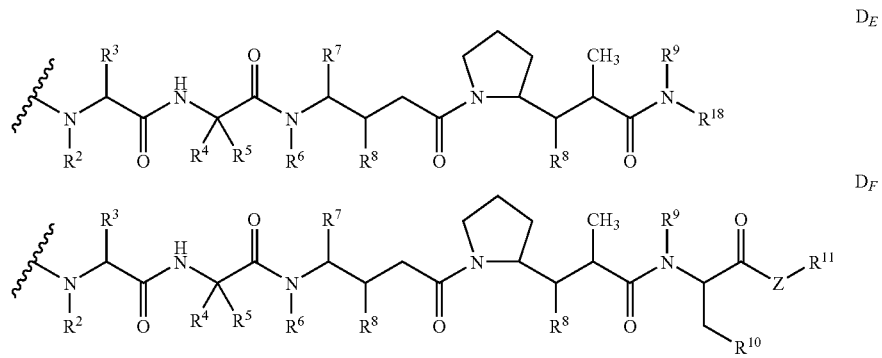

and wherein $R^2$ and $R^6$ are each methyl, $R^3$ and $R^4$ are each isopropyl, $R^7$ is sec-butyl, each $R^8$ is independently selected from $CH_3$, $O-CH_3$, OH, and H; $R^9$ is H; $R^{10}$ is aryl; Z is —O— or —NH—; $R^{11}$ is H, $C_1$-$C_8$ alkyl, or —$(CH_2)_2$—O—$(CH_2)_2$—$OCH_2)_2$—O—$CH_3$; and $R^{18}$ is —$C(R^8)_2$—$C(R^8)_2$-aryl; and (d) p ranges from about 1 to 8.

The following embodiments are further provided for any of the above immunoconjugates. In one embodiment, an immunoconjugate has in vitro or in vivo cell killing activity. In one embodiment, the linker is attached to the antibody through a thiol group on the antibody. In one embodiment, the linker is cleavable by a protease. In one embodiment, the linker comprises a val-cit dipeptide. In one embodiment, the linker comprises a p-aminobenzyl unit. In one embodiment, the p-aminobenzyl unit is disposed between the drug and a protease cleavage site in the linker. In one embodiment, the p-aminobenzyl unit is p-aminobenzyloxycarbonyl (PAB). In one embodiment, the linker comprises 6-maleimidocaproyl. In one embodiment, the 6-maleimidocaproyl is disposed between the antibody and a protease cleavage site in the linker. The above embodiments may occur singly or in any combination with one another.

In one embodiment, the drug is selected from MMAE and MMAF. In one embodiment, the immunoconjugate has the formula

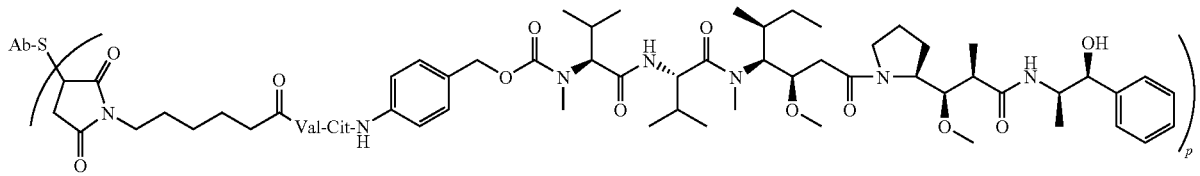

wherein Ab is any of the above anti-STEAP-1 antibodies, S is a sulfur atom, and p ranges from about 2 to about 5. In one embodiment, the immunoconjugate has the formula

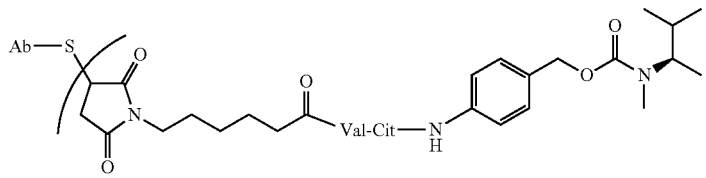
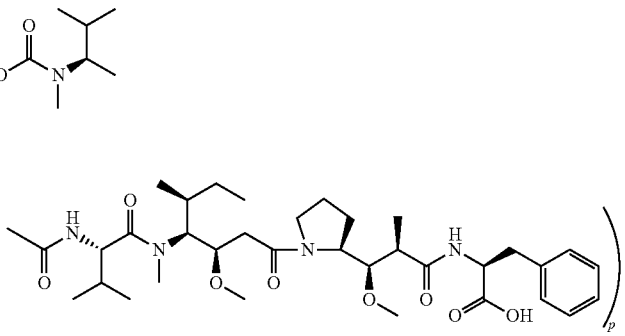

wherein Ab is any of the above anti-STEAP-1 antibodies, S is a sulfur atom, and p ranges from about 1 to about 6, from about 2 to about 5, from about 2 to about 6, from about 2 to about 4, from about 2 to about 3, from about 3 to about 4, from about 3 to about 5, from about 3 to about 6, or from about 4 to about 6.

Labelled Antibody Imaging Methods:

In another embodiment of the invention, cysteine engineered antibodies may be labelled through the cysteine thiol with radionuclides, fluorescent dyes, bioluminescence-triggering substrate moieties, chemiluminescence-triggering substrate moieties, enzymes, and other detection labels for imaging experiments with diagnostic, pharmacodynamic, and therapeutic applications. Generally, the labelled cysteine engineered antibody, i.e. "biomarker" or "probe", is administered by injection, perfusion, or oral ingestion to a living organism, e.g. human, rodent, or other small animal, a perfused organ, or tissue sample. The distribution of the probe is detected over a time course and represented by an image.

Articles of Manufacture:

In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds an antibody-drug conjugate (ADC) composition which is effective for treating the condition and may have a sterile access port (for example the container may be an intravenous solution bag or a vial having a stopper pierceable by a hypodermic injection needle). At least one active agent in the composition is an ADC. The label or package insert indicates that the composition is used for treating the condition of choice, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Pharmaceutical Compositions:

In one aspect, a pharmaceutical composition is provided comprising any of the above immunoconjugates and a pharmaceutically acceptable carrier. In one aspect, a method of treating a prostate, lung, colon, bladder, or ovarian cell proliferative disorder, or Ewing's sarcoma is provided, wherein the method comprises administering to an individual the pharmaceutical composition. In one embodiment, the prostate, lung, colon, bladder, and ovarian cancer and Ewing's sarcoma cell proliferative disorder is a metastasis of a primary prostate, lung, colon, bladder, or ovarian cancer or Ewing's sarcoma. In one embodiment, the cell proliferative disorder is associated with increased expression of STEAP-1 on the surface of a cell.

In one aspect, a method of inhibiting cell proliferation is provided, wherein the method comprises exposing a cell to any of the above immunoconjugates under conditions permissive for binding of the immunoconjugate to STEAP-1. In one embodiment, the prostate, lung, colon, bladder, or ovary cell or Ewing's sarcoma is a tumor cell. In one embodiment, the tumor cell is a prostate, lung, colon, bladder, or ovarian tumor cell or Ewing's sarcoma celll of a mammal experiencing or suspected of experiencing prostate, lung, colon, bladder cell or Ewing's sarcoma proliferative disorder including, but not limited to, a metastasis of a primary prostate, lung, colon, bladder cell cancer tumor or Ewing's sarcoma tumor. In one embodiment, the prostate, lung, colon, bladder cell or Ewing's sarcoma is a xenograft. In one embodiment, the exposing takes place in vitro. In one embodiment, the exposing takes place in vivo.

In one aspect, a method of using the anti-STEAP-1 antibody of the invention is provided to assay serum soluble STEAP-1 in a mammal experiencing prostate lung or colon cell proliferative disorder (or metastasis of a primary incidence of such disorder), measuring clinical progression or regression of the diseases, or assess tumor burden or relapse.

BRIEF DESCRIPTION OF THE FIGURES

The patent or application file contains at least one drawing executed in color. Copies of this patent or patent application publication with color drawings(s) will be provided by the Office upon request and payment of the necessary fees.

FIGS. 2A-2B: FIG. 2A depicts the amino acid sequence of the light chain variable region of murine 120.545 anti-STEAP-1 antibody aligned with the chimera antibody (120 chimera) and humanized antibody (120 graft) and aligned with the human subgroup III sequence. The CDRs are boxed (CDR-L1, CDR-L2, and CDR-L3). The sequences bracketing the CDRs are the framework sequences (FR-L1 to FR-LA). The sequences are numbered according to Kabat numbering. The Kabat, Chothia, and contact CDRs are indicated about the boxed CDRs. FIG. 2B depicts the amino acid sequence of the heavy chain variable region of murine anti- STEAP-1 antibody (120.545) aligned with the chimera antibody (120 chimera) and humanized antibody (120 graft) and aligned with the human kappa I sequence. Humanized variants 24, 37, 48, 67, and 37/48, 67, 71, and 78 were prepared by making the following amino acid changes: A24V, V37I, V48M, F67I, and L78F in the heavy chain of the 120 graft antibody. The CDRs are boxed. The FR-H1, FR-H2, FR-H3 and FR-H4 sequences bracket the CDRs (CDR-H1, CDR-H2, and CDR-H3). The sequences are numbered according to Kabat numbering. The Kabat, Chothia, and contact CDRs are indicated about the boxed CDRs.

FIGS. 3A and 3B show exemplary acceptor human variable heavy (VH) consensus framework sequences for use in practicing the instant invention with sequence identifiers as follows, where the FR SEQ ID NOs are listed in the order FR-H1, FR-H2, FR-H3, FR-H4:

human VH subgroup I consensus framework "A" minus Kabat CDRs (SEQ ID NOs:26, 27, 28, 29).
human VH subgroup I consensus frameworks "B," "C," and "D" minus extended hypervariable regions (SEQ ID NOs:30, 31, 28, 29; SEQ ID NOs:30, 31, 32, 29; and SEQ ID NOs:30, 31, 33, 29).
human VH subgroup II consensus framework "A" minus Kabat CDRs (SEQ ID NOs:34, 35, 36, 29).
human VH subgroup II consensus frameworks "B," "C," and "D" minus extended hypervariable regions (SEQ ID NOs:37, 38, 36, 29; SEQ ID NOs:37, 38, 39, 29; and SEQ ID NOs:37, 38, 40, 29).
human VH subgroup III consensus framework "A" minus Kabat CDRs (SEQ ID NOs:41, 42, 43, 29).
human VH subgroup III consensus frameworks "B," "C," and "D" minus extended hypervariable regions (SEQ ID NOs:44, 45, 43, 29; SEQ ID NOs:44, 45, 46, 29; and SEQ ID NOs:44, 45, 46, 29).
human VH acceptor 1 framework "A" minus Kabat CDRs (SEQ ID NOs:48, 42, 49, 29).
human VH acceptor frameworks "B" and "C" minus extended hypervariable regions (SEQ ID NOs:44, 45, 49, 29; and SEQ ID NOs:44, 45, 50, 29).
human VH acceptor 2 framework "A" minus Kabat CDRs (SEQ ID NOs:48, 42, 51, 29).
human VH acceptor 2 framework "B," "C," and "D" minus extended hypervariable regions (SEQ ID NOs:44, 45, 51, 29; SEQ ID NOs:44, 45, 52, 29; and SEQ ID NOs: 44, 45, 53, 29).

FIGS. 4A and 4B show exemplary acceptor human variable light (VL) consensus framework sequences for use in practicing the instant invention with sequence identifiers as follows:

human VL kappa subgroup I-1 consensus framework (κv1-1): SEQ ID NOs:54, 55, 56, 57:
human VL kappa subgroup I consensus framework (κv1): SEQ ID NOs:54, 58, 56, 57
human VL kappa subgroup II consensus framework (κv2): SEQ ID NOs:58, 59, 60, 57
human VL kappa subgroup III consensus framework (κv3): SEQ ID NOs:61, 62, 63, 57
human VL kappa subgroup IV consensus framework (κv4): SEQ ID NOs:64, 65, 66, 57.

FIG. 5 depicts alignments of native sequence human IgG Fc region sequences, humIgG1 (non-A allotype, SEQ ID NO:85; and A allotype, where the amino acid sequence SREEM within SEQ ID NO:85 is changed to SRDEL), humIgG2 (SEQ ID NO:86), humIgG3 (SEQ ID NO:87) and humIgG4 (SEQ ID NO:88) with differences between the sequences marked with asterisks. Numbers above the sequences represent the EU numbering system. An exemplary kappa constant region is also shown.

Figure 6C:
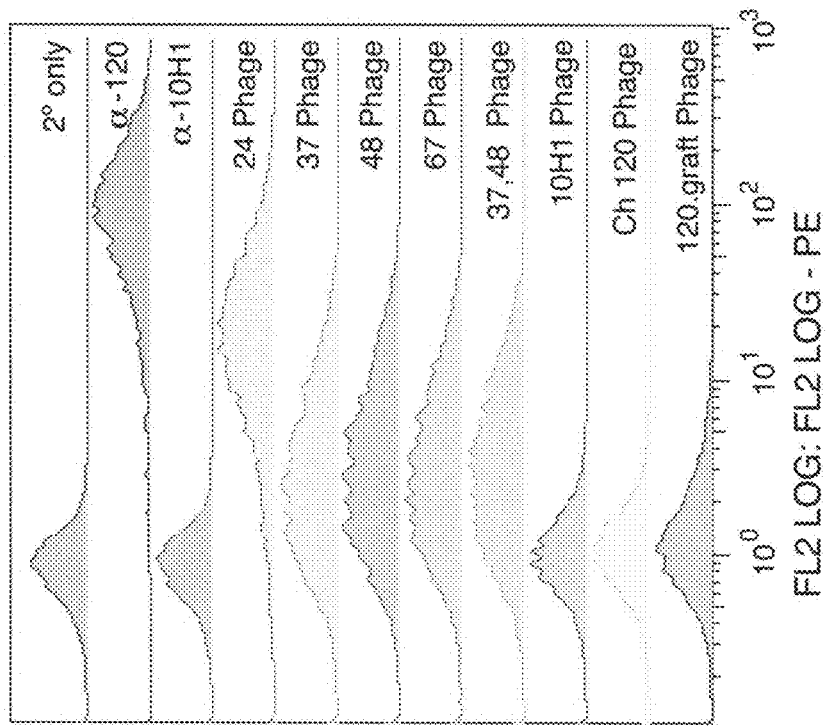
Figure 6A:
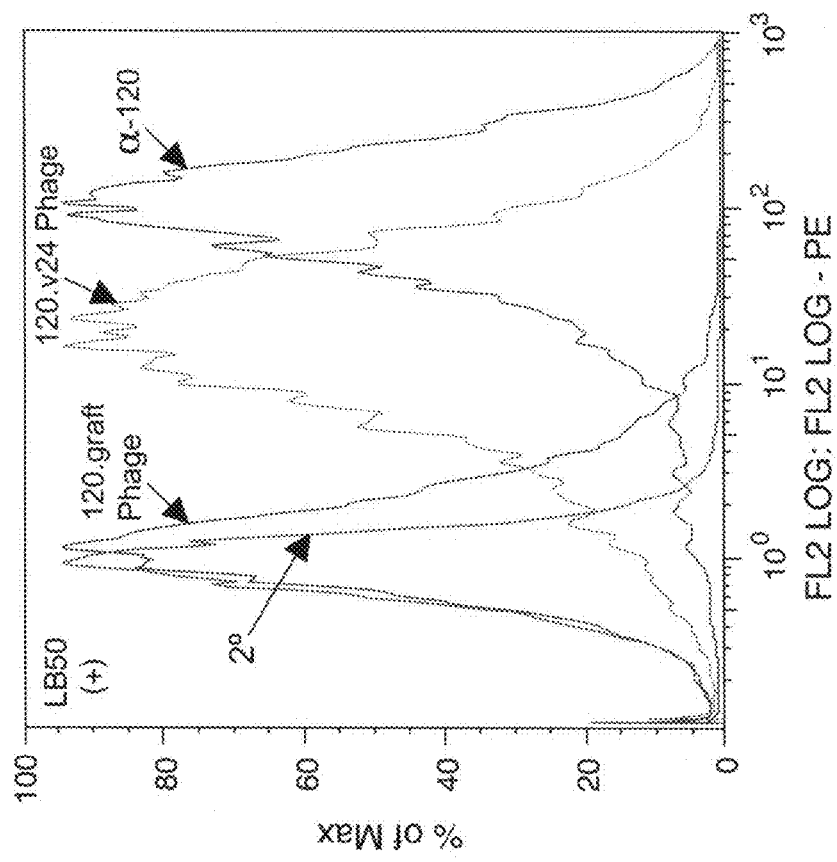
Figure 6B:
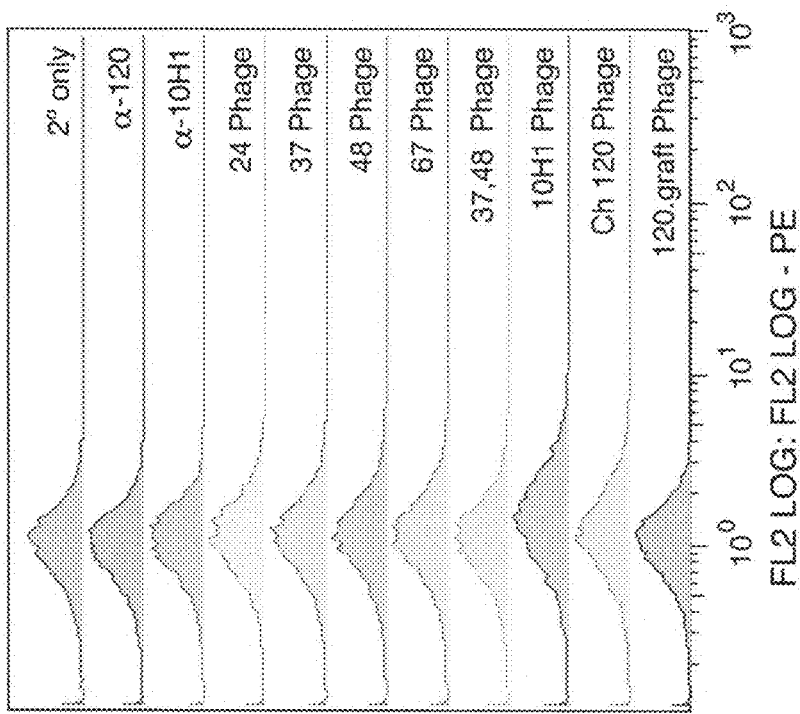
Figure 6D:
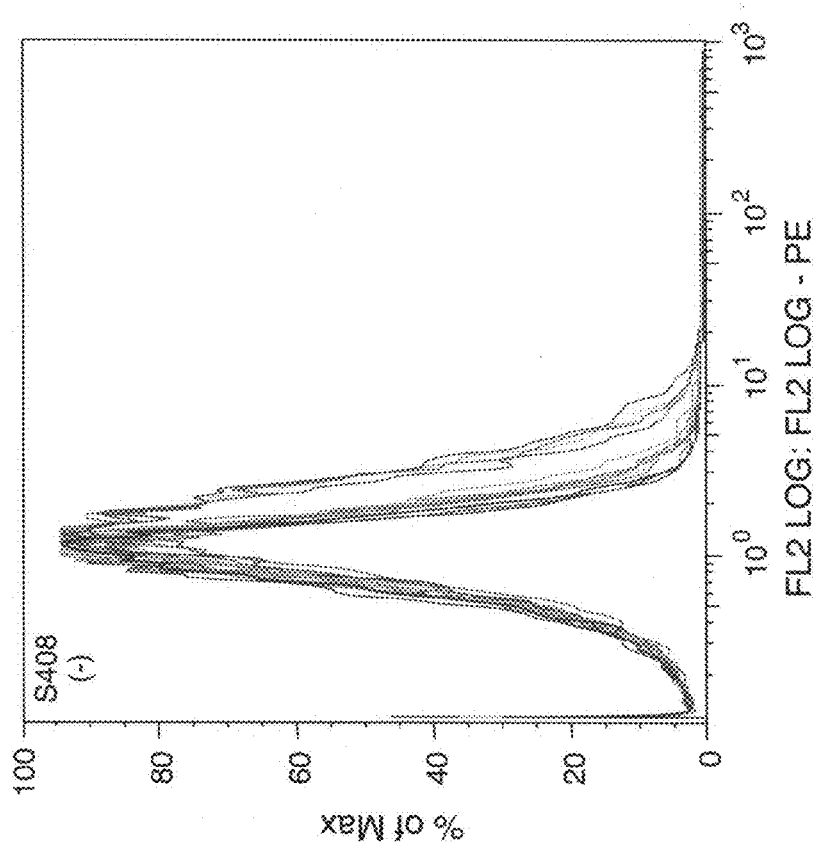

FIGS. 6A-6D depicts a FACS analysis normalized for the level of display of each antibody or variant on phage. FIG. 6A shows FACS shifts on STEAP-1 expressing cells (LB50) for four exemplary antibodies. FIG. 6B shows FACS shifts on STEAP-1 non-expressing cells (S408) for several antibodies as indicated in the figure and in Example 1. FIGS. 6C and 6D are FACS shift alignments after normalization for phage display levels.

Figure 7A:
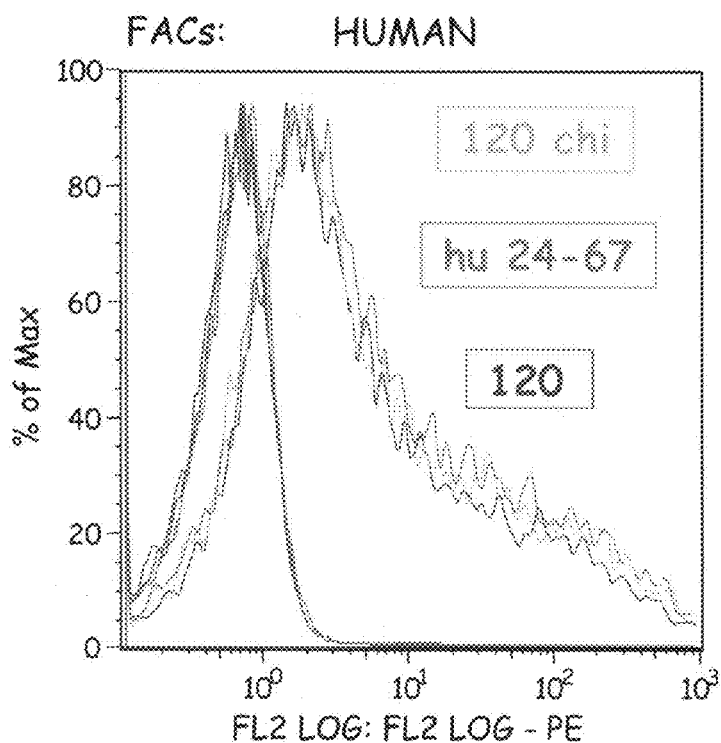
Figure 7B:
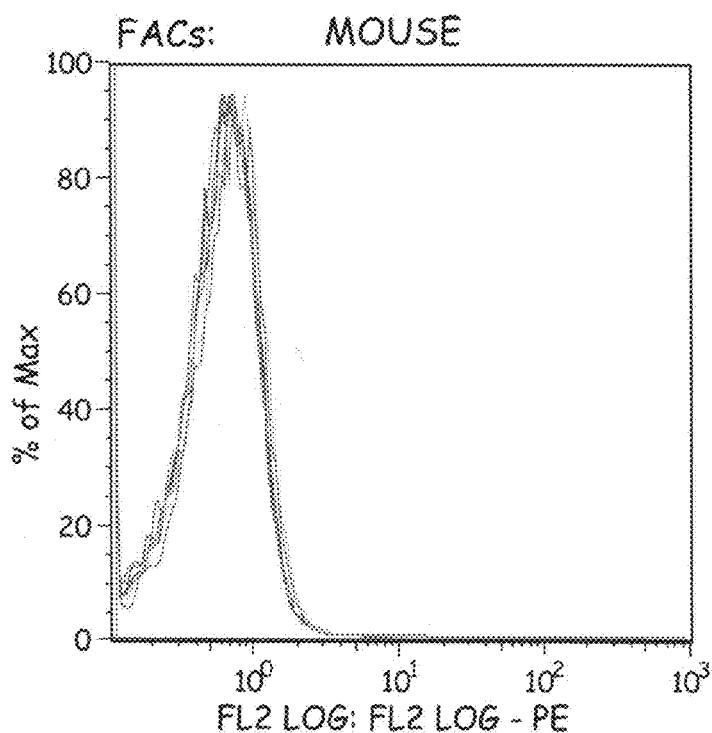
Figure 7C:
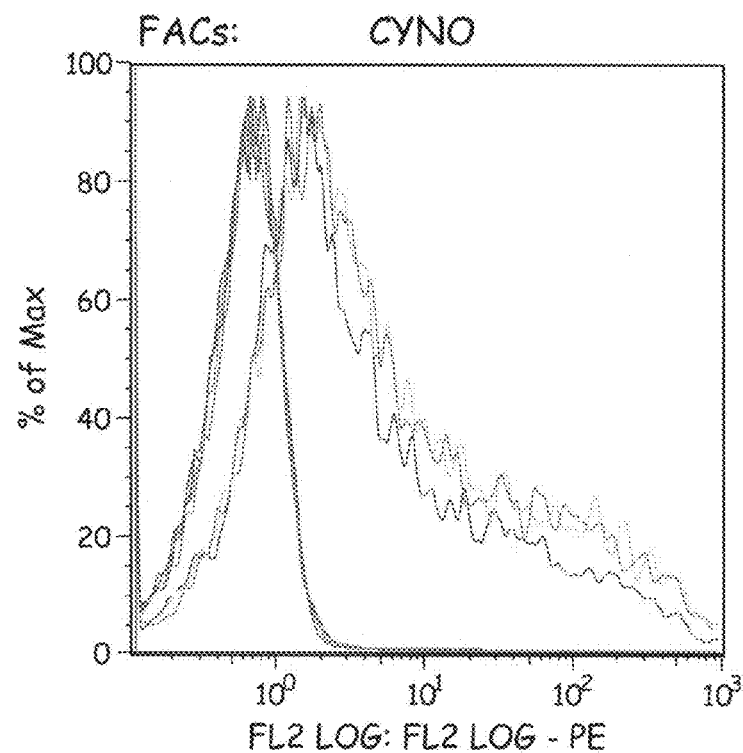
Figure 7D:
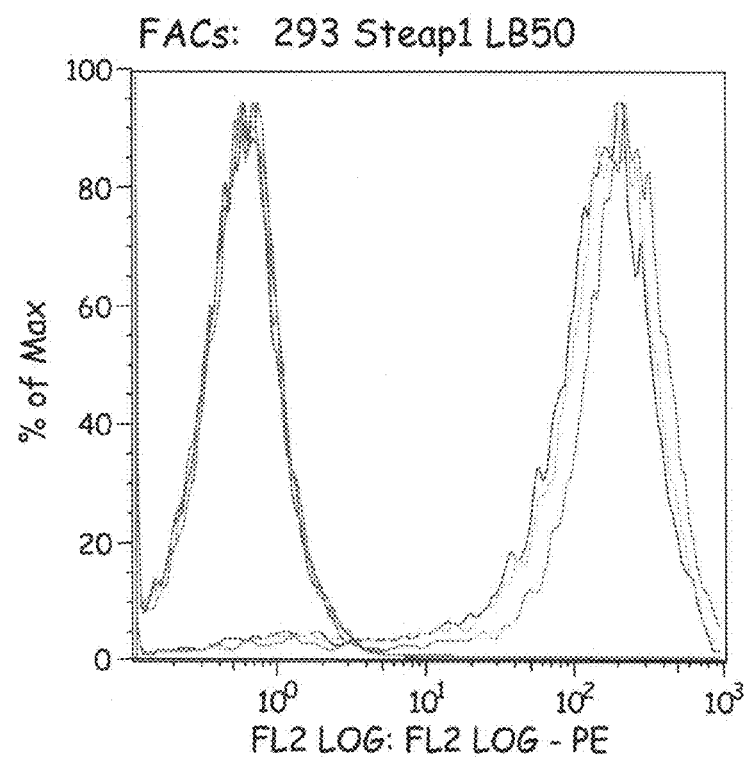
Figure 7E:
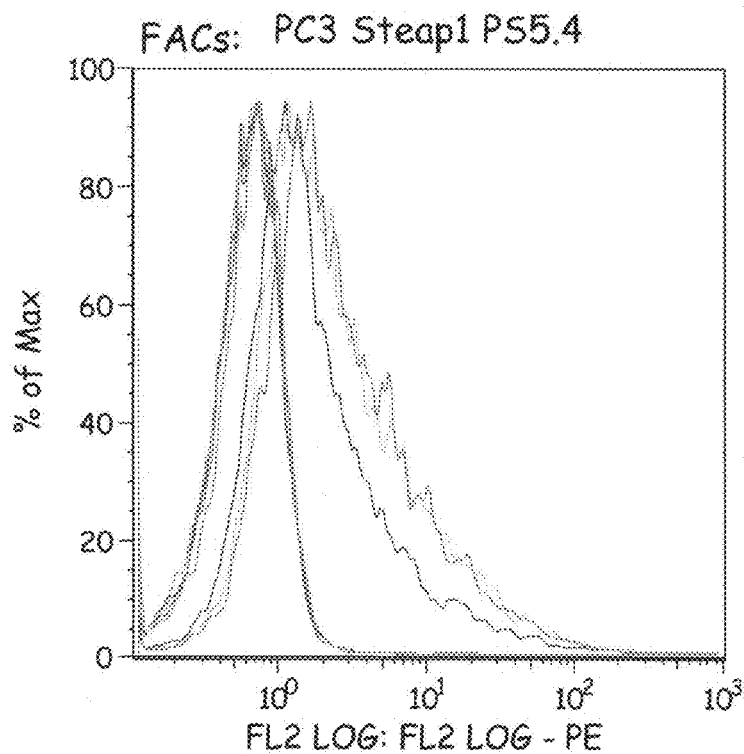
Figure 7F:
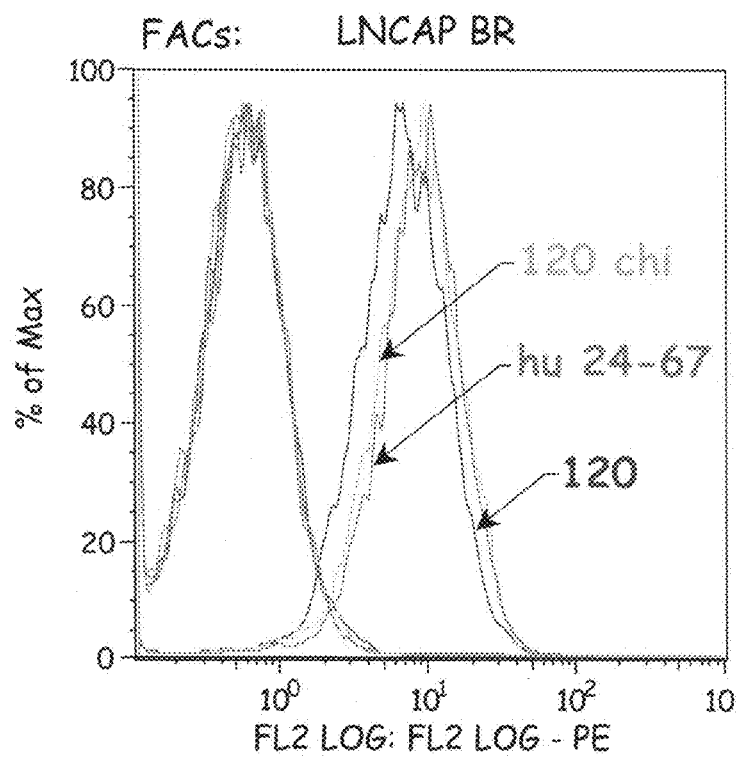

FIGS. 7A-7F graphically depict FACS analyses showing binding of anti-STEAP-1 murine, chimera and humanized version 24 antibodies to human STEAP-1 expressed on the cell surface. FIGS. 7A-7C indicate that anti-STEAP-1 murine 120, chimera 120 and humanized 120v.24 bind human and cynomolgus monkey STEAP-1, but not mouse STEAP-1. FIGS. 7D-7F are FACS plots showing binding of murine 120, 120 chimera, and humanized 120v.24 (clone 67) to human STEAP-1 expressed on the cell surface. Exogenous STEAP-1 was stably expressed in 293 cells (designated LB50 cells) and PC3 cells (designated PS5.4 cells) (FIGS. 7D and 7E), and endogenously expressed in LNCaP BR cells (FIG. 7F).

FIGS. 8A and 8B. FIG. 8A is a graph showing that administration of murine anti-STEAP-1 120-MC-vc-PAB-MMAE at 3 mg/kg was efficacious in a prostate tumor (LNCaP-Ner cells) xenograft model. See Example 4. FIG. 8B is a graph showing that single dose administration of humanized anti-STEAP-1 antibody 120v.24-MC-vc-PAB-MMAE (3 mg/kg), 120v.24-MC-MMAF (6 mg/kg), 120v.24-MC-MMAF (12 mg/kg), and anti-STEAP-1 120 chimera-MC-vc-PAB-MMAE (3 mg/kg) was shown to be efficacious in a LNCAP cell xenograft prostate tumor model. See Example 4.

Figure 9:
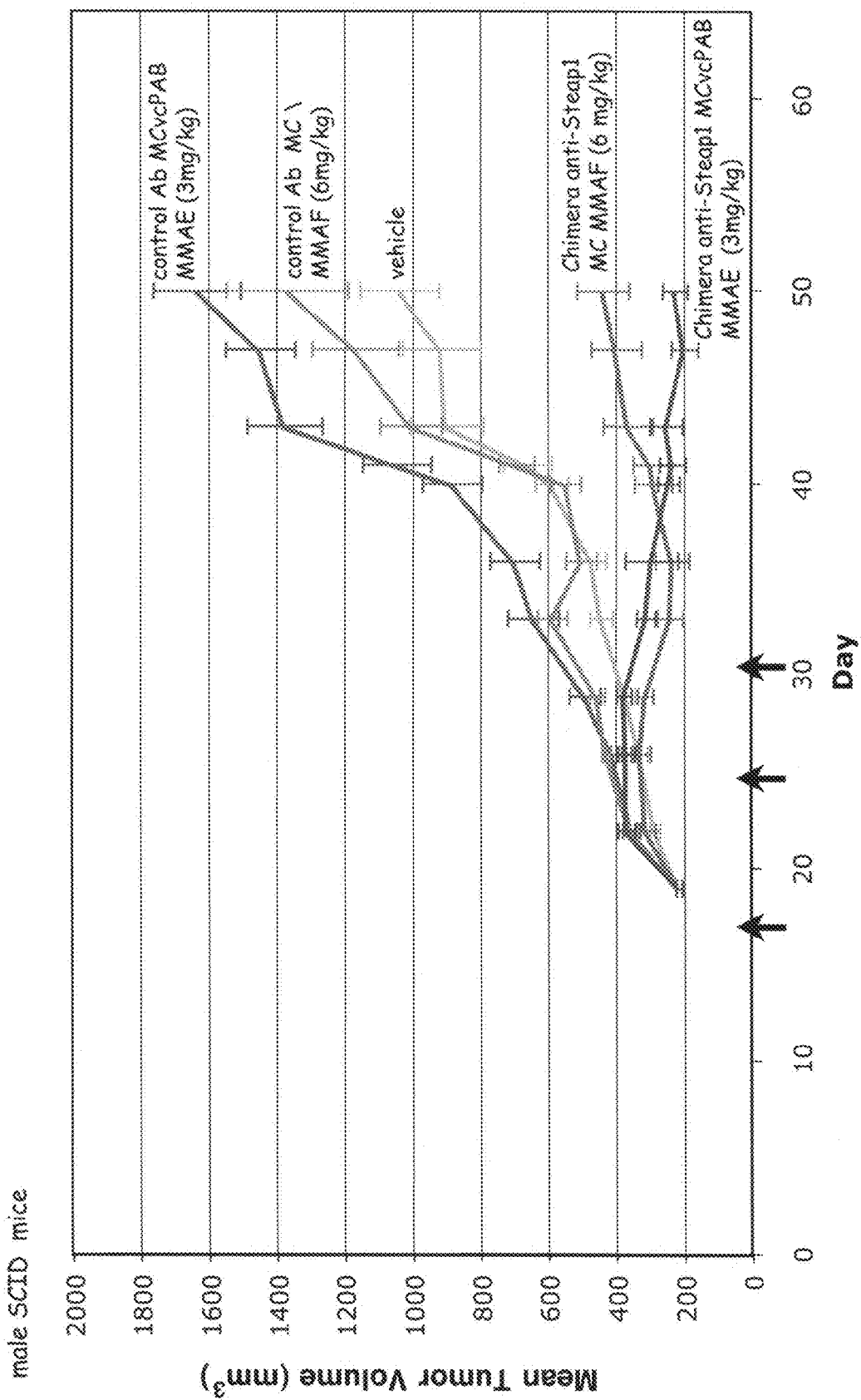

FIG. 9 is a graph showing that administration of anti-STEAP-1 antibody 120 chimera-MC-vc-PAB-MMAE (abbreviated anti-STEAP vcMMAE) at 3 mg/kg, or anti-STEAP-1 120 chimera-MC-MMAF (abbreviated anti-STEAP mcMMAF) at 6 mg/kg, was shown to be efficacious in a prostate cancer xenograft model of castrated SCID-beige mice transplanted with LNCaP cells. See Example 4.

Figure 10:
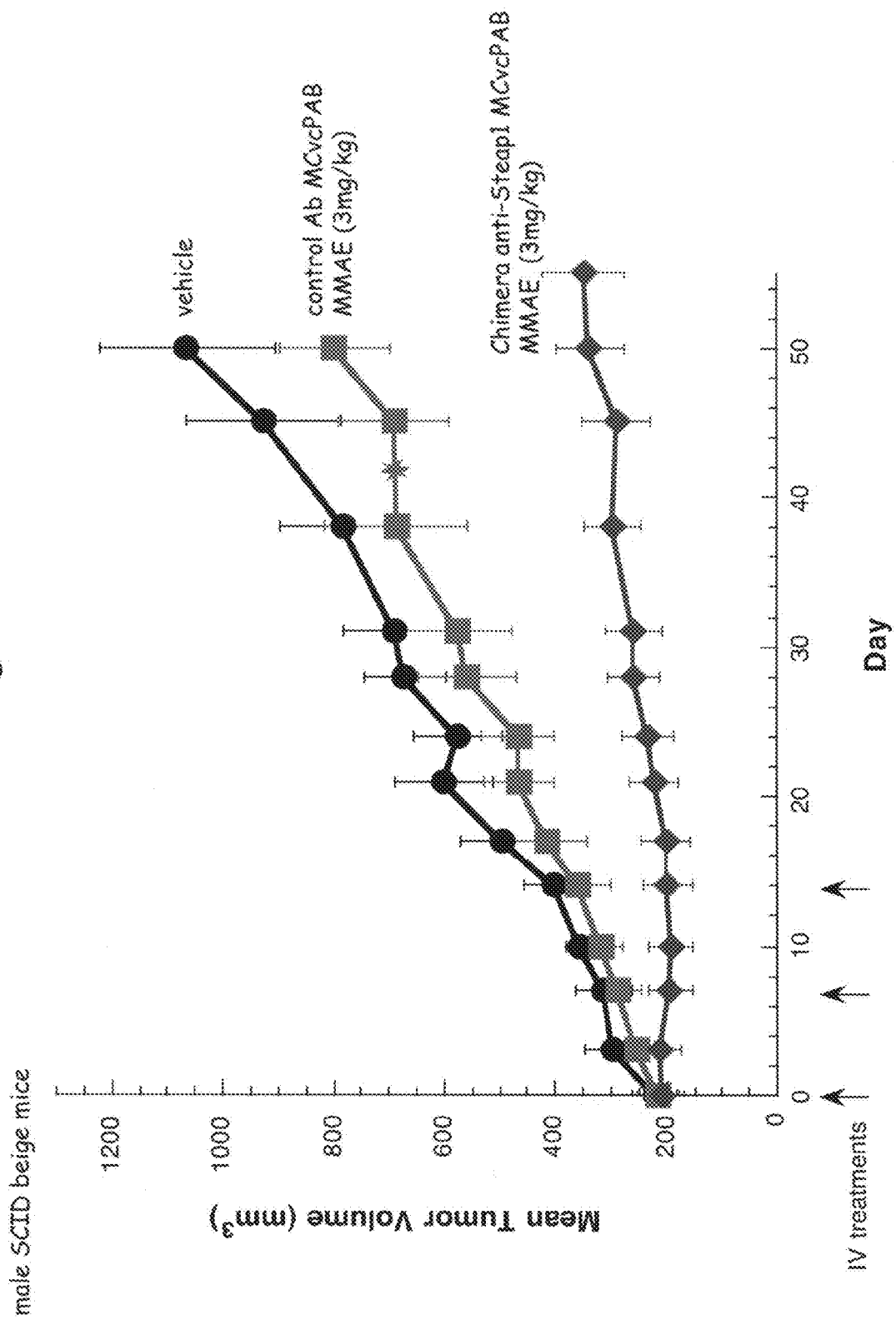

FIG. 10 is a graph showing that administration of anti-STEAP-1 antibody 120 chimera-MC-vc-PAB-MMAE (abbreviated anti-STEAP vcMMAE (at 3 mg/kg) was shown to be efficacious in a prostate cancer xenograft model of SCID beige male mice (androgen dependent) transplanted with LuCap 77 cells. See Example 4.

Figure 11:
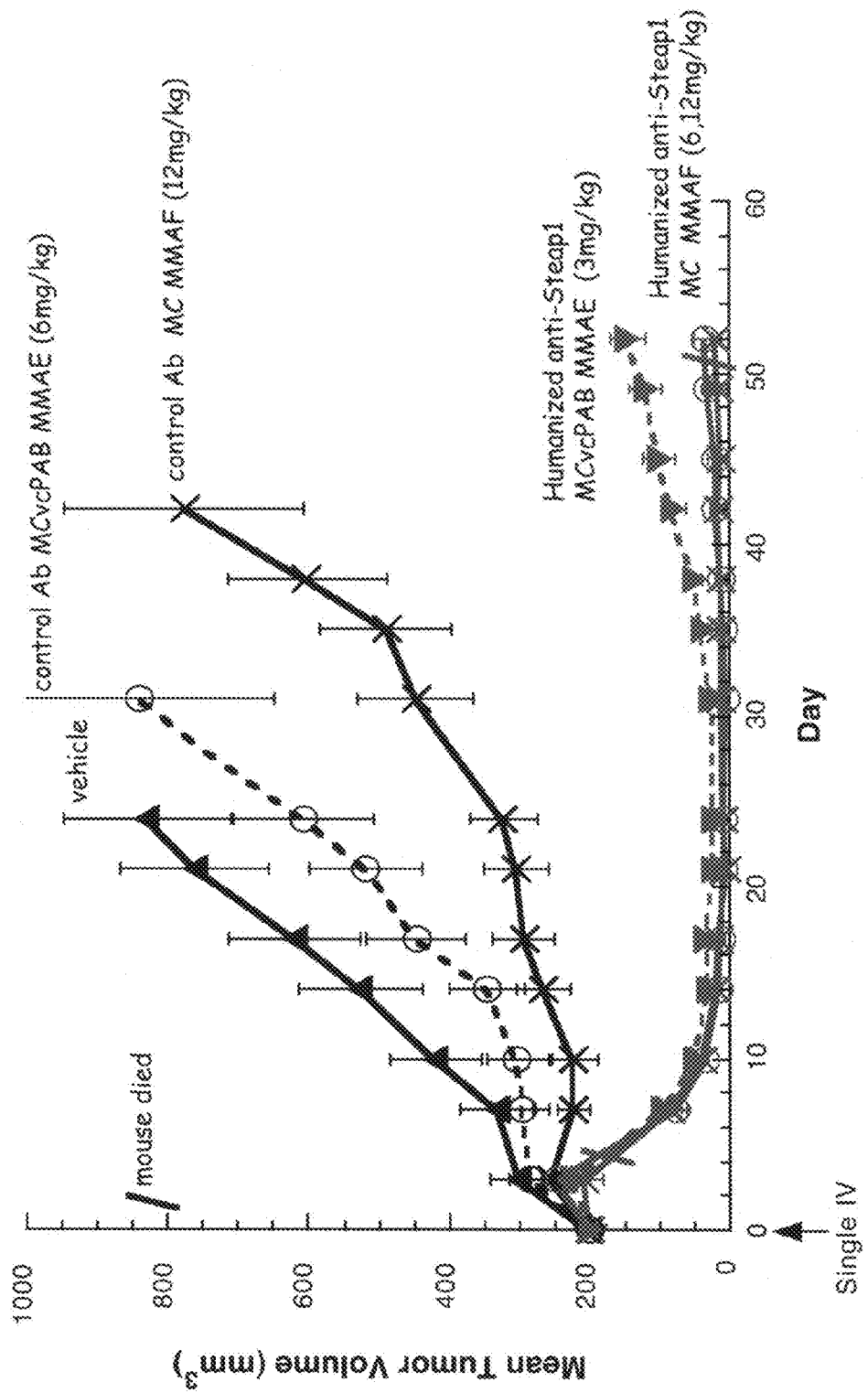

FIG. 11 is a graph showing that administration of humanized anti-STEAP-1 antibody 120v.24-MC-vc-PAB-MMAE at 3 mg/kg, humanized anti-STEAP-1 antibody 120v.24-MC-MMAF at 6 mg/kg and 12 mg/kg to castrated SCID-beige mice transplanted with LuCap35V prostate tumor was shown to be efficacious relative to controls. See Example 4.

Figure 12:
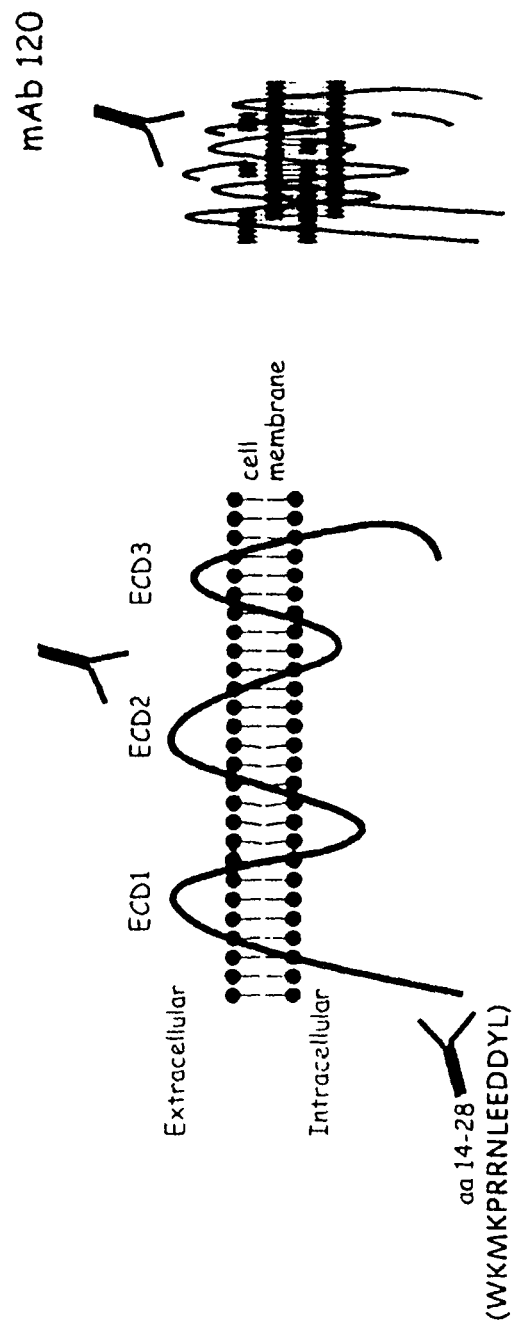
Figure 14A:
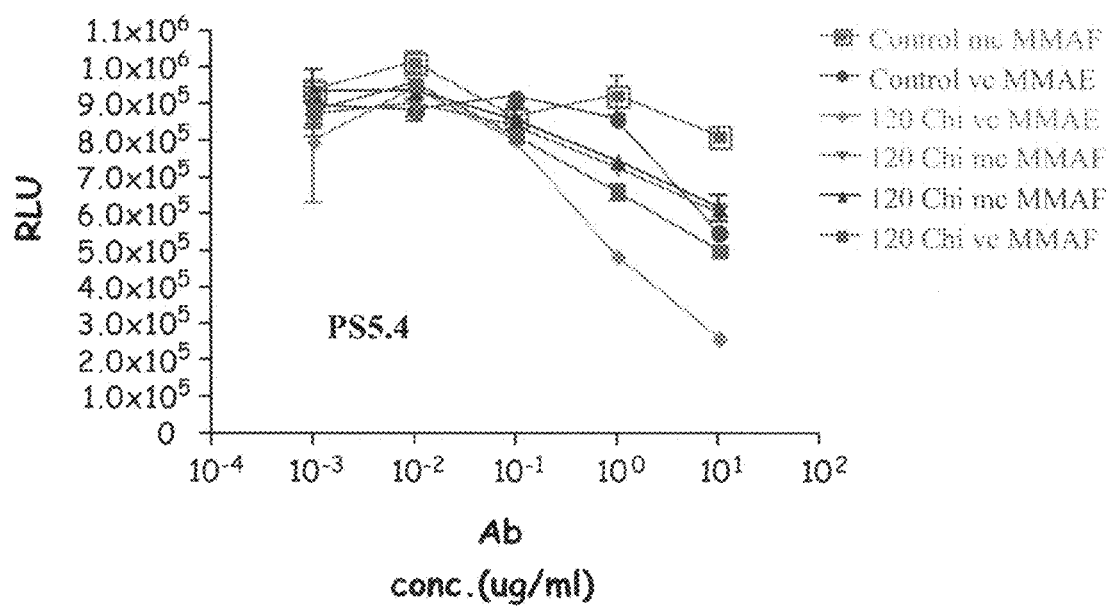
Figure 14B:
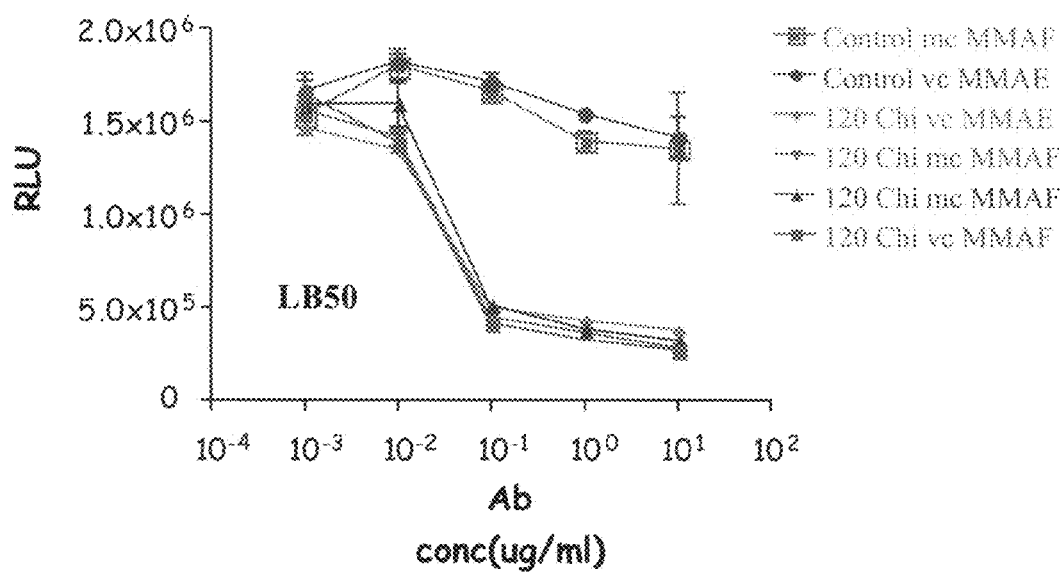
Figure 14C:
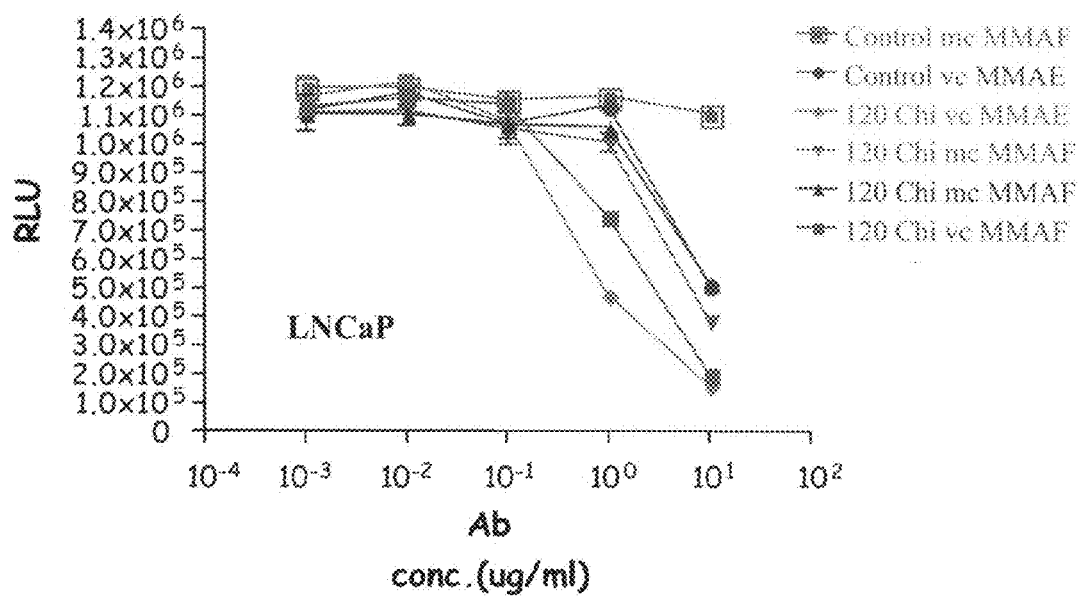
Figure 14D:
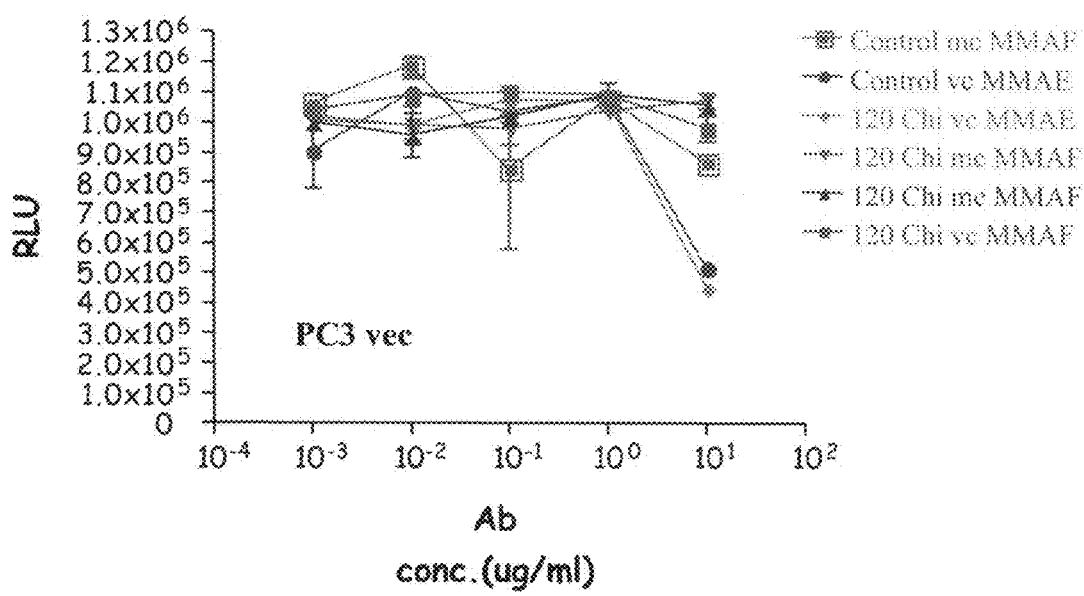
Figure 14E:
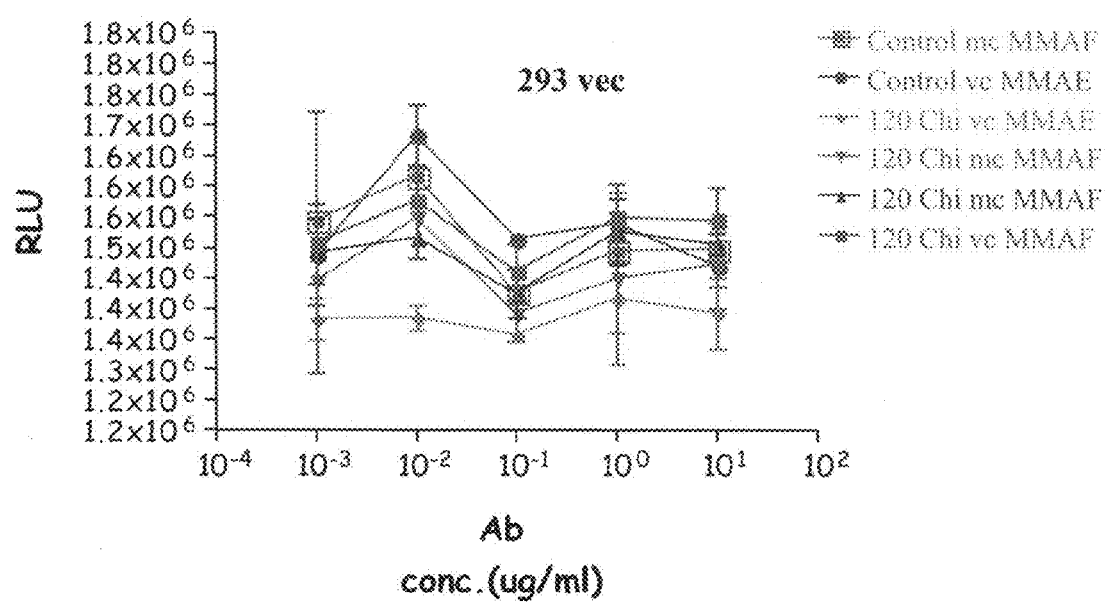

FIG. 12 is a diagram depicting STEAP-1 embedded in a cell membrane. Anti-STEAP-1 antibody 120 binding is conformation dependent and does not recognize a linear epitope of STEAP-1.

FIGS. 13A-13D show STEAP-1 expressed on the surface of cells as detected by immunohistochemistry. FIG. 13A shows an immunohistochemical stain of 293 cells expressing exogenous STEAP-1 on the cell surface. FIG. 13B shows an immunohistochemical stain of PC3 cells expressing exogenous STEAP-1 on the cell surface. FIG. 13C shows an immunohistochemical stain of LNCaP cells expressing endogenous STEAP-1 on the cell surface. FIG. 13D shows an immunohistochemica stain of LuCAP 77 cells expressing endogenous STEAP-1 on the cell surface.

FIGS. 14A-14E are graphs showing the relative effectiveness of anti-STEAP-1 antibody 120v.24-MCMMAF and anti-STEAP-1 antibody 120v.24-MC-vc-PAB-MMAE to kill STEAP-1 expressing cells in vitro. PS5.4 cells (FIG. 14A) are PC3 cells transformed with a vector encoding STEAP-1 such that STEAP-1 is expressed on the cell surface. LB50 cells (FIG. 14B) are 293 cells transformed with a vector encoding STEAP-1 such that STEAP-1 is expressed on the cell surface. LNCaP cells (FIG. 14C) express STEAP-1 endogenously. "PC3 vec" (FIG. 14D) and "293 vec" (FIG. 14E) refer to 293 cells and PC3 cells, respectively, transformed with a vector control.

Figure 15:
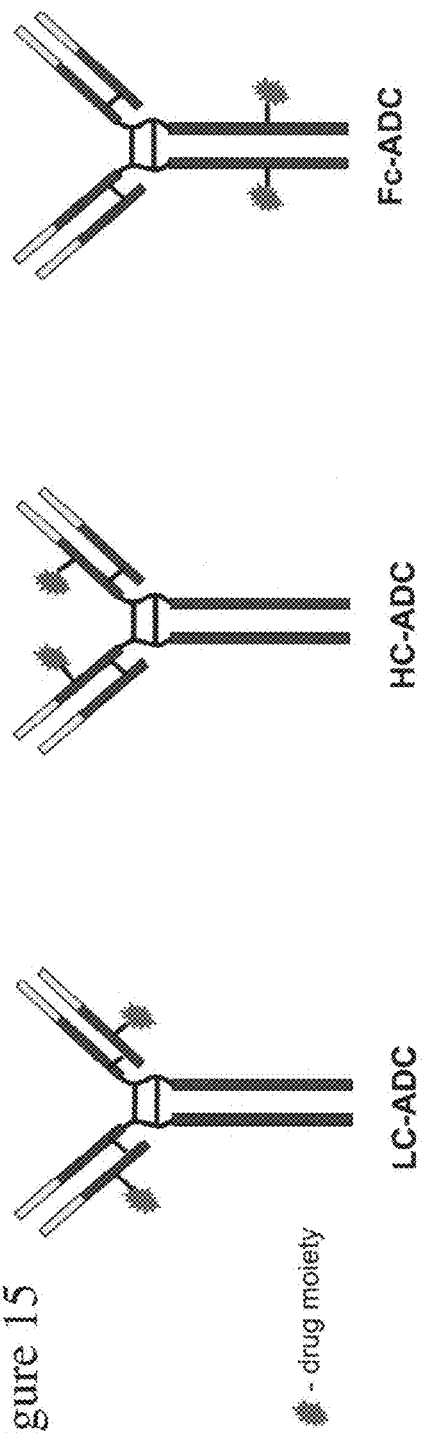

FIG. 15 shows depictions of cysteine engineered anti-STEAP-1 antibody drug conjugates (ADC) where a drug moiety is attached to an engineered cysteine group in: the light chain (LC-ADC); the heavy chain (HC-ADC); and the Fc region (Fc-ADC).

Figure 16:
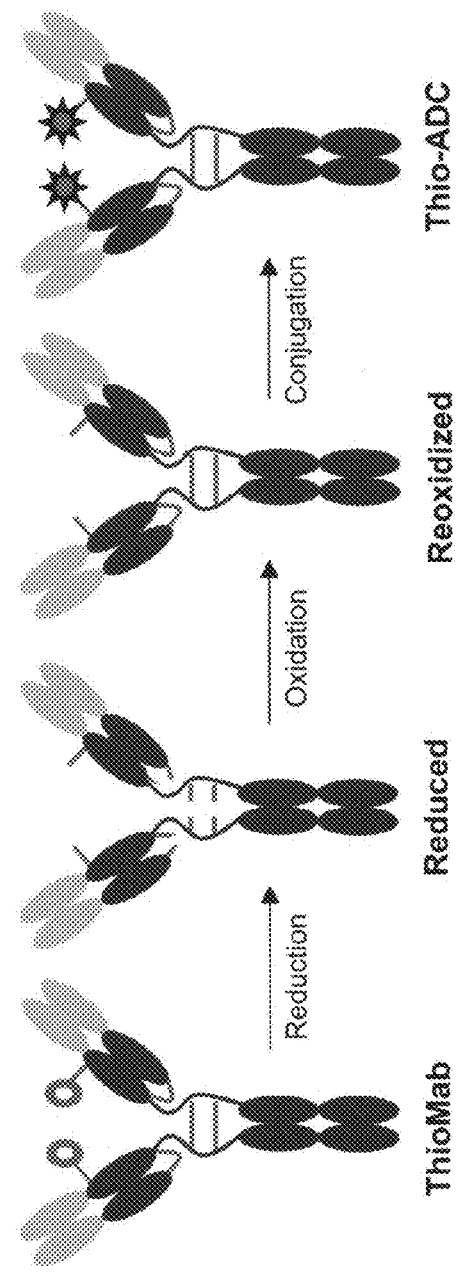

FIG. 16 shows the steps of: (i) reducing cysteine disulfide adducts and interchain and intrachain disulfides in a cysteine engineered anti-STEAP-1 antibody (ThioMab) with reducing agent TCEP (tris(2-carboxyethyl)phosphine hydrochloride); (ii) partially oxidizing, i.e. reoxidation to reform interchain and intrachain disulfides, with dhAA (dehydroascorbic acid); and (iii) conjugation of the reoxidized antibody with a drug-linker intermediate to form a cysteine engineered anti-STEAP-1 antibody drug conjugate (ADC).

FIGS. 17A-C show the sites of amino acid substitutions made to generate cysteine-engineered anti-STEAP-1 antibodies (thio-mAbs). FIG. 17A shows the thio-LC variant V205C with corresponding sequential numbering and standardized numbering according to the Kabat system. FIG. 17B shows the thio-HC variant A118C with corresponding sequential numbering and standardized numbering according to the EU system. FIG. 17C shows the thio-Fc variant S400C with corresponding sequential numbering and standardized numbering according to the EU system.

Figure 18A:
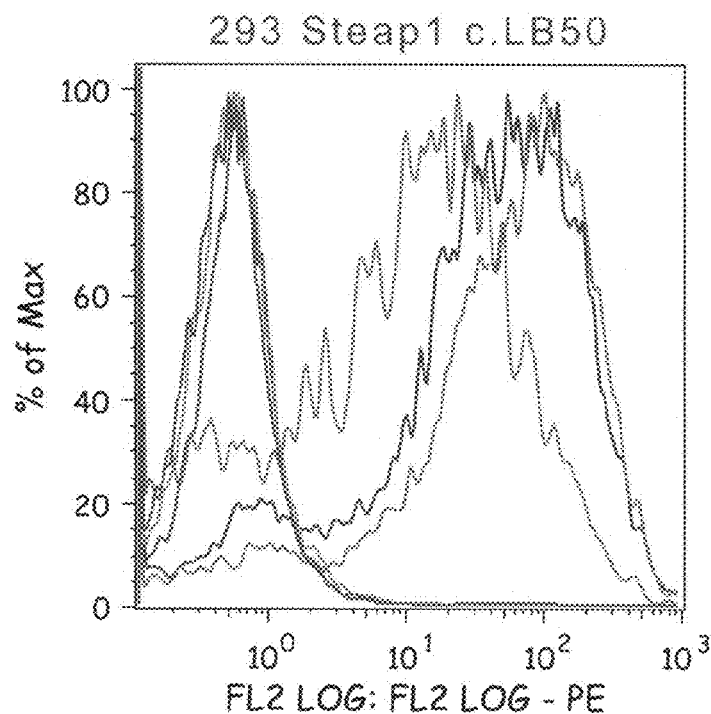
Figure 18D:
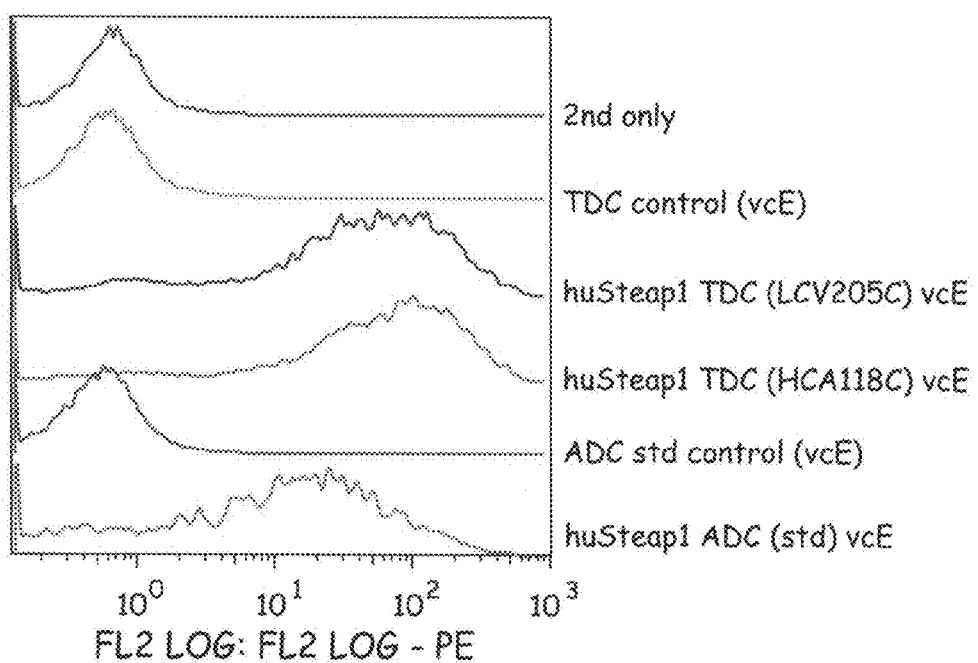
Figure 18B:
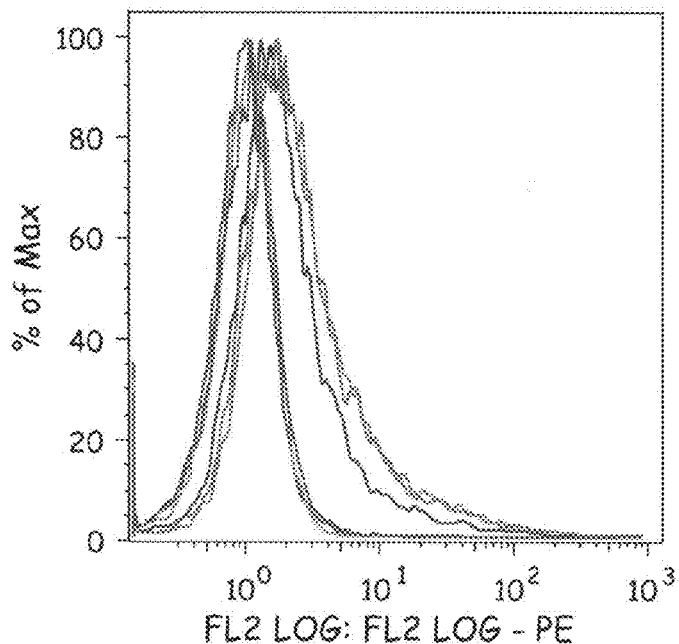
Figure 18E:
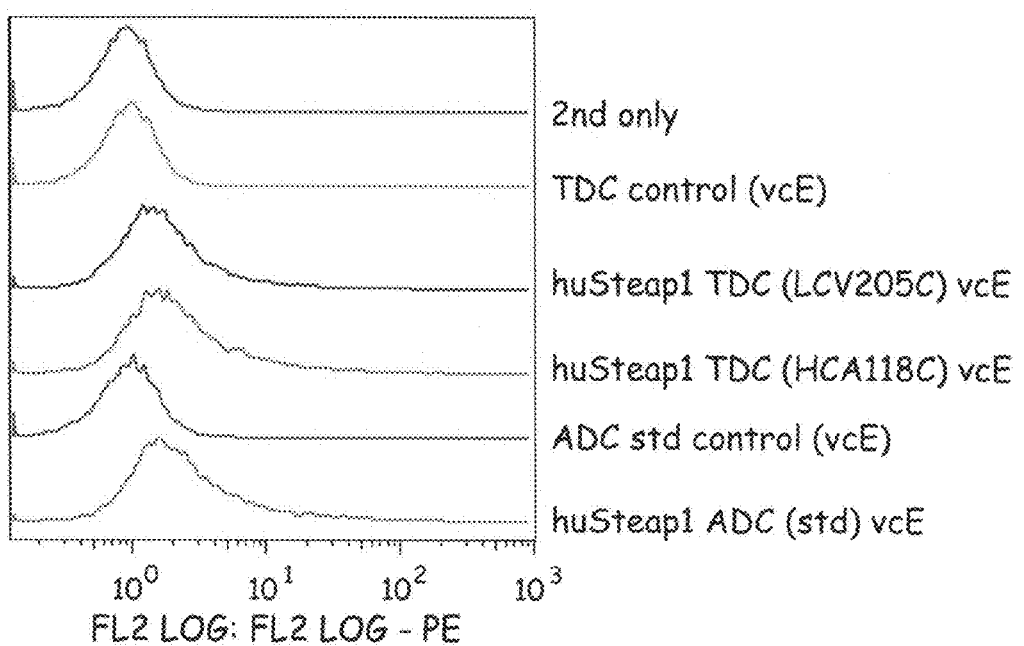
Figure 18C:
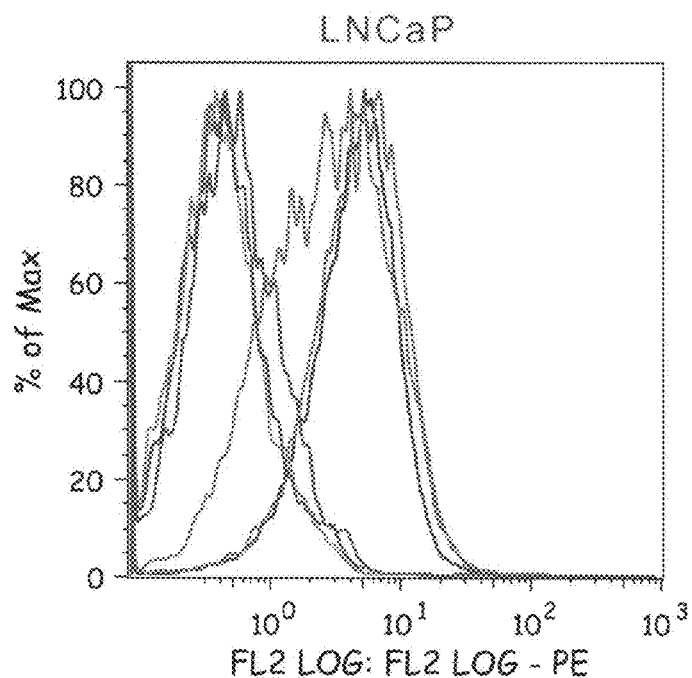
Figure 18F:
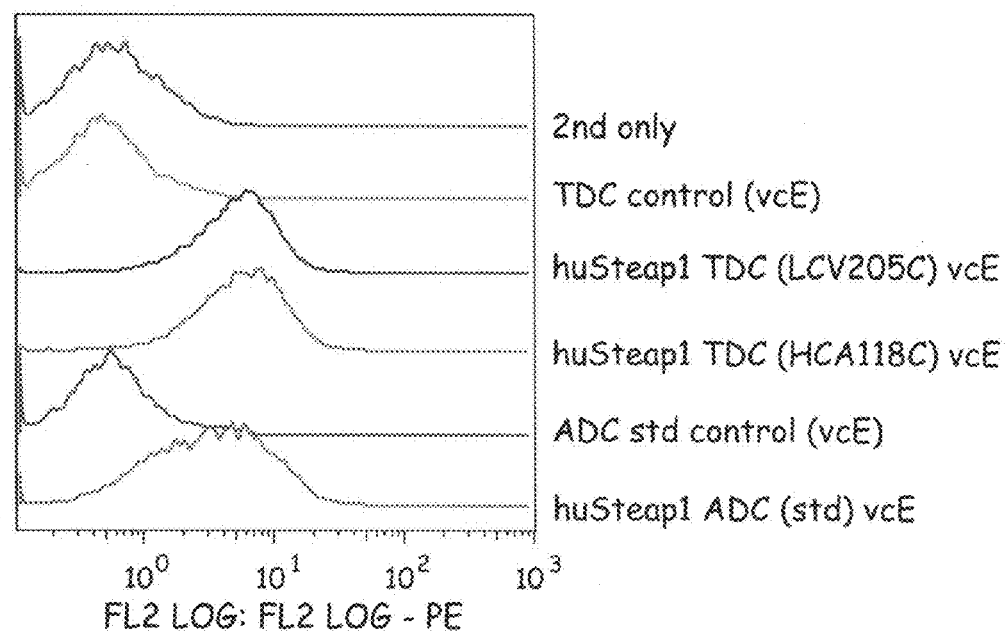

FIGS. 18A-F depict FACS analyses showing that the anti-STEAP-1 thio antibody drug conjugates (TDCs) retain the ability to bind to STEAP-1 expressed on the cell surface. FIGS. 18A-18C are FACS plots showing binding of the anti-STEAP-1 TDCs thio-human120-vc-PAB-MMAE (LCV205C) (abbreviated as huSteap1 TDC (L205C) vcE and thio-human120-vc-PAB-MMAE (HCA118C) (abbreviated as huSteap1 TDC (HCA 118C) vcE) to human STEAP-1 expressed on the cell surface. Exogenous STEAP-1 was stably expressed in 293 cells (designated LB50 cells) and PC3 cells (designated PS5.4 cells) (FIGS. 18A and 18B), and endogenously expressed in LNCaP BR cells (FIG. 18C). FIGS. 18D, 18E and 18F are alignments of the FACS shifts shown in FIGS. 7A, 7B and 7C, respectively.

Figure 19A:
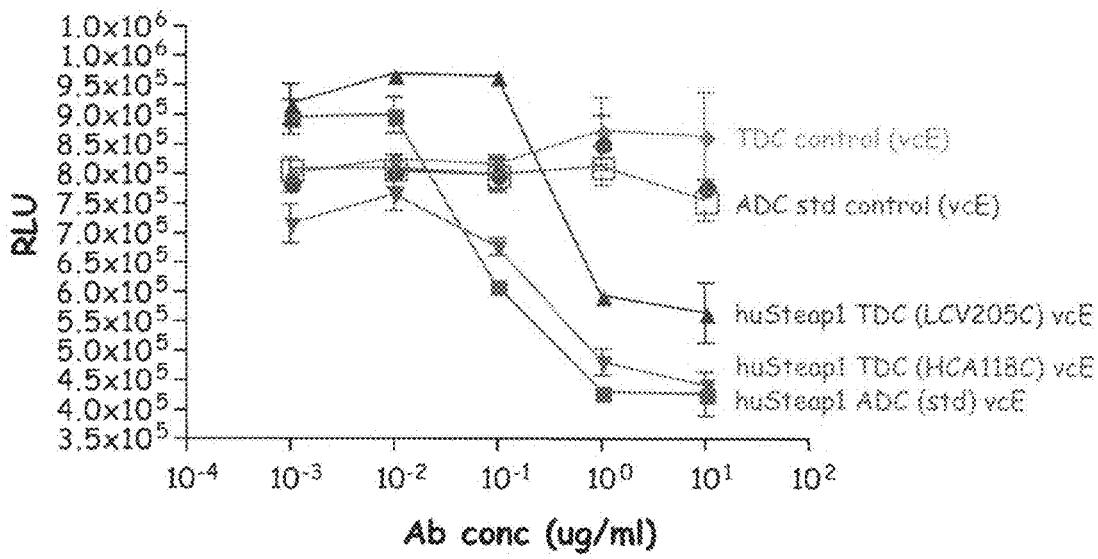
Figure 19B:
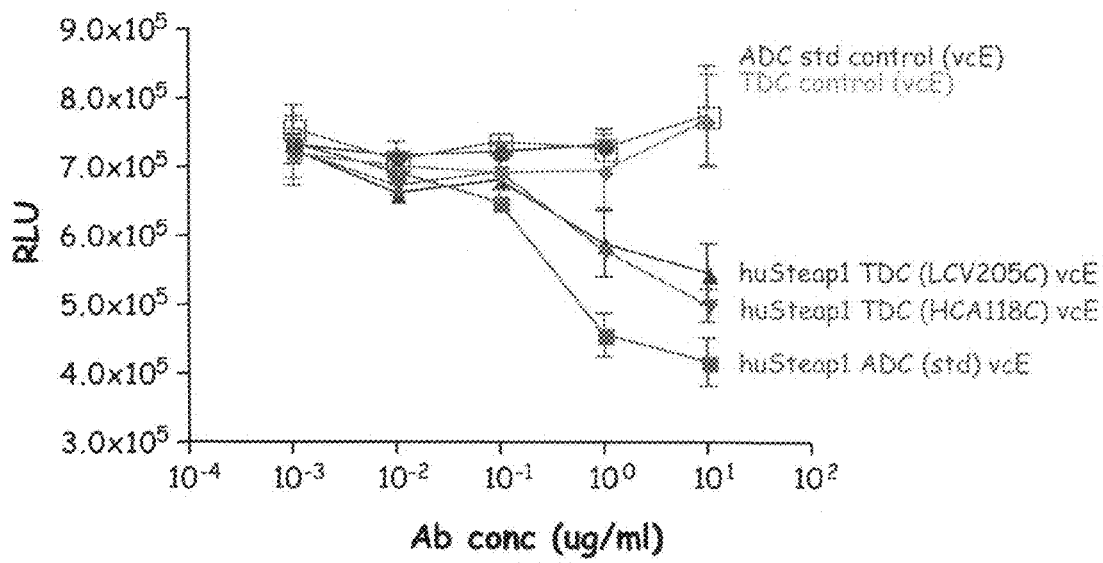
Figure 19C:
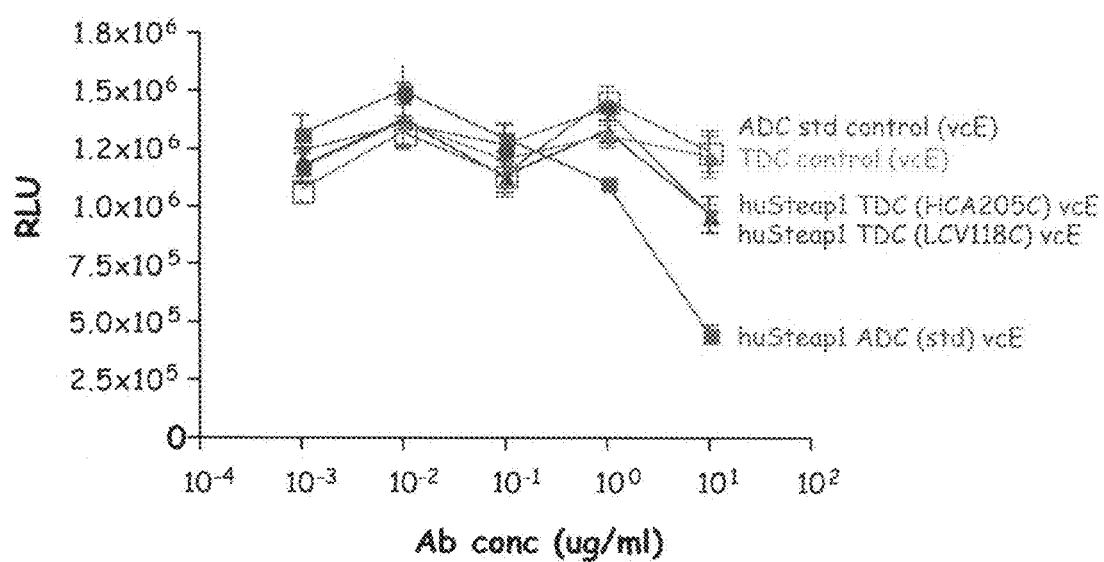

FIGS. 19A-C show the relative effectiveness of the anti-STEAP-1 thio antibody drug conjugates (TDCs) thio-human120-vc-PAB-MMAE (LCV205C) (abbreviated as huSteap1 TDC (L205C) vcE) and thio-human120-vc-PAB-MMAE (HCA118C) (abbreviated as huSteap1 TDC (HCA118C) vcE) to kill STEAP-1 expressing cells in vitro. LB50 cells (FIG. 19A) are 293 cells transformed with a vector encoding STEAP-1 such that STEAP-1 is expressed on the cell surface. PS5.4 cells (FIG. 19B) are PC3 cells transformed with a vector encoding STEAP-1 such that STEAP-1 is expressed on the cell surface. LNCaP cells (FIG. 19C) express STEAP-1 endogenously.

Figure 20:
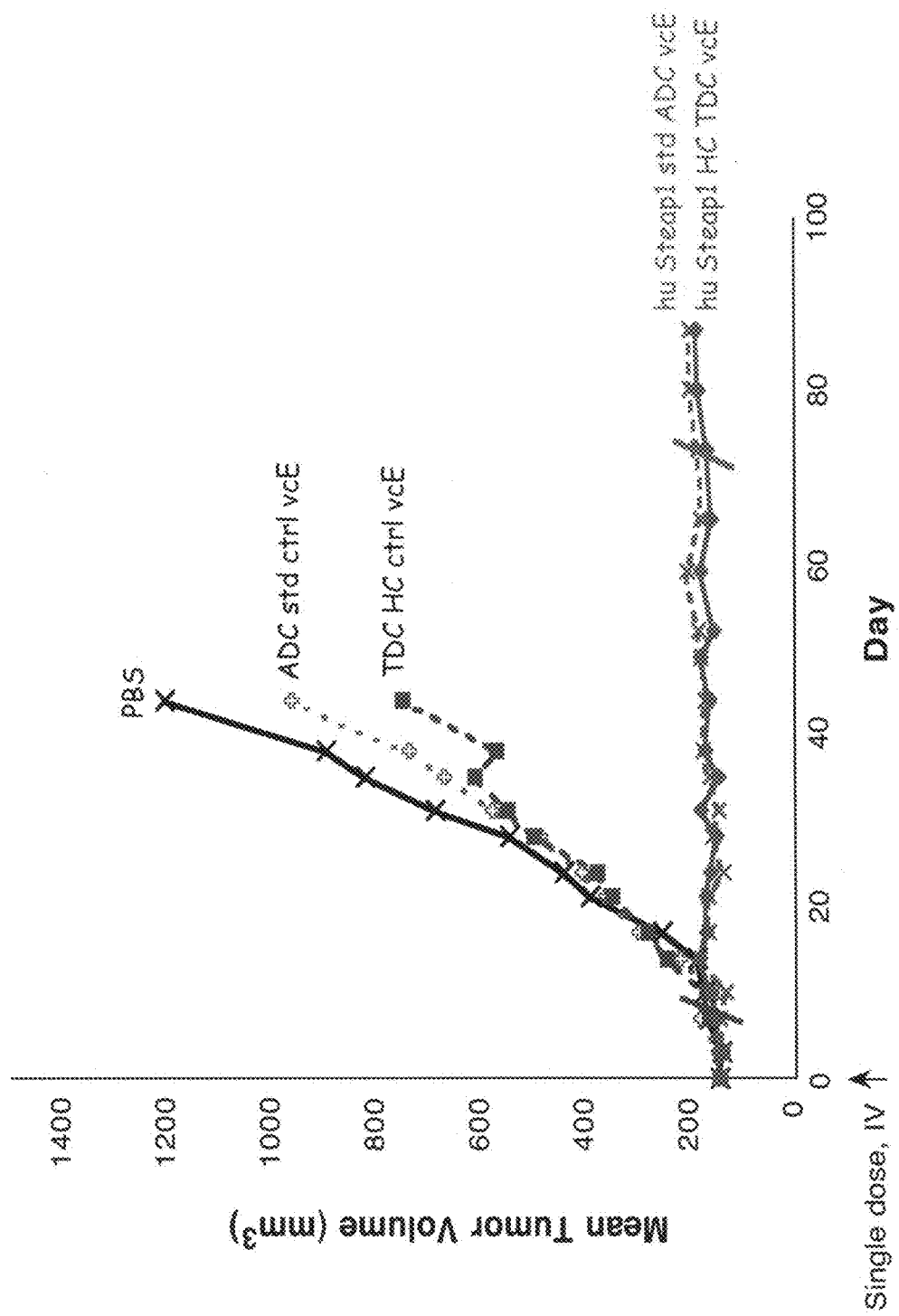

FIG. 20 is a graph showing that administration of anti-STEAP-1 TDC thio-human120-vc-PAB-MMAE (HCA118C) (abbreviated as hu Steap1 HC TDC vcE) at 3 mg/kg was shown to be efficacious relative to controls in a prostate cancer xenograft model of male SCID-beige mice (androgen-dependent) transplanted with LNCaP cells. See Example 8.

Figure 21:
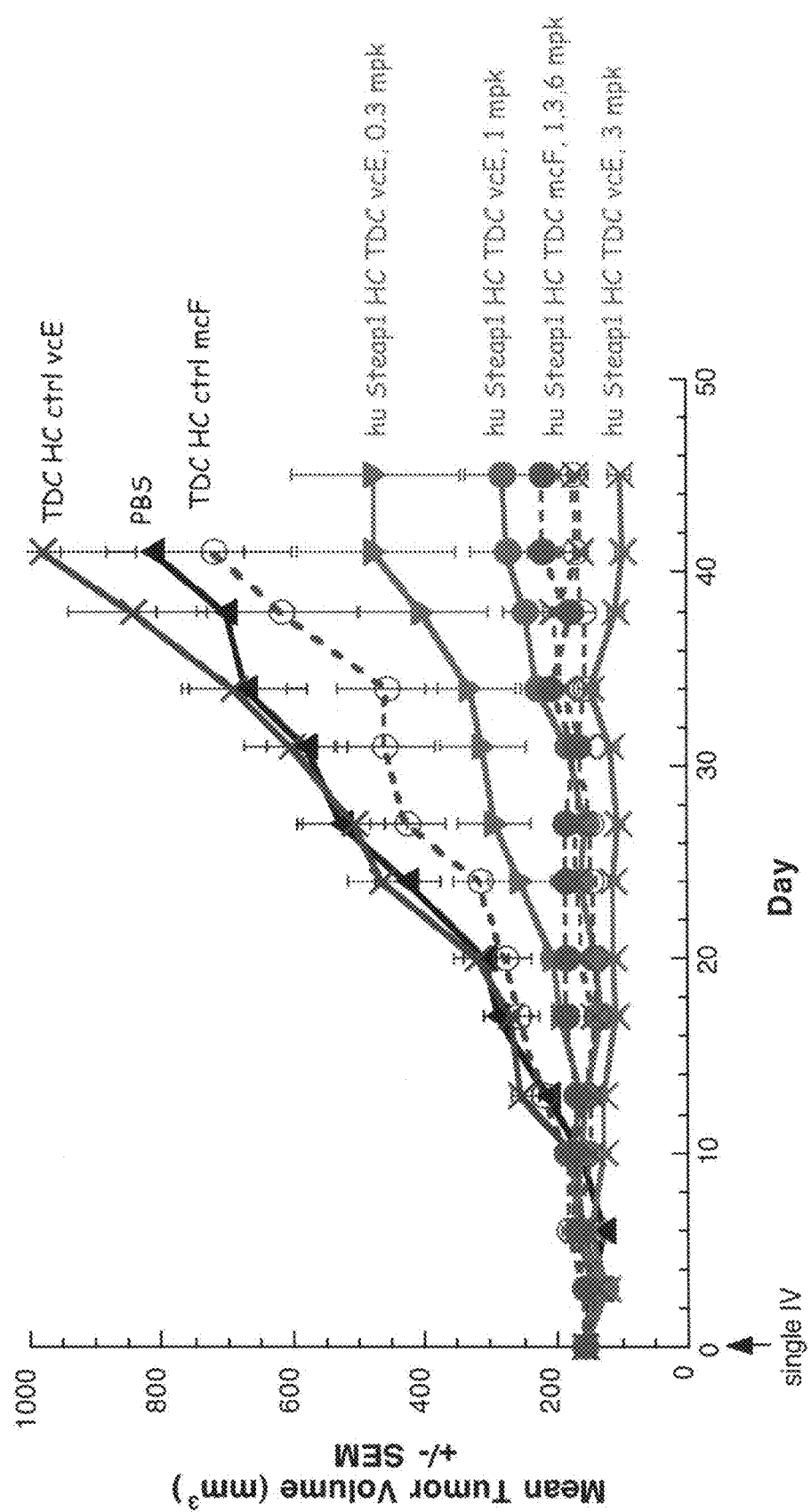

FIG. 21 is a graph showing that administration of anti-STEAP-1 TDC thio-human120-vc-PAB-MMAE (HCA118C) (abbreviated as hu Steap1 HC TDC vcE) at 3 mg/kg, or thio-human120-MC-MMAF (HCA118C) (abbreviated as hu Steap1 HC TDC mcF) at 1, 3 or 6 mg/kg, was shown to be efficacious relative to controls in a prostate cancer xenograft model of male SCID-beige mice (androgen-dependent) transplanted with LNCaP cells. See Example 8.

Figure 22:
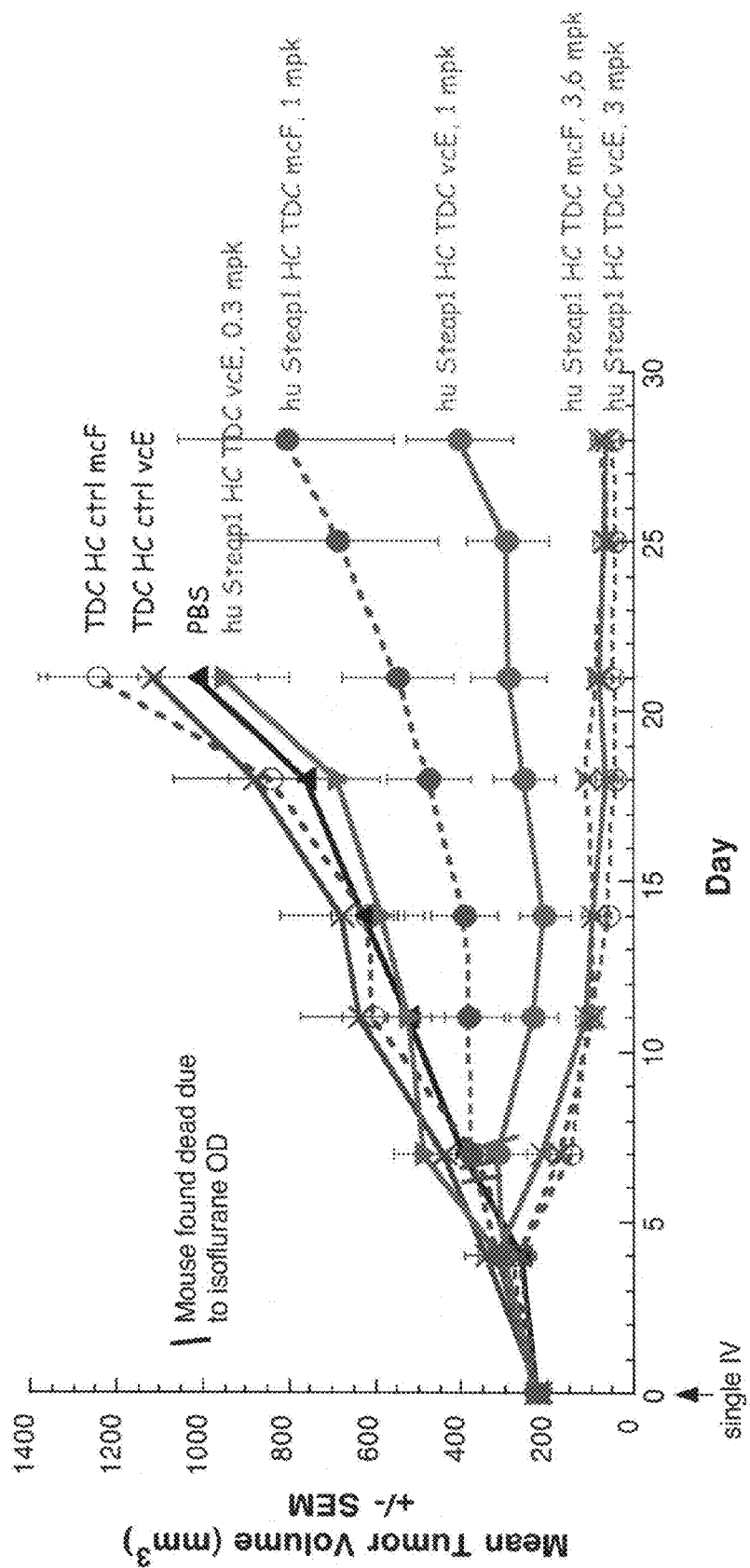

FIG. 22 is a graph showing that administration of anti-STEAP-1 TDC thio-human120-vc-PAB-MMAE (HCA118C) (abbreviated as hu Steap1 HC TDC vcE) at 3 mg/kg, or thio-human120-MC-MMAF (HCA125C) (abbreviated as hu Steap1 HC TDC mcF) at 3 or 6 mg/kg, was shown to be efficacious relative to controls in a prostate cancer xenograft model of castrated SCID-beige mice transplanted with LuCaP 35V prostate tumor. See Example 8.

Figure 23:
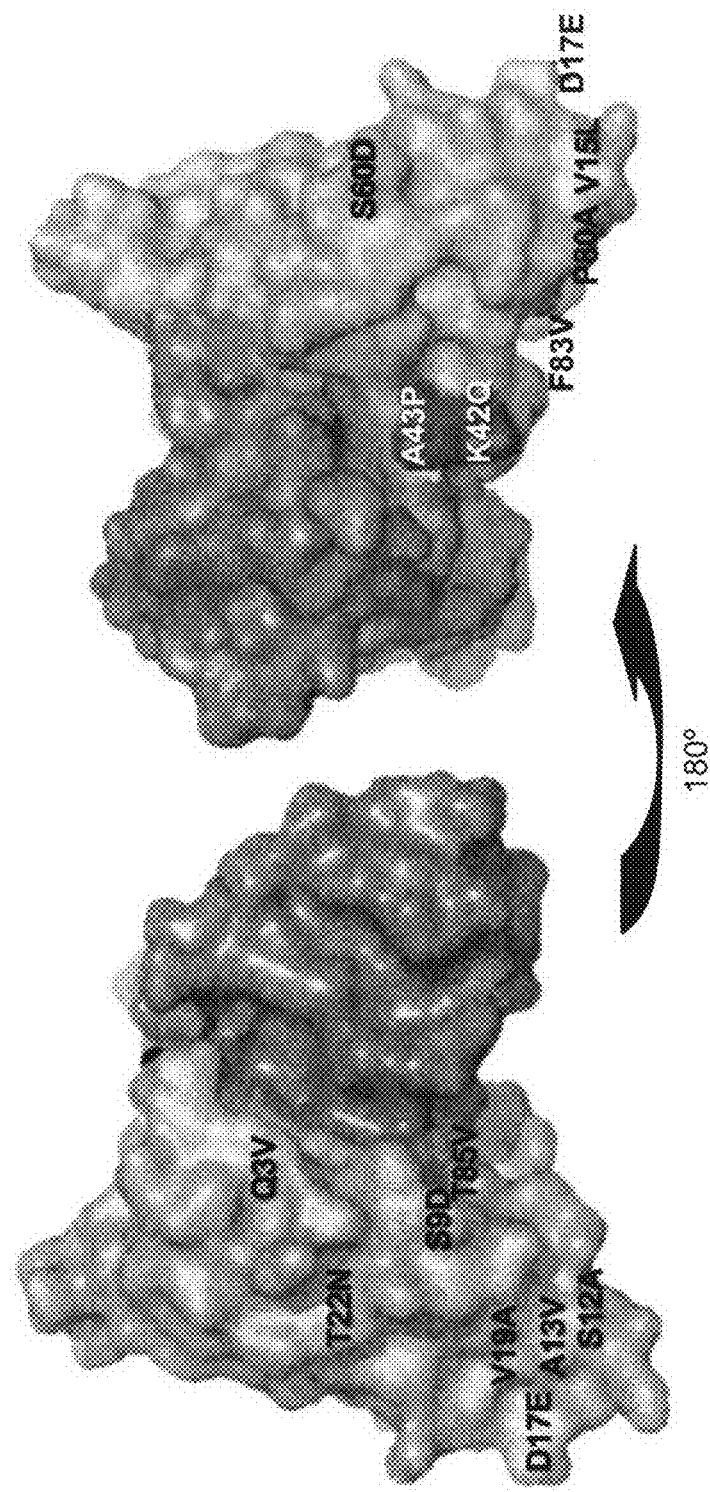

FIG. 23 shows the sites of amino acid substitutions made to generate the cysteine-engineered anti-STEAP-1 antibody (thio-mAb) designated "Simmons IV" or simply "SGIV." The amino acid sequence of the light chain of SGIV (SEQ ID NO:90) is shown in alignment with the light chain of mu 120 antibody (SEQ ID NO:89) and 120.v24 antibody (SEQ ID NO:91). The thio-LC variant SGIV with corresponding sequential numbering and standardized numbering according to the Kabat system is shown aligned with the parent antibody mu 120 as well as the thio-LC variant 120.v24 with corresponding sequential numbering and standardized numbering according to the Kabat system. The CDRs are boxed (CDR-L1, CDR-L2, and CDR-L3). The sequences bracketing the CDRs are the framework sequences (FR-L1 to FR-L4). The sequences are numbered according to Kabat numbering. The Kabat, Chothia, and contact CDRs are indicated about the boxed CDRs. See Example 9.

Figure 24:
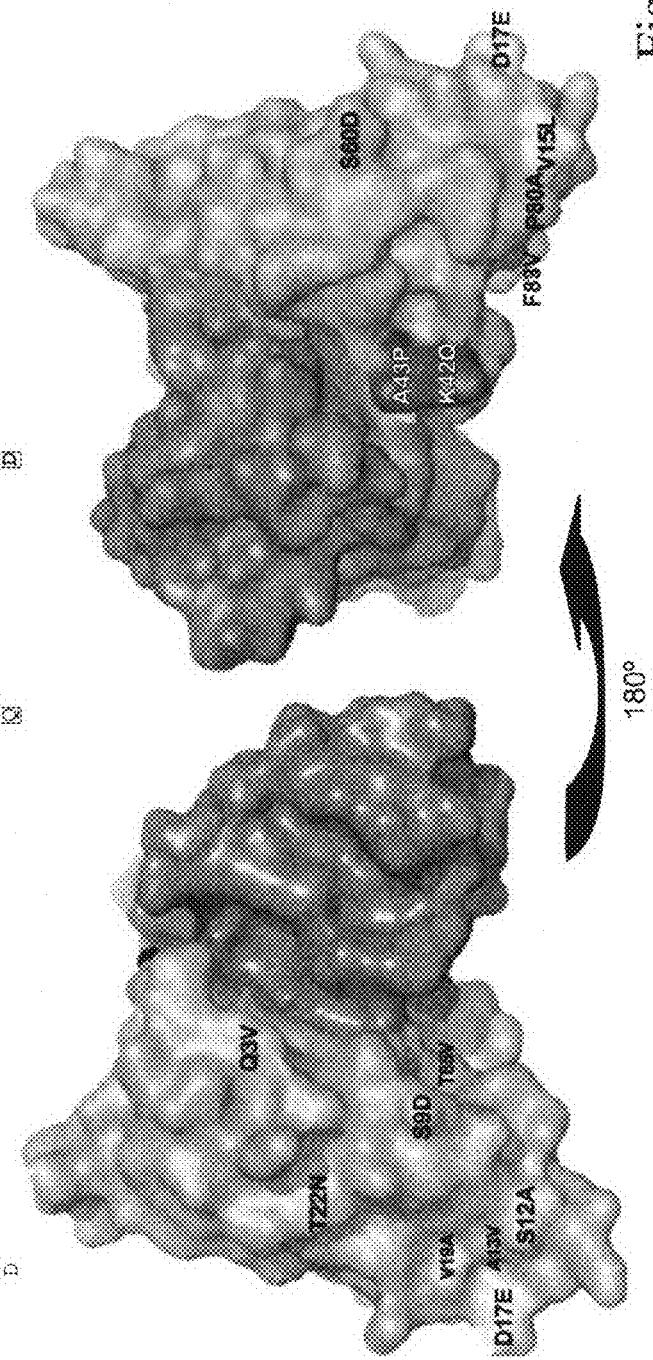
Figure 25A:
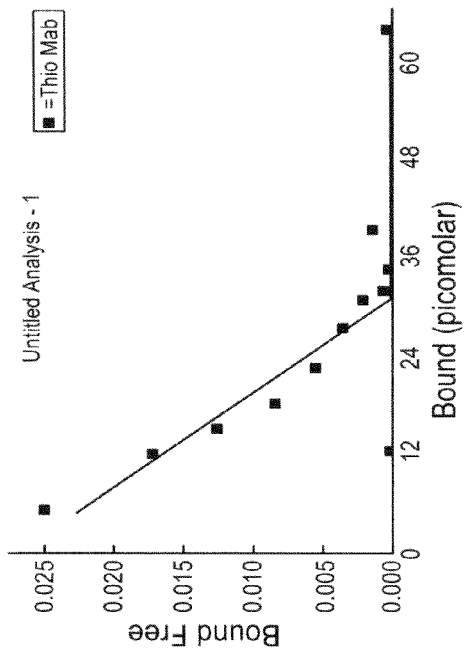
Figure 25B:
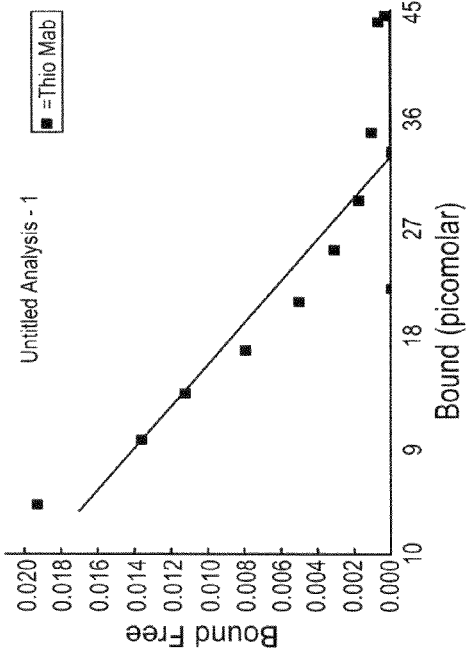
Figure 25C:
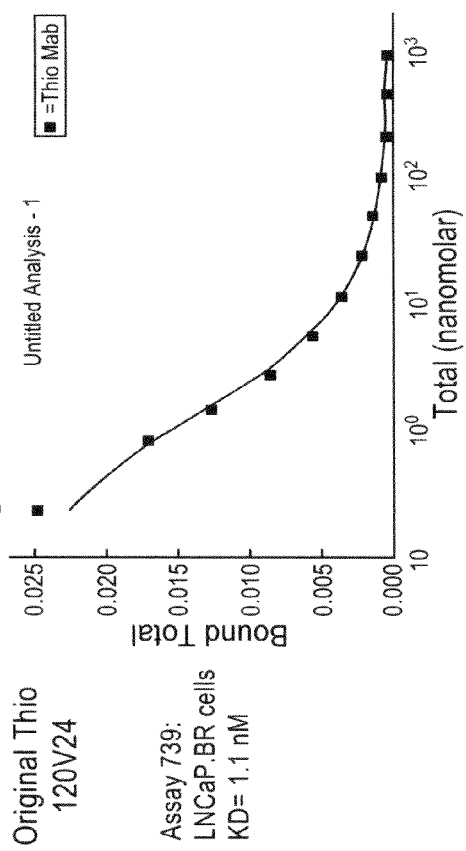
Figure 25D:
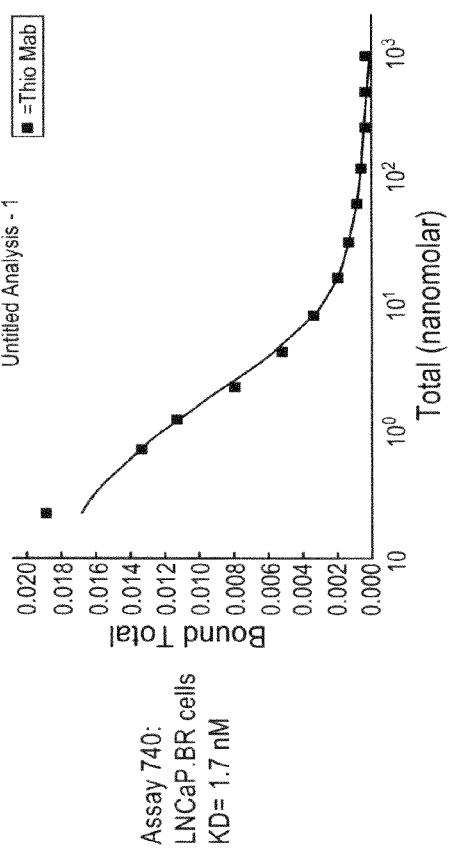
Figure 26A:
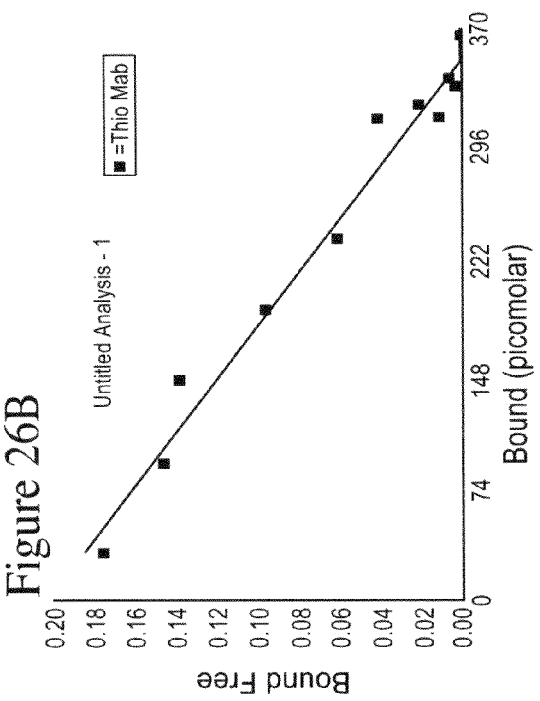
Figure 26B:
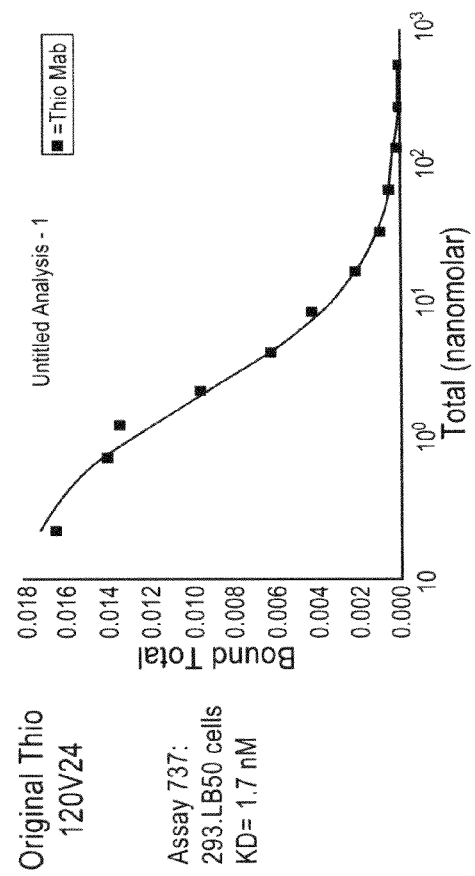
Figure 26C:
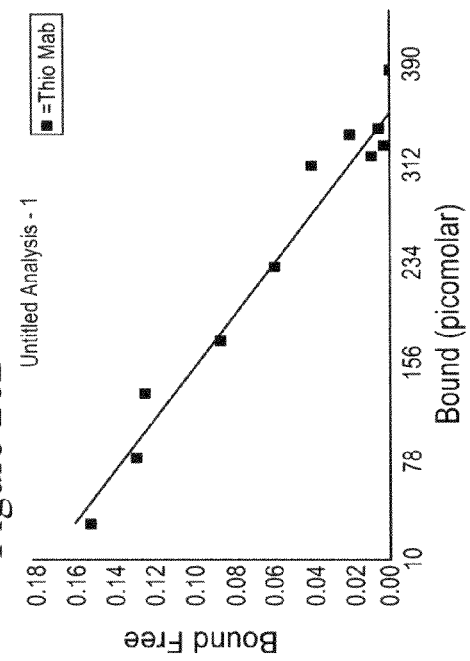
Figure 26D:
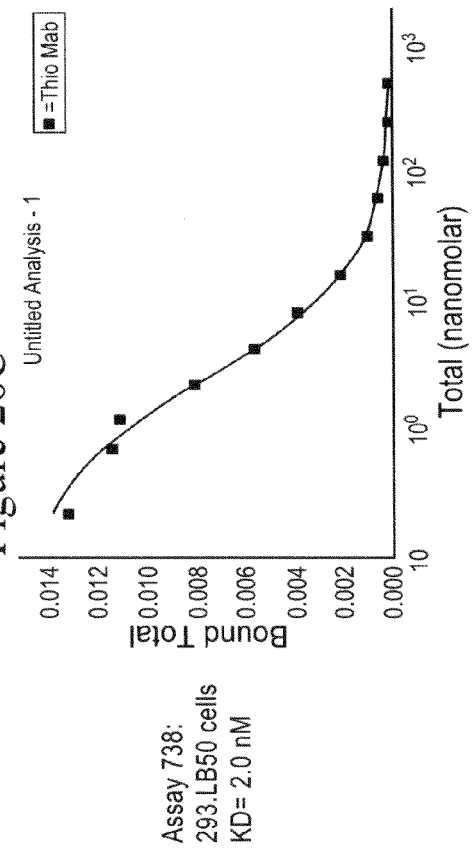
Figure 26E:
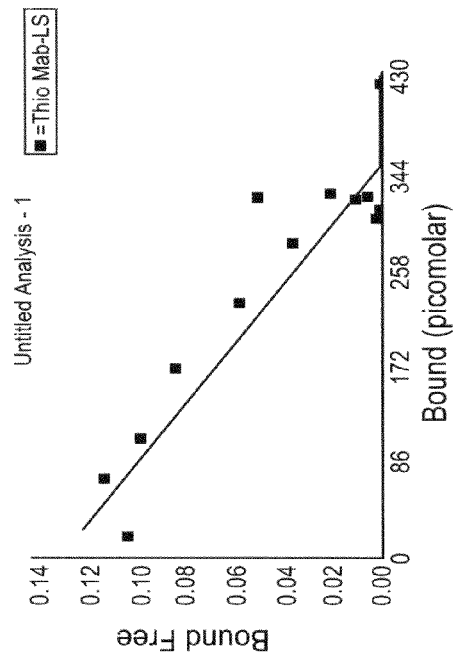
Figure 26F:
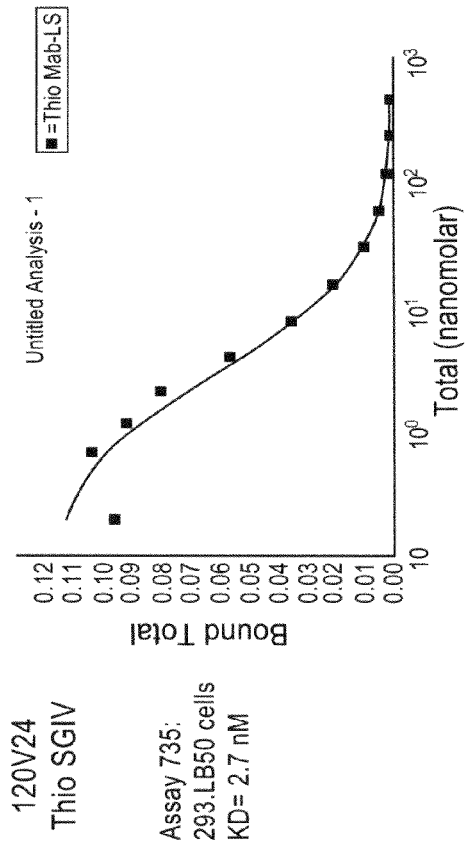
Figure 26G:
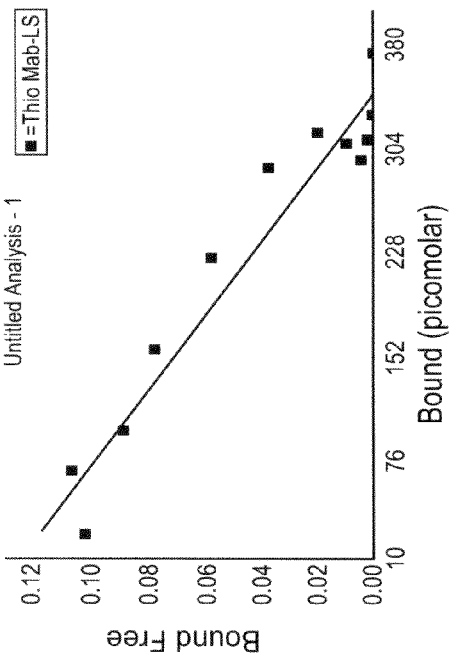
Figure 26H:
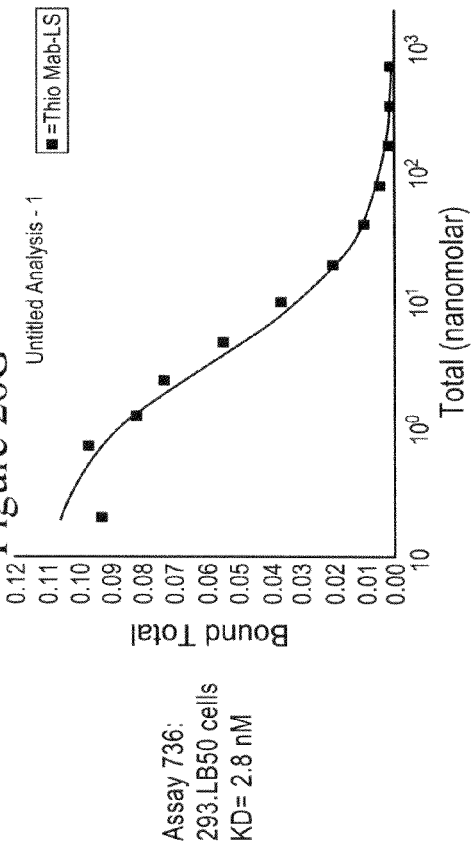

FIG. 24 shows the sites of framework amino acid substitutions made to generate various cysteine-engineered anti-STEAP-1 antibody (thio-mAb) variants of the SGIV and 120v.24 antibodies. The amino acid sequence of the light chain of SGIV is shown with standardized numbering according to the Kabat system, in alignment with variants LS.V-LVH1 (SEQ ID NO:92); LS.VLVH2 (SEQ ID NO:93); LS.Q (SEQ ID NO:94); and LS.CH1 (SEQ ID NO:95). The amino acid sequence of the light chain of 120.v24 with standardized numbering according to the Kabat system is shown in alignment with variants ED.FW1 (SEQ ID NO:96); ED.FW2 (SEQ ID NO:97); ED.FW3 (SEQ ID NO:98); ED.all (SEQ ID NO:99); ED.Pro (SEQ ID NO:100); and ED.pI (SEQ ID NO:101). The CDRs are boxed. The sequences are numbered according to Kabat numbering. See Example 9.

FIG. 25 shows Scatchard plots of antibody binding to STEAP-1 expressed on the surface of LNCaP.BR cells. Duplicate samples were measured using the 120.v24 antibody (FIGS. 25(A)-(D)) and the SGIV variant (FIGS. 25(E)-(H)). See Example 9.

FIG. 26 shows Scatchard plots of antibody binding to STEAP-1 expressed on the surface of 293.LB50 cells. Duplicate samples were measured using the 120.v24 antibody (FIGS. 26(A)-(D)) and the SGIV variant (FIGS. 26(E)-(H)). See Example 9.

Figure 27:
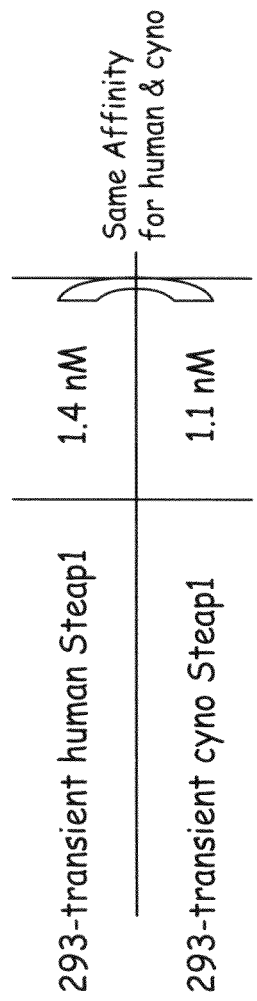

FIG. 27 is a table comparing the average binding affinities, as measured by Scatchard analysis, for the mu 1789, mu 120, Fc chimera, humanized 120.v24, thio-120.v24 and thio-SGIV antibodies in PC-3-PS5.4, 293-LB50 and LNCaP-BR cells, as well as in 293 cells transiently expressing STEAP-1. See Example 9.

FIG. 28 depicts a FACS analysis showing FACS shifts on cells stably transfected with STEAP-1 (293 STEAP-1 LB48, 293 STEAP-1 LB50 and 293 STEAP-1 LB53) with SGIV and 120.v24 antibody samples. See Example 9.

Figure 29:
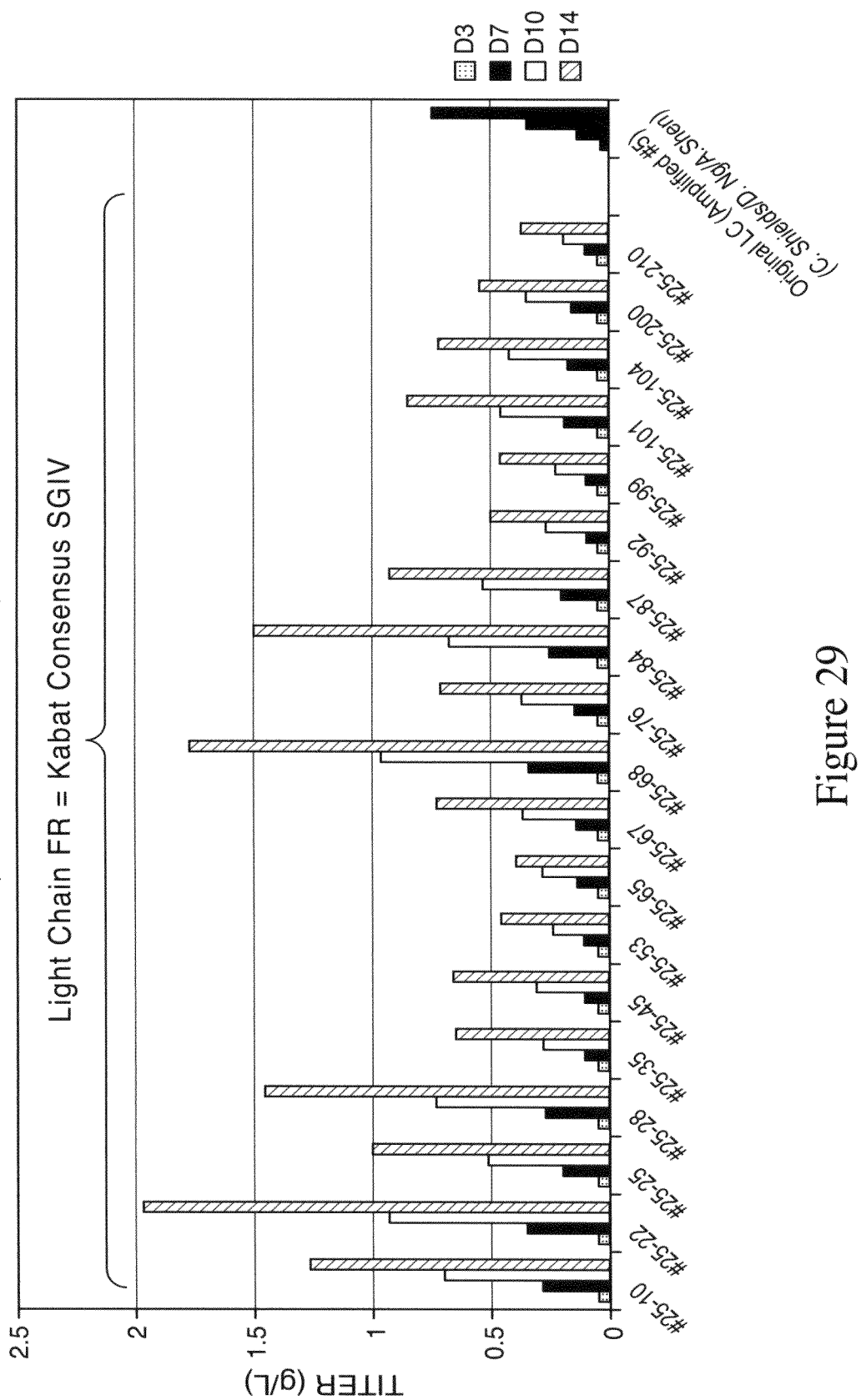

FIG. 29 shows the antibody titer observed in different harvests from cells producing SGIV or 120.v24 antibody.

DETAILED DESCRIPTION OF EMBODIMENTS OF THE INVENTION

Isolated antibodies that bind to STEAP-1 are provided. Immunoconjugates comprising anti-STEAP-1 antibodies are further provided. Antibodies and immunoconjugates of the invention are useful, e.g., for the diagnosis or treatment of disorders associated with altered expression, e.g., increased expression, of STEAP-1. In certain embodiments, antibodies or immunoconjugates of the invention are useful for the diagnosis or treatment of a cell proliferative disorder, such as a tumor or cancer. In certain embodiments, STEAP-1 is expressed in tumor or cancer of prostate, lung, or colon tissue. In certain embodiments, antibodies or immunoconjugates of the invention are useful for the detection of STEAP-1, e.g., STEAP-1 expressed on the cell surface. In certain embodiments, antibodies or immunoconjugates of the invention are useful for the detection of STEAP-1 expression on the surface of normal and/or tumor or cancer cells of prostate, lung or colon tissue.

Polynucleotides encoding anti-STEAP-1 antibodies are provided. Vectors comprising polynucleotides encoding anti-STEAP-1 antibodies are provided, and host cells comprising such vectors are provided. Compositions, including pharmaceutical formulations, comprising any one or more of the polynucleotides, anti-STEAP-1 antibodies, or immunoconjugates of the invention are also provided.

Methods of treating a cell proliferative disorder, including but not limited to tumor or cancer, with an anti-STEAP-1 antibody, antibody drug conjugate or immunoconjugate are provided. Such methods include, but are not limited to, treatment of tumor or cancer in prostate, lung or colon of a mammal. Methods of detecting STEAP-1 expression on a tissue cell using an anti-STEAP-1 antibody, antibody drug conjugate or immunoconjugate are provided. Such methods include, but are not limited to, detection of STEAP-1 expression on, as a non-limiting example, a normal cell, tumor cell, or cancer cell of prostate, lung, or colon cell.

General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3rd. edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *Pcr 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Definitions and Abbreviations

Definitions

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is separated from at least one other nucleic acid molecule with which it is ordinarily associated, for example, in its natural environment. An isolated nucleic acid molecule further includes a nucleic acid molecule contained in cells that ordinarily express the nucleic acid molecule, but the nucleic acid molecule is present extrachromosomally or at a chromosomal location that is different from its natural chromosomal location.

"Purified" means that a molecule is present in a sample at a concentration of at least 95% by weight, or at least 98% by weight of the sample in which it is contained.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O) OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Figure 1:
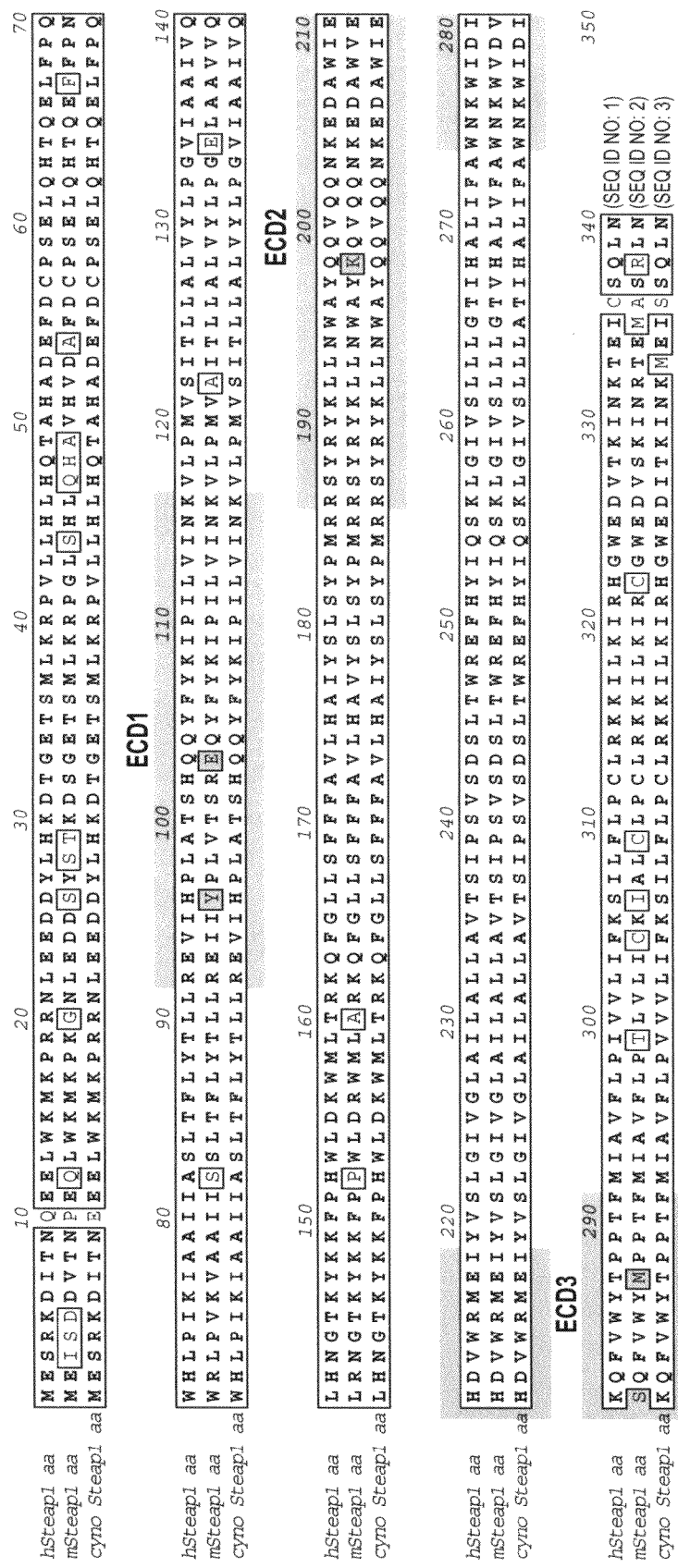
FIG. 1 depicts the amino acid sequence of human STEAP-1 (SEQ ID NO:1) aligned with STEAP-1 from mouse and cynomolgus monkey (cyno) (SEQ ID NOs:2 and 3, respectively). Extracellular domains 1, 2, and 3 are labeled and marked by shaded boxes.

The term "STEAP-1," as used herein, refers to any native STEAP-1 from any vertebrate source, including mammals such as primates (e.g. humans, cynomolgus monkey (cyno)) and rodents (e.g., mice and rats), unless otherwise indicated. The term encompasses "full-length," unprocessed STEAP-1 as well as any form of STEAP-1 that results from processing in the cell. The term also encompasses naturally occurring variants of STEAP-1, e.g., splice variants, allelic variants, and isoforms. The amino acid sequence of human STEAP-1 is depicted in FIG. 1 (SEQ ID NO:1). In one embodiment, STEAP-1 is expressed on the cell surface, such as on the surface of a normal prostate, lung or colon cell, and has increased expression in prostate, lung or colon cancer cells or metastases of such cancer cells. FIG. 1 also depicts the amino acid sequence of STEAP-1 from mouse and cynomolgus monkey (SEQ ID NOs:2 and 3, respectively).

"Antibodies" (Abs) and "immunoglobulins" (Igs) are glycoproteins having similar structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity) and may also include certain antibody fragments (as described in greater detail herein). An antibody can be chimeric, human, hunanized and/or affinity matured.

The term "anti-STEAP-1 antibody" or "an antibody that binds to STEAP-1" refers to an antibody that is capable of binding STEAP-1 with sufficient affinity such that the antibody is useful as a diagnostic and/or therapeutic agent in targeting STEAP-1. Preferably, the extent of binding of an anti-STEAP-1 antibody to an unrelated, non-STEAP-1 protein is less than about 10% of the binding of the antibody to STEAP-1 as measured, e.g., by a radioimmunoassay (RIA). In certain embodiments, an antibody that binds to STEAP-1 has a dissociation constant (Kd) of $\leq 1$ µM, $\leq 100$ nM, $\leq 10$ nM, $\leq 1$ nM, or $\leq 0.1$ nM. In certain embodiments, an anti-STEAP-1 antibody binds to an epitope of STEAP-1 that is conserved among STEAP-1 from different species.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and µ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO93/1161; Hudson et al. (2003) Nat. Med. 9:129-134; and Hollinger et al., Proc. Natl. Acad. Sci. USA 90: 6444-6448 (1993). Triabodies and tetrabodies are also described in Hudson et al. (2003) Nat. Med. 9:129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2$^{nd}$ ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody.

These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

The term "hypervariable region," "HVR," or "HV," when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). In native antibodies, H3 and L3 display the most diversity of the six hypervariable regions, and H3 in particular is believed to play a unique role in conferring fine specificity to antibodies. Xu et al. (2000) Immunity 13:37-45; Johnson and Wu (2003) in Methods in Molecular Biology 248:1-25 (Lo, ed., Human Press, Totowa, N.J.). Indeed, naturally occurring camelid antibodies consisting of a heavy chain only are functional and stable in the absence of light chain. Hamers-Casterman et al. (1993) Nature 363:446-448; Sheriff et al. (1996) Nature Struct. Biol. 3:733-736.

A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact | |
|---|---|---|---|---|---|
| L1 | L24-L34 | L24-L34 | L26-L32 | L30-L36 | |
| L2 | L50-L56 | L50-L56 | L50-L52 | L46-L55 | |
| L3 | L89-L97 | L89-L97 | L91-L96 | L89-L96 | |
| H1 | H31-H35B | H26-H35B | H26-H32 | H30-H35B | (Kabat Numbering) |
| H1 | H31-H35 | H26-H35 | H26-H32 | H30-H35 | (Chothia Numbering) |
| H2 | H50-H65 | H50-H58 | H53-H55 | H47-H58 | |
| H3 | H95-H102 | H95-H102 | H96-H101 | H93-H101 | |

Hypervariable regions may comprise "extended hypervariable regions" as follows: 24-36 or 24-34 (L1), 46-56 or 50-56 (L2) and 89-97 or 89-96 (L3) in the VL and 26-35 or 26-35A (H1), 50-65 or 49-65 (H2) and 93-102, 94-102, or 95-102 (H3) in the VH. The variable domain residues are numbered according to Kabat et al., supra, for each of these definitions. The HVR-H1, HVR-H2, and HVR-H3 hypervariable regions of the humanized anti-STEAP-1 120v.24 antibodies of the invention are H26-H35A, H49-H6, and H95-H102 using Kabat numbering. The HVR-L1, HVR-L2, and HVR-L3 hypervariable regions of the humanized anti-STEAP-1 120v.24 antibodies of the invention are L24-34, L50-56, and L89-97 using Kabat numbering. As used herein, the terms "HVR" and "CDR" are used interchangeably.

"Framework" or "FR" residues are those variable domain residues other than the hypervariable region residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of HVR and/or framework residues is described by: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody," as used herein, is an antibody which mimics at least one of the functional activities of a polypeptide of interest.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daëron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides.

WO00/42072 (Presta) describes antibody variants with improved or diminished binding to FcRs. The content of that patent publication is specifically incorporated herein by reference. See, also, Shields et al. J. Biol. Chem. 9(2): 6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., J. Immunol. Methods 202:163 (1996), may be performed.

Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. J. Immunol. 164: 4178-4184 (2000).

The term "Fc region-comprising polypeptide" refers to a polypeptide, such as an antibody or immunoadhesin, which comprises an Fc region. The C-terminal lysine (residue 447 according to the EU numbering system) of the Fc region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

An "acceptor human framework" for the purposes herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferably those changes occur at only three, two, or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5$^{th}$ Ed. Public Health Service, National Institutes of Health, Bethesda, Md. (1991). In one embodiment, for the VL, the subgroup is subgroup kappa I as in Kabat et al., supra. In one embodiment, for the VH, the subgroup is subgroup III as in Kabat et al., supra.

A "VH subgroup III consensus framework" comprises the consensus sequence obtained from the amino acid sequences in variable heavy subgroup III of Kabat et al., supra. In one embodiment, the VH subgroup III consensus framework amino acid sequence comprises at least a portion or all of each of the following sequences: EVQLVESGGGLVQPGGSLRLSCAAS (FR-H1, SEQ ID NO:21)-HVR-H1-

WVRQAPGKGLEWV (FR-H2, SEQ ID NO:22)-HVR-H2-RFTISRDTSKNTLYLQMNSLRAEDTAVYYCAR (FR-H3, SEQ ID NO:138)-HVR-H3-WGQGTLVTVSS (FR-H4, SEQ ID NO:24).

A "VL subgroup I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences: DIQMTQSPSSLSASVGDRVTITC (FR-L1, SEQ ID NO:17)-HVR-L1-WYQQKPGKAP-KLLIY (FR-L2, SEQ ID NO:18)-HVR-L2-GVPSRF-SGSGSGTDFTLTISSLQPEDFATYYC (FR-L3, SEQ ID NO:19)-HVR-L3-FGQGTKVEIKR (FR-L4, SEQ ID NO:20). "Secretion signal sequence" or "signal sequence" refers to a nucleic acid sequence encoding a short signal peptide that can be used to direct a newly synthesized protein of interest through a cellular membrane, usually the inner membrane or both inner and outer membranes of prokaryotes. As such, the protein of interest such as the immunoglobulin light or heavy chain polypeptide is secreted into the periplasm of the prokaryotic host cells or into the culture medium. The signal peptide encoded by the secretion signal sequence may be endogenous to the host cells, or they may be exogenous, including signal peptides native to the polypeptide to be expressed. Secretion signal sequences are typically present at the amino terminus of a polypeptide to be expressed, and are typically removed enzymatically between biosynthesis and secretion of the polypeptide from the cytoplasm. Thus, the signal peptide is usually not present in a mature protein product.

A "free cysteine amino acid" refers to a cysteine amino acid residue which has been engineered into a parent antibody, has a thiol functional group (—SH), and is not paired as, or otherwise part of, an intramolecular or intermolecular disulfide bridge.

The term "thiol reactivity value" is a quantitative characterization of the reactivity of free cysteine amino acids. The thiol reactivity value is the percentage of a free cysteine amino acid in a cysteine engineered antibody which reacts with a thiol-reactive reagent, and converted to a maximum value of 1. For example, a free cysteine amino acid on a cysteine engineered antibody which reacts in 100% yield with a thiol-reactive reagent, such as a biotin-maleimide reagent, to form a biotin-labelled antibody has a thiol reactivity value of 1.0. Another cysteine amino acid engineered into the same or different parent antibody which reacts in 80% yield with a thiol-reactive reagent has a thiol reactivity value of 0.8. Another cysteine amino acid engineered into the same or different parent antibody which fails totally to react with a thiol-reactive reagent has a thiol reactivity value of 0. Determination of the thiol reactivity value of a particular cysteine may be conducted by ELISA assay, mass spectroscopy, liquid chromatography, autoradiography, or other quantitative analytical tests. Thiol-reactive reagents which allow capture of the cysteine engineered antibody and comparison and quantitation of the cysteine reactivity include biotin-PEO-maleimide ((+)-biotinyl-3-maleimidopropionamidyl-3,6-dioxaoctainediamine, Oda et al (2001) Nature Biotechnology 19:379-382, Pierce Biotechnology, Inc.) Biotin-BMCC, PEO-Iodoacetyl Biotin, Iodoacetyl-LC-Biotin, and Biotin-HPDP (Pierce Biotechnology, Inc.), and Nα-(3-maleimidyl-propionyl)biocytin (MPB, Molecular Probes, Eugene, Oreg.). Other commercial sources for biotinylation, bifunctional and multifunctional linker reagents include Molecular Probes, Eugene, Oreg., and Sigma, St. Louis, Mo.

A "parent antibody" is an antibody comprising an amino acid sequence from which one or more amino acid residues are replaced by one or more cysteine residues. The parent antibody may comprise a native or wild type sequence. The parent antibody may have pre-existing amino acid sequence modifications (such as additions, deletions and/or substitutions) relative to other native, wild type, or modified forms of an antibody. A parent antibody may be directed against a target antigen of interest, e.g. a biologically important polypeptide. Antibodies directed against nonpolypeptide antigens (such as tumor-associated glycolipid antigens; see U.S. Pat. No. 5,091,178) are also contemplated.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity." refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (Chen, et al., (1999) J. Mol. Biol. 293: 865-881). To establish conditions for the assay, microtiter plates (Dynex) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., (1997) Cancer Res. 57:4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 μl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays.

According to another embodiment, the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore® Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. Association rates (kon) and dissociation rates (koff) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio koff/kon. See, e.g., Chen, Y., et al., (1999) J. Mol. Biol. 293:865-881. If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

An "on-rate," "rate of association," "association rate," or "$k_{on}$" according to this invention can also be determined as described above using a BIAcore™-2000 or a BIAcore™-3000 system (BIAcore®, Inc., Piscataway, N.J.).

A "disorder" is any condition or disease that would benefit from treatment with an substance/molecule or method of the invention. This includes chronic and acute disorders including those pathological conditions which predispose the mammal to the disorder in question. Non-limiting examples of disorders to be treated herein include cancerous conditions such as cancers or metastases of prostate, lung, and colon.

The terms "cell proliferative disorder" and "proliferative disorder" refer to disorders that are associated with some degree of abnormal cell proliferation. In one embodiment, the cell-proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

A "STEAP-1-expressing cell" is a cell which expresses endogenous or transfected STEAP-1 on the cell surface. A "STEAP-1-expressing cancer" is a cancer comprising cells that have STEAP-1 protein present on the cell surface. A "STEAP-1-expressing cancer" produces sufficient levels of STEAP-1 on the surface of cells thereof, such that an anti-STEAP-1 antibody can bind thereto and have a therapeutic effect with respect to the cancer. A cancer which "overexpresses" STEAP-1 is one which has significantly higher levels of STEAP-1 at the cell surface thereof, compared to a noncancerous cell of the same tissue type. Such overexpression may be caused by gene amplification or by increased transcription or translation. STEAP-1 overexpression may be determined in a diagnostic or prognostic assay by evaluating increased levels of the STEAP-1 protein present on the surface of a cell (e.g. via an immunohistochemistry assay; FACS analysis). Alternatively, or additionally, one may measure levels of STEAP-1-encoding nucleic acid or mRNA in the cell, e.g. via fluorescent in situ hybridization; (FISH; see WO98/45479 published October, 1998), Southern blotting, Northern blotting, or polymerase chain reaction (PCR) techniques, such as real time quantitative PCR (RT-PCR). One may also study STEAP-1 overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody. A STEAP-1-expressing cancer includes prostate, lung, and colon cancer.

As used herein, "treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder or to slow the progression of a disease or disorder.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). For prostate cancer, the progress of therapy can be assessed by routine methods, usually by measuring serum PSA (prostate specific antigen) levels; the higher the level of PSA in the blood, the more extensive the cancer. Commercial assays for detecting PSA are available, e.g., Hybitech Tandem-E and Tandem-R PSA assay kits, the Yang ProsCheck polyclonal assay (Yang Labs, Bellevue, Wash.), Abbott Imx (Abbott Labs, Abbott Park, Ill.), etc. Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

An "individual" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

An "effective amount" refers to an amount effective, at dosages and for periods of time necessary, to achieve the desired therapeutic or prophylactic result. A "therapeutically effective amount" of a substance/molecule of the invention may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "treating". To the extent the drug may prevent growth and/or kill existing cancer cells, it may be cytostatic and/or cytotoxic.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Label" as used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

The term "epitope tagged" used herein refers to a chimeric polypeptide comprising an anti-PSCA antibody polypeptide fused to a "tag polypeptide". The tag polypeptide has enough residues to provide an epitope against which an antibody can be made, yet is short enough such that it does not interfere with activity of the Ig polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The term "package insert" is used to refer to instructions customarily included in commercial packages of therapeutic products, that contain information about the indications, usage, dosage, administration, contraindications and/or warnings concerning the use of such therapeutic products.

An "isolated nucleic acid" is a nucleic acid, e.g., an RNA, DNA, or a mixed polymer, which is substantially separated from other genome DNA sequences as well as proteins or complexes such as ribosomes and polymerases, which naturally accompany a native sequence. The term embraces a nucleic acid sequence which has been removed from its naturally occurring environment, and includes recombinant or cloned DNA isolates and chemically synthesized analogues or analogues biologically synthesized by heterologous systems. A substantially pure molecule includes isolated forms of the molecule.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below.

The cell that produces an anti-STEAP-1 antibody of the invention will include the parent hybridoma cell e.g., the hybridomas that are deposited with the ATCC, as well as bacterial and eukaryotic host cells into which nucleic acid encoding the antibodies have been introduced. Suitable host cells are disclosed below.

A "growth inhibitory agent" when used herein refers to a compound or composition which inhibits growth of a cell, especially a PSCA expressing cancer cell, either in vitro or in vivo. Thus, the growth inhibitory agent may be one which significantly reduces the percentage of PSCA expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs"

by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "cytotoxic agent" as used herein refers to a substance that inhibits or prevents a cellular function and/or causes cell death or destruction. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, toxins, growth inhibitory agents, drug moieties, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the -growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX®) alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell (such as a cell expressing STEAP-1) either in vitro or in vivo. Thus, the growth inhibitory agent may be one which significantly reduces the percentage of cells (such as a cell expressing STEAP-1) in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "intracellular metabolite" refers to a compound resulting from a metabolic process or reaction inside a cell on an antibody-drug conjugate (ADC). The metabolic process or reaction may be an enzymatic process, such as proteolytic cleavage of a peptide linker of the ADC, or hydrolysis of a functional group such as a hydrazone, ester, or amide. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an antibody-drug conjugate (ADC) whereby the covalent attachment, i.e. linker, between the drug moiety (D) and the antibody (Ab) is broken, resulting in the free drug dissociated from the antibody inside the cell. The cleaved moieties of the ADC are thus intracellular metabolites.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The term "cytotoxic activity" refers to a cell-killing, cytostatic or growth inhibitory effect of an antibody-drug conjugate or an intracellular metabolite of an antibody-drug conjugate. Cytotoxic activity may be expressed as the $IC_{50}$ value, which is the concentration (molar or mass) per unit volume at which half the cells survive.

"Alkyl" is C1-C18 hydrocarbon containing normal, secondary, tertiary or cyclic carbon atoms. Examples are methyl (Me, —CH3), ethyl (Et, —CH2CH3), 1-propyl (n-Pr, n-propyl, —CH2CH2CH3), 2-propyl (i-Pr, i-propyl, —CH(CH3)2), 1-butyl (n-Bu, n-butyl, —CH2CH2CH2CH3), 2-methyl-1-propyl (1-Bu, 1-butyl, —CH2CH(CH3)2), 2-butyl (s-Bu, s-butyl, —CH(CH3)CH2CH3), 2-methyl-2-propyl (t-Bu, t-butyl, —C(CH3)3), 1-pentyl (n-pentyl, —CH2CH2CH2CH2CH3), 2-pentyl (—CH(CH3)CH2CH2CH3), 3-pentyl (—CH(CH2CH3)2), 2-methyl-2-butyl (—C(CH3)2CH2CH3), 3-methyl-2-butyl (—CH(CH3)CH(CH3)2), 3-methyl-1-butyl (—CH2CH2CH(CH3)2), 2-methyl-1-butyl (—CH2CH(CH3)CH2CH3), 1-hexyl (—CH2CH2CH2CH2CH2CH3), 2-hexyl (—CH(CH3)CH2CH2CH2CH3), 3-hexyl (—CH(CH2CH3)(CH2CH2CH3)), 2-methyl-2-pentyl (—C(CH3)2CH2CH2CH3), 3-methyl-2-pentyl (—CH(CH3)CH(CH3)CH2CH3), 4-methyl-2-pentyl (—CH(CH3)CH2CH(CH3)2), 3-methyl-3-pentyl (—C(CH3)(CH2CH3)2), 2-methyl-3-pentyl (—CH(CH2CH3)CH(CH3)2), 2,3-dimethyl-2-butyl (—C(CH3)2CH(CH3)2), 3,3-dimethyl-2-butyl (—CH(CH3)C(CH3)3.

The term "C1-C8 alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexylacetylenyl, -propynyl, -1-butynyl, -2-butynyl, -1-pentynyl, -2-pentynyl, -3-methyl-1 butynyl, methyl, ethyl, propyl, isopropyl, n-butyl, isobutyl, sec-butyl, tert-butyl, n-pentyl, isopentyl, neopentyl, n-hexyl, isohexyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$ —NHC(O)R', —SO$_3$R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

"Alkenyl" is C2-C18 hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—CH═CH₂), allyl (—CH₂CH═CH₂), cyclopentenyl (—C₅H₇), and 5-hexenyl (—CH₂CH₂CH₂CH₂CH═CH₂)

"Alkynyl" is C2-C18 hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—CH₂C≡CH), "Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH₂—) 1,2-ethyl (—CH₂CH₂—), 1,3-propyl (—CH₂CH₂CH₂—), 1,4-butyl (—CH₂CH₂CH₂CH₂—), and the like.

A "C₁-C₁₀ alkylene" is a straight chain, saturated hydrocarbon group of the formula —(CH₂)₁₋₁₀—. Examples of a C₁-C₁₀ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—CH₂C≡C—), and 4-pentynyl (—CH₂CH₂CH₂C≡C—).

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —C₁-C₈ alkyl, —O—(C₁-C₈ alkyl), -aryl, —C(O)R', —OC(O)R', —C(O)OR', —C(O)NH₂, —C(O)NHR', —C(O)N(R')₂— NHC(O)R', —S(O)₂R', —S(O)R', —OH, —halogen, —N₃, —NH₂, —NH(R'), —N(R')₂ and —CN; wherein each R' is independently selected from H, —C₁-C₈ alkyl and aryl.

An "arylene" is an aryl group which has two covalent bonds and can be in the ortho, meta, or para configurations as shown in the following structures:

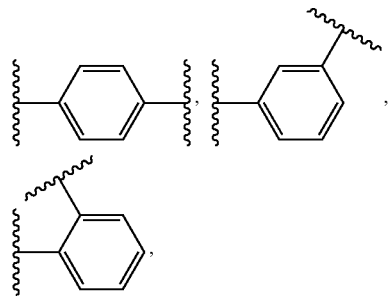

in which the phenyl group can be unsubstituted or substituted with up to four groups including, but not limited to, —C₁-C₈ alkyl, —O—(C₁-C₈ alkyl), -aryl, —C(O)R', —OC(O)R', —C(O)OR', —C(O)NH₂, —C(O)NHR', —C(O)N (R')₂ —NHC(O)R', —S(O)₂R', —S(O)R', —OH, —halogen, —N₃, —NH₂, —NH(R'), —N(R')₂ and —CN; wherein each R' is independently selected from H, —C₁-C₈ alkyl and aryl.

"Arylalkyl" refers to an acyclic alkyl radical in which one of the hydrogen atoms bonded to a carbon atom, typically a terminal or sp³ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or sp³ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl," "substituted aryl," and "substituted arylalkyl" mean alkyl, aryl, and arylalkyl respectively, in which one or more hydrogen atoms are each independently replaced with a substituent. Typical substituents include, but are not limited to, —X, —R, —O⁻, —OR, —SR, —S⁻, —NR₂, —NR₃, ═NR, —CX₃, —CN, —OCN, —SCN, —N═C═O, —NCS, —NO, —NO₂, ═N₂, —N₃, NC(═O)R, —C(═O)R, —C(═O)NR₂, —SO₃⁻, —SO₃H, —S(═O)₂R, —OS(═O)₂OR, —S(═O)₂NR, —S(═O)R, —OP(═O)(OR)₂, —P(═O)(OR)₂, —PO⁻₃, —PO₃H₂, —C(═O)R, —C(═O)X, —C(═S)R, —CO₂R, —CO₂⁻, —C(═S)OR, —C(═O)SR, —C(═S)SR, —C(═O)NR₂, —C(═S)NR₂, —C(═NR)NR₂, where each X is independently a halogen: F, Cl, Br, or I; and each R is independently —H, C₂-C₁₈ alkyl, C₆-C₂₀ aryl, C₃-C₁₄ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g. nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O) NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —(CR$_2$)$_n$O(CR$_2$)$_n$—, repeating units of alkyloxy (e.g. polyethylenoxy, PEG, polymethyleneoxy), and alkylamino (e.g. polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

Abbreviations
Linker Components:
MC=6-maleimidocaproyl
Val-Cit or "vc"=valine-citrulline (an exemplary dipeptide in a protease cleavable linker)
Citrulline=2-amino-5-ureido pentanoic acid
PAB=p-aminobenzyloxycarbonyl (an example of a "self immolative" linker component)
Me-Val-Cit=N-methyl-valine-citrulline (wherein the linker peptide bond has been modified to prevent its cleavage by cathepsin B)
MC(PEG)6-OH=maleimidocaproyl-polyethylene glycol (can be attached to antibody cysteines).
SPP=N-succinimidyl-4-(2-pyridylthio)pentanoate
SPDP=N-succinimidyl-3-(2-pyridyldithio) propionate
SMCC=succinimidyl-4-(N-maleimidomethyl)cyclohexane-1-carboxylate
IT=iminothiolane
Cytotoxic Drugs:
MMAE=mono-methyl auristatin E (MW 718)
MMAF=variant of auristatin E (MMAE) with a phenylalanine at the C-terminus of the drug (MW 731.5)
MMAF-DMAEA=MMAF with DMAEA (dimethylaminoethylamine) in an amide linkage to the C-terminal phenylalanine (MW 801.5)
MMAF-TEG=MMAF with tetraethylene glycol esterified to the phenylalanine
MMAF-NtBu=N-t-butyl, attached as an amide to C-terminus of MMAF
DM1=N(2')-deacetyl-N(2')-(3-mercapto-1-oxopropyl)-maytansine
DM3=N(2')-deacetyl-N2-(4-mercapto-1-oxopentyl)-maytansine
DM4=N(2')-deacetyl-N2-(4-mercapto-4-methyl-1-oxopentyl)-maytansine Further abbreviations are as follows: AE is auristatin E, Boc is N-(t-butoxycarbonyl), cit is citrulline, dap is dolaproine, DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, dil is dolaisoleucine, DMA is dimethylacetamide, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN(CH$_3$CN) is acetonitrile, MeOH is methanol, Mtr is 4-anisyldiphenylmethyl (or 4-methoxytrityl), nor is (1S,2R)-(+)-norephedrine, PBS is phosphate-buffered saline (pH 7.4), PEG is polyethylene glycol, Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TFA is trifluoroacetic acid, TLC is thin layer chromatography, UV is ultraviolet, and val is valine.

Compositions and Methods of Making the Same

Antibodies that bind to STEAP-1 are provided. Immunoconjugates comprising anti-STEAP-1 antibodies are provided. Antibodies and immunoconjugates of the invention are useful, e.g., for the diagnosis or treatment of disorders associated with altered expression, e.g., increased expression, of STEAP-1. In certain embodiments, antibodies or immunoconjugates of the invention are useful for the diagnosis or treatment of a cell proliferative disorder, such as cancer.

Anti-STEAP-1 Antibodies

In one aspect, the invention provides antibodies that bind to STEAP-1. In some embodiments, antibodies are provided that bind to a mature form of human and cynomolgus monkey (cyno) STEAP-1. In one such embodiment, a mature form of human STEAP-1 has an amino acid sequence of SEQ ID NO:1 (FIG. 1). The cyno STEAP-1 has an amino acid sequence of SEQ ID NO:3 (FIG. 1). In some embodiments, an antibody to STEAP-1 binds to a mature form of STEAP-1 expressed on the cell surface. In some embodiments, an antibody that binds to a mature form of STEAP-1 expressed on the cell surface inhibits the growth of the cell. In some embodiments, an anti-STEAP-1 antibody binds to a mature form of STEAP-1 expressed on the cell surface and inhibits cell proliferation. In certain embodiments, an anti-STEAP-1 antibody binds to a mature form of STEAP-1 expressed on the cell surface and induces cell death. In some embodiments, an anti-STEAP-1 antibody binds to a mature form of STEAP-1 expressed on the surface of cancer cells. In some embodiments, an anti-STEAP-1 antibody binds to a mature form of STEAP-1 that is overexpressed on the surface of cancer cells relative to normal cells of the same tissue origin. In some embodiments, an anti-STEAP-1 antibody is conjugated to a cytotoxin or a detectable label and binds to STEAP-1 on a cell surface. In some embodiments, the antibody-toxin conjugate inhibits growth of the cell. In some embodiments, the antibody-detectable label conjugate causes a cell expressing STEAP-1 on its surface to be detectable in vitro or in vivo.

In one aspect, an anti-STEAP-1 antibody is a monoclonal antibody. In one aspect, an anti-STEAP-1 antibody is an antibody fragment, e.g., a Fab, Fab'-SH, Fv, scFv, or (Fab')$_2$ fragment. In one aspect, an anti-STEAP-1 antibody is a chimeric, humanized, or human antibody. In one aspect, any of the anti-STEAP-1 antibodies described herein are purified.

Exemplary monoclonal antibodies derived from a phage library are provided herein. The antigen used for screening the library was a polypeptide having the sequence of amino acid sequences of SEQ ID NO:28 or SEQ ID NO:30, corresponding to the extracellular domains (ECDs) of STEAP-1 beta and alpha. The antibodies resulting from the library screen are affinity matured.

In one aspect, monoclonal antibodies that compete with murine 120.545, 120 graft, and humanized 120v.24 binding to STEAP-1 are provided. Monoclonal antibodies that bind to the same epitope as murine 120.545, 120 graft, and humanized 120v.24 are also provided.

In one aspect of the invention, polynucleotides encoding anti-STEAP-1 antibodies are provided. In certain embodiments, vectors comprising polynucleotides encoding anti-STEAP-1 antibodies are provided. In certain embodiments, host cells comprising such vectors are provided. In another aspect of the invention, compositions comprising anti-STEAP-1 antibodies or polynucleotides encoding anti-STEAP-1 antibodies are provided. In certain embodiments, a composition of the invention is a pharmaceutical formulation for the treatment of a cell proliferative disorder, such as those enumerated herein.

A detailed description of exemplary anti-STEAP-1 antibodies is as follows:

1. Specific Embodiments of Anti-STEAP-1 Antibodies

Figure 2B:
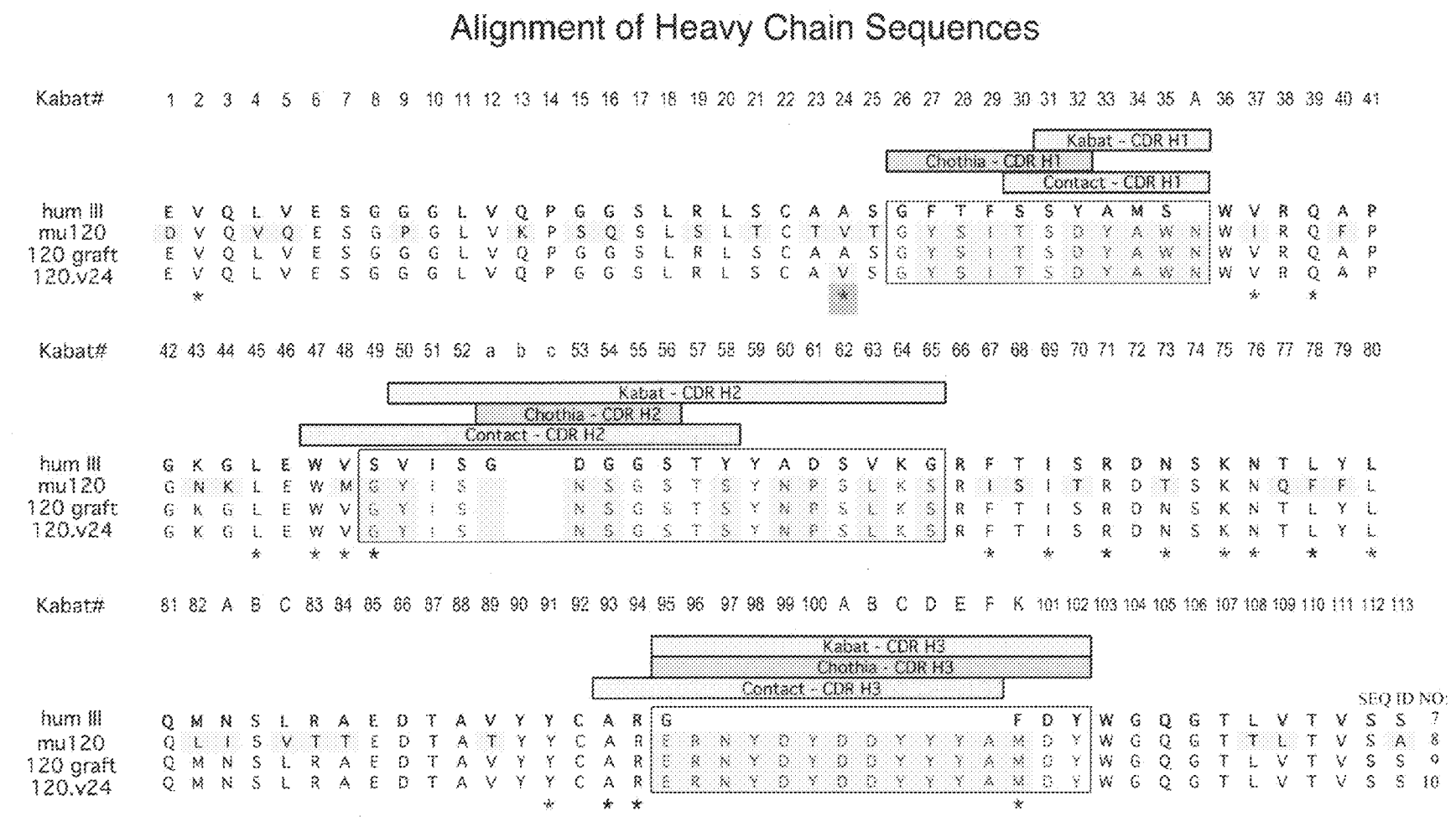

In one aspect, the invention provides an anti-STEAP-1 antibody comprising a heavy chain variable domain comprising SEQ ID NO:9 or 10 of FIG. 2B. In one aspect, the invention provides an anti-STEAP-1 antibody comprising a light chain variable domain comprising SEQ ID NO:6 of FIG. 2A.

In one aspect, the invention provides an anti-STEAP-1 antibody comprising a heavy chain comprising SEQ ID NO:9, having one or more of the following amino changes at the indicated Kabat position: A24V, V37I, V48M, F67I, and L78F. In one embodiment, the heavy chain comprises a heavy chain framework region selected from SEQ ID NOs:25, 75, 76, 77, 78, and 79. As used herein, heavy chain framework regions are designated "FR-H1-H4" or "HC-FR1-FR4," and light chain framework regions are designated "FR-L1-L4" or "LC-FR1-FR4." In one aspect, the invention provides an anti-STEAP-1 antibody comprising a light chain comprising SEQ ID NO:6.

In one aspect, the invention provides an anti-STEAP-1 antibody comprising 1, 2, 3, 4, 5, or 6 of the HVR sequences of the antibody 120.v24 shown in FIGS. 2A and 2B.

An anti-STEAP-1 antibody may comprise any suitable framework variable domain sequence, provided that the antibody retains the ability to bind STEAP-1. For example, in some embodiments, anti-STEAP-1 antibodies of the invention comprise a human subgroup III heavy chain framework consensus sequence. In one embodiment of these antibodies, the heavy chain framework consensus sequence comprises substitution(s) at position 24, 37, 48, 67, and/or 78. In one embodiment of these antibodies, position 24 is A or V, position 37 is I or V, position 48 is M or V, position 67 is I or F, and/or position 78 is F or L. In one embodiment, these antibodies comprise a heavy chain variable domain framework sequence of huMAb4D5-8, e.g., SEQ ID NO:21, 22, 49, and 24 (FR-H1, FR-H2, FR-H3, FR-H4, respectively). huMAb4D5-8 is commercially known as HERCEPTIN® anti-HER2 antibody, Genentech, Inc., South San Francisco, Calif., USA; also referred to in U.S. Pat. Nos. 6,407,213 & 5,821,337, and Lee et al., J. Mol. Biol. (2004), 340(5): 1073-93. In one such embodiment, these antibodies further comprise a human κI light chain framework consensus sequence.

In one such embodiment, these antibodies comprise a light chain variable domain framework sequence of huMAb4D5-8, e.g. SEQ ID NO:17, 18, 139, and 20 (FR-L1, FR-L2, FR-L3, FR-L4, respectively).

In one embodiment, an anti-STEAP-1 antibody comprises a heavy chain variable domain comprising a framework sequence and hypervariable regions, wherein the framework sequence comprises the FR-H1-FR-H4 sequences SEQ ID NO:21 or 25 (FR-H1), 22 (FR-H2), 23 (FR-H3), and 24 (FR-H4), respectively; the HVR H1 comprises the amino acid sequence of SEQ ID NO:14; the HVR-H2 comprises the amino acid sequence of SEQ ID NO:15; and the HVR-H3 comprises an amino acid sequence of SEQ ID NO:16. In one embodiment, an anti-STEAP-1 antibody comprises a light chain variable domain comprising a framework sequence and hypervariable regions, wherein the framework sequence comprises the FR-L1-FR-L sequences of SEQ ID NOs:17, 18, 19 and 20, respectively; the HVR-L1 comprises the amino acid sequence selected from SEQ ID NOs:11, 12, and 13. In one embodiment of these antibodies, the heavy chain variable domain comprises SEQ ID NOs:9 or 10 and the light chain variable domain comprises SEQ ID NO:6.

In some embodiments, the invention provides an anti-STEAP-1 antibody comprising a heavy chain variable domain comprising an amino acid sequence having at least 90%, 91%, 92%, 93%, 94%, 95%, 96%, 97%, 98%, or 99% sequence identity to an amino acid sequence SEQ ID NO:9 or 10. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to STEAP-1. In some embodiments, a total of 1 to 10 amino acids have been substituted, inserted, or deleted in a sequence SEQ ID NOs:9, 10, 14, 15, 16, 21, 22, 23, 24, 25, 75, 76, 77, 78, and/or 79. In some embodiments, the substitutions, insertions, or deletions occur in regions outside the HVRs (i.e., in the FRs). In some embodiments, an anti-STEAP-1 antibody comprises a heavy chain variable domain comprising an amino acid sequence selected from SEQ ID NO:9 or 10.

In some embodiments, the invention provides an anti-STEAP-1 antibody comprising a heavy chain variable domain as depicted in FIG. 2B (SEQ ID NOs:9 or 10).

In some embodiments, the heavy chain HVR and FR sequences comprise the following:

```
HVR-H1
(GYSITSDYAWN, SEQ ID NO: 14)

HVR-H2
(GYISNSGSTSYNPSLKS, SEQ ID NO: 15)

HVR-H3
(ERNYDYDDYYYAMDY, SEQ ID NO: 16)

FR-H1
(EVQLVESGGGLVQPGGSLRLSCAAS, SEQ ID NO: 21)

FR-H1
(EVQLVESGGGLVQPGGSLRLSCAVS, SEQ ID NO: 25)

FR-H2
(WVRQAPGKGLEWV, SEQ ID NO: 22)

FR-H2
(WIRQAPGKGLEWV, SEQ ID NO: 75)
```

```
FR-H2
(WVRQAPGKGLEWM, SEQ ID NO: 76)

FR-H2
(WIRQAPGKGLEWM, SEQ ID NO: 77)

FR-H3
(RFTISRDNSKNTLYLQMNSLRAEDTAVYYCAR, SEQ ID NO: 23)

FR-H3
(RITISRDNSKNTLYLQMNSLRAEDTAVYYCAR, SEQ ID NO: 78)

FR-H3
(RFTISRDNSKNTFYLQMNSLRAEDTAVYYCAR, SEQ ID NO: 79)

FR-H4
(WGQGTLVTVSS, SEQ ID NO: 24)
```

In some embodiments, the invention provides an anti-STEAP-1 antibody comprising a light chain variable domain as depicted in FIG. 2A (SEQ ID NO:6).

In some embodiments, the light chain HVR sequences comprise the following:

```
HVR-L1    (KSSQSLLYRSNQKNYLA, SEQ ID NO: 11)
HVR-L2    (WASTRES, SEQ ID NO: 12)
HVR-L3    (QQYYNYPRT, SEQ ID NO: 13).
```

In some embodiments, the light chain FR sequences comprise the following:

```
FR-L1
(DIQMTQSPSSLSASVGDRVTITC, SEQ ID NO: 17);

FR-L2
(WYQQKPGKAPKLLIY, SEQ ID NO: 18);

FR-L3
(GVPSRFSGSGSGTDFTLTISSLQPEDFATYYC, SEQ ID NO: 19)

FR-L4
(FGQGTKVEIKR, SEQ ID NO: 20).
```

In one aspect, the invention provides an anti-STEAP-1 antibody comprising a light chain variable domain comprising an amino acid sequence having at least 90%, 91%, 92%, 93%, 94%, 95%, 96%, 97%, 98%, or 99% sequence identity to an amino acid sequence SEQ ID NO:6. In some embodiments, an amino acid sequence having at least 90%, 91%, 92%, 93%, 94%, 95%, 96%, 97%, 98%, or 99% sequence identity contains substitutions, additions, or deletions relative to the reference sequence, but an antibody comprising that amino acid sequence retains the ability to bind to STEAP-1. In some embodiments, a total of 1 to 10 amino acids have been substituted, inserted, or deleted in a sequence selected from SEQ ID NOs:6, 11, 12, 13, 17, 18, 19, and 20. In some embodiments, the substitutions, insertions, or deletions occur in regions outside the HVRs (i.e., in the FRs). In some embodiments, an anti-STEAP-1 antibody comprises a light chain variable domain comprising the amino acid sequence SEQ ID NO:6.

In one aspect, the invention provides an anti-STEAP-1 antibody comprising (a) a heavy chain variable domain comprising an amino acid sequence having at least 90%, 91%, 92%, 93%, 94%, 95%, 96%, 97%, 98%, or 99% sequence identity to an amino acid sequence selected from SEQ ID NO:9 and 10; and (b) a light chain variable domain comprising an amino acid sequence having at least 90%, 91%, 92%, 93%, 94%, 95%, 96%, 97%, 98%, or 99% sequence identity to an amino acid sequence SEQ ID NO:6. In some embodiments, an amino acid sequence having at least 90%, 91%, 92%, 93%, 94%, 95%, 96%, 97%, 98%, or 99% sequence identity contains substitutions, additions, or deletions relative to the reference sequence, but an antibody comprising that amino acid sequence retains the ability to bind to STEAP-1. In some embodiments, a total of 1 to 10 amino acids have been substituted, inserted, or deleted in the reference sequence, including but not limited to a sequence selected from SEQ ID NOs:9, 10, 14, 15, 16, 21, 22, 23, 24, 25, 75, 76, 77, 78, 79. In some embodiments, the substitutions, insertions, or deletions occur in regions outside the HVRs (i.e., in the FRs). In some embodiments, an anti-STEAP-1 antibody comprises a heavy chain variable domain comprising an amino acid sequence of SEQ ID NO:9 or 10 and a light chain variable domain comprising an amino acid sequence selected from SEQ ID NO:6.

In one aspect, the invention provides an anti-STEAP-1 antibody comprising (a) one, two, or three VH HVRs selected from those shown in FIG. 2B and/or (b) one, two, or three VL HVRs selected from those shown in FIG. 2A. In one aspect, the invention provides an anti-STEAP-1 antibody comprising a heavy chain variable domain selected from those shown in FIG. 2B and a light chain variable domain selected from those shown in FIG. 2A.

2. Antibody Fragments

The present invention encompasses antibody fragments. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10: 163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

3. Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those, skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

4. Human Antibodies

Human anti-STEAP-1 antibodies of the invention can be constructed by combining Fv clone variable domain sequence(s) selected from human-derived phage display libraries with known human constant domain sequences(s) as described above. Alternatively, human monoclonal anti-STEAP-1 antibodies of the invention can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255 (1993); Bruggermann et al., Year in Immunol., 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

5. Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for STEAP-1 and the other is for any other antigen. In certain embodiments, bispecific antibodies may bind to two different epitopes of STEAP-1. Bispecific antibodies may also be used to localize cytotoxic agents to cells which express STEAP-1. These antibodies possess a STEAP-L1-binding arm and an arm which binds a cytotoxic agent, such as, e.g., saporin, anti-interferon-α, vinca alkaloid, ricin A chain, methotrexate or radioactive isotope hapten. Bispecific antibodies can be prepared as full length antibodies or antibody fragments (e.g. F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., EMBO J., 10: 3655 (1991).

According to a different approach, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the imumunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules can be engineered to maximize the percentage of heterodimers which are recovered from recombinant cell culture. The interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/00373, and EP 03089). Heteroconjugate antibodies may be made using any convenient cross-linking method. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

6. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-

(X1)n-VD2-(X2)n-Fc, wherein VD1 is a first variable domain, VD2 is a second variable domain, Pc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

7. Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

8. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

In certain embodiments, a glycosylation variant comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. J. Mol. Biol. 336: 1239-1249 (2004); Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. Biotech. Bioeng. 87: 614 (2004)).

In one embodiment, the antibody is altered to improve its serum half-life. To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule (US 2003/0190311, U.S. Pat. No. 6,821,505; U.S. Pat. No. 6,165,745; U.S. Pat. No. 5,624,821; U.S. Pat. No. 5,648,260; U.S. Pat. No. 6,165,745; U.S. Pat. No. 5,834,597).

Another type of variant is an amino acid substitution variant. These variants have at least one amino acid residue in the antibody molecule replaced by a different residue. Sites of interest for substitutional mutagenesis include the hypervariable regions, but FR alterations are also contemplated. Conservative substitutions are shown in Table 1 under the heading of "preferred substitutions." If such substitutions result in a desirable change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gln (Q)

(3) acidic: Asp (D), Glu (E)

(4) basic: Lys (K), Arg (R), His (H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. J. Immunol. 164: 4178-4184 (2000).

In one aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

9. Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylenelmaleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Certain Methods of Making Antibodies

1. Certain Hybridoma-Based Methods

The anti-STEAP-1 monoclonal antibodies of the invention can be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized to elicit lymphocytes that produce or are capable of producing antibodies that will specifically bind to the protein used for immunization. Antibodies to STEAP-1 generally are raised in animals by multiple subcutaneous (sc) or intraperitoneal (ip) injections of STEAP-1 and an adjuvant. STEAP-1 may be prepared using methods well-known in the art, some of which are further described herein. For example, STEAP-1 may be produced recombinantly. In one embodiment, animals are immunized with a derivative of STEAP-1 that contains an extracellular portion of STEAP-1 fused to the Fc portion of an immunoglobulin heavy chain. In one embodiment, animals are immunized with an STEAP-1-IgG1 fusion protein. In one embodiment, animals are immunized with immunogenic derivatives of STEAP-1 in a solution with monophosphoryl lipid A (MPL)/trehalose dicrynomycolate (TDM) (Ribi Immunochem. Research, Inc., Hamilton, Mont.), and the solution is injected intradermally at multiple sites. Two weeks later the animals are boosted. Seven to fourteen days later the animals are bled, and the serum is assayed for anti-STEAP-1 titer. Animals are boosted until titer plateaus.

Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In certain embodiments, myeloma cells are those that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies that bind to STEAP-1. Preferably, the binding specificity of monoclonal antibodies produced by hybridoma cells is determined by immunoprecipitation or by an in vitro binding assay, such as radioimmunoassay (RIA) or enzyme-linked immunoadsorbent assay (ELISA). The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

2. Certain Library Screening Methods

Anti-STEAP-1 antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. (2001) in Methods in Molecular Biology 178:1-37 (O'Brien et al., ed., Human Press, Totowa, N.J.), and in certain embodiments, in Lee et al. (2004) J. Mol. Biol. 340:1073-1093.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-STEAP-1 antibodies of the invention can be obtained by designing a suitable antigen screening procedure to select for the phage clone of interest followed by construction of a full length anti-STEAP-1 antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., J. Mol. Biol., 222: 581-597 (1991), or as Fab fragments, in which one chain is fused to pIII and the other is secreted into the bacterial host cell periplasm where, assembly of a Fab-coat protein structure which becomes displayed on the phage surface by displacing some of the wild type coat proteins, e.g. as described in Hoogenboom et al., Nucl. Acids Res., 19: 4133-4137 (1991).

In general, nucleic acids encoding antibody gene fragments are obtained from immune cells harvested from humans or animals. If a library biased in favor of anti-STEAP-1 clones is desired, the subject is immunized with STEAP-1 to generate an antibody response, and spleen cells and/or circulating B cells other peripheral blood lymphocytes (PBLs) are recovered for library construction. In a preferred embodiment, a human antibody gene fragment library biased in favor of anti-STEAP-1 clones is obtained by generating an anti-STEAP-1 antibody response in transgenic mice carrying a functional human immunoglobulin gene array (and lacking a functional endogenous antibody production system) such that STEAP-1 immunization gives rise to B cells producing human antibodies against STEAP-1. The generation of human antibody-producing transgenic mice is described below.

Additional enrichment for anti-STEAP-1 reactive cell populations can be obtained by using a suitable screening procedure to isolate B cells expressing STEAP-1-specific membrane bound antibody, e.g., by cell separation using STEAP-1 affinity chromatography or adsorption of cells to fluorochrome-labeled STEAP-1 followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which STEAP-1 is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). However, for amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes can be derived in vitro from V gene segments. Most of the human VH-gene segments have been cloned and sequenced (reported in Tomlinson et al., J. Mol. Biol., 227: 776-798 (1992)), and mapped (reported in Matsuda et al., Nature Genet., 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, J. Mol. Biol., 227: 381-388 (1992). VH repertoires can also be made with all the sequence diversity focused in a long H3 loop of a single length as described in Barbas et al., Proc. Natl. Acad. Sci. USA, 89: 4457-4461 (1992). Human Vκ and Vλ segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., Gene, 128: 119-126 (1993), or in vivo by combinatorial infection, e.g., the loxP system described in Waterhouse et al., Nucl. Acids Res., 21: 2265-2266 (1993). The in vivo recombination approach exploits the two-chain nature of Fab fragments to overcome the limit on library size imposed by E. coli transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., Proc. Natl. Acad. Sci. USA, 88: 7978-7982 (1991), or assembled together by PCR and then cloned, e.g. as described in Clackson et al., Nature, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity ($K_d^{-1}$ of about $10^6$ to $10^7$ M$^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci. USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of fight chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities of about $10^{-9}$ M or less.

Screening of the libraries can be accomplished by various techniques known in the art. For example, STEAP-1 can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized STEAP-1 under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., Proc. Natl. Acad. Sci. USA, 88: 7978-7982 (1991), or by alkali, e.g. as described in Marks et al., J. Mol. Biol., 222: 581-597 (1991), or by STEAP-1 antigen competition, e.g. in a procedure similar to the antigen competition method of Clackson et al., Nature, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

It is possible to select between phage antibodies of different affinities, even with affinities that differ slightly, for STEAP-1. However, random mutation of a selected antibody (e.g. as performed in some affinity maturation techniques) is likely to give rise to many mutants, most binding to antigen, and a few with higher affinity. With limiting STEAP-1, rare high affinity phage could be competed out. To retain all higher affinity mutants, phages can be incubated with excess biotinylated STEAP-1, but with the biotinylated STEAP-1 at a concentration of lower molarity than the target molar affinity constant for STEAP-1. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-STEAP-1 clones may be selected based on activity. In certain embodiments, the invention provides anti-STEAP-1 antibodies that bind to living cells that naturally express STEAP-1. In one embodiment, the invention provides anti-STEAP-1 antibodies that block the binding between a STEAP-1 ligand and STEAP-1, but do not block the binding between a STEAP-1 ligand and a second protein. Fv clones corresponding to such anti-STEAP-1 antibodies can be selected by (1) isolating anti-STEAP-1 clones from a phage library as described above, and optionally amplifying the isolated population of phage clones by growing up the population in a suitable bacterial host; (2) selecting STEAP-1 and a second protein against which blocking and non-blocking activity, respectively, is desired; (3) adsorbing the anti-STEAP-1 phage clones to immobilized STEAP-1; (4) using an excess of the second protein to elute any undesired clones that recognize STEAP-1-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., Curr. Opinion in Immunol., 5: 256 (1993) and Pluckthun, Immunol. Revs, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-STEAP-1 antibody derived from a hybridoma of the invention can also be modified, for example, by substituting the coding sequence for human heavy- and light-chain constant domains in place of homologous murine sequences derived from the hybridoma clone (e.g. as in the method of Morrison et al., Proc. Natl. Acad. Sci. USA, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

3. Vectors, Host Cells, and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokarvotic Host Cells:

Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes-encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB⁻ strains) provide cytoplasm conditions that are favorable for disulfide bond formation, thereby permitting proper folding and assembly of expressed protein subunits. Proba and Pluckthun Gene, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include Escherichia (e.g., E. coli), Bacilli (e.g., B. subtilis), Enterobacteria, Pseudomonas species (e.g., P. aeruginosa), Salmonella typhimurium, Serratia marcescans, Klebsiella, Proteus, Shigella, Rhizobia, Vitreoscilla, or Paracoccus. In one embodiment, gram-negative cells are used. In one embodiment, E. coli cells are used as hosts for the invention. Examples of E. coli strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli*λ 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. In certain embodiments, for *E. coli* growth, growth temperatures range from about 20° C. to about 39° C.; from about 25° C. to about 37° C.; or about 30° C. The pH of the medium may be any pH ranging from about 5 to about 9, depending mainly on the host organism. In certain embodiments, for *E. coli*, the pH is from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In certain embodiments, the phosphate-limiting medium is the C.R.A.P. medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, and in certain embodiments, about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized can be a column comprising a glass or silica surface, or a controlled pore glass column or a silicic acid column. In some applications, the column is coated with a reagent, such as glycerol, to possibly prevent nonspecific adherence of contaminants.

As the first step of purification, a preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies Using Eukaryotic Host Cells:

A vector for use in a eukaryotic host cell generally includes one or more of the following non-limiting components: a signal sequence, an origin of replication, one or more marker genes, an enhancer element, a promoter, and a transcription termination sequence.

Signal Sequence Component

A vector for use in a eukaryotic host cell may also contain a signal sequence or other polypeptide having a specific cleavage site at the N-terminus of the mature protein or polypeptide of interest. The heterologous signal sequence selected may be one that is recognized and processed (i.e., cleaved by a signal peptidase) by the host cell. In mammalian cell expression, mammalian signal sequences as well as viral secretory leaders, for example, the herpes simplex gD signal, are available. The DNA for such a precursor region is ligated in reading frame to DNA encoding the antibody.

Origin of Replication

Generally, an origin of replication component is not needed for mammalian expression vectors. For example, the SV40 origin may typically be used only because it contains the early promoter.

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, in some embodiments, cells transformed with the DHFR selection gene are first identified by culturing all of the transformants in a culture medium that contains methotrexate (Mtx), a competitive antagonist of DHFR. In some embodiments, an appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

Promoter Component

Expression and cloning vectors usually contain a promoter that is recognized by the host organism and is operably linked to nucleic acid encoding a polypeptide of interest (e.g., an antibody). Promoter sequences are known for eukaryotes. For example, virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. In certain embodiments, any or all of these sequences may be suitably inserted into eukaryotic expression vectors.

Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982), describing expression of human β-interferon cDNA in mouse cells under the control of a thymidine kinase promoter from herpes simplex virus. Alternatively, the Rous Sarcoma Virus long terminal repeat can be used as the promoter.

Enhancer Element Component

Transcription of DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) describing enhancer elements for activation of eukaryotic promoters. The enhancer may be spliced into the vector at a position 5' or 3' to the antibody polypeptide-encoding sequence, but is generally located at a site 5' from the promoter.

Transcription Termination Component

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described-expression or cloning vectors for antibody production and cultured in conventional nutrient media modified as appropriate for inducing promoters, selecting transformants, or amplifying the genes encoding the desired sequences.

Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Antibody

When using recombinant techniques, the antibody can be produced intracellularly, or directly secreted into the medium. If the antibody is produced intracellularly, as a first step, the particulate debris, either host cells or lysed fragments, may be removed, for example, by centrifugation or ultrafiltration. Where the antibody is secreted into the medium, supernatants from such expression systems may be first concentrated using a commercially available protein concentration filter, for example, an Amicon or Millipore Pellicon ultrafiltration unit. A protease inhibitor such as PMSF may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a convenient technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Methods 62:1-13 (1983)). Protein G is recommended for all mouse isotypes and for human γ3 (Guss et al., EMBO J. 5:15671575 (1986)). The matrix to which the affinity ligand is attached may be agarose, but other matrices are available. Mechanically stable matrices such as controlled pore glass or poly(styrenedivinyl) benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification, for example, by low pH hydrophobic interaction chromatography using an elution buffer at a pH between about 2.5-4.5, preferably performed at low salt concentrations (e.g., from about 0-0.25M salt).

In general, various methodologies for preparing antibodies for use in research, testing, and clinical use are well-established in the art, consistent with the above-described methodologies and/or as deemed appropriate by one skilled in the art for a particular antibody of interest.

Immunoconjugates

The invention also provides immunoconjugates (interchangeably referred to as "antibody-drug conjugates," or "ADCs") comprising any of the anti-STEAP-1 antibodies of the invention conjugated to one or more cytotoxic agents, such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

In certain embodiments, an immunoconjugate comprises an anti-STEAP-1 antibody and a chemotherapeutic agent or other toxin. Chemotherapeutic agents useful in the generation of immunoconjugates are described herein (e.g., above). Enzymatically active toxins and fragments thereof can also be used and are described herein.

In certain embodiments, an immunoconjugate comprises an anti-STEAP-1 antibody and one or more small molecule toxins, including, but not limited to, small molecule drugs such as a calicheamicin, maytansinoid, dolastatin, auristatin, trichothecene, and CC1065, and the derivatives of these drugs that have cytotoxic activity. Examples of such immunoconjugates are discussed in further detail below.

1. Exemplary Immunoconjugates

An immunoconjugate (or "antibody-drug conjugate" ("ADC")) of the invention may be of Formula I, below, wherein an anti-STEAP-1 antibody is conjugated (i.e., covalently attached) to one or more drug moieties (D) through an optional linker (L).

Ab-(L-D)$_p$     Formula I

Accordingly, the anti-STEAP-1 antibody may be conjugated to the drug either directly or via a linker. In Formula I, p is the average number of drug moieties per antibody, which can range, e.g., from about 1 to about 20 drug moieties per antibody, and in certain embodiments, from 1 to about 8 drug moieties per antibody.

Exemplary Linkers

Exemplary linkers and drug moieties are disclosed herein. A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), N-succinimidyl 4-(N-maleimidomethyl)cyclohexane-1 carboxylate ("SMCC"), N-Succinimidyl (4-iodo-acetyl)aminobenzoate ("SIAB"), and ethyleneoxy —CH$_2$CH$_2$O— as one or more repeating units ("EO" or "PEO"). Various linker components are known in the art, some of which are described below.

A linker may be a "cleavable linker," facilitating release of a drug in the cell. For example, an acid-labile linker (e.g., hydrazone), protease-sensitive (e.g., peptidase-sensitive) linker, photolabile linker, dimethyl linker or disulfide-containing linker (Chari et al., Cancer Research 52:127-131 (1992); U.S. Pat. No. 5,208,020) may be used.

In one embodiment, linker L of an ADC has the formula:

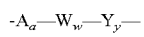

-A$_a$—W$_w$—Y$_y$— wherein:
-A- is a Stretcher unit covalently attached to a cysteine thiol of the antibody (Ab);
a is 0 or 1;
each —W— is independently an Amino Acid unit;
w is independently an integer ranging from 0 to 12;
—Y— is a Spacer unit covalently attached to the drug moiety; and
y is 0, 1 or 2.

Stretcher Unit

The Stretcher unit (-A-), when present, is capable of linking an antibody unit to an amino acid unit (—W—). In this regard an antibody (Ab) has a free cysteine thiol group that can form a bond with an electrophilic functional group of a Stretcher Unit. Exemplary stretcher units in Formula I conjugates are depicted by Formulas II and III, wherein Ab-, —W—, —Y—, -D, w and y are as defined above, and R$^{17}$ is a divalent radical selected from (CH$_2$)$_r$—, C$_3$-C$_8$ carbocyclyl, O—(CH$_2$)$_r$, arylene, (CH$_2$)$_r$-arylene, -arylene-(CH$_2$)$_r$—, (CH$_2$)$_r$—(C$_3$-C$_8$ carbocyclyl), (C$_3$-C$_8$ carbocyclyl)-(CH$_2$)$_r$, C$_3$-C$_8$ heterocyclyl, (CH$_2$)$_r$—(C$_3$-C$_8$ heterocyclyl), —(C$_3$-C$_8$ heterocyclyl)-(CH$_2$)$_r$—, —(CH$_2$)$_r$C(O)NR$^b$(CH$_2$)$_r$—, —(CH$_2$CH$_2$O)$_r$—, —(CH$_2$CH$_2$O)$_r$—CH$_2$—, —(CH$_2$)$_r$C(O)NR(CH$_2$CH$_2$O)$_r$—, —(CH$_2$)$_r$C(O)NR$^b$(CH$_2$CH$_2$O)$_r$—CH$_2$—, —(CH$_2$CH$_2$O)$_r$C(O)NR$^b$(CH$_2$CH$_2$O)$_r$, —(CH$_2$CH$_2$O)$_r$C(O)NR$^b$(CH$_2$CH$_2$O)$_r$—CH$_2$—, and —(CH$_2$CH$_2$O)$_r$C(O)NR$^b$(CH$_2$)$_r$—; where R$^b$ is H, C$_1$-C$_6$ alkyl, phenyl, or benzyl; and r is independently an integer ranging from 1-10.

Arylene includes divalent aromatic hydrocarbon radicals of 6-20 carbon atoms derived by the removal of two hydrogen atoms from the aromatic ring system. Typical arylene groups include, but are not limited to, radicals derived from benzene, substituted benzene, naphthalene, anthracene, biphenyl, and the like.

Heterocyclyl groups include a ring system in which one or more ring atoms is a heteroatom, e.g. nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4Ah-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

Carbocyclyl groups include a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

It is to be understood from all the exemplary embodiments of Formula I ADC such as II-VI, that even where not denoted expressly, from 1 to 4 drug moieties are linked to an antibody (p=1-4), depending on the number of engineered cysteine residues.

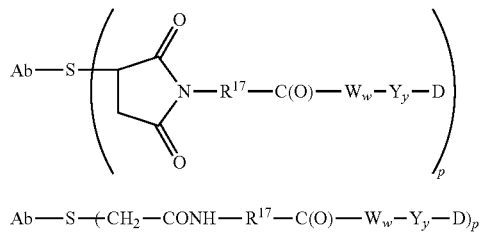

II

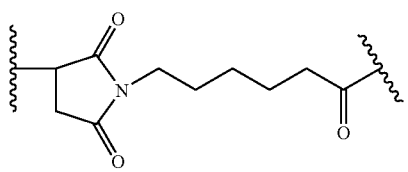

III

An illustrative Formula II Stretcher unit is derived from maleimido-caproyl (MC) wherein $R^{17}$ is —(CH$_2$)$_5$—:

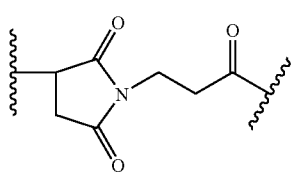

MC

An illustrative Stretcher unit of Formula II, and is derived from maleimido-propanoyl (MP) wherein $R^{17}$ is —(CH$_2$)$_2$—:

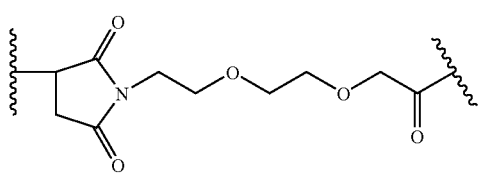

MP

Another illustrative Stretcher unit of Formula II wherein $R^{17}$ is —(CH$_2$CH$_2$O)$_r$—CH$_2$— and r is 2:

Another illustrative Stretcher unit of Formula II wherein $R^{17}$ is —(CH$_2$)$_r$C(O)NR$^b$(CH$_2$CH$_2$O)$_r$—CH$_2$— where $R^b$ is H and each r is 2:

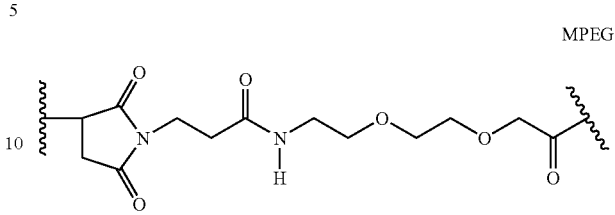

MPEG

An illustrative Stretcher unit of Formula III wherein $R^{17}$ is —(CH$_2$)$_5$—:

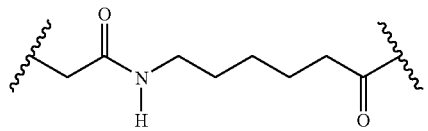

In another embodiment, the Stretcher unit is linked to the cysteine engineered anti-_antibody via a disulfide bond between the engineered cystein sulfur atom of the antibody and a sulfur atom of the Stretcher unit. A representative Stretcher unit of this embodiment is depicted by Formula IV, wherein R17, Ab-, —W—, —Y—, -D, w and y are as defined above.

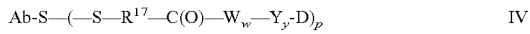   IV

In yet another embodiment, the reactive group of the Stretcher contains a thiol-reactive functional group that can form a bond with a free cysteine thiol of an antibody. Examples of thiol-reaction functional groups include, but are not limited to, maleimide, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted by Formulas Va and Vb, wherein —$R^{17}$—, Ab-, —W—, —Y—, -D, w and y are as defined above;

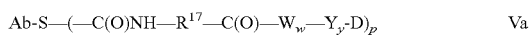   Va

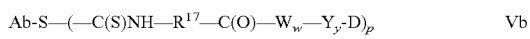   Vb

In another embodiment, the linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11: 1761-1768; King (2002) Tetrahedron Letters 43:1987-1990). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

Amino Acid Unit

The linker may comprise amino acid residues. The Amino Acid unit (—W$_w$—), when present, links the antibody (Ab) to the drug moiety (D) of the cysteine engineered antibody-drug conjugate (ADC) of the invention.

—W$_w$— is a dipeptide, tripeptide, tetrapeptide, pentapeptide, hexapeptide, heptapeptide, octapeptide, nonapeptide, decapeptide, undecapeptide or dodecapeptide unit. Amino acid residues which comprise the Amino Acid unit include those occurring naturally, as well as minor amino acids and non-naturally occurring amino acid analogs, such as citrulline. Each —W— unit independently has the formula denoted below in the square brackets, and w is an integer ranging from 0 to 12:

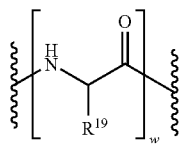

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3$ $NHCHO$, —$(CH_2)_4NHC(=NH)NH_2$, —$(CH_2)_4NH_2$, $(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

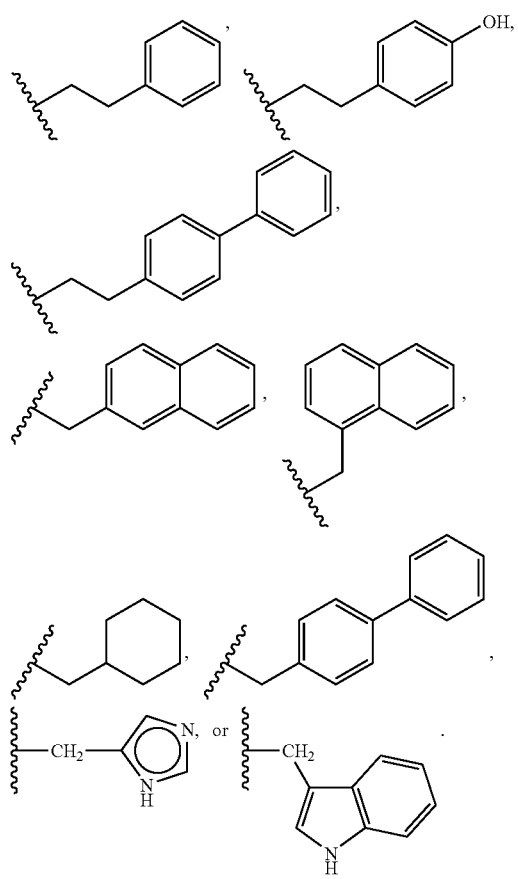

When $R^{19}$ is other than hydrogen, the carbon atom to which $R^{19}$ is attached is chiral. Each carbon atom to which $R^{19}$ is attached is independently in the (S) or (R) configuration, or a racemic mixture. Amino acid units may thus be enantiomerically pure, racemic, or diastereomeric.

Exemplary —$W_w$— Amino Acid units include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline.

The Amino Acid unit can be enzymatically cleaved by one or more enzymes, including a tumor-associated protease, to liberate the Drug moiety (-D), which in one embodiment is protonated in vivo upon release to provide a Drug (D). Amino acid linker components can be designed and optimized in their selectivity for enzymatic cleavage by a particular enzymes, for example, a tumor-associated protease, cathepsin B, C and D, or a plasmin protease.

Spacer Unit

The Spacer unit (—$Y_y$—), when present (y=1 or 2), links an Amino Acid unit (—$W_w$—) to the drug moiety (D) when an Amino Acid unit is present (w=1-12). Alternately, the Spacer unit links the Stretcher unit to the Drug moiety when the Amino Acid unit is absent. The Spacer unit also links the drug moiety to the antibody unit when both the Amino Acid unit and Stretcher unit are absent (w, y=0). Spacer units are of two general types: self-immolative and non self-immolative. A non self-immolative Spacer unit is one in which part or all of the Spacer unit remains bound to the Drug moiety after cleavage, particularly enzymatic, of an Amino Acid unit from the antibody-drug conjugate or the Drug moiety-linker. When an ADC containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from Ab-$A_a$-Ww—. In one embodiment, an independent hydrolysis reaction takes place within the target cell, cleaving the glycine-Drug moiety bond and liberating the Drug.

In another embodiment, —$Y_y$— is a p-aminobenzylcarbamoyl (PAB) unit whose phenylene portion is substituted with $Q_m$ wherein Q is —$C_1$-$C_8$ alkyl, —O—($C_1$-$C_8$ alkyl), -halogen, -nitro or -cyano; and m is an integer ranging from 0-4.

Exemplary embodiments of a non self-immolative Spacer unit (—Y—) are: -Gly-Gly-; -Gly-; -Ala-Phe-; -Val-Cit-.

In one embodiment, a Drug moiety-linker or an ADC is provided in which the Spacer unit is absent (y=0), or a pharmaceutically acceptable salt or solvate thereof.

Alternatively, an ADC containing a self-immolative Spacer unit can release -D. In one embodiment, —Y— is a PAB group that is linked to —$W_w$— via the amino nitrogen atom of the PAB group, and connected directly to -D via a carbonate, carbamate or ether group, where the ADC has the exemplary structure:

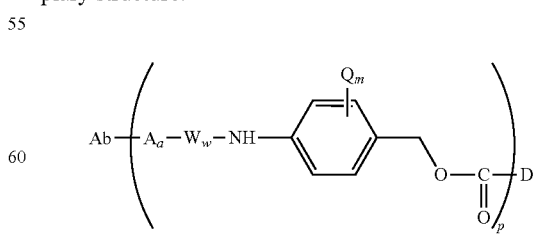

wherein Q is —$C_1$-$C_8$ alkyl, —O—($C_1$-$C_8$ alkyl), -halogen, -nitro or -cyano; m is an integer ranging from 0-4; and p ranges from 1 to 4.

Other examples of self-immolative spacers include, but are not limited to, aromatic compounds that are electronically similar to the PAB group such as 2-aminoimidazol-5-methanol derivatives (Hay et al. (1999) Bioorg. Med. Chem. Lett. 9:2237), heterocyclic PAB analogs (US 2005/0256030), beta-glucuronide (WO 2007/011968), and ortho or para-aminobenzylacetals. Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacer useful in ADCs.

Exemplary Spacer units (—$Y_{y'}$—) are represented by Formulas X-XII:

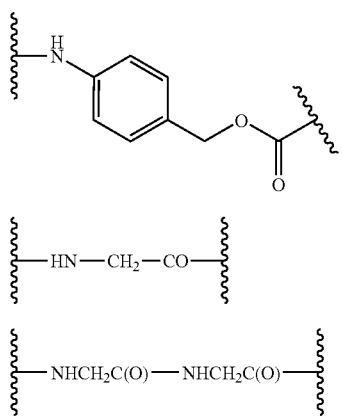

Dendritic Linkers

In another embodiment, linker L may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker. Exemplary embodiments of branched, dendritic linkers include 2,6-bis(hydroxymethyl)-p-cresol and 2,4,6-tris(hydroxymethyl)-phenol dendrimer units (WO 2004/01993; Szalai et al (2003) J. Amer. Chem. Soc. 125: 15688-15689; Shamis et al (2004) J. Amer. Chem. Soc. 126: 1726-1731; Amir et al (2003) Angew. Chem. Int. Ed. 42:4494-4499).

In one embodiment, the Spacer unit is a branched bis (hydroxymethyl)styrene (BHMS), which can be used to incorporate and release multiple drugs, having the structure:

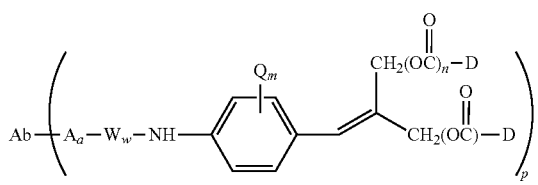

comprising a 2-(4-aminobenzylidene)propane-1,3-diol dendrimer unit (WO 2004/043493; de Groot et al (2003) Angew. Chem. Int. Ed. 42:4490-4494), wherein Q is —$C_1$-$C_8$ alkyl, —O—($C_1$-$C_8$ alkyl), -halogen, -nitro or -cyano; m is an integer ranging from 0-4; n is 0 or 1; and p ranges ranging from 1 to 4.

Exemplary embodiments of the Formula I antibody-drug conjugate compounds include XIIIa (MC), XIIIb (val-cit), XIIIc (MC-val-cit), and XIIId (MC-val-cit-PAB):

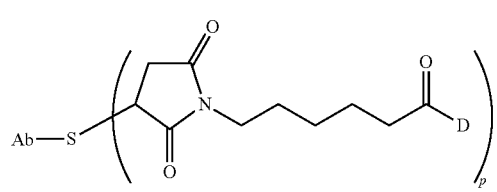

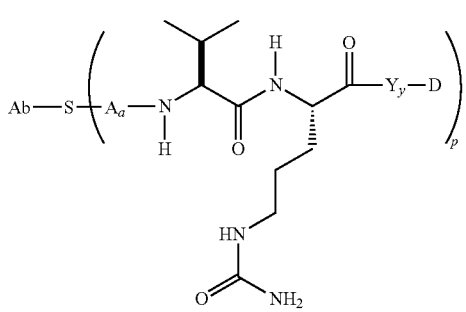

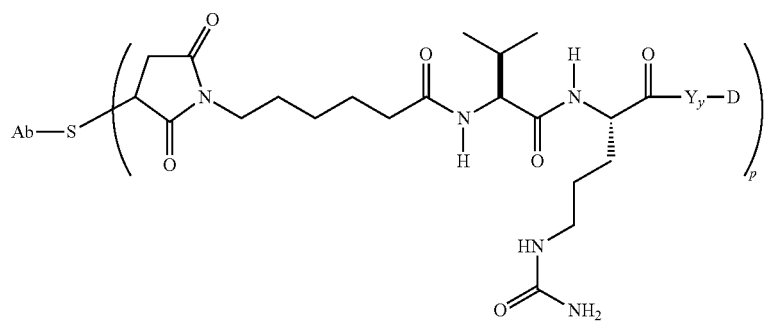

Other exemplary embodiments of the Formula Ia antibody-drug conjugate compounds include XIVa-e:

XIVa

XIVb

XIVc

XIVd

XIVe where X is:

—CH₂—⟨cyclohexyl⟩—, —(CH$_2$)$_n$—,

—(CH$_2$CH$_2$O)$_n$—,

—CH$_2$—⟨cyclohexyl⟩—C(O)—N(R)—(CH$_2$)$_n$—,

—⟨phenyl⟩—, —⟨phenyl⟩—(CH$_2$)$_n$—, or

—(CH$_2$)$_n$—C(O)—N(R)—(CH$_2$)$_n$—;

Y is:

—N(R)—⟨phenyl⟩— or —N(R)—(CH$_2$)$_n$—;

and R is independently H or $C_1$-$C_6$ alkyl; and n is 1 to 12.

In another embodiment, a Linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Typically, peptide-type Linkers can be prepared by forming a peptide bond between two or more amino acids and/or peptide fragments. Such peptide bonds can be prepared, for example, according to the liquid phase synthesis method (E. Schröder and K. Lübke (1965) "The Peptides", volume 1, pp 76-136, Academic Press) which is well known in the field of peptide chemistry. Linker intermediates may be assembled with any combination or sequence of reactions including Spacer, Stretcher, and Amino Acid units. The Spacer, Stretcher, and Amino Acid units may employ reactive functional groups which are electrophilic, nucleophilic, or free radical in nature. Reactive functional groups include, but are not limited to carboxyls, hydroxyls, para-nitrophenylcarbonate, isothiocyanate, and leaving groups, such as O-mesyl, O-tosyl, —Cl, —Br, —I; or maleimide.

In another embodiment, the Linker may be substituted with groups which modulated solubility or reactivity. For example, a charged substituent such as sulfonate (—SO$_3^-$) or ammonium, may increase water solubility of the reagent and facilitate the coupling reaction of the linker reagent with the antibody or the drug moiety, or facilitate the coupling reaction of Ab-L (antibody-linker intermediate) with D, or D-L (drug-linker intermediate) with Ab, depending on the synthetic route employed to prepare the ADC.

Exemplary Drug Moieties

Maytansine and Maytansinoids

In some embodiments, an immunoconjugate comprises an antibody of the invention conjugated to one or more maytansinoid molecules. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Maytansine compounds suitable for use as maytansinoid drug moieties are well known in the art and can be isolated from natural sources according to known methods or produced using genetic engineering techniques (see Yu et al (2002) PNAS 99:7968-7973). Maytansinol and maytansinol analogues may also be prepared synthetically according to known methods.

Exemplary embodiments of maytansinoid drug moieities include: DM1; DM3; and DM4, as disclosed herein.

Auristatins and Dolastatins

In some embodiments, an immunoconjugate comprises an antibody of the invention conjugated to dolastatin or a dolastatin peptidic analog or derivative, e.g., an auristatin (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in Senter et al, Proceedings of the American Association for Cancer Research, Volume 45, Abstract Number 623, presented Mar. 28, 2004, the disclosure of which is expressly incorporated by reference in its entirety.

A peptidic drug moiety may be selected from Formulas $D_E$ and $D_F$ below:

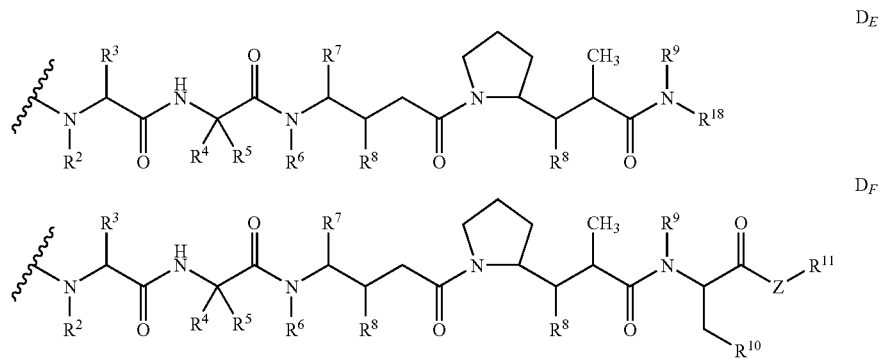

wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or $(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —OCH$_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —OCH$_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —CH($R^{15}$)$_2$, wherein $R^{15}$ is —(CH$_2$)$_n$—N($R^{16}$)$_2$, and $R^{16}$ is —C$_1$-C$_8$ alkyl or —(CH$_2$)$_n$—COOH.

In another embodiment, when Z is —NH, $R^{11}$ is —CH($R^5$)$_2$, wherein $R^{15}$ is —(CH$_2$)$_n$—SO$_3$H.

An exemplary auristatin embodiment of formula $D_E$ is MMAE, wherein the wavy line indicates the covalent attachment to a linker (L) of an antibody-drug conjugate:

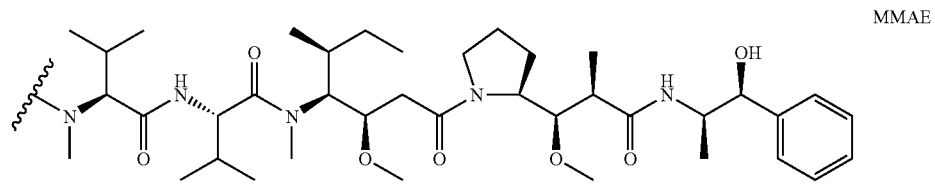 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

An exemplary auristatin embodiment of formula $D_F$ is MMAF, wherein the wavy line indicates the covalent attachment to a linker (L) of an antibody-drug conjugate (see US 2005/0238649 and Doronina et al. (2006) *Bioconjugate Chem.* 17:114-124):

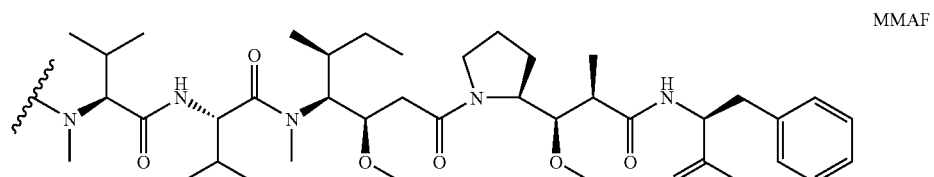

MMAF

Other drug moieties include the following MMAF derivatives, wherein the wavy line indicates the covalent attachment to a linker (L) of an antibody-drug conjugate:

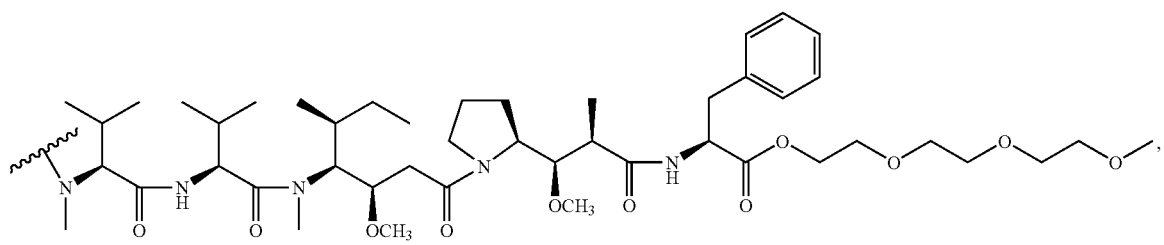

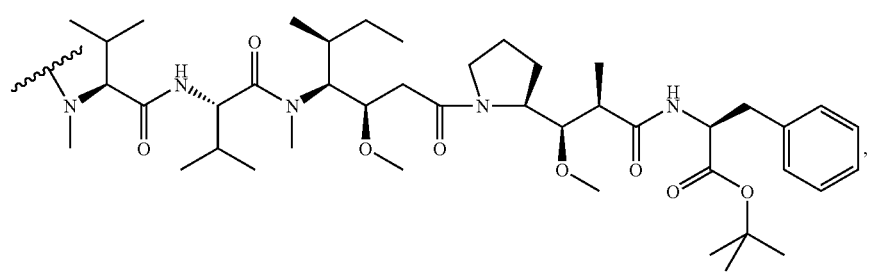

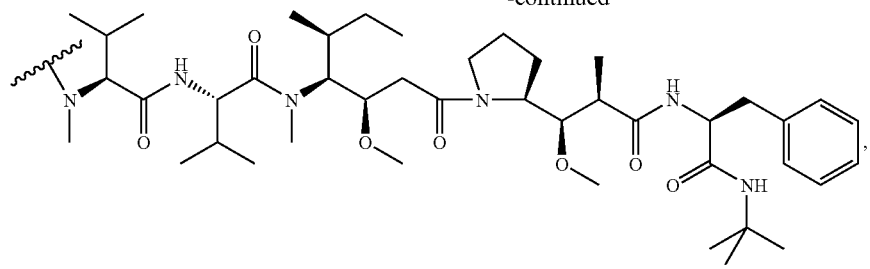
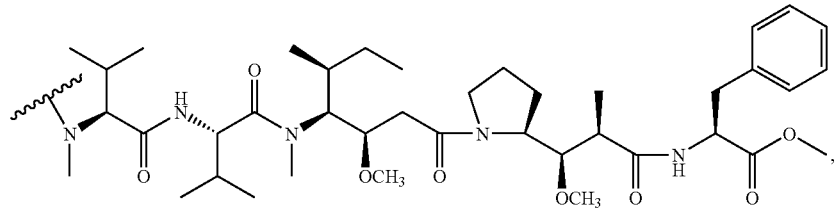
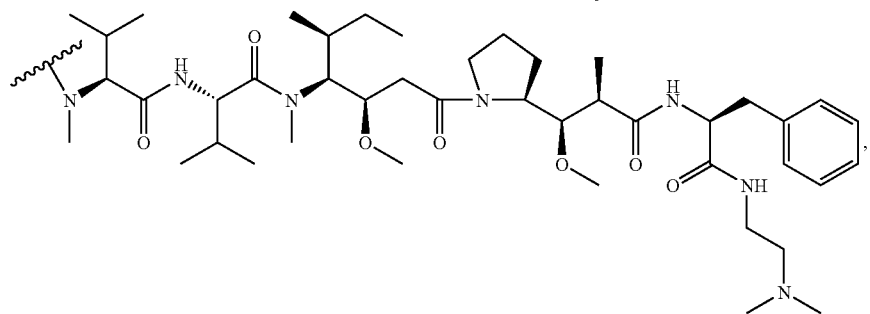
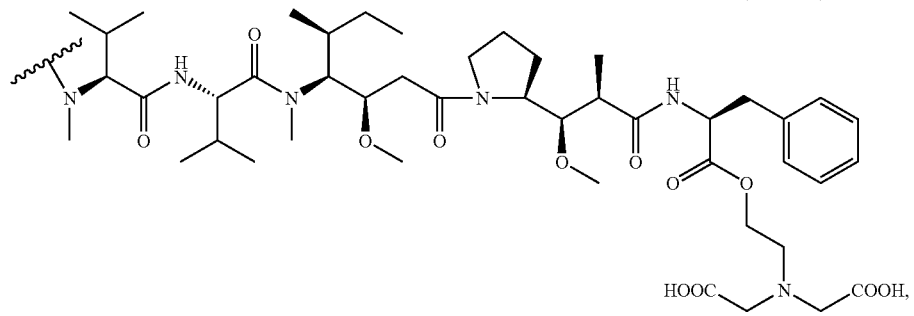
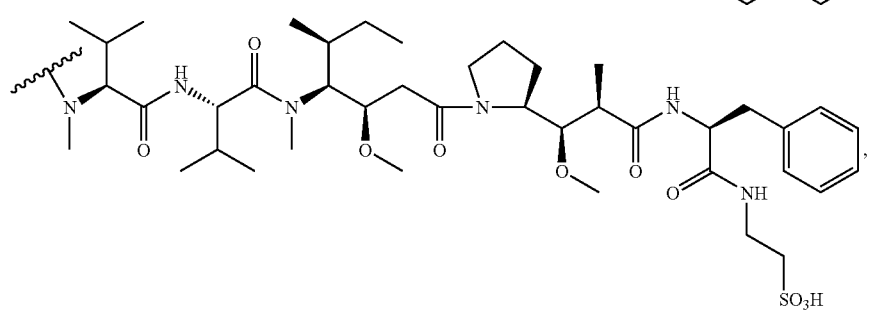
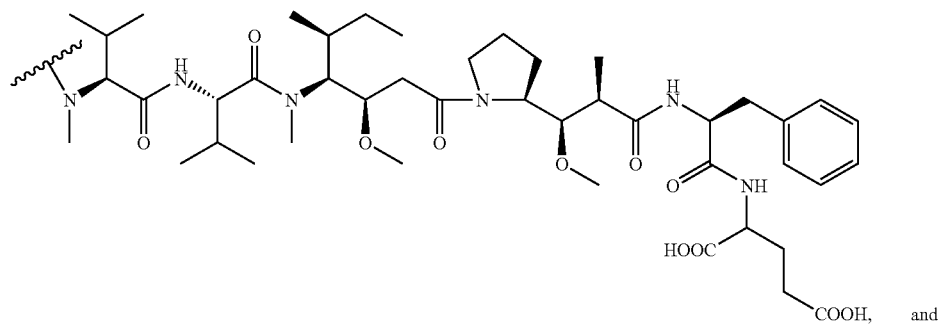
and

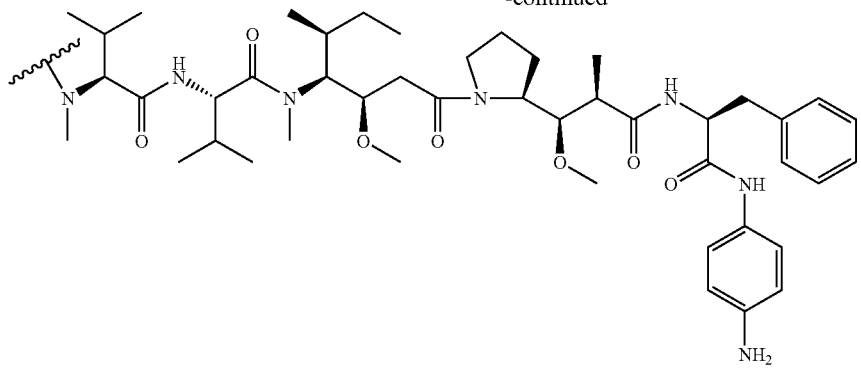

In one aspect, hydrophilic groups including but not limited to, triethylene glycol esters (TEG), as shown above, can be attached to the drug moiety at $R^{11}$. Without being bound by any particular theory, the hydrophilic groups assist in the internalization and non-agglomeration of the drug moiety.

Exemplary embodiments of ADCs of Formula I comprising an auristatin/dolastatin or derivative thereof are described in US 2005-0238649 A1 and Doronina et al. (2006) Bioconjugate Chem. 17:114-124, which is expressly incorporated herein by reference. Exemplary embodiments of ADCs of Formula I comprising MMAE or MMAF and various linker components have the following structures and abbreviations (wherein "Ab" is an antibody; p is 1 to about 8, "Val-Cit" is a valine-citrulline dipeptide; and "S" is a sulfur atom:

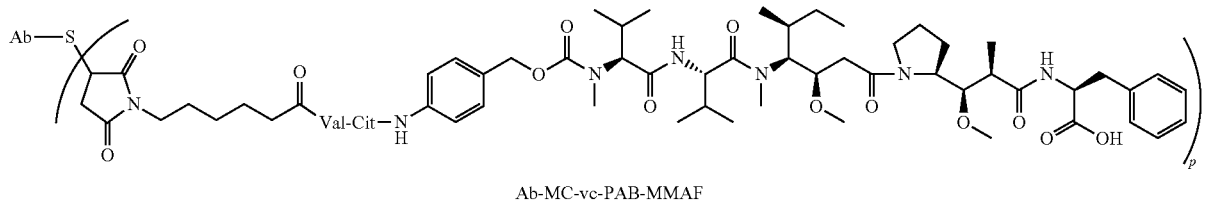

Ab-MC-vc-PAB-MMAF

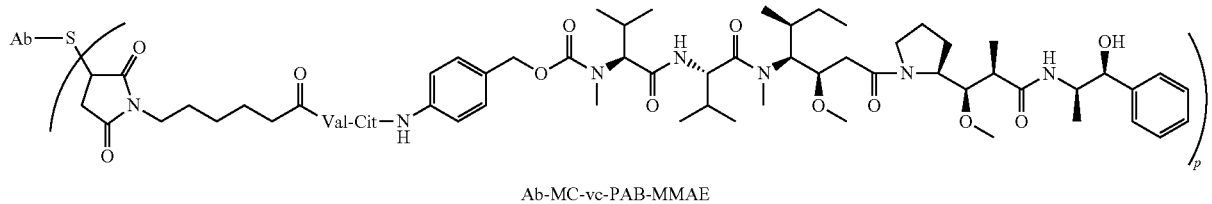

Ab-MC-vc-PAB-MMAE

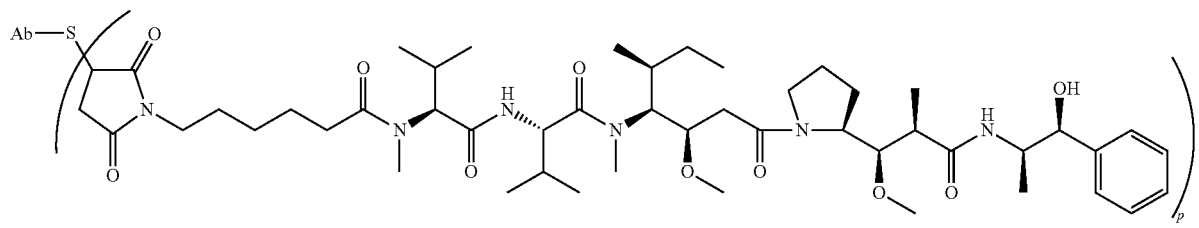

Ab-MC-MMAE

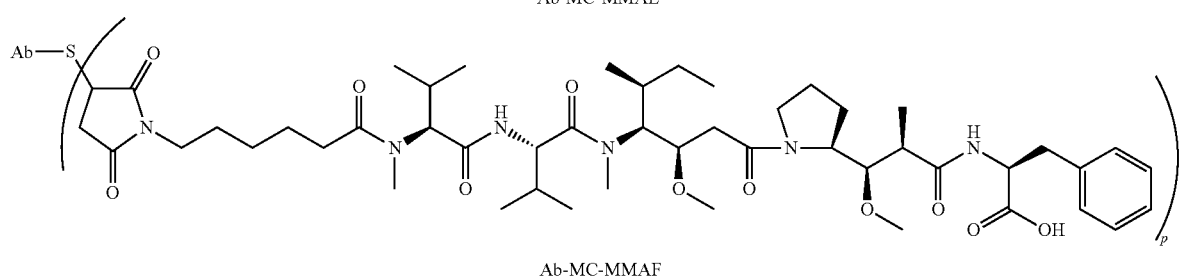

Ab-MC-MMAF

Exemplary embodiments of ADCs of Formula I comprising MMAF and various linker components further include Ab-MC-PAB-MMAF and Ab-PAB-MMAF. Interestingly, immunoconjugates comprising MMAF attached to an antibody by a linker that is not proteolytically cleavable have been shown to possess activity comparable to immunoconjugates comprising MMAF attached to an antibody by a proteolytically cleavable linker. See, Doronina et al. (2006) Bioconjugate Chem. 17:114-124. In such instances, drug release is believed to be effected by antibody degradation in the cell. Id.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. Auristatin/dolastatin drug moieties may be prepared according to the methods of: US 2005-0238649 A1; U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat. Biotechnol. 21(7):778-784.

In particular, auristatin/dolastatin drug moieties of formula $D_F$, such as MMAF and derivatives thereof, may be prepared using methods described in US 2005-0238649 A1 and Doronina et al. (2006) Bioconjugate Chem. 17:114-124. Auristatin/dolastatin drug moieties of formula $D_E$, such as MMAE and derivatives thereof, may be prepared using methods described in Doronina et al. (2003) Nat. Biotech. 21:778-784. Drug-linker moieties MC-MMAF, MC-MMAE, MC-vc-PAB-MMAF, and MC-vc-PAB-MMAE may be conveniently synthesized by routine methods, e.g., as described in Doronina et al. (2003) Nat. Biotech. 21:778-784, and Patent Application Publication No. US 2005/0238649 A1, and then conjugated to an antibody of interest.

Drug Loading

Drug loading is represented by p and is the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See US 2005-0238649 A1 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

Certain Methods of Preparing Immunconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in US 20050238649 A1, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic subsituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such an aldehyde can be reacted with a drug moiety or linker nucleophile.

Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

The compounds of the invention expressly contemplate, but are not limited to, ADC prepared with the following cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A; see pages 467-498, 2003-2004 Applications Handbook and Catalog.

Immunoconjugates comprising an antibody and a cytotoxic agent may also be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Alternatively, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Preparation of Cysteine Engineered Anti-STEAP-1 Antibodies

The design, selection, and preparation methods of the invention further enable cysteine engineered anti-STEAP-1 antibodies which are reactive with electrophilic functionality. These methods further enable antibody conjugate compounds such as antibody-drug conjugate (ADC) compounds with drug molecules at designated, designed, selective sites. Reactive cysteine residues on an antibody surface allow specifically conjugating a drug moiety through a thiol reactive group such as maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London). The amount of free thiol in a protein may be estimated by the standard Ellman's assay. Immunoglobulin M is an example of a disulfide-linked pentamer, while immunoglobulin G is an example of a protein with internal disulfide bridges bonding the subunits together. In proteins such as this, reduction of the disulfide bonds with a reagent such as dithiothreitol (DTT) or selenol (Singh et al (2002) Anal. Biochem. 304:147-156) is required to generate the reactive free thiol. This approach may result in loss of antibody tertiary structure and antigen binding specificity.

The Pheselector (Phage ELISA for Selection of Reactive Thiols) Assay allows for detection of reactive cysteine groups in antibodies in an ELISA phage format thereby assisting in the design of cysteine engineered antibodies (WO 2006/034488). The cysteine engineered antibody is coated on well surfaces, followed by incubation with phage particles, addition of HRP labeled secondary antibody, and absorbance detection. Mutant proteins displayed on phage may be screened in a rapid, robust, and high-throughput manner. Libraries of cysteine engineered antibodies can be produced and subjected to binding selection using the same approach to identify appropriately reactive sites of free Cys incorporation from random protein-phage libraries of antibodies or other proteins. This technique includes reacting cysteine mutant proteins displayed on phage with an affinity reagent or reporter group which is also thiol-reactive.

The PHESELECTOR assay allows screening of reactive thiol groups in antibodies. Identification of the A121C variant by this method is exemplary. The entire Fab molecule may be effectively searched to identify more ThioFab variants with reactive thiol groups. A parameter, fractional surface accessibility, was employed to identify and quantitate the accessibility of solvent to the amino acid residues in a polypeptide. The surface accessibility can be expressed as the surface area ($Å^2$) that can be contacted by a solvent molecule, e.g. water. The occupied space of water is approximated as a 1.4 Å radius sphere. Software is freely available or licensable (Secretary to CCP4, Daresbury Laboratory, Warrington, WA4 4AD, United Kingdom, Fax: (+44) 1925 603825, or by internet: www.ccp4.ac.uk/dist/html/INDEX.html) as the CCP4 Suite of crystallography programs which employ algorithms to calculate the surface accessibility of each amino acid of a protein with known x-ray crystallography derived coordinates ("The CCP4 Suite: Programs for Protein Crystallography" (1994) Acta. Cryst. D50:760-763). Two exemplary software modules that perform surface accessibility calculations are "AREAIMOL" and "SURFACE", based on the algorithms of B. Lee and F. M. Richards (1971) J. Mol. Biol. 55:379-400. AREAIMOL defines the solvent accessible surface of a protein as the locus of the centre of a probe sphere (representing a solvent molecule) as it rolls over the Van der Waals surface of the protein. AREAIMOL calculates the solvent accessible surface area by generating surface points on an extended sphere about each atom (at a distance from the atom centre equal to the sum of the atom and probe radii), and eliminating those that lie within equivalent spheres associated with neighboring atoms. AREAIMOL finds the solvent accessible area of atoms in a PDB coordinate file, and summarizes the accessible area by residue, by chain and for the whole molecule. Accessible areas (or area differences) for individual atoms can be written to a pseudo-PDB output file. AREAIMOL assumes a single radius for each element, and only recognizes a limited number of different elements.

AREAIMOL and SURFACE report absolute accessibilities, i.e. the number of square Angstroms (Å). Fractional surface accessibility is calculated by reference to a standard state relevant for an amino acid within a polypeptide. The reference state is tripeptide Gly-X-Gly, where X is the amino acid of interest, and the reference state should be an 'extended' conformation, i.e. like those in beta-strands. The extended conformation maximizes the accessibility of X. A calculated accessible area is divided by the accessible area in a Gly-X-Gly tripeptide reference state and reports the quotient, which is the fractional accessibility. Percent accessibility is fractional accessibility multiplied by 100. Another exemplary algorithm for calculating surface accessibility is based on the SOLV module of the program xsae (Broger, C., F. Hoffman-LaRoche, Basel) which calculates fractional accessibility of an amino acid residue to a water sphere based on the X-ray coordinates of the polypeptide. The fractional surface accessibility for every amino acid in an antibody may be calculated using available crystal structure information (Eigenbrot et al. (1993) J Mol. Biol. 229:969-995).

DNA encoding the cysteine engineered antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as *E. coli* cells, simian COS cells, Chinese Hamster Ovary (CHO) cells, or other mammalian host cells, such as myeloma cells (U.S. Pat. No. 5,807,715; US 2005/0048572; US 2004/0229310) that do not otherwise produce the antibody protein, to obtain the synthesis of monoclonal antibodies in the recombinant host cells.

After design and selection, cysteine engineered antibodies, e.g. ThioFabs, with the engineered, highly reactive unpaired Cys residues, may be produced by: (i) expression in a bacterial, e.g. *E. coli*, system (Skerra et al (1993) Curr. Opinion in Immunol. 5:256-262; Plückthun (1992) Immunol. Revs. 130: 151-188) or a mammalian cell culture system (WO 01/00245), e.g. Chinese Hamster Ovary cells (CHO); and (ii) purification using common protein purification techniques (Lowman et al (1991) J. Biol. Chem. 266(17):10982-10988).

The engineered Cys thiol groups react with electrophilic linker reagents and drug-linker intermediates to form cysteine engineered antibody drug conjugates and other labelled cysteine engineered antibodies. Cys residues of cysteine engineered antibodies, and present in the parent antibodies, which are paired and form interchain and intrachain disulfide bonds do not have any reactive thiol groups (unless treated with a reducing agent) and do not react with electrophilic linker reagents or drug-linker intermediates. The newly engineered Cys residue, can remain unpaired, and able to react with, i.e. conjugate to, an electrophilic linker reagent or drug-linker intermediate, such as a drug-maleimide. Exemplary drug-linker intermediates include: MC-MMAE, MC-MMAF, MC-vc-PAB-MMAE, and MC-vc-PAB-MMAF. The structure positions of the engineered Cys residues of the heavy and light chains are numbered according to a sequential numbering system. This sequential numbering system is correlated to the Kabat numbering system (Kabat et al., (1991) Sequences of Proteins of Immunological Interest, 5th Ed. Public Health Service, National Institutes of Health, Bethesda, Md.) starting at the N-terminus, differs from the Kabat numbering scheme (bottom row) by insertions noted by a, b, c. Using the Kabat numbering system, the actual linear amino acid sequence may contain fewer or additional amino acids corresponding to a shortening of, or insertion into, a FR or CDR of the variable domain. The cysteine engineered heavy chain variant sites are identified by the sequential numbering and Kabat numbering schemes.

In one embodiment, the cysteine engineered anti-STEAP-1 antibody is prepared by a process comprising:
  (a) replacing one or more amino acid residues of a parent anti-STEAP-1 antibody by cysteine; and
  (b) determining the thiol reactivity of the cysteine engineered anti-STEAP-1 antibody by reacting the cysteine engineered antibody with a thiol-reactive reagent.

The cysteine engineered antibody may be more reactive than the parent antibody with the thiol-reactive reagent.

The free cysteine amino acid residues may be located in the heavy or light chains, or in the constant or variable domains. Antibody fragments, e.g. Fab, may also be engineered with one or more cysteine amino acids replacing amino acids of the antibody fragment, to form cysteine engineered antibody fragments.

Another embodiment of the invention provides a method of preparing (making) a cysteine engineered anti-STEAP-1 antibody, comprising:

(a) introducing one or more cysteine amino acids into a parent anti-STEAP-1 antibody in order to generate the cysteine engineered anti-STEAP-1 antibody; and (b) determining the thiol reactivity of the cysteine engineered antibody with a thiol-reactive reagent;

wherein the cysteine engineered antibody is more reactive than the parent antibody with the thiol-reactive reagent.

Step (a) of the method of preparing a cysteine engineered antibody may comprise:

(i) mutagenizing a nucleic acid sequence encoding the cysteine engineered antibody;

(ii) expressing the cysteine engineered antibody; and (iii) isolating and purifying the cysteine engineered antibody.

Step (b) of the method of preparing a cysteine engineered antibody may comprise expressing the cysteine engineered antibody on a viral particle selected from a phage or a phagemid particle.

Step (b) of the method of preparing a cysteine engineered antibody may also comprise:

(i) reacting the cysteine engineered antibody with a thiol-reactive affinity reagent to generate an affinity labelled, cysteine engineered antibody; and (ii) measuring the binding of the affinity labelled, cysteine engineered antibody to a capture media.

Another embodiment of the invention is a method of screening cysteine engineered antibodies with highly reactive, unpaired cysteine amino acids for thiol reactivity comprising:

(a) introducing one or more cysteine amino acids into a parent antibody in order to generate a cysteine engineered antibody;

(b) reacting the cysteine engineered antibody with a thiol-reactive affinity reagent to generate an affinity labelled, cysteine engineered antibody; and (c) measuring the binding of the affinity labelled, cysteine engineered antibody to a capture media; and (d) determining the thiol reactivity of the cysteine engineered antibody with the thiol-reactive reagent.

Step (a) of the method of screening cysteine engineered antibodies may comprise:

(i) mutagenizing a nucleic acid sequence encoding the cysteine engineered antibody;

(ii) expressing the cysteine engineered antibody; and (iii) isolating and purifying the cysteine engineered antibody.

Step (b) of the method of screening cysteine engineered antibodies may comprise expressing the cysteine engineered antibody on a viral particle selected from a phage or a phagemid particle.

Step (b) of the method of screening cysteine engineered antibodies may also comprise:

(i) reacting the cysteine engineered antibody with a thiol-reactive affinity reagent to generate an affinity labelled, cysteine engineered antibody; and (ii) measuring the binding of the affinity labelled, cysteine engineered antibody to a capture media.

Labelled Cysteine Engineered Anti-STEAP-1 Antibodies

Cysteine engineered anti-STEAP-1 antibodies may be site-specifically and efficiently coupled with a thiol-reactive reagent. The thiol-reactive reagent may be a multifunctional linker reagent, a capture, i.e. affinity, label reagent (e.g. a biotin-linker reagent), a detection label (e.g. a fluorophore reagent), a solid phase immobilization reagent (e.g. SEPHAROSE™, polystyrene, or glass), or a drug-linker intermediate. One example of a thiol-reactive reagent is N-ethyl maleimide (NEM). In an exemplary embodiment, reaction of a ThioFab with a biotin-linker reagent provides a biotinylated ThioFab by which the presence and reactivity of the engineered cysteine residue may be detected and measured. Reaction of a ThioFab with a multifunctional linker reagent provides a ThioFab with a functionalized linker which may be further reacted with a drug moiety reagent or other label. Reaction of a ThioFab with a drug-linker intermediate provides a ThioFab drug conjugate.

The exemplary methods described here may be applied generally to the identification and production of antibodies, and more generally, to other proteins through application of the design and screening steps described herein.

Such an approach may be applied to the conjugation of other thiol-reactive reagents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671). The thiol-reactive reagent may be a drug moiety, a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

Uses of Cysteine Engineered Anti-STEAP-1 Antibodies

Cysteine engineered anti-STEAP-1 antibodies, and conjugates thereof may find use as therapeutic and/or diagnostic agents. The present invention further provides methods of preventing, managing, treating or ameliorating one or more symptoms associated with a STEAP-1 related disorder. In particular, the present invention provides methods of preventing, managing, treating, or ameliorating one or more symptoms associated with a cell proliferative disorder, such as cancer, e.g., prostate cancer, lung cancer. colon cancer, bladder cancer, ovarian cancer, and Ewing's sarcoma. The present invention still further provides methods for diagnosing a STEAP-1 related disorder or predisposition to developing such a disorder, as well as methods for identifying antibodies, and antigen-binding fragments of antibodies, that preferentially bind cell-associated STEAP-1 polypeptides.

Another embodiment of the present invention is directed to the use of a cysteine engineered anti-STEAP-1 antibody for the preparation of a medicament useful in the treatment of a condition which is responsive to a STEAP-1 related disorder.

Preparation of Cysteine Engineered Anti-STEAP-1 Antibody-Drug Conjugates

The ADC of Formula I may be prepared by several routes, employing organic chemistry reactions, conditions, and reagents known to those skilled in the art, including: (1) reaction of a cysteine group of a cysteine engineered antibody with a linker reagent, to form antibody-linker intermediate Ab-L, via a covalent bond, followed by reaction with an activated drug moiety D; and (2) reaction of a nucleophilic group of a drug moiety with a linker reagent, to form drug-linker intermediate D-L, via a covalent bond, followed by reaction with a cysteine group of a cysteine engineered antibody. Conjugation methods (1) and (2) may be employed with a variety of cysteine engineered antibodies, drug moieties, and linkers to prepare the antibody-drug conjugates of Formula I.

Antibody cysteine thiol groups are nucleophilic and capable of reacting to form covalent bonds with electrophilic groups on linker reagents and drug-linker intermediates including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Cysteine engineered antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.), followed by reoxidation to reform interchain and intrachain disulfide bonds (Example x). For example, full length, cysteine engineered monoclonal antibodies (ThioMabs) expressed in CHO cells are reduced with about a 50 fold excess of TCEP for 3 hrs at 37° C. to reduce disulfide bonds in cysteine adducts which may form between the newly introduced cysteine residues and the cysteine present in the culture media. The reduced ThioMab is diluted and loaded onto HiTrap S column in 10 mM sodium acetate, pH 5, and eluted with PBS containing 0.3M sodium chloride. Disulfide bonds were reestablished between cysteine residues present in the parent Mab with dilute (200 nM) aqueous copper sulfate ($CuSO_4$) at room temperature, overnight. Alternatively, dehydroascorbic acid (DHAA) is an effective oxidant to reestablish the intrachain disulfide groups of the cysteine engineered antibody after reductive cleavage of the cysteine adducts. Other oxidants, i.e. oxidizing agents, and oxidizing conditions, which are known in the art may be used. Ambient air oxidation is also effective. This mild, partial reoxidation step forms intrachain disulfides efficiently with high fidelity and preserves the thiol groups of the newly introduced cysteine residues. An approximate 10 fold excess of drug-linker intermediate, e.g. MC-vc-PAB-MMAE, was added, mixed, and let stand for about an hour at room temperature to effect conjugation and form the antibody-drug conjugate. The conjugation mixture was gel filtered and loaded and eluted through a HiTrap S column to remove excess drug-linker intermediate and other impurities.

FIG. 16 shows the general process to prepare a cysteine engineered antibody expressed from cell culture for conjugation. When the cell culture media contains cysteine, disulfide adducts can form between the newly introduced cysteine amino acid and cysteine from media. These cysteine adducts, depicted as a circle in the exemplary ThioMab (left) in FIG. 12, must be reduced to generate cysteine engineered antibodies reactive for conjugation. Cysteine adducts, presumably along with various interchain disulfide bonds, are reductively cleaved to give a reduced form of the antibody with reducing agents such as TCEP. The interchain disulfide bonds between paired cysteine residues are reformed under partial oxidation conditions with copper sulfate, DHAA, or exposure to ambient oxygen. The newly introduced, engineered, and unpaired cysteine residues remain available for reaction with linker reagents or drug-linker intermediates to form the antibody conjugates of the invention. The ThioMabs expressed in mammalian cell lines result in externally conjugated Cys adduct to an engineered Cys through —S—S— bond formation. Hence the purified ThioMabs are treated with the reduction and reoxidation procedures as described in Example x to produce reactive ThioMabs. These ThioMabs are used to conjugate with maleimide containing cytotoxic drugs, fluorophores, and other labels.

FIG. 15 shows embodiments of cysteine engineered anti-STEAP-1 antibody drug conjugates (ADC) where an auristatin drug moiety is attached to an engineered cysteine group in: the light chain (LC-ADC); the heavy chain (HC-ADC); and the Fc region (Fc-ADC).

Pharmaceutical Formulations

Administration of Antibody-Drug Conjugates

The antibody-drug conjugates (ADC) of the invention may be administered by any route appropriate to the condition to be treated. The ADC will typically be administered parenterally, i.e., infusion, subcutaneous, intramuscular, intravenous, intradermal, intrathecal and epidural.

For treating cancers of, for example, prostate, lung and/or colon, in one embodiment, the antibody-drug conjugate is administered via intravenous infusion. The dosage administered via infusion is in the range of about 1 $\mu g/m^2$ to about 10,000 $\mu g/m^2$ per dose, generally one dose per week for a total of one, two, three or four doses. Alternatively, the dosage range is of about 1 $\mu g/m^2$ to about 1000 $\mu g/m^2$, about 1 $\mu g/m^2$ to about 800 $\mu g/m^2$, about 1 $\mu g/m^2$ to about 600 $\mu g/m^2$, about 1 $\mu g/m^2$ to about 400 $\mu g/m^2$, about 10 $\mu g/m^2$ to about 500 $\mu g/m^2$, about 10 $\mu g/m^2$ to about 300 $\mu g/m^2$, about 10 $\mu g/m^2$ to about 200 $\mu g/m^2$, and about 1 $\mu g/m^2$ to about 200 $\mu g/m^2$. The dose may be administered once per day, once per week, multiple times per week, but less than once per day, multiple times per month but less than once per day, multiple times per month but less than once per week, once per month or intermittently to relieve or alleviate symptoms of the disease. Administration may continue at any of the disclosed intervals until remission of the tumor or symptoms of the lymphoma, leukemia being treated. Administration may continue after remission or relief of symptoms is achieved where such remission or relief is prolonged by such continued administration.

The invention also provides a method of treating a prostate, lung, and/or colon cancer, and/or a metastasis of such cancer, comprising administering to a patient suffering from a prostate, lung or colon cancer, a therapeutically effective amount of a humanized 120v.24 antibody of any one of the preceding embodiments, which antibody is not conjugated to a cytotoxic molecule or a detectable molecule. The antibody will typically be administered in a dosage range of about 1 $\mu g/m^2$ to about 1000 $mg/m^2$.

The invention also provides a method of treating a prostate, lung, and/or colon cancer, and/or a metastasis of such cancer, comprising administering to a patient suffering from a prostate, lung or colon cancer, a therapeutically effective amount of a humanized 120v.24 antibody of any one of the preceding embodiments, which antibody is conjugated to a cytotoxic molecule or a detectable molecule. The antibody will typically be administered in a dosage range of about 1 $\mu g/m^2$ to about 1000 $mg/m^2$.

In one aspect, the invention further provides pharmaceutical formulations comprising at least one anti-STEAP-1 antibody of the invention and/or at least one immunoconjugate thereof and/or at least one anti-STEAP-1 antibody-drug conjugate of the invention. In some embodiments, a pharmaceutical formulation comprises 1) an anti-STEAP-1 antibody and/or an anti-STEAP-1 antibody-drug conjugate and/or an immunoconjugate thereof, and 2) a pharmaceutically acceptable carrier. In some embodiments, a pharmaceutical formulation comprises 1) an anti-STEAP-1 antibody and/or an immunoconjugate thereof, and optionally, 2) at least one additional therapeutic agent.

Pharmaceutical formulations comprising an antibody or immunoconjugate of the invention or the antibody-drug conjugate of the invention are prepared for storage by mixing the antibody or antibody-drug conjugate having the desired degree of purity with optional physiologically acceptable carriers, excipients or stabilizers (Remington's Pharmaceutical Sciences 16th edition, Osol, A. Ed. (1980)) in the form of aqueous solutions or lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride); phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, manmitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutical formulations to be used for in vivo administration are generally sterile. This is readily accomplished by filtration through sterile filtration membranes.

Active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody or immunoconjugate of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies or immunoconjugates remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Antibody-Drug Conjugate Treatments

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders. Still others include prostate, lung and colon cancers.

The ADC compounds which are identified in the animal models and cell-based assays can be further tested in tumor-bearing higher primates and human clinical trials. Human clinical trials can be designed to test the efficacy of the anti-STEAP-1 monoclonal antibody or immunoconjugate of the invention in patients experiencing a prostate, lung or colon cell proliferative disorder including without limitation prostate, lung and colon cancers and metastases of such cancers. The clinical trial may be designed to evaluate the efficacy of an ADC in combinations with known therapeutic regimens, such as radiation and/or chemotherapy involving known chemotherapeutic and/or cytotoxic agents.

The cancer may comprise STEAP-1-expressing cells, such that an ADC of the present invention is able to bind to the cancer cells. To determine STEAP-1 expression in the cancer, various diagnostic/prognostic assays are available. In one embodiment, STEAP-1 overexpression may be analyzed by IHC. Parrafin-embedded tissue sections from a tumor biopsy may be subjected to the IHC assay and accorded a STEAP-1 protein staining intensity criteria with respect to the degree of staining and in what proportion of tumor cells examined.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 μg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 μg/kg to 100 mg/kg or more, depending on the factors mentioned above. An exemplary dosage of ADC to be administered to a patient is in the range of about 0.1 to about 10 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of an anti-STEAP-1 antibody. Other dosage regimens may be useful. The progress of this therapy is easily monitored by conventional techniques and assays.

Combination Therapy

An antibody-drug conjugate (ADC) of the invention may be combined in a pharmaceutical combination formulation, or dosing regimen as combination therapy, with at least one additional compound having anti-cancer properties. The at lelast one additional compound of the pharmaceutical combination formulation or dosing regimen preferably has complementary activities to the ADC of the combination such that they do not adversely affect each other.

The at least one additional compound may be a chemotherapeutic agent, cytotoxic agent, cytokine, growth inhibitory agent, anti-hormonal agent, and/or cardioprotectant. Such molecules are suitably present in combination in amounts that are effective for the purpose intended. A pharmaceutical composition containing an ADC of the invention may also have a therapeutically effective amount of a chemotherapeutic agent such as a tubulin-forming inhibitor, a topoisomerase inhibitor, or a DNA binder.

In one aspect, the first compound is an anti-STEAP-1 ADC of the invention and the at least one additional compound is a therapeutic antibody other than an anti-STEAP-1 (naked antibody or an ADC). In one embodiment, the at least one additional compound is an anti-PSCA antibody. In one embodiment the at least one additional compound is an anti-HER2 antibody, trastuzumab (e.g., Herceptin®, Genentech, Inc., South San Francisco, Calif.). In one embodiment the at least one additional compound is an anti-HER2 antibody, pertuzumab (Omnitarg™, Genentech, Inc., South San Francisco, Calif., see U.S. Pat. No. 6,949,245). In one embodiment, the at least one additional compound is an anti-VEGF antibody (e.g., Avastin®, Genentech, Inc.). In each case, the at least one compound is either a naked antibody or an ADC). In an embodiment, the at least one additional compound is an antibody (either a naked antibody or an ADC), and the additional antibody is a second, third, fourth, fifth, sixth antibody or more, such that a combination of such second, third, fourth, fifth, sixth, or more antibodies (either naked or as an ADC) is efficacious in treating a cell proliferative disease in a tissue expressing STEAP-1.

Other therapeutic regimens may be combined with the administration of an anticancer agent identified in accordance with this invention, including without limitation radiation therapy and/or bone marrow and peripheral blood transplants, and/or a cytotoxic agent, a chemotherapeutic agent, or a growth inhibitory agent. In one of such embodiments, a chemotherapeutic agent is an agent or a combination of agents such as, for example, cyclophosphamide, hydroxydaunorubicin, adriamycin, doxorubincin, vincristine (Oncovin™), prednisolone, CHOP, CVP, or COP, or immunotherapeutics such as anti-PSCA, anti-HER2 (e.g., Herceptin®, Omnitarg™) or anti-VEGF (e.g., Avastin®). The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

In one embodiment, treatment with an ADC involves the combined administration of an anticancer agent identified herein, and one or more chemotherapeutic agents or growth inhibitory agents, including coadministration of cocktails of different chemotherapeutic agents. Chemotherapeutic agents include taxanes (such as paclitaxel and docetaxel) and/or anthracycline antibiotics. Preparation and dosing schedules for such chemotherapeutic agents may be used according to manufacturer's instructions or as determined empirically by the skilled practitioner. Preparation and dosing schedules for such chemotherapy are also described in "Chemotherapy Service", (1992) Ed., M. C. Perry, Williams & Wilkins, Baltimore, Md.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Antibody-Drug Conjugates

Also falling within the scope of this invention are the in vivo metabolic products of the ADC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabelled (e.g. $^{14}C$ or $^{3}H$) ADC, administering it parenterally in a detectable dose e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the ADC compounds of the invention.

Further Methods of Using Anti-STEAP-1 Antibodies and Immunoconjugates

Diagnostic Methods and Methods of Detection

In one aspect, anti-STEAP-1 antibodies and immunoconjugates of the invention are useful for detecting the presence of STEAP-1 in a biological sample. The term "detecting" as used herein encompasses quantitative or qualitative detection. In certain embodiments, a biological sample comprises a cell or tissue. In certain embodiments, such tissues include normal and/or cancerous tissues that express STEAP-1 at higher levels relative to other tissues, for example, prostate, lung and colon.

In one aspect, the invention provides a method of detecting the presence of STEAP-1 in a biological sample. In certain embodiments, the method comprises contacting the biological sample with an anti-STEAP-1 antibody under conditions permissive for binding of the anti-STEAP-1 antibody to STEAP-1, and detecting whether a complex is formed between the anti-STEAP-1 antibody and STEAP-1.

In one aspect, the invention provides a method of diagnosing a disorder associated with increased expression of STEAP-1. In certain embodiments, the method comprises contacting a test cell with an anti-STEAP-1 antibody; determining the level of expression (either quantitatively or qualitatively) of STEAP-1 by the test cell by detecting binding of the anti-STEAP-1 antibody to STEAP-1; and comparing the level of expression of STEAP-1 by the test cell with the level of expression of STEAP-1 by a control cell (e.g., a normal cell of the same tissue origin as the test cell or a cell that expresses STEAP-1 at levels comparable to such a normal cell), wherein a higher level of expression of STEAP-1 by the test cell as compared to the control cell indicates the presence of a disorder associated with increased expression of STEAP-1. In certain embodiments, the test cell is obtained from an individual suspected of having a disorder associated with increased expression of STEAP-1. In certain embodiments, the disorder is a cell proliferative disorder, such as a cancer or a tumor.

Exemplary cell proliferative disorders that may be diagnosed using an antibody of the invention include a prostate, lung and colon cancers or metastases of such cancers.

In certain embodiments, a method of diagnosis or detection, such as those described above, comprises detecting binding of an anti-STEAP-1 antibody to STEAP-1 expressed on the surface of a cell or in a membrane preparation obtained from a cell expressing STEAP-1 on its surface. In certain embodiments, the method comprises contacting a cell with an anti-STEAP-1 antibody under conditions permissive for binding of the anti-STEAP-1 antibody to STEAP-1, and detecting whether a complex is formed between the anti-STEAP-1 antibody and STEAP-1 on the cell surface. An exemplary assay for detecting binding of an anti-STEAP-1 antibody to STEAP-1 expressed STEAP-1 on the surface of a cell is a "FACS" assay.

Certain other methods can be used to detect binding of anti-STEAP-1 antibodies to STEAP-1. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-STEAP-1 antibodies are labeled. Labejs include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable fiee radicals, and the like.

In certain embodiments, anti-STEAP-1 antibodies are immobilized on an insoluble matrix. Immobilization entails separating the anti-STEAP-1 antibody from any STEAP-1 that remains free in solution. This conventionally is accomplished by either insolubilizing the anti-STEAP-1 antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-STEAP-1 antibody after formation of a complex between the anti-STEAP-1 antibody and STEAP-1, e.g., by immunoprecipitation.

Any of the above embodiments of diagnosis or detection may be carried out using an immunoconjugate of the invention in, place of or in addition to an anti-STEAP-1 antibody.

Therapeutic Methods

An antibody or immunoconjugate of the invention may be used in, for example, in vitro, ex vivo, and in vivo therapeutic methods. In one aspect, the invention provides methods for inhibiting cell growth or proliferation, either in vivo or in vitro, the method comprising exposing a cell to an anti-STEAP-1 antibody or immunoconjugate thereof under conditions permissive for binding of the immunoconjugate to STEAP-1. "Inhibiting cell growth or proliferation" means decreasing a cell's growth or proliferation by at least 10%, 20%, 30%, 40%, 50%, 60%, 70%, 80%, 90%, 95%, or 100%, and includes inducing cell death. In certain embodiments, the cell is a tumor cell. In certain embodiments, the cell is a prostate, lung, colon, bladder, or ovary cell, or Ewing's sarcoma cell. In certain embodiments, the cell is a xenograft, e.g., as exemplified herein.

In one aspect, an antibody or immunoconjugate of the invention is used to treat or prevent a prostate, lung, colon, bladder, or ovary cell or Ewing's sarcoma cell proliferative disorder. In certain embodiments, the cell proliferative disorder is associated with increased expression and/or activity of STEAP-1. For example, in certain embodiments, the prostate, lung, colon, bladder, or ovary cell or Ewing's sarcoma cell proliferative disorder is associated with increased expression of STEAP-1 on the surface of a prostate, lung, colon, bladder, or ovary cell or Ewing's sarcoma cell. In certain embodiments, the prostate, lung, colon, bladder, or ovary cell or Ewing's sarcoma cell proliferative disorder is a tumor or a cancer or metastasis of such cancer.

In one aspect, the invention provides methods for treating a prostate, lung or colon cell proliferative disorder comprising administering to an individual an effective amount of an anti-STEAP-1 antibody or immunoconjugate thereof. In certain embodiments, a method for treating a prostate, lung or colon cell proliferative disorder comprises administering to an individual an effective amount of a pharmaceutical formulation comprising an anti-STEAP-1 antibody or anti-STEAP-1 immunoconjugate and, optionally, at least one additional therapeutic agent, such as those provided herein.

In one aspect, at least some of the antibodies or immunoconjugates of the invention can bind STEAP-1 from species other than human. Accordingly, antibodies or immunoconjugates of the invention can be used to bind STEAP-1, e.g., in a cell culture containing STEAP-1, in humans, or in other mammals having a STEAP-1 with which an antibody or immunoconjugate of the invention cross-reacts (e.g. chimpanzee, baboon, marmoset, cynomolgus and rhesus monkeys, dog, pig, rat, or mouse). In one embodiment, an anti- STEAP-1 antibody or immunoconjugate can be used for targeting STEAP-1 on prostate, lung or colono cells by contacting the antibody or immunoconjugate with STEAP-1 to form an antibody or immunoconjugate-antigen complex such that a conjugated cytotoxin of the immunoconjugate accesses the interior of the cell. In one embodiment, the STEAP-1 to which the anti-STEAP-1 antibody binds is human STEAP-1. In one embodiment, the STEAP-1 to which the anti-STEAP-1 antibody binds is cynomolgus monkey STEAP-1. In one embodiment, the humanized anti-STEAP-1 antibody binds to human and/or cynomolgus monkey STEAP-1.

In one embodiment, an anti-STEAP-1 antibody or immunoconjugate can be used in a method for binding STEAP-1 in an individual suffering from a disorder associated with increased STEAP-1 expression and/or activity, the method comprising administering to the individual the antibody or immunoconjugate such that STEAP-1 in the individual is bound. In one embodiment, the bound antibody or immunoconjugate is internalized into the prostate, lung, colon, bladder, or ovary cell or Ewing's sarcoma cell expressing STEAP-1. In one embodiment, the STEAP-1 is human STEAP-1, and the individual is a human individual. Alternatively, the individual can be a mammal expressing STEAP-1 to which an anti-STEAP-1 antibody binds. Still further the individual can be a mammal into which STEAP-1 has been introduced (e.g., by administration of STEAP-1 or by expression of a transgene encoding STEAP-1).

An anti-STEAP-1 antibody or immunoconjugate can be administered to a human for therapeutic purposes. Moreover, an anti-STEAP-1 antibody or immunoconjugate can be administered to a non-human mammal expressing STEAP-1 with which the antibody cross-reacts (e.g., a primate, dog, pig, rat, or mouse) for veterinary purposes or as an animal model of human disease. Regarding the latter, such animal models may be useful for evaluating the therapeutic efficacy of antibodies or immunoconjugates of the invention (e.g., testing of dosages and time courses of administration).

Antibodies or immunoconjugates of the invention can be used either alone or in combination with other compositions in a therapy. For instance, an antibody or immunoconjugate of the invention may be co-administered with at least one additional therapeutic agent and/or adjuvant. In certain embodiments, an additional therapeutic agent is a cytotoxic agent, a chemotherapeutic agent, or a growth inhibitory agent. In one of such embodiments, a chemotherapeutic agent is an agent or a combination of agents such as, for example, cyclophosphamide, hydroxydaunorubicin, adriamycin, doxorubincin, vincristine (Oncovin™), prednisolone, CHOP, CVP, or COP, or immunotherapeutics such as anti-PSCA (see, for example, U.S. Pat. No. 6,824,780), anti-VEGF (e.g., Avastin®, Genentech, Inc.), anti-HER2 (e.g., Herceptin®, Omnitarg™ Genentech, Inc.), or anti-HER2 in combination with Taxol® (see, for example, BioWorld Today, Nov. 17, 1999, page 1), wherein the combination therapy is useful in the treatment of cell proliferative disorders, cancers, and/or metastases of cancers of prostate, lung and/or colon.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody or immunoconjugate is suitably administered by pulse infusion, particularly with declining doses of the antibody or immunoconjugate. Dosing can be by any suitable route, e.g. by injections, such as intravenous or subcutaneous injections, depending in part on whether the administration is brief or chronic.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents, such as chemotherapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 100 mg/kg (e.g. 0.1 mg/kg-20 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) of antibody or immunoconjugate may be administered to the patient. Such doses may be administered intermittently, e.g. every week or every three weeks (e.g. such that the patient receives from about two to about twenty, or e.g. about six doses of the antibody or immunoconjugate). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Assays

Anti-STEAP-1 antibodies and immunoconjugates of the invention may be characterized for their physical/chemical properties and/or biological activities by various assays known in the art.

Activity Assays

In one aspect, assays are provided for identifying anti-STEAP-1 antibodies or immunoconjugates thereof having biological activity. Biological activity may include, e.g., the ability to inhibit cell growth or proliferation (e.g., "cell killing" activity), or the ability to induce cell death, including programmed cell death (apoptosis). Antibodies or immunoconjugates having such biological activity in vivo and/or in vitro are also provided.

In certain embodiments, an anti-STEAP-1 antibody or immunoconjugate thereof is tested for its ability to inhibit cell growth or proliferation in vitro. Assays for inhibition of cell growth or proliferation are well known in the art. Certain assays for cell proliferation, exemplified by the "cell killing" assays described herein, measure cell viability. One such assay is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) J. Immunol. Meth. 160:81-88, U.S. Pat. No. 6,602,677. The assay may be conducted in 96- or 384-well format, making it amenable to automated high-throughput screening (HTS). See Cree et al (1995) AntiCancer Drugs 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

Another assay for cell proliferation is the "MTT" assay, a colorimetric assay that measures the oxidation of 3-(4,5-dimethylthiazol-2-yl)-2,5-diphenyltetrazolium bromide to formazan by mitochondrial reductase. Like the CellTiter-Glo™ assay, this assay indicates the number of metabolically active cells present in a cell culture. See, e.g., Mosmann (1983) J. Immunol. Meth. 65:55-63, and Zhang et al. (2005) Cancer Res. 65:3877-3882.

In one aspect, an anti-STEAP-1 antibody is tested for its ability to induce cell death in vitro. Assays for induction of cell death are well known in the art. In some embodiments, such assays measure, e.g., loss of membrane integrity as indicated by uptake of propidium iodide (PI), trypan blue (see Moore et al. (1995) Cytotechnology, 17:1-11), or 7AAD. In an exemplary PI uptake assay, cells are cultured in Dulbecco's Modified Eagle Medium (D-MEM):Ham's F-12 (50:50) supplemented with 10% heat-inactivated FBS (Hyclone) and 2 mM L-glutamine. Thus, the assay is performed in the absence of complement and immune effector cells. Cells are seeded at a density of $3 \times 10^6$ per dish in 100×20 mm dishes and allowed to attach overnight. The medium is removed and replaced with fresh medium alone or medium containing various concentrations of the antibody or immunoconjugate. The cells are incubated for a 3-day time period. Following treatment, monolayers are washed with PBS and detached by trypsinization. Cells are then centrifuged at 1200 rpm for 5 minutes at 4° C., the pellet resuspended in 3 ml cold $Ca^{2+}$ binding buffer (10 mM Hepes, pH 7.4, 140 mM NaCl, 2.5 mM $CaCl_2$) and aliquoted into 35 mm strainer-capped 12×75 mm tubes (1 ml per tube, 3 tubes per treatment group) for removal of cell clumps. Tubes then receive PI (10 μg/ml). Samples are analyzed using a FACSCAN™ flow cytometer and FACSCONVERT™ CellQuest software (Becton Dickinson). Antibodies or immunoconjugates which induce statistically significant levels of cell death as determined by PI uptake are thus identified.

In one aspect, an anti-STEAP-1 antibody or immunoconjugate is tested for its ability to induce apoptosis (programmed cell death) in vitro. An exemplary assay for antibodies or immunoconjugates that induce apoptosis is an annexin binding assay. In an exemplary annexin binding assay, cells are cultured and seeded in dishes as discussed in the preceding paragraph. The medium is removed and replaced with fresh medium alone or medium containing 0.001 to 10 μg/ml of the antibody or immunoconjugate. Following a three-day incubation period, monolayers are washed with PBS and detached by trypsinization. Cells are then centrifuged, resuspended in $Ca^{2+}$ binding buffer, and aliquoted into tubes as discussed in the preceding paragraph. Tubes then receive labeled annexin (e.g. annexin V-FITC) (1 μg/ml). Samples are analyzed using a FACSCAN™ flow cytometer and FACSCONVERT™ CellQuest software (BD Biosciences). Antibodies or immunoconjugates that induce statistically significant levels of annexin binding relative to control are thus identified. Another exemplary assay for antibodies or immunoconjugates that induce apoptosis is a histone DNA ELISA colorimetric assay for detecting internucleosomal degradation of genomic DNA. Such an assay can be performed using, e.g., the Cell Death Detection ELISA kit (Roche, Palo Alto, Calif.).

Cells for use in any of the above in vitro assays include cells or cell lines that naturally express STEAP-1 or that have been engineered to express STEAP-1. Such cells include tumor cells that overexpress STEAP-1 relative to normal cells of the same tissue origin. Such cells also include cell lines (including tumor cell lines) that express STEAP-1 and cell lines that do not normally express STEAP-1 but have been transfected with nucleic acid encoding STEAP-1.

In one aspect, an anti-STEAP-1 antibody or immunoconjugate thereof is tested for its ability to inhibit cell growth or proliferation in vivo. In certain embodiments, an anti-STEAP-1 antibody or immunoconjugate thereof is tested for its ability to inhibit tumor growth in vivo. In vivo model systems, such as xenograft models, can be used for such testing. In an exemplary xenograft system, human tumor cells are introduced into a suitably immunocompromised non-human animal, e.g., a SCID mouse. An antibody or immunoconjugate of the invention is administered to the animal. The ability of the antibody or immunoconjugate to inhibit or decrease tumor growth is measured. In certain embodiments of the above xenograft system, the human tumor cells are tumor cells from a human patient. Such cells useful for preparing xenograft models include human prostate, lung, or colon tumor cell lines, which include without limitation PC3 cells expressing exogenous STEAP-1, and cells naturally expressing STEAP-1 which include, without limitation, LnCAP cells (Southern Research Institute, Birmingham, Ala.), LuCAP 77 cells, and LuCAP35V cells (University of Washington, Seattle, Wash.). In certain embodiments, the human tumor cells are introduced into a suitably immunocompromised non-human animal by subcutaneous injection or by transplantation into a suitable site, such as a mammary fat pad.

Binding Assays and Other Assays

In one aspect, an anti-STEAP-1 antibody is tested for its antigen binding activity. For example, in certain embodiments, an anti-STEAP-1 antibody is tested for its ability to bind to exogenous or endogenous STEAP-1 expressed on the surface of a cell. A FACS assay may be used for such testing.

In one aspect, competition assays may be used to identify a monoclonal antibody that competes with 120 graft or humanized variants thereof, including without limitation, 120v.24 antibody for binding to STEAP-1. In certain embodiments, such a competing antibody binds to the same epitope (e.g., a linear epitope peptide or a conformational epitope formed by expression of STEAP1 on a cell surface) that is bound by 120 graft antibody, or humanized 120 graft antibody, including variant 120v.24 humanized anti-STEAP-1 antibody. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). Two antibodies are said to bind to the same epitope if each blocks binding of the other by 50% or more.

In an exemplary competition assay, immobilized STEAP-1 is incubated in a solution comprising a first labeled antibody that binds to STEAP-1 (e.g., murine 120.545 antibody, 120 graft antibody, or humanized 120v.24 antibody) and a second unlabeled antibody that is being tested for its ability to compete with the first antibody for binding to STEAP-1. The second antibody may be present in a hybridoma supernatant. As a control, immobilized STEAP-1 is incubated in a solution comprising the first labeled antibody but not the second unlabeled antibody. After incubation under conditions permissive for binding of the first antibody to STEAP-1, excess unbound antibody is removed, and the amount of label associated with immobilized STEAP-1 is measured. If the amount of label associated with immobilized STEAP-1 is substantially reduced in the test sample relative to the control sample, then that indicates that the second antibody is competing with the first antibody for binding to STEAP-1. In certain embodiments, immobilized STEAP-1 is present on the surface of a cell or in a membrane preparation obtained from a cell expressing STEAP-1 on its surface.

In one aspect, purified anti-STEAP-1 antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In one embodiment, the invention contemplates an altered antibody that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, Annu. Rev. Immunol. 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, e.g. as described in Gazzano-Santoro et al., J. Immunol. Methods 202:163 (1996), may be performed. FcRn binding and in vivo clearance/half life determinations can also be performed using methods known in the art.

EXAMPLES

The following are examples of methods and compositions of the invention. It is understood that various other embodiments may be practiced, given the general description provided above.

Example 1

Preparation of Humanized Anti-STEAP-1 Antibodies

Nucleic acid molecules encoding amino acid sequence variants of the antibody, antibody fragment, VL domain or VH domain are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody, antibody fragment, VL domain or VH domain. For example, libraries can be created by targeting VL accessible amino acid positions in VH, and optionally in one or more CDRs, for amino acid substitution with variant amino acids using the Kunkel method. See, for e.g., Kunkel et al., Methods Enzymol. (1987), 154:367-382 and the examples herein. Generation of randomized sequences is also described below in the Examples.

The sequence of oligonucleotides includes one or more of the designed codon sets for a particular position in a CDR (HVR) or FR region of a polypeptide of the invention. A codon set is a set of different nucleotide triplet sequences used to encode desired variant amino acids. Codon sets can be represented using symbols to designate particular nucleotides or equimolar mixtures of nucleotides as shown in below according to the IUB code.

IUB Codes
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T)
N (A or C or G or T)

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al, 1987, Nucleic Acids Res. 10:6487-6504. Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., Proc. Nat'l. Acad. Sci. USA, 75:5765 (1978).

The DNA template is generated by those vectors that are either derived from bacteriophage M13 vectors (the commercially available M13 mp18 and M13 mp19 vectors are suitable), or those vectors that contain a single-stranded phage origin of replication as described by Viera et al., Meth. Enzymol., 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as E. coli JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. ((1987) Meth. Enzymol., 153:3). Thus, the DNA that is to be mutated must be inserted into one of these vectors in order to generate single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

Oligonucleotide sets can be used in a polymerase chain reaction using a variable domain nucleic acid template sequence as the template to create nucleic acid cassettes. The variable domain nucleic acid template sequence can be any portion of the heavy immunoglobulin chains containing the target nucleic acid sequences (i.e., nucleic acid sequences encoding amino acids targeted for substitution). The variable region nucleic acid template sequence is a portion of a double stranded DNA molecule having a first nucleic acid strand and complementary second nucleic acid strand. The variable domain nucleic acid template sequence contains at least a portion of a variable domain and has at least one CDR. In some cases, the variable domain nucleic acid template sequence contains more than one CDR. An upstream portion and a downstream portion of the variable domain nucleic acid template sequence can be targeted for hybridization with members of an upstream oligonucleotide set and a downstream oligonucleotide set.

A first oligonucleotide of the upstream primer set can hybridize to the first nucleic acid strand and a second oligonucleotide of the downstream primer set can hybridize to the second nucleic acid strand. The oligonucleotide primers can include one or more codon sets and be designed to hybridize to a portion of the variable region nucleic acid template sequence. Use of these oligonucleotides can introduce two or more codon sets into the PCR product (i.e., the nucleic acid cassette) following PCR. The oligonucleotide primer that hybridizes to regions of the nucleic acid sequence encoding the antibody variable domain includes portions that encode CDR residues that are targeted for amino acid substitution.

The upstream and downstream oligonucleotide sets can also be synthesized to include restriction sites within the oligonucleotide sequence. These restriction sites can facilitate the insertion of the nucleic acid cassettes (i.e., PCR reaction products) into an expression vector having additional antibody sequence. In one embodiment, the restriction sites are designed to facilitate the cloning of the nucleic acid cassettes without introducing extraneous nucleic acid sequences or removing original CDR or framework nucleic acid sequences.

Nucleic acid cassettes can be cloned into any suitable vector for expression of a portion or the entire light or heavy chain sequence containing the targeted amino acid substitutions generated via the PCR reaction. According to methods detailed in the invention, the nucleic acid cassette is cloned into a vector allowing production of a portion or the entire light or heavy chain sequence fused to all or a portion of a viral coat protein (i.e., creating a fusion protein) and displayed on the surface of a particle or cell. While several types of vectors are available and may be used to practice this invention, phagemid vectors are the preferred vectors for use herein, as they may be constructed with relative ease, and can be readily amplified. Phagemid vectors generally contain a variety of components including promoters, signal sequences, phenotypic selection genes, origin of replication sites, and other necessary components as are known to those of ordinary skill in the art.

When a particular variant amino acid combination is to be expressed, the nucleic acid cassette contains a sequence that is able to encode all or a portion of the heavy or light chain variable domain, and is able to encode the variant amino acid combinations. For production of antibodies containing these variant amino acids or combinations of variant amino acids, as in a library, the nucleic acid cassettes can be inserted into an expression vector containing additional antibody sequence, for example all or portions of the variable or constant domains of the light and heavy chain variable regions. These additional antibody sequences can also be fused to other nucleic acids sequences, such as sequences that encode viral coat proteins and therefore allow production of a fusion protein.

Humanization of murine anti-human STEAP-1 antibody is described herein.

Materials and Methods

Residue numbers are according to Kabat (Kabat et al., *Sequences of proteins of immunological interest,* 5th Ed., Public Health Service, National Institutes of Health, Bethesda, Md. (1991)). Single letter amino acid abbreviations are used. DNA degeneracies are represented using the IUB code (N=A/C/G/T, D=A/G/T, V=A/C/G, B=C/G/T, H=A/C/T, K=G/T, M=A/C, R=A/G, S=G/C, W=A/T, Y=C/T).

Cloning of murine 120 variable domains and generation of a chimeric 120 antibody—Total RNA was extracted from hybridoma cells producing M2-120.545 (designated as "murine 120" or "mu120" herein) using standard methods. The variable light (VL) and variable heavy (VH) domains were amplified using RT-PCR with degenerate primers to the heavy and light chains. The forward primers were specific for the N-terminal amino acid sequence of the VL and VH regions. Respectively, the LC and HC reverse primers were designed to anneal to a region in the constant light (CL) and constant heavy domain 1 (CH1), which are highly conserved across species. Amplified VL and VH were cloned into mammalian expression vectors. The polynucleotide sequence of the inserts was determined using routine sequencing methods. The M2-120.545 ("mu 120") VL and VH amino acid sequences are shown in FIGS. 2A and 2B, respectively.

Generation of murine 120 chimera—A chimeric anti-STEAP-1 antibody was prepared by fusing the murine 120 variable heavy (VH) and variable light (VL) regions to the constant domains of a human IgG. The resultant antibody is designated "120 chimera," "chimera 120," "chimeric 120 IgG," or "Fc chimera" herein.

Direct hypervaiiable region grafts onto the acceptor human consensus framework—Variants constructed during the humanization of murine 120 were assessed both as protein in the form of an IgG or as a Fab displayed on phage.

The phagemid used for this work is a monovalent Fab-g3 display vector and consists of two open reading frames under control of the phoA promoter. The first open reading frame consists of the stII signal sequence fused to the VL and CH1 domains of the acceptor light chain and the second consists of the stII signal sequence fused to the VH and CH1 domains of the acceptor heavy chain followed by the minor phage coat protein P3.

The VL and VH domains from murine 120 were aligned with the human VL kappa I (huKI) and human VH subgroup III (huIII) consensus sequences. To make the CDR grafts, hypervariable regions from the murine 120 antibody were grafted into the huKI and huIII acceptor frameworks.

Hypervariable regions from murine 120 antibody (mu120) were engineered into the acceptor human consensus framework to generate the direct CDR-graft (designated as "120 graft," or "graft 120" herein). In the VL domain the following regions were grafted to the human consensus acceptor: positions 24-34 (L1), 50-56 (L2) and 89-97 (L3). In the VH domain, positions 26-35a (H1), 49-65 (H2) and 95-102 (H3) were grafted. The sequences of the light and heavy chain variable regions of the 120 graft are shown in FIGS. 2A-2B. The CDRs (also designated here as HVRs) are shown in boxes (FIGS. 2A-2B). These CDR definitions include positions defined by their sequence hypervariability (Kabat ref), their structural location (Chothia ref) and their involvement in antigen-antibody contacts (MacCallum et al. *J. Mol. Biol.* 262: 732-745 (1996)).

The direct-graft variants expressed as a Fab displayed on phage or as an IgG were generated by Kunkel mutagenesis using a separate oligonucleotide foreach hypervariable region. Correct clones were assessed by DNA sequencing.

Generation of humanized 120 phage variants—Humanized 120 variants were generated as Fab displayed on phage by Kunkle mutagenesis. A phosphorylated oligonucleotide was added to 300 ng Kunkel template in 50 mM Tris pH 7.5, 10 mM MgCl$_2$ in a final volume of 10 μl. The mixture was annealed at 90° C. for 2 min, 50° C. for 5 min and then cooled on ice. The annealed template was then filled in by adding 0.5 μl 10 mM ATP, 0.5 μl 10 mM dNTPs (10 mM each of DATP, dCTP, dGTP and dTTP), 1 μl 100 mM DTT, 1 μl 10×TM buffer (0.5 M Tris pH 7.5, 0.1 M MgCl$_2$), 80 U T4 ligase, and 4 U T7 polymerase in a total volume of 20 µl for 2 h at room temperature. The filled in and ligated product was then transformed into XL1-blue cells (Stratagene). Correct clones were identified by DNA sequencing.

Correct phage clones were grown in 25 ml of 2YT containing 50 µg/ml carbenacillin and M13/KO7 helper phage (MOI 10) overnight at 37° C.

Assessment of humanized 120 variants—Humanized variants expressed as IgG were assessed by FACS analysis using Steap1 positive (293 Steap1 NT LB50) and negative (293 vector S408) cell lines.

Humanized variants expressed as a Fab displayed on phage were also assessed by FACS analysis. Phage expressing Fab variants were first assessed for their Fab display level using an phage ELISA used to detect a flag-tag fused to the light chain of the Fab. MaxiSorp microtiter plates were coated with anti-gD 1766 at 10 µg/ml in PBS over night and then blocked with Casein Blocker. Phage from culture supernatants were serially diluted in PBST containing 0.5% BSA in a tissue culture microtiter plate and transferred to the coated wells for 1 h to capture the Fab displaying phage. The plate was washed with PBST and HRP conjugated anti-M13 (Amersham Pharmacia Biotech) was added (1:5000 in PBST containing 0.5% BSA) for 40 min. The plate was washed with PBST and developed by adding Tetramethylbenzidine substrate (Kirkegaard and Perry Laboratories, Gaithersburg, Md.). The absorbance at 405 nm was used as an estimate of the Fab display level on the surface of the phage. Phage preparations were normalized for display by dilution. Low displaying phage (e.g. the chimera) were used neat for FACS analysis.

For FACS analysis of phage binding, cells were removed from the plate using 2 mM EDTA, collected in a 15 mL conical bottom tube and pelleted by centrifugation. Cells (5×10$^5$ cells per sample) were re-suspended in 100 µL of phage (normalized by display level) in FACS buffer (1% FBS, PBS with 2 mM EDTA) and incubated for 1-2 hours on ice. Samples were washed twice with FACS buffer by centrifugation. Anti-M13 5G7 control antibody (Genentech, Inc. South San Francisco, Calif.) was added at 2 µg/mL and incubated on ice for at least 45 minutes. Samples were washed twice with FACS buffer by centrifugation. A 1:200 dilution of anti-mouse PE (R-phycoerythrin goat anti-mouse IgG Fcy Fragment, Jackson Immunoresearch) was added and incubated on ice for 30 minutes. Samples were again washed twice with FACS buffer by centrifugation and analyzed by FACS.

For analysis of IgG by FACS, cells were prepared as in the phage FACS. Each IgG was added at 5 µl/mL on ice for 1 hour. Samples were washed twice with FACS buffer by centrifugation and a 1:200 dilution of anti-human PE conjugate (R-phycoerythrin goat anti-human IgG Fcy Fragment, Jackson Immunoresearch) was added for 30 minutes. Samples were again washed twice with FACS buffer by centrifugation and samples were analyzed by FACS.

IgG Production and Affinity Determination -IgG was purified with Protein G affinity chromatography. Affinity determinations were performed by Scatchard analysis on 293 STEAP-1 NT LB50 cells.

Results and Discussion

Murine 120 variable domain sequences and CDR assignment graft design—The human acceptor framework used for humanization of M2-120.545 is based on the consensus human kappa I VL domain and the human subgroup mI consensus VH domain. The VL and VH domains of murine M2-120.545 were each aligned with the human kappa I and subgroup III domains; each complimentarily region (CDR) was identified and grafted into the human acceptor framework to generate a CDR graft that could be displayed as an Fab on phage and expressed as an IgG. The sequences of humanized anti-STEAP-1 antibody version 24 variable regions are shown in FIGS. 2A and 2B. The 120-graft Fab displayed on phage and 120-graft IgG were tested for binding to exogenous STEAP-1 expressing cells (293 STEAP-1 NT LB50) by FACS analysis. Although the 120-graft IgG bound specifically to the STEAP-1 expressing cells, the FACS signal observed for the 120-graft IgG was smaller than that observed for the chimeric 120 IgG indicating a loss in binding affinity. Phage displaying the 120-graft Fab also generated a FACS signal that was only observed on STEAP-1 expressing cells. This shift was less than that observed for the chimeric 120 IgG. Scatchard analysis of the 120-graft IgG also indicated a significant (approximately 50-fold) loss in binding affinity (KD=36 nM for the 120v.78; KD=260 nM for 120 graft).

Humanization of M2-120.545—Approximately 30 vernier positions that influence CDR conformation and VL:VH domain packing have been identified and changes at these positions between the donor and human frameworks should be considered when humanizing antibodies (Foote, J. and Winter, G., J. Mol. Biol. 224(2):487-499 (1992)). An assessment of the alignment of murine M2-120.545 with the consensus human kappa I VL domain and the human subgroup III consensus VH domain revealed sequence differences at 6 key vernier positions in the VH domain: 24, 37, 48, 67, 73, 78 (see FIG. 2B). To assess the influence of these positions, murine residues were individually introduced into the human consensus subgroup III VH domain of the Fab on phage. This involved making the following mutations to the 120-graft Fab displayed on phage individually: A24V (120.v24), V37I (120.v37), V48M (120.v48), F67I (120.v67), and L78F (120.v78). N73T was not tested. Each phage variant was normalized by dilution to an equivalent Fab display level determined by titration of an epitope tag fused to the light chain displayed on the phage and then assessed for binding to STEAP-1 by FACS analysis on STEAP-1-expressing cells (293 STEAP-1 NT LB50) and non-expressing (293 vector S408) cells. The term "2°" refers to the secondary antibody in the FACS analysis. The term "α-120" refers to the murine 120 anti-STEAP-1 antibody. The term "α-10H1" refers to a control antibody. The terms "24 Phage," "37 Phage," and the like refer to humanized anti-STEAP-1 variants as disclosed herein displayed on phage. "Ch 120 Phage" refers to the 120 Chimera displayed on phage, and "120.graft Phage" refers to the 120 graft displayed on Phage. (FIG. 6). The importance of normalizing phage clones by their Fab display level is illustrated by a FACS analysis of the 120-graft at different phage titers: 7×10$^{12}$ phage/ml in FIG. 6 and 2×10$^{11}$ phage/ml in FIG. 6. Once diluted to the lower phage concentration, the 120-graft phage no longer produced an observable FACS shift. Thus normalization of the different phage clones for their display level was important step for assessing their affinity differences for Steap1.

Following normalization for Fab display levels, the variant of the 120-graft containing the additional mutation A24V (120.v24) produced a FACS shift superior to other variants (FIG. 6). When expressed as an IgG, 120.v24 produced a similar FACS shift to the chimeric 120 antibody at all concentrations tested. Subsequent Scatchard analysis of 120.v24 indicated a Kd of 2.2 nM for binding to 293 STEAP-1 NT LB50 cells, a two-fold improvement over the 120 chimera and the original murine M2-120.545 (Table 2).

TABLE 2

Anti-STEAP-1 antibody binding affinity for cell surface STEAP-1 (Kd (nM))

| Cell line | Murine anti-STEAP-1 MAb 120.545 nM | 120 Chimera | Humanized anti-STEAP-1 120v.24 |
|---|---|---|---|
| PC3-PS5.4 (exogenous STEAP-1) | 17.5 nM<br>187,256 sites per cell | 9.9 nM<br>103,204 sites per cell | — |
| 293.LB50 (exogenous STEAP-1) | 4.7 nM<br>301,100 sites per cell | 4.9 nM<br>252,892 sites per cell | 2.2 nM<br>264,172 sites per cell |
| LNCaP-BR (endogenous STEAP-1) | 1.5 nM<br>37,207 sites per cell | 0.9 nM<br>22,021 sites per cell | — |

Binding activity of anti-STEAP-1 naked antibodies, murine 120 and chimera 120 was also tested using FACS analysis. Binding was compared for exogenous STEAP-1 in 293 stable STEAP-1 NT LB50, PC3 stable STEAP-1 PS5.4, and endogenous STEAP-1 in LNCaP cells. The results are also shown in FIGS. 7D-7F. NT LB50 cells expressing exogenous human STEAP-1 on the cell surface were prepared by stably transforming 293 cells (ATCC CRL-1573) with human STEAP-1 DNA. PS5.4 cells expressing exogenous human STEAP-1 on the cell surface were prepared by stably transforming PC3 (ATCC CLL-1435) with human STEAP-1 DNA. LNCAP cells (ATCC CRL-1740) express STEAP-1 endogenously.

Example 2

Characterization of Anti-STEAP-1 Antibodies

Anti-STEAP-1 antibodies (naked antibodies and antibody drug conjugates disclosed herein) were characterized or may be characterized according to standard methods.

ELISA-based assays: Anti-STEAP-1 antibody screening by ELISA is performed as follows, with all incubations done at room temperature. Test plates (Nunc Immunoplate) were coated for 2 hours with purified STEAP-1 in 50 mM sodium carbonate buffer, pH 9.6, then blocked with 0.5% bovine serum albumin in phosphate buffered saline (PBS) for 30 minutes, then washed four times with PBS containing 0.05% Tween 20 (PBST). Test antibody supernatants are added and incubated two hours with shaking, then washed four times with PBST. The plates are developed by adding 100 µl/well of a solution containing 10 mg of o-phenylenediamine dihydrochloride (Sigma, #P8287) and 10 µl of a 30% hydrogen peroxide solution in 25 ml phosphate citrate buffer, pH. 5.0, and incubating for 15 minutes. The reaction is stopped by adding 100 µl/well of 2.5 M sulfuric acid. Data is obtained by reading the plates in an automated ELISA plate reader at an absorbance of 490 nm.

Characterization of Anti-STEAP-1 Binding by Scatchard Analysis:

The binding affinity of the monoclonal antibody can, for example, be determined by the Scatchard analysis described in Munson et al., Anal. Biochem., 107:220 (1980) using standard techniques well know in the relevant art. See also Scatchard, G., Ann. N.Y. Acad. Sci. 51:660 (1947).

Example 3

Production of Anti-STEAP-1 Antibody Drug Conjugates

Production of anti-STEAP-1 auristatin ADCs—Anti-STEAP-1 ADCs were produced by conjugating anti-STEAP-1 antibodies murine 120.545, 120 chimera, 120 graft, and humanized 120 framework variants to the following drug-linker moieties: spp-DM1, smcc-DM1, MC-vc-PAB-MMAE; MC-vc-PAB-MMAF; MC-MMAE, MC-MMAF, vc-MMAE, and vc-MMAF, which drug and linker moieties and methods of attachment are disclosed herein as well as in WO 2004/010957, published Feb. 5, 2004, WO2006/034488, published Sep. 9, 2005, and in Doronina, S. O. et al., Nature Biotechnol. 21:778-784 (2003), (each of which references is herein incorporated by reference in its entirety). Prior to conjugation, the antibodies were partially reduced with TCEP using standard methods in accordance with the methodology described in WO 2004/010957. The partially reduced antibodies were conjugated to the above drug-linker moieties using standard methods in accordance with the methodology described in Doronina et al. (2003) Nat. Biotechnol. 21:778-784 and US 2005/0238649 A1. Briefly, the partially reduced antibodies were combined with the drug linker moieties to allow conjugation of the moieties to cysteine residues. The conjugation reactions were quenched, and the ADCs were purified. The drug load (average number of drug moieties per antibody) for each ADC was determined by HPLC. As used herein, the linker-drug component of an ADC, "-MC-vc-PAB-MMAE" or "-MC-vc-PAB-MMAF" is sometimes abbreviated as "-vcMMAE" or "-vcMMAF," and the component "-MC-MMAF" is sometimes abbreviated as "MCM-MAF" or "mcMMAF."

Production of anti-STEAP-1 maytansinoid ADCs—Anti-STEAP-1 ADCs were produced by conjugating anti-STEAP-1 antibodies, murine 120, 120 chimera, 120 graft, and humanized 120 framework variants to the linker drug moiety—smcc-DM1. Such conjugation may be performed according to the method disclosed in WO 2005/037992 for conjugation of Herceptin® anti-HER2 antibody.

Example 4

In Vivo Tumor Volume Reduction Assay

To test the efficacy of toxin-conjugated or unconjugated anti-STEAP-1 monoclonal antibodies for the ability to reduce tumor volume in vivo and in vitro, the following protocol was employed.

Mammalian cell lines and human tumor xenografts: 293 is a human immortalized embryonic kidney cell line (ATCC reference CRL1573), PC-3 is a human prostate adenocarcinoma cell line (ATCC reference CRL1435) and LNCAP is a prostate carcinoma cell line (ATCC CRL1740). All cells were grown in 50/50 Dulbecco modified Eagle high glucose medium, Ham's F12 supplemented with 10% fetal bovine serum (FBS), 2 mM glutamine, 1% penicillin-streptomycin and cultured at 37° C. in 5% CO2. 293 and PC-3 stable cell lines were generated by transfection (Fugene, Roche) with a cytomegalovirus-driven vector encoding either full length STEAP1 (LB50 and PS5.4 respectively) or an empty vector and selected in 400 µg/ml G418 (Geneticin, Life Technologies). Human prostate explant models, LuCAP 77 and LuCAP 35V, were obtained from the University of Seattle.

Expression of exogenous and endogenous STEAP-1 on the cell surface was demonstrated by immunohistochemistry (IHC) and FACS analysis as follows. Sheep and mouse anti-STEAP-1 antibodies (Agensys, Inc., Santa Monica, Calif.) were generated against an intracellular amino-terminal peptide of STEAP-1 (see Hubert, R. S., Vivanco, I. et al., PNAS 25:14523-14528 (1999)). Monoclonal antibodies against the extracellular domains of STEAP-1 (Agensys, Inc.) were generated by immunization of mice with 293T cells transiently transfected with STEAP-1. For IHC analysis, the primary sheep anti-STEAP-1 antibody was used for detection. For FACS analysis, cells were grown to 90% confluence and removed from plates using 2 mM EDTA in PBS. Cells were washed and resuspended in FACS buffer (PBS with 1% BSA) and incubated for 60 minutes with anti-STEAP1 antibodies at room temperature followed by 60 minutes with the appropriate secondary antibody conjugated to phycoerythrin. Analysis was performed on FACSscan (BD Biosciences). For immunoflourescence, cells were grown in chamber slides overnight and then incubated with primary antibody at 37° C. for 60 minutes. Cells were fixed in paraformaldehyde, blocked in 1% BSA and incubated with the appropriate secondary antibody conjugated to flourescin.

In vivo prostate cancer xenograft models were used to test the efficacy of anti-STEAP-1 ADCs. These models included human cell line LNCaP (ATCC CRL-1740 or Southern Research Institute, Birmingham, Ala.). Prostate explant models included LuCaP 77 and LuCaP35V (University of Washington, Seattle, Wash.). Each prostate explant model was maintained by serial transplanting in castrated (androgen independent model, LuCAP 35V) or uncastrated (androgen dependent model, LuCAP 77), male SCID-beige mice from Charles River Lab. The uncastrated mice received a testosterone pellet prior to implantation, while castration was done at least two weeks prior to tumor implantation to allow testosterone levels to nadir. When donor mice had tumors of between 800-1000 mm$^3$, tumor tissue were aseptically removed and dissected into small implantable sized pieces (approximately 20 mm$^3$) for study animals. The tumor is placed into a pocket at the implantation site and the skin is closed using wound clips. For the LNCap cell line model, in vitro grown LNCaP cells were injected subcutaneously at 8-10 million cells per mouse in 50% matrigel into male SCID-beige mice which had received a testosterone pellet. When mean tumor size reached 100-200 mm$^3$, animals were randomly grouped in ten groups of ten mice each and given a single IV administration of test antibody ADC or control antibody (naked or control). In some experiments, multiple doses of test or control antibody were administered (see FIGS. 8A, 9, and 10). In some experiments, a single dose of test and control antibody were administered as seen in FIGS. 8B and 11. Where the prostate explant model was LuCap 77, a testosterone pellet was implanted in the mice approximately 3-7 days before transplantation of exogenous tumor. Tumors were measured twice per week for 4 weeks, then once or twice per week for the remainder of the study or once per week throughout the study. A significantly lower tumor volume in test animals over time was considered to an indication of efficacy. In some cases, tumor volume decreased significantly from the initial volume and remained low throughout the study. Results are plotted in FIGS. 8-11.

Anti-STEAP-1 Auristatin Drug Conjugates Reduce Prostate Tumor Volume In Vivo

Administration of murine anti-STEAP-1 120-MC-vc-PAB-MMAE at 3 mg/kg was efficacious in a prostate tumor (LNCaP-Ner cells) xenograft model. PBS and anti-gp120-MC-vc-PAB-MMAE (3 mg/kg) were used as controls. Doses were administered on days 0, 7, and 14. See FIG. 8A.

Administration of Humanized Anti-STEAP-1 Antibody 120v.24-MC-vc-PAB-MMAE (3 mg/kg), 120v.24-MC-MMAF (6 mg/kg), 120v.24-MC-MMAF (12 mg/kg), and anti-STEAP-1 120 chimera-MC-vc-PAB-MMAE (3 mg/kg) to SCID beige mice transplanted with LNCap-Ner tumor (treated with a testosterone pellet as described herein) was shown to be efficacious. Vehicle, anti-ragweed-MC-vc-PAB-MMAE (3 mg/kg) and anti-ragweed-MC-MMAF (12 mg/kg) were used as controls. Doses were administered on the days indicated in FIG. 8. The results are plotted in FIG. 8B.

Administration of anti-STEAP-1 antibody 120 chimera-MC-vc-PAB-MMAE (3 mg/kg) and anti-STEAP-1 120 chimera-MC-MMAF (6 mg/kg) was shown to be efficacious in a prostate cancer xenograft model of SCID-beige mice transplanted with LNCaP cells. Three doses at approximately days 15, 25, and 30 at 3 mg/kg (anti-STEAP-vcMMAE) or 6 mg/kg (anti-STEAP-mcMMAF) were administered to the mice. Control anti-ragweed-MC-vc-PAB-MMAE (3 mg/kg) and anti-ragweed-MC-MMAF (6 mg/kg) were used. See FIG. 9.

Administration of humanized anti-STEAP-1 antibody 120 chimera-MC-vc-PAB-MMAE (3 mg/kg) was shown to be efficacious in a prostate cancer xenograft model of SCID beige male mice (androgen dependent) transplanted with LuCap 77 cells. Controls were vehicle and anti-ragweed-MC-vc-PAB-MMAE. Three doses at 3 mg/kg of test and control antibodies were administered. See FIG. 10.

Administration of humanized anti-STEAP-1 antibody 120v.24-MC-vc-PAB-MMAE at 3 mg/kg, anti-STEAP-1 antibody 120v.24-MC-MMAF at 6 mg/kg and 12 mg/kg to castrated SCID-beige mice transplanted with LuCap35V prostate tumor was shown to be efficacious relative to controls. Drug load was 3.1 per antibody. Control antibodies were anti-ragweed-MC-MMAF administered at 12 mg/kg, and anti-gp120-MC-vc-PAB-MMAE administered at 6 mg/kg. See FIG. 11.

Anti-STEAP-1 Auristatin Drug Conjugates Reduce Prostate Tumor Volume In Vitro

In vitro cell killing assays were performed to assess the effectiveness of anti-STEAP-1 drug conjugates to inhibit growth and/or kill cells expressing STEAP-1. Briefly, cells expressing STEAP-1 were plated at approximately 2,000 cells/well in a 96-well plate and treated 24 hours later in duplicate with antibody drug conjugate. Plates were incubated for 5-7 days at 37° C. and developed with CellTiter-Glo® luminescent cell viability assay kit (Promega, Madison, Wis., USA). Test cells included PS5.4 (PC3 cells expressing exogenous STEAP-1), LB50 (293 cells expressing exogenous STEAP-1), PC3 cells transfected with vector alone, 293 cells transfected with vector alone, and LNCaP cells expressing endogenous STEAP-1. Tested antibody drug conjugates included control antibody-MC-MMAF, control antibody-vc-MMAE, anti-STEAP-1 antibody 120 chimera-vc-MMAE, anti-STEAP-1 antibody 120 chimera-MC-MMAF (two different lots of material), and anti-STEAP-1 antibody chimera-vc-MMAF. The results are shown in FIG. 14A-E.

Example 5

Preparation of Cysteine Engineered Anti-STEAP-1 Antibodies for Conjugation by Reduction and Reoxidation Full length, cysteine engineered anti-STEAP-1 monoclonal antibodies (ThioMabs) expressed in CHO cells are dissolved in 500 mM sodium borate and 500 mM sodium chloride at about pH 8.0 and reduced with about a 50-100 fold excess of 1 mM TCEP (tris(2-carboxyethyl)phosphine hydrochloride (Getz et al (1999) Anal. Biochem. Vol 273:73-80; Soltec Ventures, Beverly, Mass.) for about 1-2 hrs at 37° C. The reduced ThioMab is diluted and loaded onto a HiTrap S column in 10 mM sodium acetate, pH 5, and eluted with PBS containing 0.3M sodium chloride. The eluted reduced ThioMab is treated with 2 mM dehydroascorbic acid (dhAA)

at pH 7 for 3 hours, or 2 mM aqueous copper sulfate (CuSO$_4$) at room temperature overnight. Ambient air oxidation may also be effective. The buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm.

Example 6

Preparation of Cysteine Engineered Anti-STEAP-1 Antibody Drug Conjugates By Conjugation of Cysteine Engineered Anti-STEAP-1 Antibodies and Drug-linker Intermediates After the reduction and reoxidation procedures of Example 5, the cysteine engineered anti-STEAP antibody is dissolved in PBS (phosphate buffered saline) buffer and chilled on ice. About 1.5 molar equivalents relative to engineered cysteines per antibody of an auristatin drug linker intermediate, such as MC-MMAE (maleimidocaproyl-monomethyl auristatin E), MC-MMAF, MC-val-cit-PAB-MMAE, or MC-val-cit-PAB-MMAF, with a thiol-reactive functional group such as maleimido, is dissolved in DMSO, diluted in acetonitrile and water, and added to the chilled reduced, reoxidized antibody in PBS. After about one hour, an excess of maleimide is added to quench the reaction and cap any unreacted antibody thiol groups. The reaction mixture is concentrated by centrifugal ultrafiltration and the cysteine engineered anti-STEAP-1 antibody drug conjugate is purified and desalted by elution through G25 resin in PBS, filtered through 0.2 µm filters under sterile conditions, and frozen for storage.

By the procedure above, the following cysteine engineered anti-STEAP-1 antibody drug conjugates were prepared (where numbering for the variants is standardized (Kabat numbering for the light chain and EU numbering for the heavy chain), as provided herein and in FIG. 17):

thio human120-MC-MMAF by conjugation of light chain V205C thio hu 120 and MC-MMAF;

thio human120-MC-MMAF by conjugation of heavy chain a118C thio hu 120 and MC-MMAF;

thio human120-MC-val-cit-PAB-MMAE by conjugation of light chain V205C thio hu 120 and MC-val-cit-PAB-MMAE; and thio human120-MC-val-cit-PAB-MMAE by conjugation of heavy chainA 118C thio hu 120 and MC-val-cit-PAB-MMAE.

Example 7

Characterization of Cysteine Engineered Anti-STEAP-1 Antibodies

The cysteine engineered anti-STEAP-1 antibody drug conjugates (TDCs) prepared as described above were assayed to confirm that they retained the activity of the parent antibody in vitro. The anti-STEAP-1 TDCs thio-human120-vc-PAB-MMAE (LCV205C) (abbreviated as huSteap1 TDC (L205C) vcE and thio-human120-vc-PAB-MMAE (HCA118C) (abbreviated as huSteap 1 TDC (HCA 118C) vcE) were assessed for binding to STEAP-1 by FACS analysis on STEAP-1-expressing cells (293 STEAP-1 NT LB50) and non-expressing (293 vector S408) cells. The term "2$^{nd}$ only" refers to the secondary antibody in the FACS analysis. The TDC control (vcE) and ADC std control (vcE) are control antibody thio and non-thio vc-PAB-MMAE drug conjugates, respectively. The huSteap1 ADC (std) is a vc-PAB-MMAE drug conjgate derived from the parent human anti-STEAP-1 antibody. As shown, the TDCs produced FACS shifts similar to that of the parent huSteap1 ADC.

In vitro cell killing assays were also performed, to assess the effectiveness of the cysteine engineered anti-STEAP-1 antibody drug conjugates to inhibit growth and/or kill cells expressing STEAP-1. Briefly, cells expressing STEAP-1 were plated at approximately 2,000 cells/well in a 96-well plate and treated 24 hours later in duplicate with antibody drug conjugate. Plates were incubated for 5-7 days at 37° C. and developed with CellTiter-Glo® luminescent cell viability assay kit (Promega, Madison, Wis., USA). Test cells included PS5.4 (PC3 cells expressing exogenous STEAP-1), LB50 (293 cells expressing exogenous STEAP-1), and LNCaP cells expressing endogenous STEAP-1. Tested antibody drugconjugates included control antibody-vc-MMAE (ADC std control (vcE)), control thio antibody-vc-MMAE (TDC control (vcE)), the anti-STEAP-1 TDCs thio-human120-vc-PAB-MMAE (LCV205C) (abbreviated as huSteap 1 TDC (L205C) vcE and thio-human120-vc-PAB-MMAE (HCA118C) (abbreviated as huSteap1 TDC (HCA118C) vcE), and huSteap1 ADC (std), a vc-PAB-MMAE drug conjgate derived from the parent human anti-STEAP-1 antibody. As shown in FIGS. 19A-C, the anti-STEAP-1 TCDs retain the activyt of the parent ADC in vitro.

Example 8

In Vivo Tumor Volume Reduction Assays for Cysteine Engineered Anti-STEAP-1 Antibody Drug Conjugates In vivo prostate cancer xenograft models were used to test the efficacy of cysteine-engineeered anti-STEAP-1 ADCs. These models and the test protocols employed correspond to those described in Example 4.

Administration of the anti-STEAP-1 TDC thio-human120-vc-PAB-MMAE (HCA118C) (abbreviated as huSteap1 HC TDC vcE) (3 mg/kg) to SCID beige mice transplanted with LNCap-Ner tumor (treated with a testosterone pellet as described herein) was shown to be efficacious. Vehicle (PBS), control antibody-vc-MMAE (ADC std ctrl vcE) and control thio antibody-vc-MMAE (TDC HC ctrl vcE) were used as controls. The effect of the anti-STEAP-1 TDC was also compared to human anti-STEAP-1 antibody 120-MC-vc-PAB-MMAE (hu Steap 1 std ADC vcE) as a positive control. A single dose was administered at day 0. All antibodies were administered at 3 mg/kg. The results are plotted in FIG. 20.

FIG. 21 shows that administration of anti-STEAP-1 TDC thio-human120-vc-PAB-MMAE (HCA118C) (abbreviated as huSteap1 HC TDC vcE) at 3 mg/kg and anti-STEAP-1 TDC thio-human120-MC-MMAF (HCA118C) (abbreviated as huSteap1 HC TDC mcF) at 1, 3 or 6 mg/kg was shown to be efficacious in a prostate cancer xenograft model of SCID-beige mice transplanted with LNCaP cells. Single doses at day 0 at 0.3, 1 or 3 mg/kg (huSteap1 HC TDC vcE) or 1, 3 or 6 mg/kg (huSteap1 HC TDC mcF) were administered to the mice. Vehicle (PBS), control antibody-vc-MMAE (ADC std ctrl vcE) and control thio antibody-vc-MMAE (TDC HC ctrl vcE) were used as controls.

FIG. 22 shows that administration of anti-STEAP-1 TDC thio-human120-vc-PAB-MMAE (HCA 118C) (abbreviated as huSteap IHC TDC vcE) at 3 mg/kg and anti-STEAP-1 TDC thio-human120-MC-MMAF (HCA118C) (abbreviated as huSteap1 HC TDC mcF) at 3 or 6 mg/kg was shown to be efficacious in a prostate cancer xenograft model of SCID beige male mice (androgen dependent) transplanted with LuCap 35V cells. Single doses at day 0 at 0.3, 1 or 3 mg/kg (huSteap1 HC TDC vcE) or 1, 3 or 6 mg/kg (huSteap1 HC TDC mcF) were administered to the mice. Vehicle (PBS), control antibody-vc-MMAE (ADC std ctrl vcE) and control thio antibody-vc-MMAE (TDC HC ctrl vcE) were used as controls.

Example 9

Preparation and Characterization of the Anti-STEAP-1 Antibody SGIV from Antibody 120 Variant 24

Another LC anti-STEAP-1 antibody variant was prepared wherein the light chain and framework regions were further modified to obtain improved antibody expression levels.

Materials and Methods

Residue numbers are according to Kabat (Kabat et al., *Sequences of proteins of immunological interest*, 5th Ed., Public Health Service, National Institutes of Health, Bethesda, Md. (1991)). Single letter amino acid abbreviations are used. DNA degeneracies are represented using the IUB code (N=A/C/G/T, D=A/G/T, V=A/C/G, B=C/G/T, H=A/C/T, K=G/T, M=A/C, R=A/G, S=G/C, W=A/T, Y=C/T).

Preparation of a Revised Light Chain Variant: A variant of the 120.v24 antibody, designated "Simmons IV" or simply "SGIV," was generated and characterized. The amino acid sequence of the SGIV light chain is provided in SEQ ID NO:90. This sequence, aligned with the corresponding regions of the mu 120 antibody (SEQ ID NO:89) and the 120.v24 antibody (SEQ ID NO:91) is shown in FIG. 23.

Assessment of variant SGIV compared to variant 120.v24-SGIV and 120.v24 antibodies, expressed as IgG, were assessed by FACS analysis using the stably transformed Steap1 positive cell lines 293 Steap1 NT LB48, 293 Steap1 NT LB50, and 293 Steap1 NT LB53 as well as in LNCaP cells, which express endogenous STEAP-1 (FIG. 28). Cells were prepared as described in Example 1. Each IgG was added at 5 µg/mL on ice for 1 hour. Samples were washed twice with FACS buffer by centrifugation and a 1:200 dilution of anti-human PE conjugate (R-phycoerythrin goat anti-human IgG Fcγ Fragment, Jackson Immunoresearch) was added for 30 minutes. Samples were again washed twice with FACS buffer by centrifugation and samples were analyzed by FACS.

Scatchard-Based Affinity Determination of SGIV and 120.v24 binding to STEAP-1—The binding affinities of 120.v24 and the Simmons IV ("SGIV") antibodies to STEAP-1 were determined using Scatchard analysis according to standard methods. JgG was purified with Protein G affinity chromatography. Affinity determinations were performed by Scatchard analysis in PC-3-PS5.4, 293-LB50 and LNCaP-BR cells in duplicate. Scatchard plots of 120.v24 and SGIV in LNCaP BR cells and 293.LB50 cells are shown in FIGS. 25 and 26 respectively. A table comparing the average binding affinities for the mu 1789, mu 120, Fc chimera, humanized 120.v24, thio-120.v24 and thio-SGIV in PC-3-PS5.4, 293-LB50 and LNCaP-BR cells, as well as in 293 cells transiently expressing STEAP-1, is shown in FIG. 27.

Site Directed Mutagenesis Of SGIV and 120.v24: Variants of the SGIV and 120.v24 antibodies were prepared using standard mutagenesis protocols as described above. The first class of variants resulted from site-directed mutagenesis whereby particular residues of Simmons IV ("SGIV") were replaced with the corresponding residue of 120.v24 to further improve binding affinity. The specific variants produced, as shown in FIG. 24, were as follows:

(1) LS.VLVH1, wherein residues 42 ("Q") and 43 ("P") were modified to "K" and "A" respectively (SEQ ID NO:92)

(2) LS.VLVH2, wherein residue 3 ("V") were modified to "Q," residues 42 ("Q") and 43 ("P") were modified to "K" and "A" respectively, and residue 85 ("V") was modified to "T" (SEQ ID NO:93)

(3) LS.Q, wherein residue 3 ("V") was modified to "Q" (SEQ ID NO:94)

(4) LS.CH1, wherein residue 15 ("L") was modified to "V" and residue 83 ("V") was modified to "F" (SEQ ID NO:95)

A second class of variants was generated through site-directed mutagenesis wherein particular residues of 120.v24 were replaced with the corresponding residue of Simmons IV (SGIV) in an attempt to improve antibody expression levels. The specific variants, as shown in FIG. 24, were as follows:

(1) ED.FW1, wherein residue 3 ("Q") was modified to "V"; residue 9 ("S") was modified to "D"; residue 12 ("S") was modified to "A"; residue 13 ("A") was modified to "V"; residue 15 ("V") was modified to "L"; residue 17 ("D") was modified to "E"; residue 19 ("V") was modified to "A"; and residue 22 ("T") was modified to "N" (SEQ ID NO:96)

(2) ED.FW2, wherein residues 42 ("K") and 43 ("A") of 120.v24 were modified to "Q" and "P" respectively (SEQ ID NO:97)

(3) ED.FW3, wherein residue 60 ("S") was modified to "D"; residue 80 ("P") was modified to "A"; residue 83 ("F") was modified to "V"; and residue 85 ("T") was modified to "V" (SEQ ID NO:98)

(4) ED.all, wherein residue 3 ("Q") was modified to "V"; residue 9 ("S") was modified to "D"; residue 12 ("S") was modified to "A"; residue 13 ("A") was modified to "V"; residue 15 ("V") was modified to "L"; residue 17 ("D") was modified to "E"; residue 19 ("V") was modified to "A"; residue 22 ("T") was modified to "N"; residues 42 ("K") and 43 ("A") of 120.v24 were modified to "Q" and "P"; residue 60 ("S") was modified to "D"; residue 80 ("P") was modified to "A"; residue 83 ("F") was modified to "V"; and residue 85 ("T") was modified to "V" (SEQ ID NO:99)

(5) ED.Pro, wherein residue 43 ("A") was modified to "P" and residue 80 ("P") was modified to "A" (SEQ ID NO:100)

(6) ED.pl, wherein residue 9 ("S") was moedified to "D"; residue 42 ("K") was modified to "Q" and residue 60 ("S") was modified to "D" (SEQ ID NO:101)

Results and Discussion

Preparation of SGIV Antibody—The sequences of anti-STEAP-1 antibody version 24 (120.v24) variable region is shown in FIGS. 23 and 24 (SEQ ID NO:91). Using site-directed mutagenesis, another variant termed "Simmons IV" or simply "SGIV" was prepared using standard mutagenesis protocols as described above. FIGS. 23 and 24 show the sequence of SGIV light chain in alignment with that of mu 120 antibody and 120.v24. The titers of various harvests of SGIV antibody are shown in FIG. 29.

Comparison of Binding of SGIV and 120.v24 to STEAP-1 using FACs—The ability of both antibodies, 120.v24 and SGIV, to bind to STEAP-1 expressed on the cell surface was measured using FACs. Antibody binding to cell lines expressing either exogenous STEAP-1 (293 STEAP-1 LB48, 293 STEAP-1 LB50 and 293 STEAP-1 LB53) or endogenous STEAP1 (LNCaP.Br) was measured in duplicate; the results are summarized in FIG. 28. As shown in FIG. 28, both antibodies were able to bind STEAP-1 in all four cell lines.

Binding affinity of the SGIV Antibody To STEAP-1 and Comparison to 120.v24—The binding affinities of the SGIV and 120.v24 to STEAP-1 were examined using Scatchard analysis. Scatchard plots of 120.v24 and SGIV in LNCaP BR cells and 293.LB 50 cells are shown in FIGS. 25 and 26 respectively. A table comparing the average binding affinities for the mu 1789, mu 120, Fc chimera, humanized 120.v24, thio-120.v24 and thio-SGIV antibodies in PC-3-PS5.4, 293-LB50 and LNCaP-BR cells, as well as in 293 cells transiently expressing STEAP-1, is shown in FIG. 27. The results indicate that the binding affinity of the 120.v24 antibody in 293-LB50 and LNCaP.BR cells is roughly 1.5-fold that of the SGIV variant.

Although the foregoing invention has been described in some detail by way of illustration and example for purposes of clarity of understanding, the descriptions and examples should not be construed as limiting the scope of the invention. The disclosures of all patent and scientific literatures cited herein are expressly incorporated in their entirety by reference.

What is claimed is:

1. A humanized monoclonal antibody that binds to STEAP-1,
   wherein the antibody comprises (a) heavy chain variable domain comprising:
   (1) an HC-FR1 comprising the amino acid sequence of SEQ ID NO:25;
   (2) an HVR-H1 comprising the amino acid sequence of SEQ ID NO:14;
   (3) an HC-FR2 comprising the amino acid sequence of SEQ ID NO:22;
   (4) an HVR-H2 comprising the amino acid sequence of SEQ ID NO:15;
   (5) an HC-FR3 comprising the amino acid sequence of SEQ ID NO:138;
   (6) an HVR-H3 comprising the amino acid sequence of SEQ ID NO:16; and
   (7) an HC-FR4 comprising the amino acid sequence of SEQ ID NO:24,
   and (b) a light chain variable domain comprising:
   (1) an HC-FR1 comprising the amino acid sequence of SEQ ID NO:17;
   (2) an HVR-H1 comprising the amino acid sequence of SEQ ID NO:11;
   (3) an HC-FR2 comprising the amino acid sequence of SEQ ID NO:18;
   (4) an HVR-H2 comprising the amino acid sequence of SEQ ID NO:12;
   (5) an HC-FR3 comprising the amino acid sequence of SEQ ID NO:19;
   (6) an HVR-H3 comprising the amino acid sequence of SEQ ID NO:13; and
   (7) an HC-FR4 comprising the amino acid sequence of SEQ ID NO:20,
   wherein the binding affinity to STEAP-1 of said humanized antibody is higher than the binding affinity to STEAP-1 of a humanized antibody comprising a heavy chain variable domain comprising the amino acid sequence of SEQ ID NO:9 and a light chain variable domain comprising the amino acid sequence of SEQ ID NO:6.

2. The antibody of claim 1, wherein the antibody is an antibody fragment selected from a Fab, Fab'-SH, Fv, scFv, or (Fab')$_2$ fragment.

3. The antibody of claim 1 covalently attached to a cytotoxic agent.

4. The antibody covalently attached to a cytotoxic agent of claim 3, wherein the cytotoxic agent is selected from a toxin, a chemotherapeutic agent, a drug moiety, an antibiotic, a radioactive isotope, and a nucleolytic enzyme.

5. An immunoconjugate, wherein the immunoconjugate has the formula Ab-(L-D)p, and wherein: (a) Ab is the antibody of claim 1 (b) L is a linker; (c) D is a drug moiety; and (d) p is 1 to 20.

6. The immunoconjugate of claim 5, wherein L is selected from 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1carboxylate (SMCC), N-Succinimidyl (4-iodo-acetyl) aminobenzoate (SLAB), and 6-maleimidocaproyl-valine-citrulline-p-aminobenzyloxycarbonyl (MC-vc-PAB).

7. The immunoconjugate of claim 5, wherein D is selected from an auristatin and dolastatin.

8. The immunoconjugate of claim 7, wherein D is a drug moiety of formula $D_E$ or $D_F$:

$$D_E$$

$$D_F$$

and wherein $R^2$ and $R^6$ are each methyl, $R^3$ and $R^4$ are each isopropyl; $R^5$ is H; $R^7$ is sec-butyl; each $R^8$ is independently selected from $CH_3$, $O-CH_3$, OH, and H; $R^9$ is H; $R^{10}$ is aryl; Z is $-O-$ or $-NH-$; $R^{11}$ is H, $C_1$-$C_8$ alkyl, or $-(CH_2)_2-O-(CH_2)_2-OCH_2)_2-O-CH_3$; and $R^{18}$ is $-C(R^8)_2-C(R^8)_2$-aryl; and
p ranges from about 1 to 8.

9. The immunoconjugate of claim 5, having in vitro or in vivo cell killing activity.

10. The immunoconjugate of claim 5, wherein the immunoconjugate has the formula Ab-(L-MMAE)p, wherein L is a linker and p ranges from 2 to 5.

11. The immunoconjugate of claim 10, wherein L comprises val-cit.

12. The immunoconjugate of claim 10, wherein L comprises MC.

13. The immunoconjugate of claim 10, wherein L comprises PAB.

14. The immunoconjugate of claim 10, wherein L comprises MC-vc-PAB.

15. The immunoconjugate of claim 5, wherein D is a maytansinoid.

16. The immunoconjugate of claim 15, wherein D is selected from DM1, DM3, and DM4.

17. The immunoconjugate of claim 15, wherein the linker is attached to the antibody through a thiol group on the antibody.

18. The immunoconjugate of claim 15, wherein the linker, L, is selected from N-Succinimidyl 4-(2-pyridylthio) pentanoate (SPP), N-succinimidyl 4-(N-maleimidomethyl) cyclohexane-1 carboxylate (SMCC), and N-Succinimidyl (4-iodo-acetyl) aminobenzoate (SLAB).

19. The immunoconjugate of claim 18, wherein D is DM4.

20. The immunoconjugate of claim 19, wherein L comprises SPP.

21. The immunoconjugate of claim 19, wherein L comprises SMCC.

22. The immunoconjugate of claim 19, wherein p is from 2-6.

23. A pharmaceutical composition comprising the immunoconjugate of claim 5 and a pharmaceutically acceptable carrier.

24. The antibody of claim 1 comprising a heavy chain constant domain and/or a light chain constant domain in which an amino acid residue naturally occurring in said heavy chain constant domain or said light chain constant domain is replaced with a free cysteine amino acid having a thiol reactivity value in the range of 0.6 to 1.0.

25. The antibody of claim 24 wherein the free cysteine amino acid is located in a light chain constant domain.

26. The antibody of claim 24 wherein the free cysteine amino acid is located in a heavy chain constant domain.

27. An antibody of claim 24 covalently attached to a cytotoxic agent.

28. The antibody covalently attached to a cytotoxic agent of claim 27, wherein the cytotoxic agent is selected from a toxin, a chemotherapeutic agent, a drug moiety, an antibiotic, a radioactive isotope, and a nucleolytic enzyme.

29. The antibody of claim 24 wherein the antibody is covalently attached to a capture label, a detection label, or a solid support.

30. The antibody of claim 24 covalently attached to an auristatin or maytansinoid drug moiety.

31. An antibody-drug conjugate, wherein the antibody-drug conjugate has the formula Ab-(L-D)p, and wherein: (a) Ab is the antibody of claim 24; (b) L is a linker moiety attached to said free cysteine amino acid; (c) D is a drug moiety; and (d) p ranges from 1 to 4.

32. The antibody-drug conjugate compound of claim 31 wherein p is 2.

33. The antibody-drug conjugate compound of claim 31 wherein L has the formula:

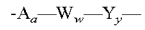

where:
A is a Stretcher unit covalently attached to a cysteine thiol of the cysteine engineered antibody (Ab);
a is 0 or 1;
each W is independently an Amino Acid unit;
w is an integer ranging from 0 to 12;
Y is a Spacer unit covalently attached to the drug moiety; and
y is 0, 1 or 2.

34. The antibody-drug conjugate compound of claim 33 having the formula:

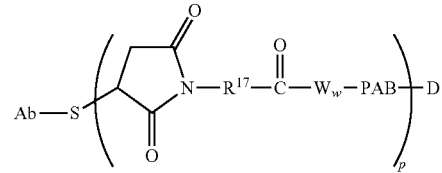

where PAB is para-aminobenzylcarbamoyl, and $R^{17}$ is a divalent radical selected from $(CH_2)_r$, $C_3$-$C_8$ carbocyclyl, O—$(CH_2)_r$, arylene, $(CH_2)_r$-arylene, -arylene-$(CH_2)_r$—, $(CH_2)_r$—($C_3$-$C_8$ carbocyclyl), ($C_3$-$C_8$ carbocyclyl)-$(CH_2)_r$, $C_3$-$C_8$ heterocyclyl, $(CH_2)_r$—$C_3$-$C_8$ heterocyclyl), —($C_3$-$C_8$ heterocyclyl)-$(CH_2)_r$—, —$(CH_2)_r$C(O)NR$^b$(CH_2)_r$—, —$(CH_2CH_2O)_r$—, —$(CH_2CH_2O)_r$—CH_2$—, —$(CH_2)_r$C(O)NR$^b$(CH_2CH_2O)_r$—, $(CH_2)_r$C(O)NR$^b$(CH_2CH_2O)_r$—CH_2$—, —$(CH_2CH_2O)_r$C(O)NR$^b$(CH_2CH_2O)_r$—, —$(CH_2CH_2O)_r$C(O)NR$^b$(CH_2CH_2O)_r$—CH_2$—, and $CH_2CH_2O)_r$C(O)NR$^b$(CH_2)_r$; where $R^b$ is H, $C_1$-$C_6$ alkyl, phenyl, or benzyl; and r is independently an integer ranging from 1 to 10.

35. The antibody-drug conjugate compound of claim 33 wherein $W_w$ is valine-citrulline.

36. The antibody-drug conjugate compound of claim 34 wherein R17 is $(CH_2)_5$ or $(CH_2)_2$.

37. The antibody-drug conjugate compound of claim 33 having the formula:

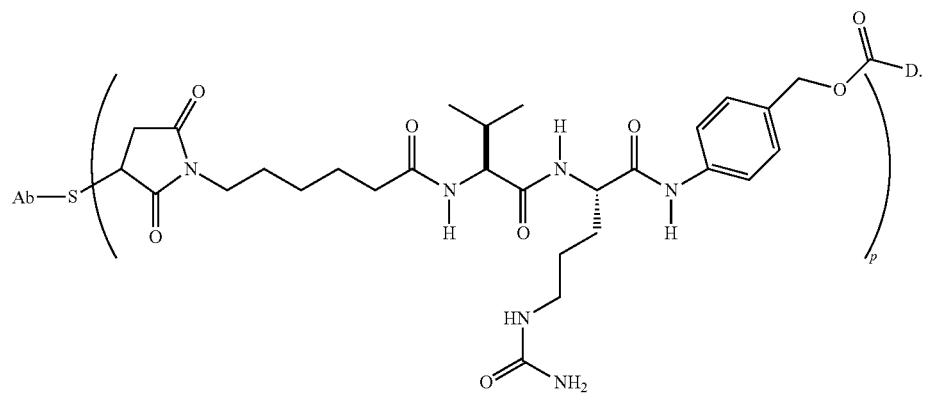

38. The antibody-drug conjugate compound of claim 31 wherein D is MMAE, having the structure:

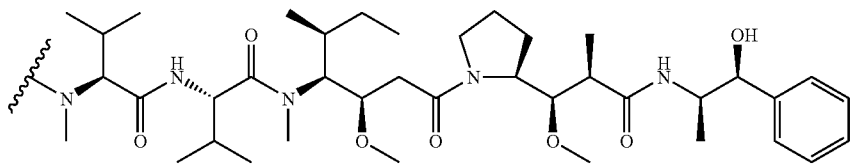 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

where the wavy line indicates the attachment site to the linker L.

39. A pharmaceutical formulation comprising the antibody covalently attached to an auristatin or maytansinoid drug moiety of claim 30, and a pharmaceutically acceptable diluent, carrier or excipient.

40. The antibody of claim 24 in which an amino acid residue naturally occurring in said heavy chain constant domain or said light chain constant domain is replaced with a cysteine at a position selected from 110, 144, 168 and 205 of the light chain constant domain according to Kabat numbering convention or a position selected from 115, 118, 120, 171,172, 282, 375, and 400 of the heavy chain constant domain according to EU numbering convention.

41. The antibody of claim 40, wherein a cysteine is at position 205 of the light chain constant domain.

42. The antibody of claim 40, wherein a cysteine is at position 118 of the heavy chain constant domain.

43. The antibody-drug conjugate compound of claim 31 wherein D is DM4, having the structure:

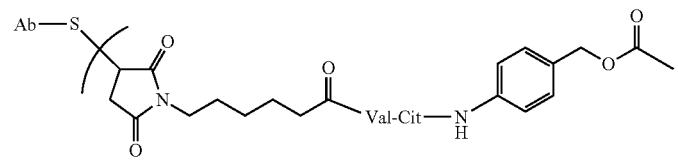

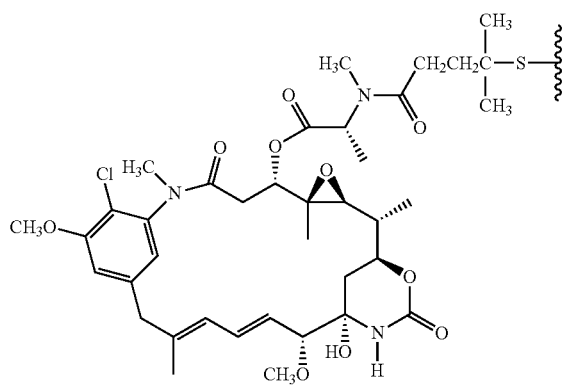

DM4 wherein the wavy lite indicates the attachment site to the linker L.

44. An antibody-drug conjugate compound selected from the structures:

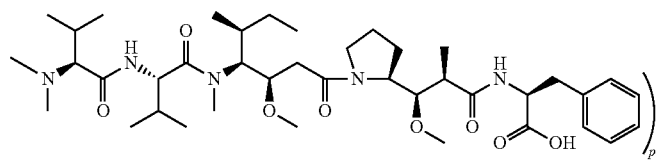

Ab-MC-vc-PAB-MMAF

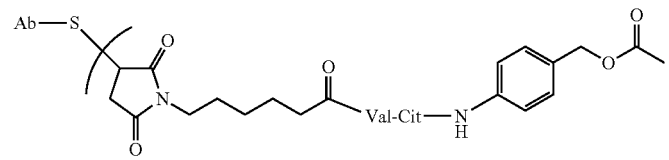

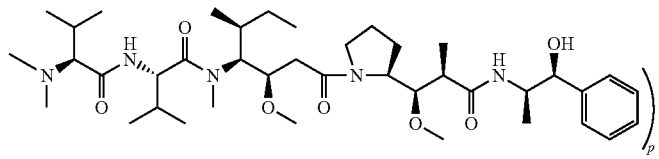

Ab-MC-vc-PAB-MMAE

-continued
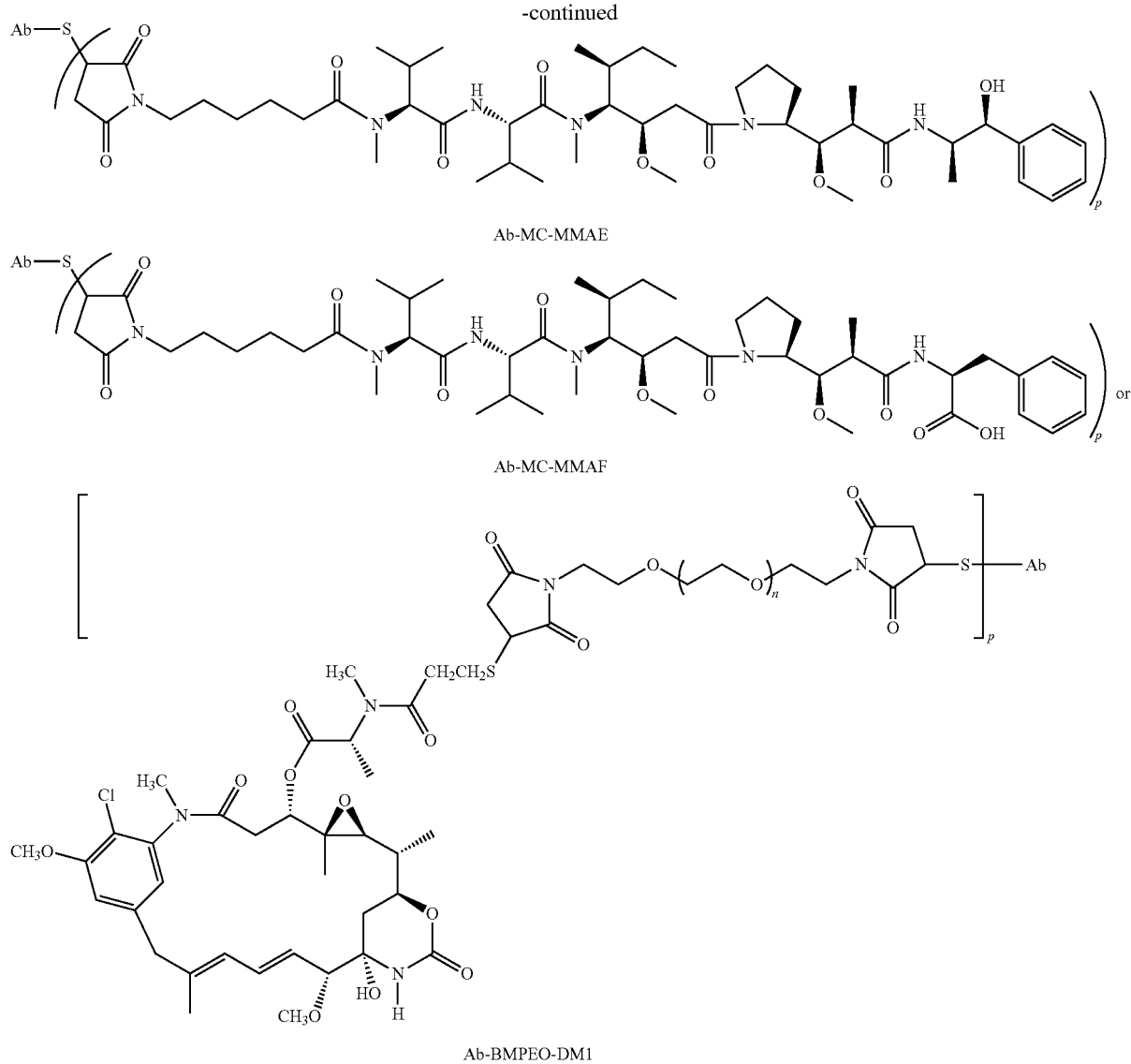
wherein Val is valine; Cit is citrulline; p ranges from 1 to 4; and Ab is an anti-STEAP-1 antibody of claim 24.
* * * * *

UNITED STATES PATENT AND TRADEMARK OFFICE
CERTIFICATE OF CORRECTION

PATENT NO. : 8,436,147 B2  
APPLICATION NO. : 11/978122  
DATED : May 7, 2013  
INVENTOR(S) : Mark S. Dennis et al.

Page 1 of 1

It is certified that error appears in the above-identified patent and that said Letters Patent is hereby corrected as shown below:

In the Claims:

Col. 213,

At claim number 1, line number 20, please replace "HC-FR1" with --LC-FR1--.

At claim number 1, line number 22, please replace "HVR-H1" with --HVR-L1--.

At claim number 1, line number 24, please replace "HC-FR2" with --LC-FR2--.

At claim number 1, line number 26, please replace "HVR-H2" with --HVR-L2--.

At claim number 1, line number 28, please replace "HC-FR3" with --LC-FR3--.

At claim number 1, line number 30, please replace "HVR-H3" with --HVR-L3--.

At claim number 1, line number 32, please replace "HC-FR4" with --LC-FR4--.

Signed and Sealed this  
Twenty-ninth Day of July, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,436,147 B2 | Page 1 of 1 |
| APPLICATION NO. | : 11/978122 | |
| DATED | : May 7, 2013 | |
| INVENTOR(S) | : Dennis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 458 days.

Signed and Sealed this
Twenty-seventh Day of January, 2015

Michelle K. Lee
*Deputy Director of the United States Patent and Trademark Office*